United States Patent
Boyer, Jr. et al.

(10) Patent No.: US 6,528,510 B1
(45) Date of Patent: Mar. 4, 2003

(54) HIV PROTEASE INHIBITORS

(75) Inventors: Frederick Earl Boyer, Jr., Canton Township, MI (US); John Michael Domagala, Canton, MI (US); Edmund Lee Ellsworth, Brighton, MI (US); Christopher Andrew Gajda, Ann Arbor, MI (US); Susan Elizabeth Hagen, Canton Township, MI (US); Michael James Lovdahl, Ann Arbor, MI (US); Elizabeth Ann Lunney, Ann Arbor, MI (US); Larry James Markoski, Champaign, IL (US); Josyula Venkata Nagendra Vara Prasad, Ann Arbor, MI (US); Bradley Dean Tait, Canton, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/674,652

(22) PCT Filed: Aug. 18, 1999

(86) PCT No.: PCT/US99/18986
§ 371 (c)(1),
(2), (4) Date: Nov. 2, 2000

(87) PCT Pub. No.: WO00/15634
PCT Pub. Date: Mar. 23, 2000

Related U.S. Application Data

(60) Provisional application No. 60/099,946, filed on Sep. 11, 1998.

(51) Int. Cl.[7] .................. A61K 31/495; A61K 31/47; C07D 239/02; C07D 401/00; C07D 333/02
(52) U.S. Cl. ................ 514/252.01; 514/227.5; 514/252.1; 514/256; 514/269; 514/314; 514/397; 544/60; 544/298; 544/315; 544/374; 546/1; 546/268; 548/304.4; 548/304.7; 548/311.1; 549/29; 549/292; 549/417
(58) Field of Search ............... 514/460, 397, 514/252.01, 252.1, 256, 227.5, 232.2, 314, 269; 549/29, 292, 417; 548/304.4, 304.7, 311.1; 546/268.1; 544/298, 60, 315, 374, 397

(56) References Cited

U.S. PATENT DOCUMENTS 3,786,063 A   1/1974  Arnold .............. 260/306.5

FOREIGN PATENT DOCUMENTS

| WO | 9514011 | | 5/1995 |
| WO | 9514012 | * | 5/1995 |
| WO | 9819997 | * | 5/1998 |

OTHER PUBLICATIONS

PCT International Search Report, PCT/US99/18986.
Chemical Abstracts, vol. 84, No. 21, 1976, abstract no. 150164.
Hagen, et al., "Synthesis of 5,6–Dihydro–4–hydroxy–2–pyrones as HIV–1 Protease Inhibitors: The Profound Effect of Polarity on Antiviral Activity", *J. Med. Chem.,* vol. 40, No. 23, 1997, pp. 3707–3711.
Ellsworth, et al., "4–Hydroxy–5, 6–dihydro–2H–pyran–2–ones. 3. Bicyclic and heteroaromatic ring systems as 3–position scaffolds to bind to S1'and S2'of the HIV–1 protease enzyme", *Bioorganic & Medicinal Chemistry Letters,* vol. 9, No. 14, 1999, pp. 2019–2024.
Vara Prasad, et al., "Nonpeptidic HIV protease inhibitors: 6–alkyl–5,6–dihydropyran–2–ones possessing achiral 3–(4–amino/carboxamide–2–t–butyl, 5–methylphenyl thio) moiety: antiviral activities and pharmacokinetic properties", *Bioorganic & Medicinal Chemistry Letters,* vol. 9, No. 11, 1999, pp. 1481–1486.

* cited by examiner

Primary Examiner—Richard L. Raymond
Assistant Examiner—Sudhaker B. Patel
(74) Attorney, Agent, or Firm—Elizabeth M. Anderson; Heidi M. Berven

(57) ABSTRACT

The present invention relates to novel dihydropyrones with tethered heterocycles having improved pharmacologic properties which potently inhibit the HIV aspartyl protease blocking HIV infectivity. The dihydropyrones are useful in the development of therapies for the treatment of viral infections and diseases, including AIDS. The present invention is also directed to methods of synthesis of the dihydropyrones and intermediates useful in the preparation of the final compounds.

33 Claims, No Drawings

HIV PROTEASE INHIBITORS

This application claims the benefit of provisional application No. 60/099,946 filed Sep. 11, 1998.

BACKGROUND OF THE INVENTION

The HIV-protease enzyme is absolutely essential for the replication and dissemination of HIV throughout the body (Navia M. A. and McKeever B. M., *Ann. New York Acad. Sci.,* 1990;616:73–85) and has become an extremely important target for the design and development of anti-HIV therapeutic agents (von der Helm K., *Biol. Chem.* 1996;377:756–774). Several peptidomimetic HIV protease inhibitors have been successfully developed (such as indinavir, saquinavir, ritonavir, and nelfinavir), which demonstrate significant clinical success in lowering plasma viral load. reducing the onset to AIDS. and decreasing the frequency of opportunistic infections (Deeks S. G., Smith M., Holodniy M., and Kahn J. O., *JAMA.,* 1997;277: 145–153).

Yet the current HIV protease inhibitors by their peptidomimetic nature have relatively poor solubility, high biliary excretion, limited bioavailabilities and significant liver metabolism. These drawbacks in turn increase the need for high doses of drug which increases the frequency of various side effects and multiple drug interactions (Barry M., Gibbons S., Back D., and Mulcahy F., *Clin Pharmacokinet.,* 1997;32: 194–209). More importantly, resistance to the current HIV protease inhibitors has emerged (Shock H. B.. Garsky V. M., and Kuo L., *J. Biol Chem,* 1996;27 1:31957–31963) resulting in treatment failures (Fatkenheuer G., Theisen A., Rockstroh J., Grabow T., et at., *AIDS,* 1997;11:F113–F1 16). From this discussion, it is apparent that while HIV protease is an excellent antiviral target for the treatment of HIV infection and AIDS, there is a critical need to identify non-peptide inhibitors with improved pharmacological properties and which are not cross resistant with the current drugs (Wallace R. W., *DDT,* 1997;2:83–84).

U.S. Pat. No. 5,789,440 recites non-peptidic HIV protease inhibitors of formula A

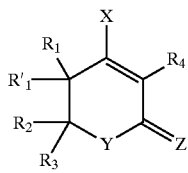

A

The patent application is hereby incorporated by reference. Excellent HIV protease inhibition was achieved, but the antiviral activity at the cellular level was in some cases less than desired for an ideal therapeutic agent due to poor overall pharmacological properties (Tummino P. J., Vara Prasad J. V. N., Ferguson D., Nauhan C., et al., *BioOrganic and Med. Chem.,* 1996;4:1401–1410). These efforts however led to a core structure B where $R_1$ and $R_2$ were alkyl groups filling the

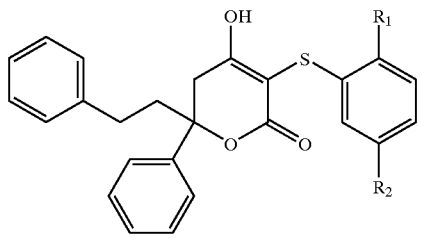

B $S_1'$ and $S_2'$ pockets, respectively, and the phenyl of the phenethyl group at $C_6$ filled the $S_2$ pocket very efficiently. This core structure was recognized as a valuable platform for additional study (Tait B. D., Hagen S., Domagala J. M., Ellsworth E. L., et al., *J. Med. Chem.,* 1997;40:3781–3792).

Additional dihydropyrones C were reported when it was unexpectedly discovered that certain polar groups judiciously placed at $R_1$–$R_5$ led to greatly

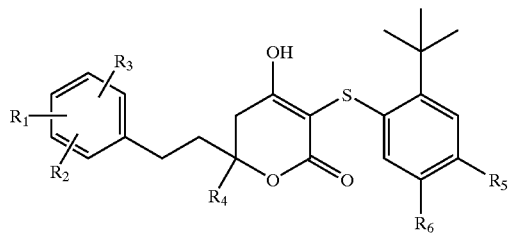

C improved antiviral cellular activity. See U.S. patent application Ser. No. 08/883,743. The patent application is hereby incorporated by reference. Among the preferred compounds were those where $R_1$ and $R_5$ were OH, $NH_2$, or $CH_2OH$. In such cases, the preferred $R_4$ included a small alkyl chain or ring and $R_6$ was methyl. In addition to improved cellular antiviral activity, the compounds also showed good pharmacokinetics in animals relative to the non-polar substituted compounds. These compounds were also not cross resistant with current HIV Protease inhibitors (Hagen S. E., Vara Prasad J. V. N., Boyer F. E., Domagala J. M., et al., *J. Med.,* 1997;40:3707–3711; Vander Roest S., Wold S., and Saunders J., *37th Interscience Conference on Antimicrobial Agents and Chemotherapy,* Sep. 28–Oct. 1, 1997, Toronto, Canada. Abstract I-84; Domagala J. M., Boyer F., Ellsworth E., Gajda C., et al., *5th Conference on Retroviruses and Opportunistic Infections,* Feb. 1–5, 1998, Chicago, Ill. Abstract 638).

While the compounds C were notable for their improved pharmacological properties relative to the non-polar substituted core molecules B, these highly favorable properties were conferred directly by the use of OH, $NH_2$ and $NR_2$ groups placed on the lipophilic rings. The rings themselves were important for binding to the enzyme "pockets" and for holding the t-butyl group and the groups $R_1$–$R_3$ and $R_5$ in their proper places within the enzyme's active site.

It is well-known in the pharmacological sciences that OH and $NH_2$ groups, especially phenols and anilines, offer distinct metabolic sites resulting in deactivation of the drug and more rapid clearance. In particular, phenols may be glucuronidated and amines and anilines are substrates for rapid acetylation (Goodman L. S. and Gilman A., *The Pharmacological Basis of Therapeutics,* Permagon Press, New York, N.Y. 1985:13–16). Such modifications generally inactivate the drug by preventing its binding to the structurally stringent active site of the enzyme. The modifications also reduce the plasma level of the active agent (Caldwell J., in *Concepts in Drug Metabolism,* edited by Jenner P. and Testa B., Marcel Dekker, New York, N.Y., Part A, 1980:235–238). Another suggested problem with amines and anilines is their possible oxidation to electropositive nitrogen species which have mutagenic potential (Sobels F. H., *Mut. Res.,* 1985;157:107–110; Bus J. S. and Popp J. A., *Fd Chem. Toxic,* 1987:25:619–626; Rodrigues-Amaiz R. and Aranda J. H., *Env. Mol. Mutagenesis,* 1994;24:75–79). Thus, while the polar groups are vital for good antiviral efficacy, solubility, and oral absorption, they also present sites for metabolism and possible mutagenesis.

This hereby incorporates by reference 5888L1-01-TMC filed on even date herewith now United States Patent Application Serial Number 60/099,944 filed Sep. 11, 1998, entitled "A Method of Making Dihydropyrone HIV Protease Inhibitors" by Victor Fedij, et al.

SUMMARY OF THE INVENTION

The present invention relates to the extraordinary discovery that the phenyl groups bearing the important polar groups (especially the OH and $NH_2$ groups) in formula C above, the very polar groups that improved cellular antiviral activity and improved pharmacokinetics in animals relative to compounds of formula B, can themselves be replaced by certain selected heterocycles. These heterocycles bind to the enzyme in the manner of the phenyls to preserve essential enzymatic activity, but additionally present the polar atoms of the heterocycle in such a way as to maintain cellular antiviral activity without requiring peripheral OH and $NH_2$ groups. Since these compounds have fewer peripheral OH and $NH_2$ groups. they have even greater pharmacokinetic improvements and less potential for amine based toxicity.

The dihydropyrones with selected heterocycles replacing the phenyls bearing polar substituents are useful in the development of treatments for infections caused by viruses, especially by retroviruses that rely on aspartyl protease activities for replication and infectivity. One such virus is HIV. These dihydropyrones provide higher plasma levels in animals and man due to reduced metabolism and/or clearance, and they provide less toxicity risk due to the removal of certain reactive anilino functionalities. For these reasons, the compounds of this invention are very useful for lowering viral load in individuals infected with HIV. Furthermore, the compounds reduce diseases and syndromes associated with viral pathogenesis. One such syndrome is AIDS.

The compounds of the instant invention will be useful according to: Guidelines for the Use of Antiretroviral Agents in HIV-Infected Adults and Adolescents, supplement to the *J. of the International Association of Physicians in AIDS Care,* Supp. No. 1, Vol. 5, pp 4–26 and David A. Katzenstein, Antiretroviral Therapy for HIV: What to do in 1999. *The Journal of Critical Illness,* April 1999; 14(4):196.

DETAILED DESCRIPTION OF THE INVENTION

The present invention relates to compounds or pharmaceutically acceptable salts thereof, of Formula I

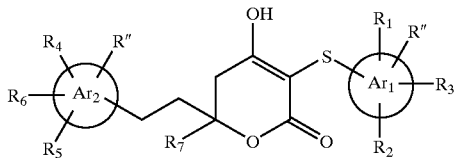

I $R_1$ is H, a straight or branched alkyl of 1–6 carbons or a carbocycle of 3–6 carbons;

$R_2$ is H, a straight or branched alkyl of 1–5 carbons;

$R_3$ is H, $(CR'_2)_nOR$, $(CR'_2)_nN(R)_2$, $(CR'_2)_nNR'COR$, $(CR'_2)_nCO_2R$, $(CR'_2)_nOCOR$, $(CR'_2)_nCON(R)_2$, $(CR'_2)_n$ $OCON(R)_2$, $(CR'_2)_nR$, $(CR'_2)_nNR'CON(R)_2$, $(CR'_2)_n$ $NR'CO_2R$, $(CR'_2)_nOSO_2N(R)_2$, $(CR'_2)_n$ $NR'SO_2OR$, $(CR'_2)_nNR'SO_2N(R)_2$, $(CR'_2)_nOSO_2R$, $(CR'_2)_n$ $NR'SO_2R$, $(CR'_2)_nSO_pR$, $(CR'_2)_nNR'CSN(R)_2$, $(CR'_2)_n$ $NR'C(NR')N(R)_2$, $(CR'_2)_nSO_2N(R)_2$, $(CR'_2)_nC$ $(NR')N(R)_2$, $(CR'_2)_nCOR$, $O(CR'_2)_mOR$, $NR(CR'_2)_mOR$, F, Cl, Br, $CF_3$, CN, or =O;

$R_4$, $R_5$, and $R_6$ are independently H, a straight or branched alkyl of 1–6 carbons, a cycloalkyl of 3–6 carbons, $(CR'_2)_nOR$, $(CR'_2)_nN(R)_2$, F, Cl, Br, CN, $CF_3$, =O, $(CR'_2)_pNR'COR$, $(CR'_2)_pSO_pR$, $(CR'_2)_pR$, $(CR'_2)_p$ $OCOR$, $O(CR'_2)_mOR$, $NR(CR'_2)_mOR$, $(CR'_2))_p$ $NR'CON(R)_2$, $(CR'_2)_pOCON(R)_2$, $(CR'_2)_pNR'CO_2R$, $(CR'_2)_pCOR$, $(CR'_2)_pCO_2R$, $(CR'_2)_pCON(R)_2$, $(CR'_2)_p$ $NR'SO_2R$, $(CR'_2)_pSO_2N(R)_2$, $(CR'_2)_pNR'SO_2OR$, $(CR'_2)_pOSO_2N(R)_2$, $(CR'_2)_pNR'SO_2N(R)_2$, $(CR'_2)_pC$ $(NR')N(R)_2$, $(CR'_2)_pNR'C(NR')N(R)_2$, $(CR'_2)_pHet$;

any two of $R_1$–$R_3$ or $R_4$–$R_6$ may together form a ring of 5–6 total atoms which may contain 0–3 heteroatoms;

n is an integer of from 0 to 3;

m is an integer of from 2 to 4;

p is an integer from 0 to 2;

$R_7$ is a straight or branched alkyl of 1–6 carbons or a carbocycle of 3–6 carbons;

R is independently H, a straight or branched alkyl of 1–4 carbons, $(CH_2)_nPh$, or a $(CH_2)_n$heterocycle of 5–6 atoms containing 1–2 heteroatoms and wherein the $(R)_2$ in $N(R)_2$ may form a heterocycle containing the nitrogen, all optionally substituted by F, Cl, Br, OR', CN, $CO_2R'$, $N(R')_2$, NR'COR', $CF_3$, or =O;

R' is independently H, a straight or branched alkyl of 1–4 carbons, or phenyl;

R" is independently H, a straight or branched alkyl of 1–4 carbons, F, Cl, Br, OR', or $N(R')_2$;

$Ar_1$ and $Ar_2$ are independently phenyl or Het with the proviso that at least one Ar is Het;

Het is a heterocycle of from 5–6 atoms having from 1–4 heteroatoms or a fused heterocycle of from 9–10 atoms having 1–3 heteroatoms.

A compound which upon administering to a human being converts into a compound according to Formula I is within the scope of this invention.

Preferred compounds of Formula I are those wherein:

$R_1$ is isopropyl or t-butyl;

$R_2$ is H, methyl, or ethyl;

$R_3$ is H, $(CR'_2)_nOR$, $(CR'_2)_nN(R)_2$, $(CR'_2)_nNR'COR$, $(CR'_2)_nCO_2R$, $(CR'_2)_nOCOR$, $(CR'_2)_nCON(R)_2$, $(CR'_2)_n$ $OCON(R)_2$, $(CR'_2)_nNR'CON(R)_2$, $(CR'_2)_n$ $NR'CO_2R$, $(CR'_2)_nOSO_2N(R)_2$, $(CR'_2)_nNR'SO_2OR$, $(CR'_2)_n$ $NR'SO_2N(R)_2$, $(CR'_2)_nOSO_2R$, $(CR'_2)_n$ $NR'SO_2R$, $(CR'_2)_nSO_pR$, $(CR'_2)_nNR'CSN(R)_2$, $(CR'_2)_nCOR$, $O(CR'_2)_mOR$, $NR(CR'_2)_mOR$, F, Cl, Br, $CF_3$, CN, or =O;

$R_4$, $R_5$, and $R_6$ are independently H, a straight or branched alkyl of 1–6 carbons, a cycloalkyl of 3–6 carbons, $(CH_2)_nOR$, $(CH_2)_nN(R)_2$, F, Cl, Br, CN, $CF_3$, =O, $(CR'_2)_pNR'COR$, $(CR'_2)_pSO_pR$, $(CR'_2)_pNR'CON(R)_2$, $(CR'_2)_pOCON(R)_2$, $(CR'_2)_pNR'COR$, $(CR'_2)_pCOR$, $(CR'_2)_pCO_2R$, $(CR'_2)_pCON(R)_2$, $(CR'_2)_pNR'SO_2R$, $(CR'_2))_pSO_2N(R)_2$, $(CR'_2)_pNR'SO_2OR$, $(CR'_2)_pOSO_2N(R)_2$, $(CR'_2)_pHet$ and any two of $R_1$–$R_3$ or $R_4$–$R_6$ may together form a ring of 5–6 total atoms which may contain 0–2 heteroatoms;

n is an integer of 0 to 3;

m is an integer of 2 to 4;

p is 0 to 2;

$R_7$ is a straight or branched alkyl of 1–6 carbons or a carbocycle of 3–6 carbons;

R is H, a straight or branched alkyl of 1–4 carbons, $(CH_2)_nPh$, or a $(CH_2)_n$heterocycle of 5–6 atoms containing 1–2 heteroatoms and wherein the $(R)_2$ in $N(R)_2$ may form a heterocycle containing the nitrogen, all optionally substituted by F, Cl, Br, OR', $N(R')_2$, NR'COR', $CF_3$, or =O;

R' is H, a straight or branched alkyl of 1–4 carbons, or phenyl;

R" is H, a straight or branched alkyl of 1–4 carbons, F, Cl, Br, OR', or $N(R')_2$;

$Ar_1$ is phenyl or Het; and $Ar_2$ is Het wherein Het is a heterocycle of from 5–6 atoms having 1–4 heteroatoms selected from: furan, pyrrole, thiophene, oxazole, isoxazole, thiazole, pyrazole, 1,2,3-triazole, 1,2,4-triazole, tetrazole, pyridine, pyridazine, pyrimidine, pyrazine, tetrahydrofuran, tetrahydrothiophene, pyrrolidine, piperazine, piperidine, morpholine, thiomorpholine, oxolane, dioxane, sulfolane; or a fused heterocycle of from 9–10 atoms having from 1–3 heteroatoms selected from: benzofuran, indole, indoline, benzothiophene, benzimidazole, benzthiazole, benzoxazole, quinoline, isoquinoline, cinnoline, quinazoline and quinoxaline.

Other preferred compounds of Formula I are those wherein:

$R_1$ is isopropyl or t-butyl;

$R_2$ is H, methyl or ethyl;

$R_3$ is H, $(CH_2)_nOR$, $(CH_2)_nN(R)_2$, $(CH_2)_nNR'COR$, $(CH_2)_nCON(R)_2$, $(CH_2)_nOCON(R)_2$, $(CH_2)_nNR'CON(R)_2$, $(CH_2)_nNR'CO_2R$, $(CH_2)_nOSO_2N(R)_2$, $(CH_2)_nNR'SO_2OR$, $(CH_2)_nNR'SO_2N(R)_2$, $(CH_2)_nOSO_2R$, $(CH_2)_nNR'SO_2R$, $(CH_2)_nSO_2R$, $(CH)_nNR'CSN(R)_2$, $(CH_2)_nCOR$, $O(CH_2)_mOR'$, $NR(CH_2)_mOR'$, or $C(CH_3)_2OR'$;

$R_4$, $R_5$, and $R_6$ are independently H, a straight or branched alkyl of 1–6 carbons, a cycloalkyl of 3–6 carbons, $(CH_2)_nOR$, $(CH_2)_nN(R)_2$, F, Cl, Br, CN, $CF_3$, =O, $(CH_2)_pNR'COR$, $(CH_2)_pNR'CON(R)_2$, $(CH_2)_pOCON(R)_2$, $(CH_2)_pNR'CO_2R$, $(CH_2)_pCOR$, $(CH_2)_pCON(R)_2$, $(CH_2)_pNR'SO_2R$, $(CH_2)_pNR'SO_2OR$, $(CH_2)_pOSO_2N(R)_2$, wherein p is 0 to 2, or $R_4$ and $R_5$ may together form a ring of 5–6 total atoms which may contain 0–2 heteroatoms;

n is an integer of 0 to 3;

m is an integer of 2 to 4;

$R_7$ is a straight or branched alkyl of 1–6 carbons or a carbocycle of 3–6 carbons;

R is H, a straight or branched alkyl of 1–4 carbons, $(CH_2)_nPh$, or a $(CH_2)_n$heterocycle of 5–6 atoms containing 1–2 heteroatoms and wherein the $(R)_2$ in $N(R)_2$ may be a heterocycle containing the nitrogen, all optionally substituted by F, Cl, Br, OR', $N(R')_2$, NR'COR', or =O;

R' is H, a straight or branched alkyl of 1–4 carbons, or phenyl;

R" is H, a straight or branched alkyl of 1–4 carbons, F, Cl, Br, OR', or $N(R')_2$;

$Ar_1$ is phenyl; and $Ar_2$ is a heterocycle of 5–6 atoms having from 1–4 heteroatoms selected from: furan, pyrrole, thiophene, oxazole, isoxazole, thiazole, pyrazole, 1,2,3-triazole, 1,2,4-triazole, tetrazole, pyridine, pyridazine, pyrimidine, pyrazine, tetrahydrofuran, tetrahydrothiophene, pyrrolidine, piperazine, piperidine, morpholine, thiomorpholine, oxolane, dioxane, sulfolane; or a fused heterocycle of 9–10 atoms having from 1–3 heteroatoms selected from: benzofuran, indole, indoline, benzothiophene, benzimidazole, benzthiazole, benzoxazole, quinoline, isoquinoline, cinnoline, quinazoline and quinoxaline.

Still other preferred compounds of Formula I are those wherein:

$R_1$ is H, a straight or branched alkyl of 1–6 carbons or a carbocycle of 3–6 carbons;

$R_2$ is H, a straight or branched alkyl of 1–5 carbons;

$R_3$ is H, $(CH_2)_nOR$, $(CH_2)_nN(R)_2$, $(CH_2)_nNR'COR$, $(CH_2)_nCON(R)_2$, $(CH_2)_nOCON(R)_2$, $(CH_2)_nNR'CON(R)_2$ $(CH_2)_nNR'CO_2R$, $(CH_2)_nOSO_2N(R)_2$, $(CH_2)_nNR'SO_2OR$, $(CH_2)_nNR'SO_2N(R)_2$, $(CH_2)_nOSO_2R$, $(CH_2)_nNR'SO_2R$, $(CH_2)_nSO_2R$, $(CH_2)_nCOR$, $O(CH_2)_mOR$, $NR(CH_2)_mOR$, $C(CH_3)_2OR'$, F, Cl, Br, $CF_3$, or =O;

$R_4$, $R_5$, and $R_6$ are independently H, a straight or branched alkyl of 1–6 carbons, a cycloalkyl of 3–6 carbons, $(CH_2)_nOR$, $(CH_2)_nN(R)_2$, F, Cl, Br, =O, $(CH_2)_pNR'COR$, $(CH_2)_pNR'CON(R)_2$, $(CH_2)_pOCON(R)_2$, $(CH_2)_pNR'CO_2R$, $(CH_2)_pCOR$, $(CH_2)_pCON(R)_2$, $(CH_2)_pNR'SO_2R$, $(CH_2)_pNR'SO_2OR$, $(CH_2)_pOSO_2N(R)_2$, wherein p is 0 to 2;

$R_4$ and $R_5$ may together form a ring of 5–6 total atoms which may contain 0–2 heteroatoms;

n is an integer of 0 to 3;

m is an integer of 2 to 4;

$R_7$ is methyl, ethyl, isopropyl, cyclopropyl, cyclobutyl, cyclopentyl or cyclohexyl;

R is H, a straight or branched alkyl of 1–4 carbons, $(CH_2)_nPh$, or a $(CH_2)_n$heterocycle of 5–6 atoms containing 1–2 heteroatoms and wherein the $(R)_2$ in $N(R)_2$ may be a heterocycle containing the nitrogen, all optionally substituted by F, Cl, Br, OR', $N(R')_2$, NR'COR', or =O;

R' is H, a straight or branched alkyl of 1–4 carbons, or phenyl;

R" is H, a straight or branched alkyl of 1–4 carbons, F, Cl, Br, OR', or $N(R')_2$;

$Ar_1$ is phenyl or Het; and $Ar_2$ is Het wherein Het is a heterocycle of 5–6 atoms having from 1–4 heteroatoms selected from: furan, pyrrole, thiophene, oxazole, isoxazole, thiazole, pyrazole, 1,2,3-triazole, 1,2,4-triazole, tetrazole, pyridine, pyridazine, pyrimidine, pyrazine, tetrahydrofuran, tetrahydrothiophene, pyrrolidine, piperazine, piperidine, morpholine, thiomorpholine, oxolane, dioxane, sulfolane; or a fused heterocycle of from 9–10 atoms having 1–3 heteroatoms selected from: benzofuran, indole, indoline, benzothiophene, benzimidazole, benzthiazole, benzoxazole, quinoline, isoquinoline, cinnoline, quinazoline and quinoxaline.

Still other preferred compounds of Formula I are those wherein:

$R_1$ is H, methyl, ethyl, isopropyl, or t-butyl;

$R_2$ is H or methyl;

$R_3$ is H, $(CH_2)_nOR$, $(CH_2)_nN(R)_2$, $(CH_2)_nNR'COR$, $(CH_2)_nCON(R)_2$, $(CH_2)_nOCON(R)_2$, $(CH_2)_nNR'CON(R)_2$, $(CH_2)_nNR'CO_2R$, $(CH_2)_nOSO_2N(R)_2$, $(CH_2)_nNR'SO_2OR$, $(CH_2)_nNR'SO_2N(R)_2$, $(CH_2)_nOSO_2R$, $(CH_2)_nNR'SO_2R$, $(CH_2)_nSO_2R$, $(CH_2)_nCOR$, $O(CH_2)_mOR'$, $NR(CH_2)_mOR'$, $C(CH_3)_2OR'$, F, Cl, Br, $CF_3$, or =O;

$R_4$, $R_5$, and $R_6$ are independently H, a straight or branched alkyl of 1–6 carbons, a cycloalkyl of 3–6 carbons, $(CH_2)_nOR$, $(CH_2)_nN(R)_2$, F, Cl, Br, $CF_3$, $(CH_2)_pNR'COR$, $(CH_2)_pNR'CON(R)_2$, $(CH_2)_pOCON(R)_2$, $(CH_2)_pNR'CO_2R$, $(CH_2)_pCOR$, $(CH_2)_pCON(R)_2$, $(CH_2)_pNR'SO_2R$, $(CH_2)_pNR'SO_2OR$, $(CH_2)_pOSO_2N(R)_2$, $(CH_2)_p$Het wherein p is 0 to 2;

any two of $R_4$–$R_6$ may together form a ring of 5–6 total atoms which may contain 0–2 heteroatoms, n is an integer of 0 to 3;

m is an integer of 2 to 4;

$R_7$ is a straight or branched alkyl of 1–6 carbons or a carbocycle of 3–6 carbons;

R is H, a straight or branched alkyl of 1–4 carbons, $(CH_2)_nPh$, or a $(CH_2)_n$heterocycle of 5–6 atoms having from 1–2 heteroatoms and wherein the $(R)_2$ in $N(R)_2$ may form a heterocycle having nitrogen, all optionally substituted by F, Cl, Br, OR', $N(R')_2$, NR'COR', or =O;

R' is H, a straight or branched alkyl of 1–4 carbons, or phenyl;

R" is H, a straight or branched alkyl of 1–4 carbons, F, Cl, Br, OR', or $N(R')_2$;

$Ar_1$ is a heterocycle of 5–6 atoms having from 1–4 heteroatoms selected from: furan, pyrrole, thiophene, oxazole, isoxazole, thiazole, pyrazole, 1,2,3-triazole, 1,2,4-triazole, tetrazole, pyridine, pyridazine, pyrimidine, pyrazine, tetrahydrofuran, tetrahydrothiophene, pyrrolidine, piperazine, piperidine, morpholine, thiomorpholine, oxolane, dioxane, sulfolane; or a fused heterocycle of 9–10 atoms having 1–3 heteroatoms selected from: benzofuran, indole, indoline, benzothiophene, benzimidazole, benzthiazole, benzoxazole, quinoline, isoquinoline, cinnoline, quinazoline and quinoxaline; and $Ar_2$ is phenyl.

More preferred compounds of Formula I are those wherein:

$R_1$ is isopropyl or t-butyl;

$R_2$ is H or methyl;

$R_3$ is H, $(CH_2)_nOR$, $(CH_2)_nN(R)_2$, $(CH_2)_nOCON(R)_2$, $(CH_2)_nNR'CON(R)_2$, $(CH_2)_nNR'CO_2R$, $(CH_2)_nOSO_2N(R)_2$, $(CH_2)_nNR'SO_2OR$, $(CH_2)_nNR'SO_2N(R)_2$, $(CH_2)_nNR'SO_2R$, $(CH_2)_nSO_2R$, $O(CH_2)_mOR'$, $NR(CH_2)_mOR'$, or $C(CH_3)_2OR'$;

$R_4$, $R_5$, and $R_6$ are independently H, a straight or branched alkyl of 1–6 carbons, a cycloalkyl of 3–6 carbons, $(CH_2)_nOR$, $(CH_2)_nN(R)_2$, F, Cl, Br, =O, $(CH_2)_pNR'COR$, $(CH_2)_pNR'CON(R)_2$, $(CH_2)_pOCON(R)_2$, $(CH_2)_pNR'CO_2R$, $(CH_2)_pCOR$, $(CH_2)_pCON(R)_2$, $(CH_2)_pNR'SO_2R$, $(CH_2)_pNR'SO_2OR$, $(CH_2)_pOSO_2N(R)_2$, wherein p is 0 to 2;

$R_4$ and $R_5$ may together form a ring of 5–6 total atoms which may contain 0–2 heteroatoms;

n is an integer of 0 to 3;

m is an integer of 2 to 4;

$R_7$ is a straight or branched alkyl of 1–6 carbons or a carbocycle of 3–6 carbons R is H, a straight or branched alkyl of 1–4 carbons, $(CH_2)_nPh$, or a $(CH_2)_n$heterocycle of 5–6 atoms having from 1–2 heteroatoms and wherein the $(R)_2$ in $N(R)_2$ may be a heterocycle containing the nitrogen, all optionally substituted by F, Cl, Br, OR', $N(R')_2$, NR'COR', or =O;

R' is H, a straight or branched alkyl of 1–4 carbons, or phenyl;

R" is H, a straight or branched alkyl of 1–4 carbons, F, Cl, Br, OR', or $N(R')_2$;

$Ar_1$ is phenyl; and $Ar_2$ is furan, pyrrole, thiophene, oxazole, isoxazole, thiazole, pyrazole, tetrazole, or pyridine.

Other more preferred compounds of Formula I are those wherein:

$R_1$ is H, a straight or branched alkyl of 1–6 carbons or a carbocycle of 3–6 carbons;

$R_2$ is H, methyl or ethyl or isopropyl;

$R_3$ is H, $(CH_2)_nOR$, $(CH_2)_nN(R)_2$, $(CH_2)_nNRCOR$, $(CH_2)_n CON(R)_2$, $(CH_2)_nOCON(R)_2$, $(CH_2)_nNR'CON(R)_2$, $(CH_2)_nNR'CO_2R$, $(CH_2)_nOSO_2N(R)_2$, $(CH_2)_nNR'SO_2OR$, $(CH_2)_nNR'SO_2N(R)_2$, $(CH_2)_nOSO_2R$, $(CH_2)_nNR'SO_2R$, $(CH_2)_nSO_2R$, $O(CH_2)_mOR$, $NR(CH_2)_mOR'$, $C(CH_3)_2OR'$, or =O;

$R_4$, $R_5$, and $R_6$ are independently H, a straight or branched alkyl of 1–6 carbons, a cycloalkyl of 1–6 carbons, $(CH_2)_nOR$, $(CH_2)_nN(R)_2$, F, Cl, Br, =O, $(CH_2)_pNR'COR$, $(CH_2)_pNR'CON(R)_2$, $(CH_2)_pOCON(R)_2$, $(CH_2)_pNR'CO_2R$, $(CH_2)_pCOR$, $(CH_2)_pCON(R)_2$, $(CH_2)_pNR'SO_2R$, $(CH_2)_pNR'SO_2OR$, $(CH_2)_pOSO_2N(R)_2$, wherein p is 0 to 2;

$R_4$ and $R_5$ may together form a ring of 5–6 total atoms which may contain 0–2 heteroatoms;

n is an integer of 0 to 3;

m is an integer of 2 to 4;

$R_7$ is a straight or branched alkyl of 1–6 carbons or a carbocycle of 3–6 carbons;

R is H, a straight or branched alkyl of 1–4 carbons, $(CH_2)_nPh$, or a $(CH_2)_n$heterocycle of 5–6 atoms containing 1–2 heteroatoms and wherein the $(R)_2$ in $N(R)_2$ may be a heterocycle having nitrogen, all optionally substituted by F, Cl, Br, OR', $N(R')_2$, NR'COR', or =O;

R' is H, a straight or branched alkyl of 1–4 carbons, or phenyl;

R" is H, a straight or branched alkyl of 1–4 carbons, F, Cl, Br, OR', or $N(R')_2$;

$Ar_1$ is thiophene, thiazole, pyridine, benzothiophene, benzthiazole, benzoxazole, quinoline or isoquinoline; and $Ar_2$ is phenyl or Het wherein Het is a heterocycle of 5–6 atoms having from 1–4 heteroatoms selected from: furan, pyrrole, thiophene, oxazole, isoxazole, thiazole, pyrazole, 1,2,3-triazole, 1,2,4-triazole, tetrazole, pyridine, pyridazine, pyrimidine, pyrazine, tetrahydrofuran, tetrahydrothiophene, pyrrolidine, piperazine, piperidine, morpholine, thiomorpholine, oxolane, dioxane, sulfolane; or a fused heterocycle of 9–10 atoms having 1–3 heteroatoms selected from: benzofuran, indole, indoline, benzothiophene, benzimidazole, benzthiazole, benzoxazole, quinoline, isoquinoline, cinnoline, quinazoline and quinoxaline.

Still other more preferred compounds of formula IV are those wherein:

$R_1$ is isopropyl or t-butyl;

$R_2$ is H, methyl, or ethyl;

$R_3$ is $CH_2OH$, $NH_2$, $OCH_2CH_2OH$, $NHCOR$, $OSO_2N(R)_2$, $NR'SO_2OR$, $NR'SO_2R$, or $OSO_2R$;

$R_4$, $R_5$ and $R_6$ are independently H, a straight or branched alkyl of 1–6 carbons, a cycloalkyl of 1–6 carbons, $(CH_2)_nOR$, $(CH_2)_nN(R)_2$, F, Cl, Br, =O, $(CH_2)_pNR'COR$, $(CH_2)_pNR'CON(R)_2$, $(CH_2)_pOCON(R)_2$, $(CH_2)_pNR'CO_2R$, $(CH_2)_pCOR$, $(CH_2)_pCON(R)_2$, $(CH_2)_pNR'SO_2R$, $(CH_2)_pNR'SO_2OR$, $(CH_2)_pOSO_2N(R)_2$, wherein p is 0 to 2;

$R_4$ and $R_5$ may together form a ring of 5–6 total atoms which may contain 0–2 heteroatoms;

$R_7$ is a straight or branched alkyl of 1–6 carbons or a carbocycle of 3–6 carbons, R is H, a straight or branched alkyl of 1–4 carbons, $(CH_2)_nPh$, or a $(CH_2)_n$heterocycle of 5–6 atoms having from 1–2 heteroatoms and wherein the $(R)_2$ in $N(R)_2$ may be a heterocycle having nitrogen, all optionally substituted by F, Cl, Br, OR', $N(R')_2$, NR'COR', or =O;

R' is H, a straight or branched alkyl of 1–4 carbons, or phenyl;

R" is H, a straight or branched alkyl of from 1–4 carbons, F, Cl, Br, OR', or $N(R')_2$;

$Ar_1$ is phenyl; and $Ar_2$ is a heterocycle of 5–6 atoms having from 1–4 heteroatoms selected from: furan, pyrrole, thiophene, oxazole, isoxazole, thiazole, pyrazole, 1,2,3-triazole, 1,2,4-triazole, tetrazole, pyridine, pyridazine, pyrimidine, pyrazine, tetrahydrofuran, tetrahydrothiophene, pyrrolidine, piperazine, piperidine, morpholine, thiomorpholine, oxolane, dioxane, sulfolane; or a fused heterocycle of 9–10 atoms having from 1–3 heteroatoms selected from: benzofuran, indole, indoline, benzothiophene, benzimidazole, benzthiazole, benzoxazole, quinoline, isoquinoline, cinnoline, quinazoline and quinoxaline.

Still other more preferred compounds of Formula I are those wherein;

$R_1$ is H, methyl, ethyl, isopropyl, or t-butyl;

$R_2$ is H or methyl;

$R_3$ is H, $(CH_2)_nOR$, $(CH_2)_nN(R)_2$, $(CH_2)_nNR'COR$, $(CH_2)_nCON(R)_2$, $(CH_2)_nOCON(R)_2$, $(CH_2)_nNR'CON(R)$, $(CH_2)_nNR'CO_2R$, $(CH_2)_nOSO_2N(R)_2$, $(CH_2)_nNR'SO_2OR$, $(CH_2)_nNR'SO_2N(R)_2$, $(CH_2)_nOSO_2R$, $(CH_2)_nNR'SO_2R$, $(CH_2)_nSO_2R$, $(CH_2)_nNR'CSN(R)_2$, $(CH_2)_nCOR$, $O(CH_2)_mOR$, $NR(CH_2)_mOR'$, $C(CH_3)_2OR'$, F, Cl, Br, or =O;

$R_4$, $R_5$ and $R_6$ are independently H, methyl, ethyl, OH, $CH_2OH$, $CH_2CH_2OH$, F, Cl, $NH_2$;

any two $R_4$–$R_6$ may form a ring of 5–6 atoms having from 1–2 heteroatoms;

n is an integer of 0 to 3;

m is an integer of 2 to 4;

$R_7$ is a straight or branched alkyl of 1–6 carbons or a carbocycle of 3–6 carbons;

R is H, a straight or branched alkyl of 1–4 carbons, $(CH_2)_nPh$, or a $(CH_2)_n$heterocycle of 5–6 atoms having from 1–2 heteroatoms or a heterocycle having a nitrogen, all optionally substituted by F, Cl, Br, OR', $N(R')_2$, NR'COR', or =O;

R' is H, a straight or branched alkyl of 1–4 carbons, or phenyl;

R" is H, a straight or branched alkyl of 1–4 carbons, F, Cl, Br, OR', or $N(R')_2$;

$Ar_1$ is furan, thiophene, thiazole, pyridine, imidazole, benzofuran, benzothiophene, benzimidazole, benzthiazole, quinoline, or isoquinoline; and $Ar_2$ is phenyl.

Still other more preferred compounds of formula IV are those wherein:

$R_1$ is H, methyl, ethyl, isopropyl, or t-butyl;

$R_2$ is H or methyl;

$R_3$ is H, $(CH_2)_nOR$, $(CH_2)_nN(R)_2$, or =O;

$R_4$, $R_5$, and $R_6$ are independently H, methyl, OH, $CH_2OH$, $CH_2CH_2OH$, $NH_2$, or F;

$R_7$ is H, isopropyl, butyl, sec-butyl, cyclobutyl, cyclopentyl, or cyclohexyl;

R is H, methyl, ethyl, phenyl, or $CH_2Ph$ and wherein the $(R)_2$ of $N(R)_2$ may be a heterocycle having a nitrogen;

R" is H, F, or $CH_3$;

$Ar_1$ is furan, thiophene, thiazole, pyridine, imidazole, benzofuran, benzothiophene, benzimidazole, benzthiazole, quinoline, or isoquinoline; and $Ar_2$ is phenyl.

Most preferred compounds of Formula I are those wherein:

$R_1$ is H, methyl, ethyl, isopropyl, or t-butyl;

$R_2$ is H, methyl, ethyl, or isopropyl;

$R_3$ is H, $NH_2$, OH, $CH_2OR$, $CH_2N(R)_2$, $CH_2CON(R)_2$, $CH_2OSO_2N(R)_2$, $CH_2NHSO_2OR$, $CH_2NHSO_2R$, $CH_2OSO_2R$, Cl, Br, or $OCH_2CH_2OH$;

$R_4$, $R_5$, and $R_6$ are independently H, methyl, ethyl, isopropyl, OH, $NH_2$, $CH_2OR$, $CH_2N(R)_2$, =O, F, Cl, Br, or $CH_2NRCOR$;

$R_7$ is methyl, ethyl, isopropyl, cyclopropyl, cyclobutyl, or cyclopentyl;

R is H, methyl, ethyl, Ph, $CH_2Ph$, and wherein the $(R)_2$ in $N(R)_2$ may be a heterocycle having a nitrogen;

R" is H, F, or $CH_3$;

$Ar_1$ is thiophene, thiazole, furan, pyridine, benzothiophene, benzofuran, benzthiazole, benzoxazole, quinoline, or isoquinoline; and $AR_2$ is furan, thiophene, oxazole, isoxazole, imidazale, thiazole, pyrazole, pyridine, benzofuran, benzothiophene, benzimidazole, benzthiazole, quinoline, or isoquinoline.

Other most preferred compounds of Formula I are those wherein:

$R_1$ is isopropyl or t-butyl;

$R_2$ is H, methyl, or ethyl;

$R_3$ is H, $NH_2$, OH, $CH_2OR$, $CH_2N(R)_2$, $CH_2CON(R)_2$, $OSO_2N(R)_2$, $NHSO_2OR$, $NHSO_2R$, $OSO_2R$, or $OCH_2CH_2OH$;

$R_4$, $R_5$, and $R_6$ are independently H, methyl, ethyl, isopropyl, OH, $NH_2$, $CH_2OR$, $CH_2N(R)_2$, =O, F, Cl, Br, or $CH_2NRCOR$;

$R_7$ is methyl, ethyl, isopropyl, cyclopropyl, cyclobutyl, or cyclopentyl;

R is H, methyl, ethyl, Ph, $CH_2Ph$, and wherein the $(R)_2$ in $N(R)_2$ may be a heterocycle containing the nitrogen;

R" is H, F, or $CH_3$;

$Ar_1$ is phenyl; and $Ar_2$ is furan, thiophene, oxazole, isoxazole, imidazale, thiazole, pyrazole, pyridine, benzofuran, benzothiophene, benzimidazole, benzthiazole, quinoline, or isoquinoline.

Still other most preferred compounds of Formula I are those wherein:

$R_1$ is isopropyl or t-butyl;

$R_2$ is H, methyl, or ethyl;

$R_3$ is $NH_2$, $CH_2OH$, $OCH_2CH_2OH$, or $CH_2CH_2OH$;

$R_4$, $R_5$, and $R_6$ are independently H, $NH_2$, $CH_2OH$, =O, methyl, ethyl, or isopropyl;

$R_7$ is isopropyl;

R" is H, F, or $CH_3$;

$Ar_1$ is phenyl; and $Ar_2$ is furan, thiophene, imidazole, thiazole, pyrazole, or pyridine.

Still other most preferred compounds of Formula I are those wherein:

$R_1$ is H, methyl, ethyl, isopropyl, or t-butyl;

$R_2$ is H or methyl;

$R_3$ is H, $CH_2OH$, $NH_2$, or =O;

$R_4$, $R_5$, and $R_6$ are independently H, OH, $CH_2OH$, $NH_2$, or F;

$R_7$ is isopropyl, sec-butyl, isobutyl, or cyclopentyl;

R is H, methyl, ethyl, Ph, $CH_2Ph$, and wherein the $(R)_2$ in $N(R)_2$ may be a heterocycle having a nitrogen;

R" is H, F, or $CH_3$;

$Ar_1$ is furan, thiophene, imidazole, thiazole, pyrazole, or pyridine; and $Ar_2$ is phenyl.

Especially preferred compounds of the invention are:

3-(2-tert-Butyl-4-hydroxymethyl-5-methyl-phenylsulfanyl)-4-hydroxy-6-isopropyl-6-(2-pyridin-4-yl-ethyl)-5,6-dihydro-pyran-2-one;

3-(2-tert-Butyl-4-hydroxymethyl-5-methyl-phenylsulfanyl)-4-hydroxy-6-isopropyl-6-(2-pyridin-3-yl-ethyl)-5,6-dihydro-pyran-2-one;

3-(2-tert-Butyl-4-hydroxymethyl-5-methyl-phenylsulfanyl)-4-hydroxy-6-isopropyl-6-(2-pyridin-2-yl-ethyl)-5,6-dihydro-pyran-2-one;

3-(2-tert-Butyl-4-hydroxymethyl-5-methyl-phenylsulfanyl)-6-(2-furan-3-yl-ethyl)-4-hydroxy-6-isopropyl-5,6-dihydro-pyran-2-one;

3-(2-tert-Butyl-4-hydroxymethyl-5-methyl-phenylsulfanyl)-6-(2-furan-2-yl-ethyl)-4-hydroxy-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(tetrahydro-furan-2-yl)-ethyl]-5,6-dihydro-pyran-2-one;

3-(2-tert-Butyl-4-hydroxymethyl-5-methyl-phenylsulfanyl)-4-hydroxy-6-isopropyl-6-(2-thiophen-3-yl-ethyl )-5,6-dihydro-pyran-2-one;

3-(2-tert-Butyl-4-hydroxymethyl-5-methyl-phenylsulfanyl)-4-hydroxy-6-isopropyl-6-(2-thiophen-2-yl-ethyl)-5,6-dihydro-pyran-2-one;

3-(2-tert-Butyl-4-hydroxymethyl-5-methyl-phenylsulfanyl)-4-hydroxy-6-[2-(5-hydroxymethyl-thiophen-3-yl)-ethyl]-6-isopropyl-5,6-dihydro-pyran-2-one;

3-(2-tert-Butyl-4-hydroxymethyl-5-methyl-phenylsulfanyl)-4-hydroxy-6-[2-(2-hydroxymethyl-thiophen-3-yl)-ethyl]-6-isopropyl-5,6-dihydro-pyran-2-one;

3-(4-Amino-2-tert-butyl-5-methyl-phenylsulfanyl)-4-hydroxy-6-[2-(2-hydroxymethyl-thiophen-3-yl)-ethyl]-6-isopropyl-5,6-dihydro-pyran-2-one;

(S)-3-(2-Amino-5-tert-butyl-benzothiazol-6-ylsulfanyl)-4-hydroxy-6-isopropyl-6-phenethyl-5,6-dihydro-pyran-2-one;

(S)-3-(2-Amino-5-isopropyl-benzothiazol-6-ylsulfanyl)-4-hydroxy-6-isopropyl-6-phenethyl-5,6-dihydro-pyran-2-one;

6-[-2-(4-Fluoro-phenyl)-ethyl]-4-hydroxy-6-isopropyl-3-(5-isopropyl-benzothiazol-6-ylsulfanyl)-5,6-dihydro-pyran-2-one;

3-(2-Amino-5-isopropyl-benzothiazol-6-yl-sulfanyl)-6-[2-(4-fluoro-phenyl)-ethyl]-phenethyl-4-hydroxy-6-isopropyl-5,6-dihydro-pyran-2-one;

(S)-3-(2-Amino-7-isopropyl-4-methyl-benzothiazol-6-yl-sulfanyl)-4-hydroxy-6-isopropyl-6-phenethyl-5,6-dihydro-pyran-2-one;

(S)-3-(2-Amino-7-isopropyl-4-methyl-benzothiazol-6-ylsulfanyl)-4-hydroxy-6-[2-(4-hydroxyl-phenyl)-ethyl]-6-isopropyl-5,6-dihydro-pyran-2-one;

(S)-(6-{4-Hydroxy-6-[2-(4-hydroxy-phenyl)-ethyl]-6-isopropyl-2-oxo-5,6-dihydro-2H-pyran-3-ylsulfanyl}-4-isopropyl-7-methyl-benzothiazol-2-yl)-carbamic acid methyl ester;

(S)-3-(2-Amino-6-tert-butyl-benzothiazol-4-ylsulfanyl)-4-hydroxy-6-[2-(4-hydroxy-phenyl)-ethyl]-6-isopropyl-5,6-dihydro-pyran-2-one;

(S)-3-(3-tert-Butyl-benzo[b]thiophen-2-ylsulfanyl)-4-hydroxy-6-[2-(4-hydroxy-phenyl)-ethyl]-6-isopropyl-5,6-dihydro-pyran-2-one;

3-(3-tert-Butyl-benzo[b]thiophen-2-yl-sufanyl)-4-hydroxy-6-[2-(2-hydroxymethyl-phenyl)-ethyl]-6-isopropyl-5,6-dihydro-pyran-2-one;

4-Hydroxy-3-(5-hydroxymethyl-2-isopropyl-thiophen-3-ylsulfanyl)-6-isopropyl-6-(2-thiophen-3-yl-ethyl)-5,6-dihydro-pyran-2-one;

3-(2-tert-Butyl-4-hydroxymethyl-5-methyl-phenylsulfanyl)-4-hydroxy-6-isopropyl-6-[2-(4-methyl-thiazol-5-yl)-ethyl]-5,6-dihydro-pyran-2-one;

3-(2-tert-Butyl-4-hydroxymethyl-5-methyl-phenylsulfanyl)-4-hydroxy-6-isopropyl-6-(2-thiazol-2-yl-ethyl)-5,6-dihydro-pyran-2-one;

3-(2-tert-Butyl-4-hydroxymethyl-5-methyl-phenylsulfanyl)-4-hydroxy-6-isopropyl-6-[2-(4-methyl-thiazol-2-yl)-ethyl]-5,6-dihydro-pyran-2-one;

N-(4-{2-[5-(2-tert-Butyl-4-hydroxymethyl-5-methyl-phenylsulfanyl)-4-hydroxy-2-isopropyl-6-oxo-3,6-dihydro-2H-pyran-2-yl]-ethyl}-thiazol-2-yl)-acetamide;

3-(2-tert-Butyl-4-hydroxymethyl-5-methyl-phenylsulfanyl)-4-hydroxy-6-isopropyl-6-[2-(5-methyl-thiazol-2-yl)-ethyl]-5,6-dihydro-pyran-2-one;

3-(2-tert-Butyl-4-hydroxymethyl-5-methyl-phenylsulfanyl)-4-hydroxy-6-isopropyl-6-(2-thiazol-5-yl-ethyl)-5,6-dihydro-pyran-2-one;

3-(2-tert-Butyl-4-hydroxymethyl-5-methyl-phenylsulfanyl)-4-hydroxy-6-isopropyl-6-[2-(2-methyl-thiazol-4-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(5-methyl-thiazol-4-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(2-isopropyl-thiazol-4-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(4-isopropyl-thiazol-5-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(5-isopropyl-thiazol-4-yl)-ethyl]-5,6-dihydro-pyran-2-one;

3-(4-Amino-2-tert-butyl-5-methyl-phenylsulfanyl)-4-hydroxy-6-isopropyl-6-(2-thiophen-3-yl-ethyl)-5,6-dihydro-pyran-2-one;

3-(4-Amino-2-tert-butyl-5-methyl-phenylsulfanyl)-6-(2-furan-3-yl-ethyl)-4-hydroxy-6-isopropyl-5,6-dihydro-pyran-2-one;

3-(2-tert-Butyl-4-hydroxy-5-methyl-phenylsulfanyl)-4-hydroxy-6-[2-(5-hydroxymethyl-thiophen-2-yl)-ethyl]-6-isopropyl-5,6-dihydro-pyran-2-one;

3-(4-Amino-2-tert-butyl-5-methyl-phenylsulfanyl)-4-hydroxy-6-[2-(5-hydroxymethyl-thiophen-2-yl)-ethyl]-6-isopropyl-5,6-dihydro-pyran-2-one;

3-(2-tert-Butyl-4-hydroxymethyl-5-methyl-phenylsulfanyl)-4-hydroxy-6-[2-(5-hydroxymethyl-thiophen-2-yl)-ethyl]-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(1H-pyrazol-3-yl)-ethyl]-5,6-dihydro-pyran-2-one;

3-(4-Amino-2-tert-butyl-5-methyl-phenylsulfanyl)-4-hydroxy-6-isopropyl-[2-(1H-pyrazol-3-yl)-ethyl]-5,6-dihydro-pyran-2-one;

3-(2-tert-Butyl-4-hydroxymethyl-5-methyl-phenylsulfanyl)-4-hydroxy-6-isopropyl-6-(2-pyrimidin-5-yl-ethyl)-5,6-dihydro-pyran-2-one;

3-(4-Amino-2-tert-butyl-5-methyl-phenylsulfanyl)-4-hydroxy-6-isopropyl-6-(2-pyrimidin-5-yl-ethyl)-5,6-dihydro-pyran-2-one;

6-[2-(2-Amino-pyrimidin-5-yl)-ethyl]-3-(2-tert-butyl-4-hydroxymethyl-5-methyl-phenylsulfanyl)-4-hydroxy-6-isopropyl-5,6-dihydro-pyran-2-one;

3-(4-Amino-2-tert-butyl-5-methyl-phenylsulfanyl)-6-[2-(2-amino-pyrimidin-5-yl)-ethyl]-4-hydroxy-6-isopropyl-5,6-dihydro-pyran-2-one;

3-(2-tert-Butyl-4-hydroxymethyl-5-methyl-phenylsulfanyl)-4-hydroxy-6-isopropyl-6-(2-thiazol-4-yl-ethyl)-5,6-dihydro-pyran-2-one;

(S)-4-Hydroxy-6-isopropyl-3-(5-isopropyl-benzothiazol-6-ylsulfanyl)-6-phenethyl-5,6-dihydro-pyran-2-one;

(S)-4-Hydroxy-6-[2-(4-hydroxy-phenyl)-ethyl]-6-isopropyl-3-(5-isopropyl-benzothiazol-6-ylsulfanyl)-5,6-dihydro-pyran-2-one;

3-(2-Amino-7-isopropyl-4-methyl-benzothiazol-6-ylsulfanyl)-6-[2-(4-fluoro-phenyl)-ethyl]-4-hydroxy-6-isopropyl-5,6-dihydro-pyran-2-one;

(S)-3-(2-Amino-5-tert-butyl-benzothiazol-6-ylsulfanyl)-4-hydroxy-6-[2-(4-hydroxy-phenyl)-ethyl]-6-isopropyl-5,6-dihydro-pyran-2-one;

(S)-3-(2-Amino-5-isopropyl-benzothiazol-6-ylsulfanyl)-4-hydroxy-6-[2-(4-hydroxy-phenyl)-ethyl]-6-isopropyl-5,6-dihydro-pyran-2-one;

(R)-3-(2-tert-Butyl-4-hydroxymethyl-5-methyl-phenylsulfanyl)-4-hydroxy-6-isopropyl-6-(2-thiophen-3-yl-ethyl)-5,6-dihydro-pyran-2-one;

3-(2-Amino-5-isopropyl-benzothiazol-6-ylsulfanyl)-4-hydroxy-6-isopropyl-6-[2-(2-trifluoromethyl-phenyl)-ethyl]-5,6-dihydro-pyran-2-one;

3-(4-Amino-2-tert-butyl-5-methyl-phenylsulfanyl)-4-hydroxy-6-isopropyl-6-(2-pyridin-3-yl-ethyl)-5,6-dihydro-pyran-2-one;

3-(2-tert-Butyl-5-methyl-phenylsulfanyl)-4-hydroxy-6-[2-(5-hydroxymethyl-thiophen-2-yl)-ethyl]-6-isopropyl-5,6-dihydro-pyran-2-one;

3-(4-Amino-2-tert-butyl-5-methyl-phenylsulfanyl)-4-hydroxy-6-isopropyl-6-[2-(tetrahydro-furan-2-yl)-ethyl]-5,6-dihydro-pyran-2-one;

3-(2-tert-Butyl-4-hydroxymethyl-phenylsulfanyl)-4-hydroxy-6-isopropyl-6-(2-thiophen-3-yl-ethyl)-5,6-dihydro-pyran-2-one;

3-[2-tert-Butyl-4-(2-hydroxy-ethyl)-5-methyl-phenylsulfanyl]-4-hydroxy-6-isopropyl-6-(2-thiophen-3-yl-ethyl)-5,6-dihydro-pyran-2-one;

5-Trifluoromethyl-pyridine-2-sulfonic acid {5-tert-butyl-4-[4-hydroxy-6-isopropyl-2-oxo-6-(2-thiophen-3-yl-ethyl)-5,6-dihydro-2H-pyran-3-ylsulfanyl]-2-methyl-phenyl}-amide; and 5-Trifluoromethyl-pyridine-2-sulfonic acid {5-tert-butyl-4-[4-hydroxy-6-isopropyl-2-oxo-6-(2-pyridin-3-yl-ethyl)-5,6-dihydro-2H-pyran-3-ylsulfanyl]-2-methyl-phenyl}-amide.

Other preferred compounds are:

3-(4-Amino-2-tert-butyl-5-methyl-phenylsulfanyl)-4-hydroxy-6-[2-(3-hydroxymethyl-thiophen-2-yl)-ethyl]-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(3-methyl-thiophen-2-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(2-methyl-thiophen-3-yl)-ethyl]-5,6-dihydro-pyran-2-one;

3-(4-Amino-2-tert-butyl-5-methyl-phenylsulfanyl)-4-hydroxy-6-[2-(4-hydroxymethyl-thiophen-3-yl)-ethyl]-6-isopropyl-5,6-dihydro-pyran-2-one 3-(2-tert-Butyl-4-hydroxymethyl-5-methyl-phenylsulfanyl)-4-hydroxy-6-isopropyl-6-[2-(4-methyl-thiophen-3-yl)-ethyl]-5,6-dihydro-pyran-2-one;

3-(2-Cyclopentyl-4-hydroxymethyl-5-methyl-phenylsulfanyl)-4-hydroxy-6-isopropyl-6-(2-thiophen-3-yl-ethyl)-5,6-dihydro-pyran-2-one;

3-(4-Amino-2-cyclopentyl-5-methyl-phenylsulfanyl)-4-hydroxy-6-[2-(2-hydroxymethyl-thiophen-3-yl)-ethyl]-6-isopropyl-5,6-dihydro-pyran-2-one;

3-(4-Amino-2-cyclopentyl-5-methyl-phenylsulfanyl)-4-hydroxy-6-[2-(4-hydroxymethyl-thiophen-3-yl)-ethyl]-6-isopropyl-5,6-dihydro-pyran-2-one;

3-(6-tert-Butyl-1-hydroxy-indan-5-ylsulfanyl)-4-hydroxy-6-isopropyl-6-(2-thiophen-3-yl-ethyl)-5,6-dihydro-pyran-2-one;

3-(6-tert-Butyl-1-hydroxy-indan-5-ylsulfanyl)-4-hydroxy-6-[2-(2-hydroxymethyl-thiophen-3-yl)-ethyl]-6-isopropyl-5,6-dihydro-pyran-2-one;

3-(6-tert-Butyl-1-hydroxy-indan-5-ylsulfanyl)-4-hydroxy-6-[2-(4-hydroxymethyl-thiophen-3-yl)-ethyl]-6-isopropyl-5,6-dihydro-pyran-2-one;

3-(4-Amino-2-tert-butyl-5-methyl-phenylsulfanyl)-4-hydroxy-6-[2-(2-hydroxymethyl-furan-3-yl)-ethyl]-6-isopropyl-5,6-dihydro-pyran-2-one;

3-(4-Amino-2-tert-butyl-5-methyl-phenylsulfanyl)-4-hydroxy-6-[2-(3-hydroxymethyl-furan-2-yl)-ethyl]-6-isopropyl-5,6-dihydro-pyran-2-one;

3-(4-Amino-2-tert-butyl-5-methyl-phenylsulfanyl)-4-hydroxy-6-[2-(4-hydroxymethyl-furan-3-yl)-ethyl]-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(2-methyl-furan-3-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(3-methyl-furan-2-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(4-methyl-furan-3-yl)-ethyl]-5,6-dihydro-pyran-2-one;

3-(2-Cyclopentyl-4-hydroxymethyl-5-methyl-phenylsulfanyl)-6-(2-furan-3-yl-ethyl)-4-hydroxy-6-isopropyl-5,6-dihydro-pyran-2-one:

3-(6-tert-Butyl-1-hydroxy-indan-5-ylsulfanyl)-6-(2-furan-3-yl-ethyl)-4-hydroxy-6-isopropyl-5,6-dihydro-pyran-2-one;

3-(4-Amino-2-tert-butyl-5-methyl-phenylsulfanyl)-4-hydroxy-6-[2-(4-hydroxymethyl-thiazol-5-yl)-ethyl]-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(4-methyl-thiazol-5-yl)-ethyl]-5,6-dihydro-pyran-2-one;

3-(4-Amino-2-tert-butyl-5-methyl-phenylsulfanyl)-4-hydroxy-6-[2-(5-hydroxymethyl-thiazol-4-yl)-ethyl]-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(5-methyl-thiazol-4-yl)-ethyl]-5,6-dihydro-pyran-2-one;

6-[2-(2-Amino-thiazol-4-yl)-ethyl]-3-(2-tert-butyl-4-hydroxymethyl-5-methyl-phenylsulfanyl)-4-hydroxy-6-isopropyl-5,6-dihydro-pyran-2-one;

6-[2-(2-Amino-thiazol-5-yl)-ethyl]-3-(2-tert-butyl-4-hydroxymethyl-5-methyl-phenylsulfanyl)-4-hydroxy-6-isopropyl-5,6-dihydro-pyran-2-one;

3-(2-tert-Butyl-4-hydroxymethyl-5-methyl-phenylsulfanyl)-4-hydroxy-6-isopropyl-6-(2-isothiazol-4-yl-ethyl)-5,6-dihydro-pyran-2-one;

3-(2-tert-Butyl-4-hydroxymethyl-5-methyl-phenylsulfanyl)-4-hydroxy-6-isopropyl-6-(2-isothiazol-5-yl-ethyl)-5,6-dihydro-pyran-2-one;

3-(2-tert-Butyl-4-hydroxymethyl-5-methyl-phenylsulfanyl)-4-hydroxy-6-isopropyl-6-(2-isothiazol-3-yl-ethyl)-5,6-dihydro-pyran-2-one;

3-(2-tert-Butyl-4-hydroxymethyl-5-methyl-phenylsulfanyl)-4-hydroxy-6-isopropyl-6-[2-(4-methyl-oxazol-5-yl)-ethyl]-5,6-dihydro-pyran-2-one;

3-(4-Amino-2-tert-butyl-5-methyl-phenylsulfanyl)-4-hydroxy-6-[2-(1H-indol-5-yl)-ethyl]-6-isopropyl-5,6-dihydro-pyran-2-one;

3-(2-tert-Butyl-4-hydroxymethyl-5-methyl-phenylsulfanyl)-4-hydroxy-6-[2-(1H-indol-5-yl)-ethyl]-6-isopropyl-5,6-dihydro-pyran-2-one;

3-(4-Amino-2-tert-butyl-5-methyl-phenylsulfanyl)-4-hydroxy-6-[2-(1H-indazol-5-yl)-ethyl]-6-isopropyl-5,6-dihydro-pyran-2-one;

3-(2-tert-Butyl-4-hydroxymethyl-5-methyl-phenylsulfanyl)-4-hydroxy-6-[2-(1H-indazol-5-yl)-ethyl]-6-isopropyl-5,6-dihydro-pyran-2-one;

3-(4-Amino-2-tert-butyl-5-methyl-phenylsulfanyl)-6-[2-(1H-benzoimidazol-5-yl)-ethyl]-4-hydroxy-6-isopropyl-5,6-dihydro-pyran-2-one;

6-[2-(1H-Benzoimidazol-5-yl)-ethyl]-3-(2-tert-butyl-4-hydroxymethyl-5-methyl-phenylsulfanyl)-4-hydroxy-6-isopropyl-5,6-dihydro-pyran-2-one;

3-(4-Amino-2-tert-butyl-5-methyl-phenylsulfanyl)-6-[2-(3-amino-1H-indazol-5-yl)-ethyl]-4-hydroxy-6-isopropyl-5,6-dihydro-pyran-2-one;

6-[2-(3-Amino-1H-indazol-5-yl)-ethyl]-3-(2-tert-butyl-4-hydroxymethyl-5-methyl-phenylsulfanyl)-4-hydroxy-6-isopropyl-5,6-dihydro-pyran-2-one;

3-(4-Amino-2-tert-butyl-5-methyl-phenylsulfanyl)-4-hydroxy-6-[2-(1H-indol-4-yl)-ethyl]-6-isopropyl-5,6-dihydro-pyran-2-one;

3-(2-tert-Butyl-4-hydroxymethyl-5-methyl-phenylsulfanyl)-4-hydroxy-6-[2-(1H-indol-4-yl)-ethyl]-6-isopropyl-5,6-dihydro-pyran-2-one;

3-(4-Amino-2-tert-butyl-5-methyl-phenylsulfanyl)-4-hydroxy-6-[2-(1H-indazol-4-yl)-ethyl]-6-isopropyl-5,6-dihydro-pyran-2-one;

3-(2-tert-Butyl-4-hydroxymethyl-5-methyl-phenylsulfanyl)-4-hydroxy-6-[2-(1H-indazol-4-yl)-ethyl]-6-isopropyl-5,6-dihydro-pyran-2-one;

3-(4-Amino-2-tert-butyl-5-methyl-phenylsulfanyl)-6-[2-(3-amino-1H-indazol-4-yl)-ethyl]-4-hydroxy-6-isopropyl-5,6-dihydro-pyran-2-one;

6-[2-(3-Amino-1H-indazol-4-yl)-ethyl]-3-(2-tert-butyl-4-hydroxymethyl-5-methyl-phenylsulfanyl)-4-hydroxy-6-isopropyl-5,6-dihydro-pyran-2-one;

3-(2-tert-Butyl-6-hydroxymethyl-5-methyl-pyridin-3-ylsulfanyl)-6-[2-(4-fluoro-phenyl)-ethyl]-4-hydroxy-6-isopropyl-5,6-dihydro-pyran-2-one;

3-(2-tert-Butyl-5-methyl-pyridin-3-ylsulfanyl)-4-hydroxy-6-[2-(2-hydroxymethyl-phenyl)-ethyl]-6-isopropyl-5,6-dihydro-pyran-2-one;

3-(3-tert-Butyl-2-hydroxymethyl-6-methyl-pyridin-4-ylsulfanyl)-6-[2-(4-fluoro-phenyl)-ethyl]-4-hydroxy-6-isopropyl-5,6-dihydro-pyran-2-one;

3-(5-tert-Butyl-2-methyl-pyridin-4-ylsulfanyl)-4-hydroxy-6-[2-(2-hydroxymethyl-phenyl)-ethyl]-6-isopropyl-5,6-dihydro-pyran-2-one;

3-(4-tert-Butyl-5-hydroxymethyl-thiophen-3-ylsulfanyl)-6-[2-(4-fluoro-phenyl)-ethyl]-4-hydroxy-6-isopropyl-5,6-dihydro-pyran-2-one;

3-(4-tert-Butyl-thiophen-3-ylsulfanyl)-4-hydroxy-6-[2-(2-hydroxymethyl-phenyl)-ethyl]-6-isopropyl-5,6-dihydro-pyran-2-one;

6-[2-(4-Amino-phenyl)-ethyl]-3-(2-tert-butyl-5-methyl-thiophen-3-ylsulfanyl)-4-hydroxy-6-isopropyl-5,6-dihydro-pyran-2-one;

3-(2-tert-Butyl-5-methyl-thiophen-3-ylsulfanyl)-4-hydroxy-6-[2-(2-hydroxymethyl-phenyl)-ethyl]-6-isopropyl-5,6-dihydro-pyran-2-one;

6-[2-(4-Amino-phenyl)-ethyl]-3-(4-tert-butyl-5-hydroxymethyl-thiophen-3-ylsulfanyl)-4-hydroxy-6-isopropyl-5,6-dihydro-pyran-2-one;

6-[2-(4-Amino-phenyl)-ethyl]-3-(3-tert-butyl-4-hydroxymethyl-5-methyl-thiophen-2-ylsulfanyl)-4-hydroxy-6-isopropyl-5,6-dihydro-pyran-2-one;

3-(3-tert-Butyl-5-methyl-thiophen-2-ylsulfanyl)-4-hydroxy-6-[2-(2-hydroxymethyl-phenyl)-ethyl]-6-isopropyl-5,6-dihydro-pyran-2-one;

3-(3-tert-Butyl-4-hydroxymethyl-5-methyl-thiophen-2-ylsulfanyl)-6-[2-(4-fluoro-phenyl)-ethyl]-4-hydroxy-6-isopropyl-5,6-dihydro-pyran-2-one;

3-(3-tert-Butyl-4-hydroxymethyl-5-methyl-thiophen-2-ylsulfanyl)-4-hydroxy-6-isopropyl-6-(2-thiophen-3-yl-ethyl)-5,6-dihydro-pyran-2-one:

3-(6-tert-Butyl-2,3-dihydro-1H-indol-5-ylsulfanyl)-6-[2-(4-fluoro-phenyl)-ethyl]-4-hydroxy-6-isopropyl-5,6-dihydro-pyran-2-one;

3-(6-tert-Butyl-2,3-dihydro-1H-indol-5-ylsulfanyl)-4-hydroxy-6-[2-(2-hydroxymethyl-phenyl)-ethyl]-6-isopropyl-5,6-dihydro-pyran-2-one;

3-(6-tert-Butyl-1H-indol-5-ylsulfanyl)-6-[2-(4-fluoro-phenyl)-ethyl]-4-hydroxy-6-isopropyl-5,6-dihydro-pyran-2-one;

3-(6-tert-Butyl-1H-indol-5-ylsulfanyl)-4-hydroxy-6-[2-(2-hydroxymethyl-phenyl)-ethyl]-6-isopropyl-5,6-dihydro-pyran-2-one;

3-(7-tert-Butyl-1,2,3,4-tetrahydro-quinolin-6-ylsulfanyl)-6-[2-(4-fluoro-phenyl)-ethyl]-4-hydroxy-6-isopropyl-5,6-dihydro-pyran-2-one;

3-(7-tert-Butyl-1,2,3,4-tetrahydro-quinolin-6-ylsulfanyl)-4-hydroxy-6-[2-(2-hydroxymethyl-phenyl)-ethyl]-6-isopropyl-5,6-dihydro-pyran-2-one;

N-(7-tert-Butyl-6-{6-[2-(4-fluoro-phenyl)-ethyl]-4-hydroxy-6-isopropyl-2-oxo-5,6-dihydro-2H-pyran-3-ylsulfanyl}-4-methyl-benzothiazol-2-yl)-acetamide;

N-(7-tert-Butyl-6-{4-hydroxy-6-[2-(2-hydroxymethyl-phenyl)-ethyl]-6-isopropyl-2-oxo-5,6-dihydro-2H-pyran-3-ylsulfanyl}-4-methyl-benzothiazol-2-yl)-acetamide;

N-(7-tert-Butyl-6-{6-[2-(4-fluoro-phenyl)-ethyl]-4-hydroxy-6-isopropyl-2-oxo-5,6-dihydro-2H-pyran-3-ylsulfanyl}-4-methyl-benzothiazol-2-yl)-methanesulfonamide;

N-(7-tert-Butyl-6-{4-hydroxy-6-[2-(2-hydroxymethyl-phenyl)-ethyl]-6-isopropyl-2-oxo-5,6-dihydro-2H-pyran-3-ylsulfanyl}-4-methyl-benzothiazol-2-yl)-methanesulfonamide;

3-(7-tert-Butyl-2-dimethylamino-4-methyl-benzothiazol-6-ylsulfanyl)-6-[2-(4-fluoro-phenyl)-ethyl]-4-hydroxy-6-isopropyl-5,6-dihydro-pyran-2-one;

3-(7-tert-Butyl-2-dimethylamino-4-methyl-benzothiazol-6-ylsulfanyl)-4-hydroxy-6-[2-(2-hydroxymethyl-phenyl)-ethyl]-6-isopropyl-5,6-dihydro-pyran-2-one;

3-(7-tert-Butyl-2-hydroxy-4-methyl-benzothiazol-6-ylsulfanyl)-6-[2-(4-fluoro-phenyl)-ethyl]-4-hydroxy-6-isopropyl-5,6-dihydro-pyran-2-one 3-(7-tert-Butyl-2-hydroxy-4-methyl-benzothiazol-6-ylsulfanyl)-4-hydroxy-6-[2-(2-hydroxymethyl-phenyl)-ethyl]-6-isopropyl-5,6-dihydro-pyran-2-one;

3-(2-tert-Butyl-6-hydroxymethyl-5-methyl-pyridin-3-ylsulfanyl)-4-hydroxy-6-isopropyl-6-(2-thiophen-3-yl-ethyl)-5,6-dihydro-pyran-2-one;

3-(3-tert-Butyl-2-hydroxymethyl-6-methyl-pyridin-4-ylsulfanyl)-4-hydroxy-6-isopropyl-6-(2-thiophen-3-yl-ethyl)-5,6-dihydro-pyran-2-one;

3-(6-tert-Butyl-2,3-dihydro-1H-indol-5-ylsulfanyl)-4-hydroxy-6-[2-(2-hydroxymethyl-thiophen-3-yl)-ethyl]-6-isopropyl-5,6-dihydro-pyran-2-one;

3-(6-tert-Butyl-1H-indol-5-ylsulfanyl)-4-hydroxy-6-[2-(2-hydroxymethyl-thiophen-3-yl)-ethyl]-6-isopropyl-5,6-dihydro-pyran-2-one;

3-(7-tert-Butyl-1,2,3,4-tetrahydro-quinolin-6-ylsulfanyl)-4-hydroxy-6-[2-(2-hydroxymethyl-thiophen-3-yl)-ethyl]-6-isopropyl-5,6-dihydro-pyran-2-one;

N-{7-tert-Butyl-6-[4-hydroxy-6-isopropyl-2-oxo-6-(2-thiophen-3-yl-ethyl)-5,6-dihydro-2H-pyran-3-ylsulfanyl]-4-methyl-benzothiazol-2-yl}-acetamide;

N-{7-tert-Butyl-6-[4-hydroxy-6-isopropyl-2-oxo-6-(2-thiophen-3-yl-ethyl)-5,6-dihydro-2H-pyran-3-ylsulfanyl]-4-methyl-benzothiazol-2-yl}-methanesulfonamide;

3-(7-tert-Butyl-2-dimethylamino-4-methyl-benzothiazol-6-ylsulfanyl)-4-hydroxy-6-isopropyl-6-(2-thiophen-3-yl-ethyl)-5,6-dihydro-pyran-2-one;

3-(7-tert-Butyl-2-hydroxy-4-methyl-benzothiazol-6-ylsulfanyl)-4-hydroxy-6-isopropyl-6-(2-thiophen-3-yl-ethyl)-5,6-dihydro-pyran-2-one;

(S)-3-(2-tert-Butyl-4-hydroxymethyl-5-methyl-phenylsulfanyl)-4-hydroxy-6-isopropyl-6-(2-thiophen-3-yl-ethyl)-5,6-dihydro-pyran-2-one; and compounds useful as intermediates in the preparation of the final products are:

a compound of Formula 1A

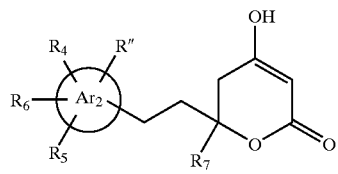

wherein $R_4$, $R_5$, and $R_6$ are independently H, a straight or branched alkyl of 1–6 carbons, a cycloalkyl of 3–6 carbons, $(CR'_2)_nOR$, $(CR'_2)_nN(R)_2$, F, Cl, Br, CN, $CF_3$, =O, $(CR'_2)_pNR'COR$, $(CR'_2)_pSO_pR$, $(CR'_2)_pR$, $(CR'_2)_pOCOR$, $O(CR'_2)_mOR$, $NR(CR'_2)_mOR$, $(CR'_2)NR'CON(R)_2$, $(CR'_2)_pOCON(R)_2$, $(CR'_2)_pNR'CO_2R$, $(CR'_2)_pCOR$, $(CR'_2)_pCO_2R$, $(CR'_2)_pCON(R)_2$, $(CR'_2)_pNR'SO_2R$, $(CR'_2)_pSO_2N(R)_2$, $(CR'_2)_pNR'SO_2OR$, $(CR'_2)_pOSO_2N(R)_2$, $(CR'_2)_pNRSO_2N(R)_2$, $(CR'_2)_pC(NR')N(R)_2$, $(CR'_2)_pNR'C(NR')N(R)_2$, $(CR'_2)_pHet$;

any two of $R_4$–$R_6$ may together form a ring of 5–6 total atoms which may contain 0–3 heteroatoms;

n is an integer of from 0 to 3;

p is an integer from 0 to 2;

$R_7$ is a straight or branched alkyl of 1–6 carbons or a carbocycle of 3–6 carbons;

R is independently H, a straight or branched alkyl of 1–4 carbons, $(CH_2)_nPh$, or a $(CH_2)_n$heterocycle of 5–6 atoms containing 1–2 heteroatoms and wherein the $(R)_2$ in $N(R)_2$ may form a heterocycle containing the nitrogen, all optionally substituted by F, Cl, Br, OR', CN, $CO_2R'$, $N(R')_2$, NR'COR', $CF_3$, or =O;

R' is independently H, a straight or branched alkyl of 1–4 carbons, or phenyl;

R" is independently H, a straight or branched alkyl of 1–4 carbons, F, Cl, Br, OR', or $N(R')_2$;

$Ar_2$ is phenyl or Het wherein Het is a heterocycle of from 5–6 atoms having from 1–4 heteroatoms.

Terms useful in describing the instant invention are as follows:

The term "alkyl" means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, and dodecyl. The alkyl groups may contain one or more sites of unsaturation such as double or triple carbon-carbon bonds. The alkyl group is unsubstituted or substituted by from 1 to 3 substituents selected from F, Cl, Br, OH, $NH_2$, CN, $NO_2$, $OCH_3$, $OCH_2CH_2OH$, $NHCH_3$, or $N(CH_3)_2$.

The term "cycloalkyl" means a hydrocarbon ring which contains from 3 to 12 carbon atoms unless otherwise specified, for example, cyclopropyl, cyclobutyl, cyclopentyl, cyclohexyl, and adamantyl. Where possible, the cycloalkyl group may contain double bonds. The cycloalkyl ring may be unsubstituted or substituted by from 1 to 3 substituents selected from alkyl, alkoxy, thioalkoxy all as defined herein, hydroxy, thiol, nitro, halogen, amino, formyl, carboxyl, nitrile, —NH—CO—R, —CO—NHR—, —$CO_2R$, —COR, aryl, or heteroaryl wherein alkyl (R), aryl, and heteroaryl are defined as herein.

The term "carbocycle" means cycloalkyl as defined above.

The term "heteroatoms" means a nitrogen, sulfur, or oxygen.

The term "heterocycle" means a heterocyclic radical which are 5–6 atoms having 1–4 heteroatoms and selected from 1–4 heteroatoms selected from: furan, pyrrole, thiophene, oxazole, isoxazole, thiazole, pyrazole, 1,2,3-triazole, 1,2,4-triazole, tetrazole, pyridine, pyridazine, pyrimidine, pyrazine, tetrahydrofuran, tetrahydrothiophene, pyrrolidine, piperazine, piperidine, morpholine, thiomorpholine, oxolane, dioxane, sulfolane, unsubstituted or substituted by 1 to 2 substituents selected from alkyl as defined above. For heterocycles containing sulfur, the oxidized sulfur heterocycles containing SO or $SO_2$ groups are also included.

The term "fused heterocycle" refers to a heterocycle that is adjoined as two consecutive positions with a phenyl ring or another heterocycle, such rings may include 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-indolinyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

For purposes of the syntheses of the compounds of the present invention, reactive functional groups present in starting materials, reaction intermediates, or reaction products may be protected during chemical reactions using protecting groups which render the reactive functional groups substantially inert to the reaction conditions (see for example, *Protective Groups in Organic Synthesis,* 2nd ed., T. W. Green and P. G. Wuts, John Wiley & Sons, New York, N.Y. 1991). Thus, for example, protecting groups such as the following may be utilized to protect suitable amino, hydroxyl, and other groups of related reactivity: carboxylic acyl groups, such as formyl, acetyl, trifluoroacetyl; alkoxycarbonyl groups, such as ethoxycarbonyl, t-butoxycarbonyl (BOC), β,β,β-trichloroethoxycarbonyl (TCEC), β-iodoethoxycarbonyl; aryloxycarbonyl groups, such as benzyloxycarbonyl, p-methoxybenzyloxycarbonyl, phenoxycarbonyl; trialkyl silyl groups such as trimethylsilyl and t-butyldimethylsilyl (TBDMS); and groups such as trityl, tetrahydropyranyl, vinyloxycarbonyl, o-nitrophenylsulfenyl, diphenylphosphinyl, p-toluenesulfonyl, and benzyl may all be utilized. The protecting group may be removed, after completion of the synthetic reaction of interest, by procedures known to those skilled in the art. For example, a BOC group may be removed by acidolysis, a trityl group by hydrogenolysis, TBDMS by treatment with fluoride ions, and TCEC by treatment with zinc.

Some of the compounds of Formula I are capable of further forming pharmaceutically acceptable acid-addition and/or base salts. All of these forms are within the scope of the present invention.

Pharmaceutically acceptable acid addition salts of the compounds of Formula I include salts derived from nontoxic inorganic acids such as hydrochloric, nitric, phosphoric sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihyrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science,* 1977;66:1–19.

The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, supra., 1977).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof. Configuration drawn is most preferred.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of a retroviral protease, as agents for the treatment of infections caused by a retrovirus including HIV, or as agents for the treatment of diseases due to AIDS, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The compounds of the instant invention, protease inhibitors, can be used as a component of initial patient antiretroviral therapy for HIV as, for example, in the following regimen:

Choose one combination of nucleoside reverse transcriptase inhibitors
Zidovudine+lamivudine
Zidovudine+didanosine
Zidovudine+zalcitabine
Didanosine+stavudine
Didanosine+lamivudine
Stavudine+lamivudine
Abacavir+zidovudine+lamivudine AND one of the compounds of the instant invention.

In addition, one may use one of the nucleoside reverse transcriptase inhibitor combinations above with one of the agents below plus a compound of the instant invention.
Nelfinavir
Indinavir
Saquinavir (soft gel-cap now preferred over hard gel-cap)
Ritonavir
Nevirapine
Delavirdine
Efavirenz The compounds of the instant invention can be used in multiple combinations with available antiretroviral drugs for combination therapy. The following are illustrative:

| Drug class/agents | Dosage |
| --- | --- |
| Nucleoside reverse transcriptase inhibitors | |
| Abacavir | 300 mg bid |
| Didanosine | 200 mg bid (for patients <60 kg, 125 mg bid) |
| Lamivudine | 150 mg bid (for patients <50 kg, 2 mg/kg bid) |
| Stavudine | 40 mg bid (for patients <60 kg, 30 mg/kg bid) |
| Zalcitabine | 0.75 mg tid |
| Zidovudine | 300 mg bid |
| Non-nucleoside reverse transcriptase inhibitors | |
| Delavirdine | 400 mg tid |
| Efavirenz | 600 mg qd |
| Nevirapine | 200 mg bid |
| Protease inhibitors | |
| Indinavir | 800 mg q8h |
| Nelfinavir | 750 mg tid |
| Ritonavir | 600 mg bid |
| Saquinavir | 600 mg tid (hard gel-cap formulation), 1200 mg tid (soft gel-cap formulation) |

The compounds of the instant invention can be used with or instead of the following for the treatment of established HIV infection.

| | |
| --- | --- |
| Preferred | Strong evidence of clinical benefit and/or sustained suppression of plasma viral load. One choice each from column A and column B. Drugs are listed in random, not priority, order: |

| Column A | Column B |
| --- | --- |
| Indinavir (AI) | ZDV + ddI (AI) |
| Nelfinavir (AII) | d4T + ddI (AII) |
| Ritonavir (AI) | ZDV + ddC (AI) |
| Saquinavir – SGC (AII) | ZDV + 3TC (AI) |
| Ritonavir + Saquinavir SGC or HGC (BII) | d4T + 3TC (AII) |
| Efavirenz (AII) | |

| | | | |
|---|---|---|---|
| -continued | | | |
| Alternative | Less likely to provide sustained virus suppression or data inadequate. Nevirapine or delavirdine + two NRTIs (Column B, above) (BII) | | |

The compounds of the instant invention can be used with the following drugs available through treatment investigational new drug protocols.

| | Drug | | |
|---|---|---|---|
| | Adefovir (Preveon) | Abacavir (1592-U89) | Amprenavir (Agenerase; 141W94) |
| Source | Gilead 800-GILEAD-5 | Glaxo-Wellcome 800-501-4672 | Vertex; Glaxo-Wellcome 800-248-9757 |
| Class | Nucleotide RT Inhibitor | Nucleoside RT Inhibitor | Protease Inhibitor |
| Usual dose | 60 mg po qd or 120 mg po qd + L-carnitine 500 mg po qd | 300 mg po bid | 1200 mg po bid |
| Side effects (major) | Proximal renal tubular dysfunction, nausea, elevated LFTs | Hypersensitivity: 2–5% usually in first 4 weeks (fever, nausea, vomiting, morbilliform rash) | Nausea, diarrhea, rash, headache |

The compounds of the present invention can be prepared according to the various synthetic schemes that follow. Protecting groups may be used when appropriate throughout many of the schemes. Although specifically noted in certain schemes, the appropriate use and choice of protecting groups is well-known by one skilled in the art, and is not limited to the specific examples below. It is also understood that such groups not only serve to protect chemically reactive sites, but also to enhance solubility or otherwise change physical properties. A good general reference for protecting group preparation and deprotection is "Protecting Groups in Organic Synthesis" by Theodora Green. A number of general reactions such as oxidations and reductions are not shown in detail but can be done by methods understood by one skilled in the art. General transformations are well-reviewed in "Comprehensive Organic Transformation" by Richard Larock, and the series "Compendium of Organic Synthetic Methods" published by Wiley-Interscience. In general, the starting materials were obtained from commercial sources unless otherwise indicated.

There are three major components of the synthesis of the desired products: the formation of a ketone precursor; the cyclization of that ketone into the dihydropyrone ring system; and the addition of the thiol component to complete the preparation of the compounds of the invention. Schemes 1 through 6 address the various methods for preparation of ketones indicated as C, D, G, and K.

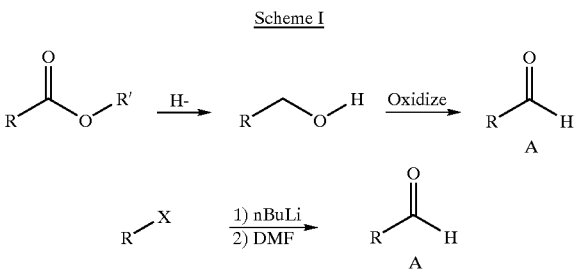

Scheme 1

Aldehyde Synthesis

The desired aldehydes which can be used in Schemes 2 and 3 are prepared by a number of methods as indicated in Scheme 1. The appropriate ester can be reduced to the corresponding alcohols and then oxidized to the aldehyde. Another method involves preparation of an anion with an appropriate base and trapping with a reagent, such as DMF, to prepare the aldehyde.

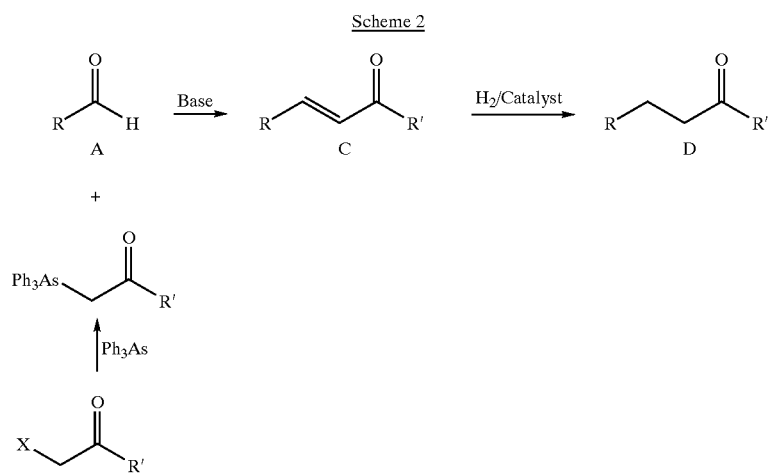

Scheme 2

The desired ketones can be prepared as shown in Schemes 2 and 3. The appropriate alpha halo ketone can be displaced with triphenylarsine to prepare an arsenate reagent. In a similar manner, triphenylphosphine can be used to prepare a Wittig reagent which will also carry out the reaction shown in Scheme 2. Upon treating the arsenate reagent and the aldehyde with base such as potassium carbonate, the chalcone derivative C is formed. Compound C can then be reduced using hydrogen with an appropriate catalyst to prepare ketone D.

Scheme 3

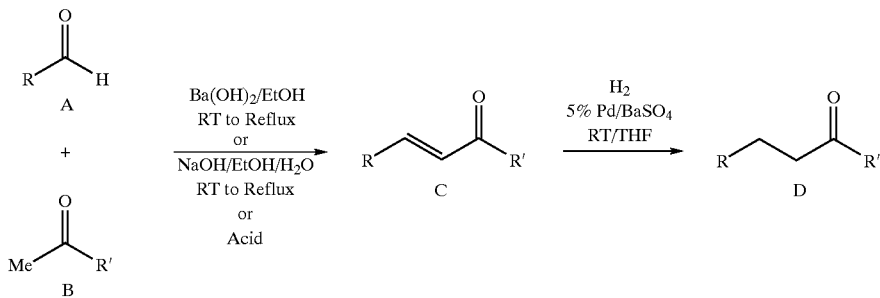

Alternatively, the desired enones C can be prepared by reaction of the appropriate methylketones and aldehydes using Ba(OH)$_2$ in EtOH as described in *Synthesis*, 1983:502–504, *An Quim, Ser. C*, 1981;77(2):222–224, and *Pol. J. Chem.*, 1982;56(10–112):1435. In a similar fashion, the enones C can also be prepared by reaction of the appropriate methylketones and aldehydes using NaOH in EtOH as described by Kohler and Chadwell, *Org Synth. Coll.*, 1941;1:78. The relative ratio of aldehyde, ketone, base, and temperature (RT to reflux) varied according to the substitution pattern of the aldehyde and ketone. There have also been reports of conversion of A and B to chalcones C under acidic conditions using H$_2$SO$_4$ and acetic anhydride. This may be accomplished by direct treatment with acid or the acid may be used to dehydrate the aldol intermediate if it does not dehydrate during the reaction with base.

The resulting chalcones C were converted into ketones D by reduction as noted previously in Scheme 2. The reduction was generally accomplished by hydrogenation using palladium on barium sulfate at room temperature in tetrahydrofuran. On occasion, overreduction to the alcohol was observed. The isolated alcohol or the crude mixture can be oxidized to the ketone with Jones reagent.

The reduction of the enone to the corresponding ketone can be carried out via a number of alternative methods including but not limited to: metals in ammonia as described in *Org. Reactions*, 1976;23:1–253; ethylene glycol and RuCl$_2$[P(Ph)$_3$]$_3$ as described in *Synthesis*, 1973:359; and copper hydride reagents as described in *J. Amer. Chem. Soc.*, 1974;96:3686.

Scheme 4

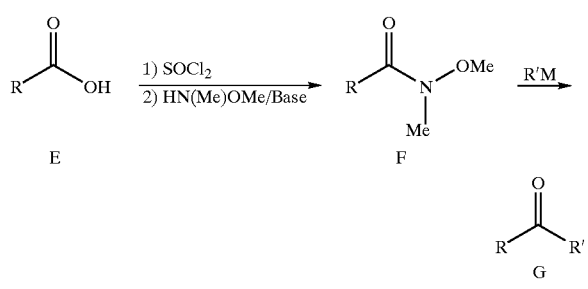

Preparation of the ketone G can be accomplished from an appropriate acid(E) and appropriate nucleophile using the Weinreb methodology described in *Tetrahedron Letters*, 1987:1857. The appropriate acid can be converted to the acid chloride by treatment with neat thionyl chloride or by treatment with oxalyl chloride in methylene chloride with a catalytic amount of DMF. Treatment of the acid chloride with N,O-dimethylhydroxylamine with bases such as pyridine or triethylamine in inert solvents such as methylene chloride from 0° C. to reflux will give intermediate F. Intermediate F can then be converted to G by treatment with the appropriate nucleophile, such as Grignard reagents, at 0° C. to reflux in solvents such as tetrahydrofuran or ether. An alternative method of converting the acid E to ketone G is by treatment with alkyl lithiums at –78° C. to reflux as described in *J. Med. Chem.*, 1996;39:2659 and *J. Amer. Chem., Soc.* 1970;92:2590. Another route is treatment of the acid chloride with nucleophiles (organomagnesium, copper, cadmium, or zinc reagents) as reviewed in *Org. React.*, 1954;8:28 and *Tetrahedron Lett.*, 1970:4647.

Scheme 5

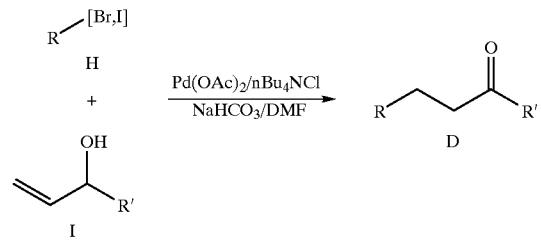

An alternative preparation of ketone D can be accomplished by reaction of an allylic alcohol I with an appropriate halide H using palladium acetate as described in *Tetrahedron*, 1979;35:329 and *Tetrahedron Lett.*, 1991;32:2121. There are a number of catalysts and conditions which will effect this transformation such as: Pd(OAc)$_2$, NaHCO$_3$, DMF, tetrabutylammonium chloride at room temperature to reflux; Pd(OAc)$_2$, triethylamine, acetonitrile at room temperature to reflux. The desired ketone D can also be prepared by acid catalyzed reaction of allylic alcohol I, or an enone, with an appropriate heterocycles as described in *Heterocycles*, 1987;25:399.

Scheme 6

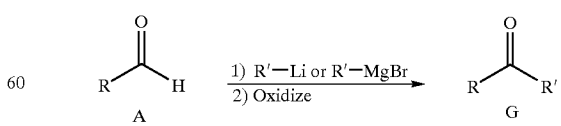

An alternate preparation of ketone G can be accomplished by reaction of aldehyde A with an appropriate nucleophile such as an organo lithium or Grignard reagents from –78° C. to room temperature in inert solvents to afford the alcohol.

The desired ketone G can by formed by oxidation of the resulting alcohol with Jones reagent or other oxidizing conditions such as the Swern oxidation which are well-known to one skilled in the art.

Scheme 7

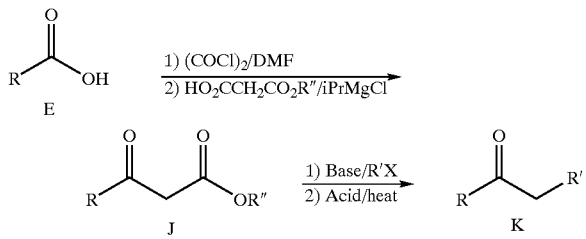

Acid E can be converted to desired ketone K utilizing a four step route indicated in Scheme 7. The appropriate acid E can be converted into the corresponding β-ketoester J utilizing conditions described in *Tetrahedron Letters*, 1992:1945 and *Angew. Chem. Int. Ed.*, 1979:72. The resulting β-ketoester L can be treated with a base, such as NaH or lithium diisopropylamide (LDA), then with an appropriate alkylating agent, R'X at 0° C. to room temperature to give the alkylated β-ketoester. The β-ketoester can be decarboxylated with acid in tetrahydrofuran at reflux. Alternatively the β-ketoester can be hydrolyzed with base to the acid, then heated with or without acid to give the desired ketone K.

The ketones C, D, G, and K and those prepared from Scheme 7 are cyclized to the dihydropyrone ring following the routes shown in Schemes 8 and 9. Scheme 9 also describes methods for obtaining optically pure forms of the dihydropyrone ring which is a recognized and important aspect of the current invention. The same methods can be used to produce racemic compounds if the resolution step is removed.

Scheme 8

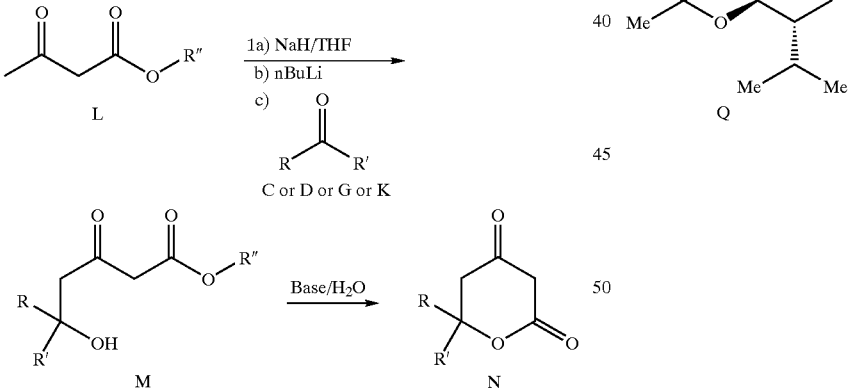

The dihydropyrone ring system can be prepared as described in *Can. J. Chem*, 1974;52:2157–2164 and *Synthetic Communications*, 1988;18(9):949–963. Reaction of the dianion of acetoacetate (L) with the appropriate ketone (C, D, G, or K) in inert solvents such as tetrahydrofuran at 0° C. to room temperature gave aldol intermediate M. $H_2O$ can be added directly to the reaction to effect closure. Alternatively the reaction can be worked up by addition of acetic acid or ammonium chloride and the aldol product isolated and characterized or taken on crude. The aldol product M can be closed by treating with dilute sodium hydroxide with or without tetrahydrofuran present. The tetrahydrofuran may be necessary to assist in solubilizing the aldol intermediate M. Protecting groups on intermediate M can be removed before closure to assist in solubilizing the intermediate in base.

Other routes are available to form the dihydropyrone ring such as those described in: *J C. S. Chem. Comm.*, 1979:578; *J. Am. Chem. Soc.*, 1984;106:4294; and *J Org. Chem.*, 1975;40:1610.

Scheme 9

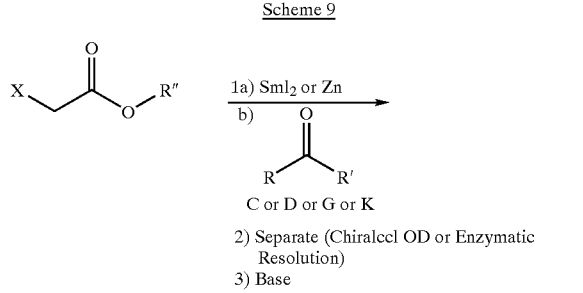

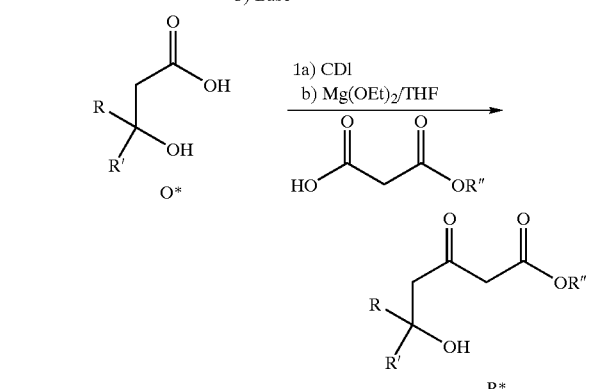

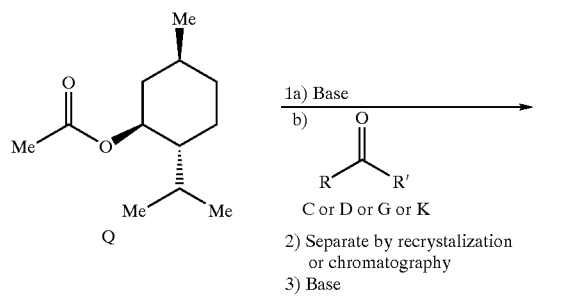

The dihydropyrone ring system can also be prepared optically enriched as shown in Scheme 9. The appropriate ketone (C, D, G, or K) can be reacted with the appropriate Reformasky reagent or the equivalent lanthanide species (*Tetrahedron*, 1981;37(Supp. 1):175; *J. Org. Chem.*, 1984;49:3904) in inert solvents such as tetrahydrofuran at −78° C. to reflux to afford the aldol intermediate. The two antipodes can be separated by a chiral HPLC column such as Chiralcel OD (90% hexane:0.1% TFA:10% isopropyl alcohol) or selective enzymatic hydrolysis with enzymes such as Candida antarctica "B" lipase in phosphate buffer with co-solvents such as isopropyl alcohol at room temperature. The resolved ester can be hydrolyzed to the acid O* using base under standard conditions.

Intermediate R* can also be prepared in a chiral form by reaction of ketone C, D, G or K with a chiral ester Q to give an intermediate which is a mixture of diastereomers (*J. Org. Chem.*, 1982;47:91; *Tetrahedron*, 1980;36:227). The aldol mixture can be separated by recrystallization or by chromatography to give each enantiomer. Hydrolysis of the ester using base affords acid R*.

Intermediate O can be prepared in racemic form and then resolved by classical means such as co-crystallization with a chiral amine such as 1-(1-naphthyl)ethylamine in solvents such as $H_2O$. Analysis of the chiral salt by x-ray may allow the determination of the absolute stereochemistry of intermediate O*.

The intermediates O* or R* can be converted to P* by activation of the acid and treatment with the magnesium salt of a half acid ester. Then P*, like M, may be converted to N or N* by base.

Schemes 10 to 14 describe the synthesis of a number of the tosyl reagents (X, BB, HH) which are used to introduce the 3-thiol moiety to the dihydropyrones of the invention.

thiol with tosyl bromide and base such as triethylamine or pyridine in inert solvents such as carbon tetrachloride at 0° C. to room temperature.

Scheme 11

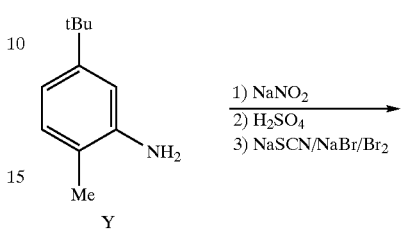

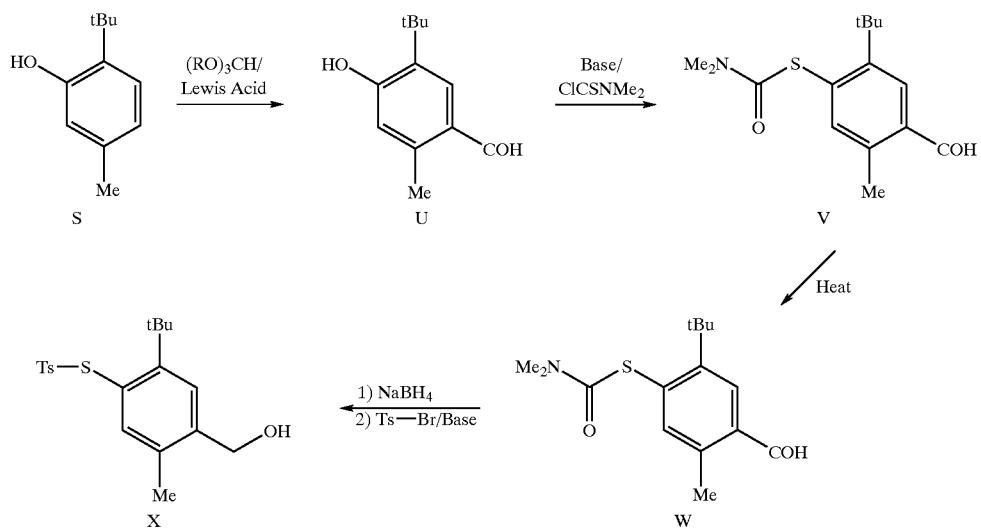

Scheme 10

Phenol S can be reacted with electrophiles, such as $HC(OEt)_3$ in inert solvents with a Lewis acid, to give the para-substituted phenol. The phenol can be protected with groups such as methoxyethoxymethyl or tertbutyldimethyl-silyl which are known to one skilled in the art. The derivatized phenol can be converted to the corresponding thiol using a variety of methods (*Tetrahedron Lett.*, 1996:4523; *Chem. Lett.*, 1985:1307, and *Tetrahedron Lett.*, 1993:393). The Newman-Kwart rearrangement is also useful for the conversion of phenol to thiophenol as described in *J. Org. Chem*, 1966:3980: *Synth.*, 1975:43; and *J. Chem. Eng. Data*, 1975;20:443. Phenol U can be treated with bases such as sodium hydride and dimethylthiocarbamoyl chloride in solvents such as DMF or tetrahydrofuran at 0° C. to reflux to give V. Vigorous heating of V at temperatures in the 200° C. to 330° C. range affords intermediate X. The free thiol can be prepared by reduction of derivatives such as W with diisobutylaluminum hydride (DIBAL-H) or sodium borohydride in inert solvents such as toluene or tetrahydrofuran from -78° C. to room temperature or by hydrolysis in base. The desired thiotosylate X can be prepared by reaction of the -continued

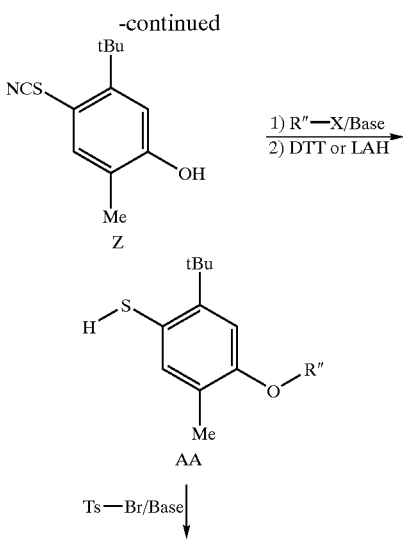

-continued

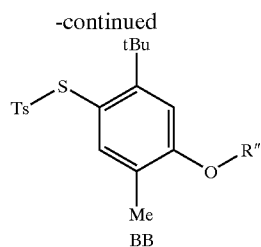

BB

-continued

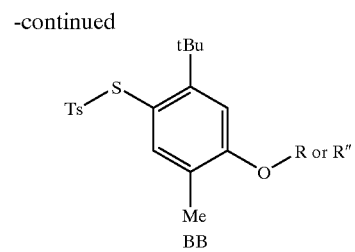

BB

Another route into desired thiotosyl reagents is indicated in Scheme 11. Aniline Y can be converted to the corresponding phenol using a variety of conditions (*J. Org. Chem.*, 1951;16:586; *Org. Synth.*, 1955;Coll. Vol. 3:130). The phenol can be treated with sodium thiocyanate, sodium bromide, and bromine in MeOH at 0° C. to 50° C. to incorporate the thiocyanate to give Z (*Synth.*, 1992:656). The phenol can be modified or protected using conditions which are understood by one skilled in the art. The thiocyanate can be converted to the thiol (AA) by treatment with dithiothreitol (DTT) in phosphate buffer in ethanol at room temperature to reflux or by treatment with lithium aluminum hydride (LAH) in inert solvents such as tetrahydrofuran at 0° C. to room temperature. The desired thiotosylate BB can be prepared by reaction of the thiol with tosyl bromide and base as described in Scheme 10.

Thiol AA can be converted to the disulfide (CC) by treatment with iodine and triethylamine in EtOAc. The disulfide can act as a protecting group for the sulfur. Various reactions can then be carried out on CC and the disulfide converted back to the thiol by treatment with dithiothreitol (DTT) using similar conditions as described in Scheme 11. Reaction of the free thiophenol with tosyl bromide as previously described affords the desired tosyl reagent BB.

Scheme 13

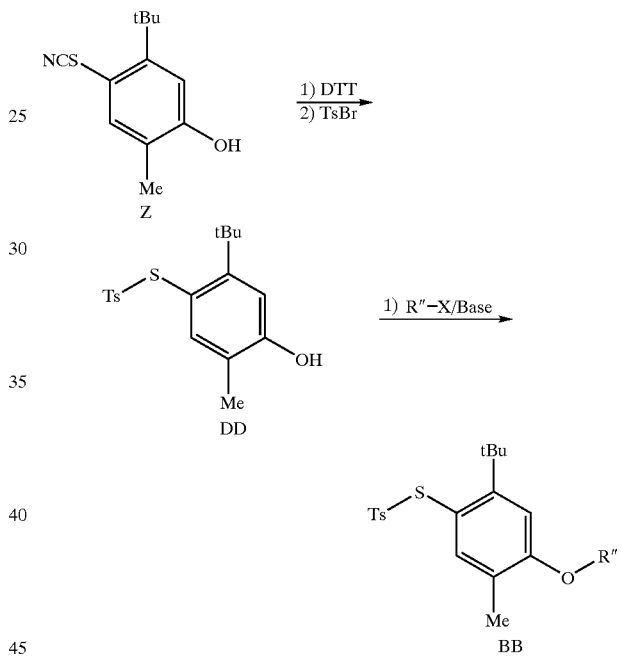

Thiocyanate Z can be converted to the thiol and then to thiotosylate DD using conditions which have been described in previous schemes. Thiotosylate DD can be derivatized or a protecting group attached using conditions known to one skilled in the art to give BB.

Scheme 12

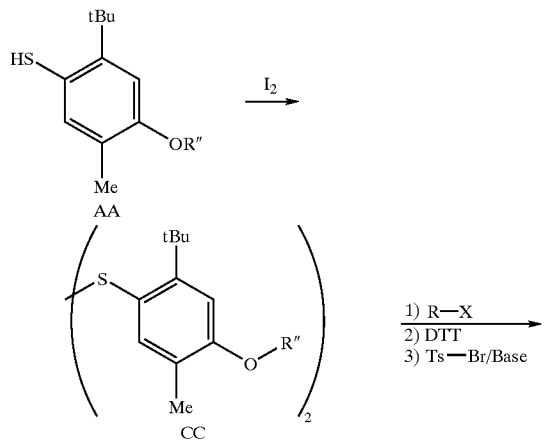

Scheme 14

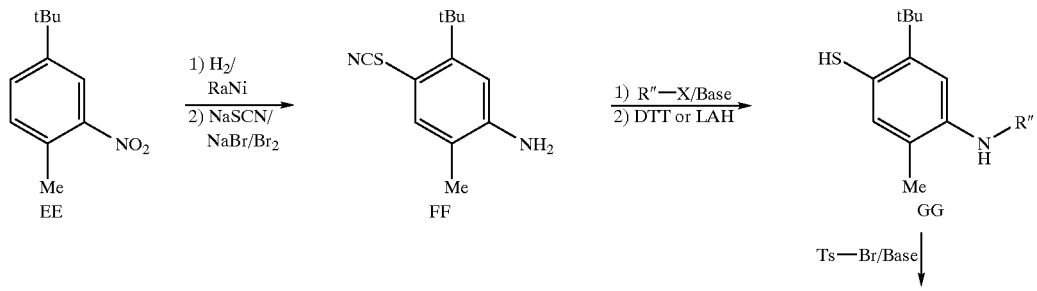

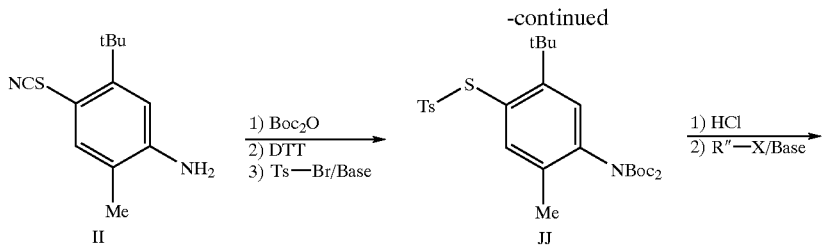
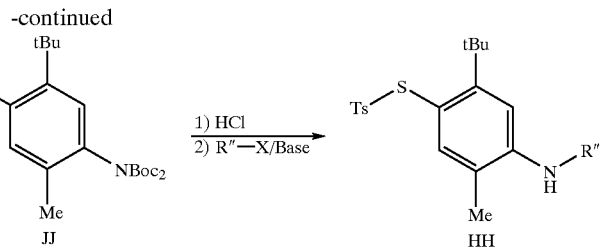

The nitro aromatic EE (*J. Org. Chem.*, 1951:586) can be reduced to the corresponding aniline by hydrogenation over Raney Nickel at room temperature. The thiocyanate can be introduced para to the amine in a similar manner as described in Scheme 11. Aniline FF can be converted to GG by modification of the amine, conversion to thiol, and tosylation as previously described. Alternatively aniline II can be protected, converted to the thiol, and reacted with tosyl bromide to give JJ. Aniline JJ can be deprotected and then modified to give HH. The reactions in this scheme have been previously described or are known to one skilled in the art.

Scheme 15 shows the convergent preparation of the desired compounds of the invention. The dihydropyrones (N) described in Schemes 8 and 9 are reacted with the tosyl reagents (X, BB, HH) described in Schemes 10 to 14 to produce the target compounds.

Scheme 15

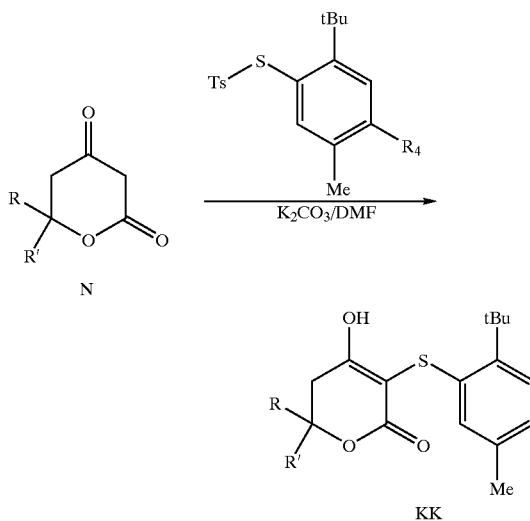

The desired dihydropyrone KK can be prepared by reaction with the appropriate dihydropyrone N or N*, thiotosylate (X, BB, HH) and potassium carbonate in dimethylformamide (DMF) at room temperature. Other bases and solvents will also effect this reaction such as triethylamine in ethanol or sodium hydride in tetrahydrofuran at 0° C. to reflux. Alternatively, the intermediate N can be brominated with NBS in tert-butanol and then displaced with the thiols such as AA and GG.

Scheme 16 describes alternative methods for effecting the separation of enantiomers into optically pure forms after formation of the dihydropyrone ring.

Scheme 16

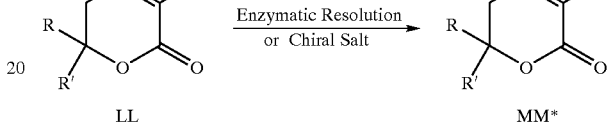

It has been shown that tetrahydropyrones can be resolved as described in the ICI patent WO 93/06235. The 4-hydroxydihydropyrone can be converted to a ester and the ester hydrolyzed with an enzyme to afford chiral material. This or other similar enzymatic processes may be applicable to the dihydropyrones as indicated in Scheme 16. The 4-hydroxydihydropyrone may also be resolved by classical means by conversion into a salt with chiral amines such as 1-(1-naphthyl)ethylamine. The salt may be recrystallized and then freed to afford the desired chiral material MM*.

Scheme 17

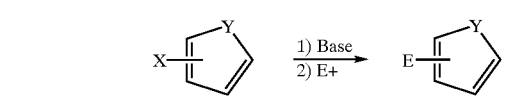

Scheme 17 shows the general preparation of a number of substituted heterocycles. When X is a halogen, a metal halogen exchange can be preformed to prepare the appropriate anion which can be trapped with an appropriate electrophile (E). This can be used to prepare heterocyclic aldehydes by trapping with DMF, thiols by trapping with sulfur, and alkyl groups by trapping with alkyl ketones or alkyl halides. In certain cases an appropriate base will deprotonate a heterocyclic hydrogen to prepare an anion directly. The following references exemplify Scheme 17: *J. Chem. Soc., Perkin Trans.* 1, 1997:3465; *J. Chem. Soc., Perkin Trans.* 1, 1995:2913; *J Org Chem.*, 1971;36(18):2690.

Preparation of Aldehydes

EXAMPLE A-1

5-Methyl-thiazole-4-carbaldehyde

A solution of 2.48 g (14.4 mmol) of 5-methyl-thiazole-4-carboxylic acid ethyl ester (*J. Chem. Soc. Perkin Trans.* 1, 1982:159–164) in dichloromethane ($CH_2Cl_2$) (50 mL) was cooled to −78° C. under nitrogen. DIBAL (Diisobutylaluminum hydride) (1.0 M in $CH_2Cl_2$, 15 mmol) was added dropwise, and the solution was stirred at low temperature for 45 minutes. Another 10 mmol of DIBAL was then added dropwise, and the mixture was stirred for another 45 minutes. A solution of methanol (MeOH):acetic acid (10 mL:5 mL) was added slowly, followed by $H_2O$. The organic layer was separated, washed with brine, and dried ($MgSO_4$). Concentration gave a residue which was chromatographed on silica gel, eluting with 2:1 hexane:ethyl acetate (EtOAc), to give the title compound.

$^1$H NMR ($CDCl_3$): δ2.76 (s, 3 H), 8.58 (s, 1 H), 10.14 (s, 1 H).

EXAMPLE A-2

2-Methyl-thiazole-4-carbaldehyde

A mixture of 5.52 g (30 mmol) of 4-chloromethyl-2-methylthiazole hydrochloride and 0.5 M NaOH (180 mL) was refluxed for 8 hours and then stirred for 18 hours at room temperature. EtOAc and $H_2O$ were added. The organic phase was separated, washed with brine, and dried ($MgSO_4$). Concentration gave 4-(hydroxymethyl)-2-methylthiazole.

$^1$H NMR ($CDCl_3$): δ2.63 (s, 3 H), 4.66 (s, 2 H), 6.96 (s, 1 H).

The crude product (2.2 g, 17 mmol) was oxidized with $MnO_2$ (20 g) in 75 mL of $CHCl_3$ for 16 hours. The suspension was filtered, and the filtrate was concentrated. The residue was chromatographed on silica gel, eluting with 2:1 hexane:EtOAc, to give the title compound.

$^1$H NMR ($CDCl_3$): δ2.71 (s, 3 H), 7.98 (s, 1 H), 9.89 (s, 1 H).

EXAMPLE A-3

2-iso-Propyl-thiazole-4-carbaldehyde

A solution of 2.7 g (13 mmol) of 2-isopropyl-thiazole-4-carboxylic acid ethyl ester (*J. Med. Chem.,* 1998:602–617) in $CH_2Cl_2$ (50 mL) was cooled to −78° C. under nitrogen and treated dropwise with DIBAL (15 mL of 1.0 M in $CH_2Cl_2$; 15 mmol). The mixture was stirred at low temperature for 45 minutes and then treated with another 15 mL of DIBAL. The solution was stirred for 1 hour at −78° C. Five percent citric acid was added, and the mixture was extracted with EtOAc (3×100 mL). The combined extracts were washed with brine, dried ($MgSO_4$), and concentrated. Chromatography of the residue over silica gel, eluting with 3:1 hexane:EtOAc, gave the title compound.

$^1$H NMR ($CDCl_3$): δ1.37 (d, 6 H), 3.30–3.35 (m, 1 H), 8.01 (s, 1 H), 9.93 (s, 1 H).

EXAMPLE A-4

4-iso-Propyl-thiazole-5-carbaldehyde

A solution of 5.9 g (30 mmol) of 4-isopropyl-thiazole-5-carboxylic acid ethyl ester (*J. Chem. Soc. Perkin Trans* 1, 1982:159–164) in toluene (100 mL) was cooled in an ice bath under nitrogen and treated dropwise with DIBAL (150 mL of 1.0 M; 150 mmol). The mixture was stirred at low temperature for 45 minutes and then allowed to warm to room temperature overnight. $H_2O$ was added cautiously, and the mixture was extracted with EtOAc (3×200 mL). The combined extracts were washed with brine, dried ($MgSO_4$), and concentrated. The crude 5-(hydroxymethyl)-4-isopropyl-thiazole thus obtained was used as is in the next step.

$^1$H NMR ($CDCl_3$): δ1.30 (d, 6 H), 3.13–3.20 (m, 1 H), 4.85 (s, 2 H), 8.67 (s, 1 H).

A mixture of 4.65 g (30 mmol) of crude 5-(hydroxymethyl)-4-isopropyl-thiazole in 200 mL of chloroform ($CHCl_3$) was treated with 45 g of $MnO_2$ and stirred at room temperature for 2.5 hours. The suspension was filtered, and the filtrate was concentrated. The residue was chromatographed on silica gel, eluting with 3:1 hexane:EtOAc, to give the title compound.

$^1$H NMR ($CDCl_3$): δ1.40 (d, 6 H), 3.62–3.69 (m, 1 H), 8.97 (s, 1 H), 10.17 (s, 1 H).

EXAMPLE A-5

5-iso-Propyl-thiazole-4-carbaldehyde

A solution of 6.8 g (37 mmol) of 5-isopropyl-thiazole-4-carboxylic acid methyl ester (*J. Chem. Soc., Perkin Trans.* 1, 1982:159–164) in $CH_2Cl_2$ (120 mL) was cooled to −78° C. under nitrogen and treated dropwise with DIBAL (37 mL of 1.0 M in $CH_2Cl_2$; 37 mmol). The mixture was stirred at low temperature for 45 minutes and then treated with another 20 mL of DIBAL. The solution was stirred for 1 hour at −78° C. $H_2O$ was added, and the mixture was extracted with EtOAc (3×150 mL). The combined extracts were washed with brine, dried ($MgSO_4$), and concentrated. Chromatography of the residue over silica gel, eluting with 2:1 hexane:EtOAc, gave the title compound.

$^1$H NMR ($CDCl_3$): δ1.34 (d, 6 H), 4.09–4.16 (m, 1 H), 8.63 (s, 1 H), 10.20 (s, 1 H).

EXAMPLE A-6

4-iso-Propyl-thiazole-2-carbaldehyde

A solution of 2.1 g (11 mmol) of 4-isopropyl-thiazole-2-carboxylic acid ethyl ester (*J. Med. Chem.,* 1998:602–617) in $CH_2Cl_2$ (50 mL) was cooled to −78° C. under nitrogen and treated dropwise with DIBAL (12 mL of 1.0 M in $CH_2Cl_2$; 12 mmol). The mixture was stirred at low temperature for 1 hour and then treated with another 7 mL of DIBAL. The solution was stirred for 30 minutes at −78° C. $H_2O$ was added, and the mixture was extracted with EtOAc (3×100 mL). The combined extracts were washed with brine, dried ($MgSO_4$), and concentrated. Chromatography of the residue over silica gel, eluting with 3:1 hexane:EtOAc, gave the title compound.

$^1$H NMR ($CDCl_3$): δ1.35 (d, 6 H), 3.16–3.23 (m, 1 H), 7.33 (s, 1 H), 9.96 (s, 1 H).

The remaining aldehydes were either commercially available or known in the chemical literature, as summarized in Table A below.

TABLE A

Preparation of Aldehydes

| Example | Aryl | Method of Preparation | $^1$H NMR Data |
|---|---|---|---|
| A-7 | 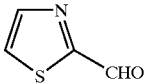 | Commercially available | |
| A-8 | 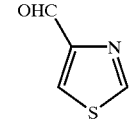 | Synthesis, 1987: 998–1001 | (CDCl$_3$): δ 8.22 (s, 1 H), 8.88 (s. 1 H), 10.10 (s, 1 H). |
| A-9 | 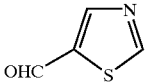 | Synthesis, 1987: 998–1001 | (CDCl$_3$): δ 8.51 (s, 1 H), 9.10 (s, 1 H), 10.10 (s, 1 H). |
| A-10 | 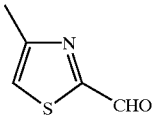 | Acta. Chemica Scandinavica, 1966; 20: 2649–2657 | (CDCl$_3$): δ 2.49 (s, 3 H), 7.29 (s, 1 H), 9.86 (s, 1 H). |
| A-11 | 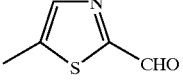 | Acta. Chemica Scandinavica, 1966; 20: 2649–2657 | (CDCl$_3$): δ 2.51 (s, 3 H), 7.71 (s, 1 H), 9.80 (s, 1 H). |
| A-12 | 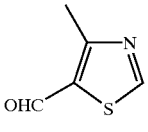 | J. Amer. Chem. Soc., 1982: 4934–4943 | (CDCl$_3$): δ 2.76 (s, 3 H), 8.94 (s, 1 H), 10.11 (s, 1 H). |
| A-13 | 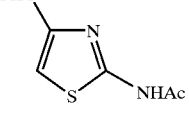 | Bull. Chim. France, 1967: 2235–2238 | (CDCl$_3$): δ 2.19 (s, 3 H), 7.74 (s, 1 H), 9.77 (s, 1 H), 11.69 (br s, 1 H). |
| A-14 | 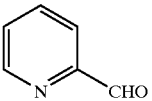 | Commercially available | |
| A-15 | 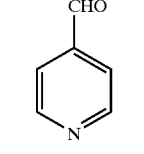 | Commercially available | |
| A-16 | 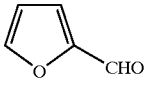 | Commercially available | |
| A-17 | 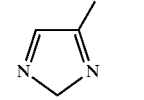 | Commercially available | |
| A-18 | 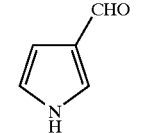 | J Org. Chem., 1990; 55 (26): 6317–6328 | (CDCl$_3$): δ 6.69 (m, 1 H), 6.85 (m, 1 H), 7.46 (m, 1 H), 9.2 (br s, 1 H), 9.82 (s, 1 H). |

TABLE A-continued
Preparation of Aldehydes
| Example | Aryl | Method of Preparation | $^1$H NMR Data |
|---|---|---|---|
| A-19 | 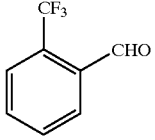 | Commercially available | |
| A-20 | 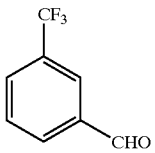 | Commercially available | |
| A-21 | 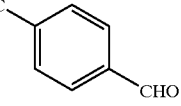 | Commercially available | |
| A-22 | 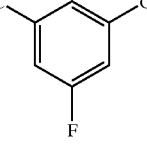 | Commercially available | |
| A-23 | 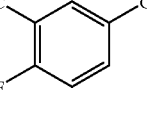 | Commercially available | |
| A-24 | 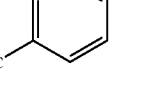 | Commercially available | |
| A-25 | 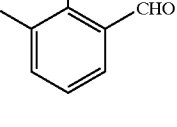 | Commercially available | |
| A-26 | 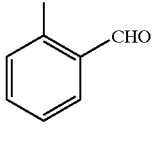 | Commercially available | |
| A-27 | 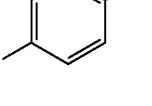 | Commercially available | |
| A-28 | 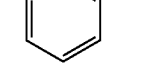 | Commercially available | |

TABLE A-continued

Preparation of Aldehydes

| Example | Aryl | Method of Preparation | $^1$H NMR Data |
|---------|------|----------------------|----------------|
| A-29 | F-[benzene]-CHO, F | Commercially available | |
| A-30 | OHC-[indole] | Chem Pharm. Bull., 1986; 34(10): 4116–4125 | (CDCl$_3$): δ 6.67 (m, 1 H), 7.25 (m, 1 H), 7.45 (d, 1 H), 7.74 (d, 1 H), 8.15 (s, 1 H), 8.70 (br s, 1 H), 10.00 (s, 1 H). |
| A-31 | OHC-[methylthiophene] | J.O.C., 1987; 53: 107–109 | |
| A-32 | F-[benzene]-CHO, F | Commercially available | |
| A-33 | F-[benzene]-CHO, F | Commercially available | |
| A-34 | [benzene]-CHO, F, F | Commercially available | |
| A-35 | F-[benzene]-CHO, F, F | Commercially available | |

Methods for the Preparation of Enones: General Method 1. Preparation of Enones Via Triphenylarsonium Salts A mixture of the appropriate aldehyde from Examples A-1 to A-29 (1.0 equiv.), the crude arsonate salt (usually (3-methyl-2-oxobutyl)triphenylarsonium bromide, prepared in *Synthesis*, 1988:975–977; 1.1 equiv.), potassium carbonate (1.1 equiv.), and 1% H$_2$O in CH$_3$CN was stirred for 1 to 18 hours at room temperature. The solids were filtered, and the filtrate was chromatographed on silica gel to remove the arsenate by-products.

EXAMPLE B-1

4-Methyl-1-(4-methyl-thiazol-5-yl)-pent-1-en-3-one

The title compound was prepared as described in General Method 1 using 1.4 g (11.0 mmol) of 4-methyl-5-thiazolecarbaldehyde (Example A-12), 6.2 g (13.1 mmol) of (3-methyl-2-oxobutyl)triphenylarsonium bromide, 1.8 g (13.1 mmol) of potassium carbonate, 75 mL of acetonitrile, and 0.75 mL of H$_2$O. Chromatography of the residue, eluting with 3:1 hexane:EtOAc gave the title compound.

$^1$H NMR (CDCl$_3$): δ1.13 (d, 6 H), 2.54 (s, 3 H), 2.75–2.82 (m, 1 H), 6.50 (d, 1 H), 7.73 (d, 1 H), 8.66 (s, 1 H).

General Method 2. Preparation of Enones Via Condensation with Ba(OH)$_2$

The desired enones were prepared by reaction of the appropriate methylketones and aldehydes by the methods described in *Synthesis*, 1983:502–504; *An. Quim, Ser. C*, 1981;77(2):222–224; *Org. Synth Coll.*, 1941;1:78; and *Pol. J. Chem.*, 1982;56(10–112):1435. To a reaction flask was added aldehyde (1–2 equiv.), ketone (1–2 equiv.), 95% EtOH, and anhydrous or hydrated Ba(OH)$_2$ (23 mg/mmol). The reaction was stirred at room temperature or heated at reflux for up to 2 days. The reaction was cooled to room temperature. The EtOH was evaporated, and the crude reaction was partitioned between EtOAc and 1N HCl. The aqueous layer was extracted with EtOAc. The combined organic extracts were dried (MgSO$_4$) and concentrated. The crude product was purified by flash chromatography or recrystallization.

EXAMPLE B-2

1-Furan-2-yl-4-methyl-pent-1-en-3-one

The titled compound was prepared according to General Method 2 by reacting 2-furaldehyde (117 mmol), 2-methyl-butan-3-one (117 mmol), anhydrous Ba(OH)$_2$ (2.2 g) and EtOH (200 mL) to afford the desire compound.

$^1$H NMR (CDCl$_3$): δ1.18. (d, 6 H), 2.83 (m, 1 H), 6.46 (m, 1 H), 6.65 (m, 1 H), 6.73 (d, 1 H), 7.38 (d, 1 H), 7.50 (m, 1 H).

The following enones were prepared using either General Method 1 (the arsonate salt) or General Method 2 (the Ba(OH)$_2$ method) from the corresponding aldehydes in Examples A-1 to A-35:

TABLE B

Preparation of Enones

| Example | R$_7$ | General Method | NMR Data (δ for vinyl protons. Solvent: CDCl$_3$) or Mass Spec |
|---|---|---|---|
| B-3 | 2-thiazolyl | Gen. Method 1 | 7.05, 7.64 |
| B-4 | 4-thiazolyl | Gen. Method 1 | 7.14, 7.53 |
| B-5 | thiazolyl | Gen. Method 1 | 6.58, 7.72 |
| B-6 | 5-methyl-2-thiazolyl | Gen. Method 1 | 6.90, 7.52 |
| B-7 | 4-methyl-2-thiazolyl | Gen. Method 1 | 7.01, 7.57 |
| B-8 | 2-methyl-4-thiazolyl | Gen Method 1 | 7.06, 7.43 |
| B-9 | 5-methyl-4-thiazolyl | Gen. Method 1 | 7.12, 7.54 |

TABLE B-continued
Preparation of Enones
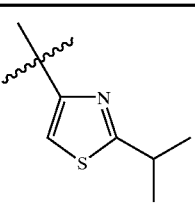
| Example | R₇ | General Method | NMR Data (δ for vinyl protons. Solvent: CDCl₃) or Mass Spec |
|---|---|---|---|
| B-10 | 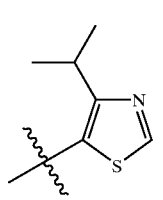 | Gen. Method 1 | 7.11, 7.49 |
| B-11 | 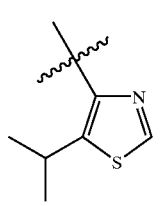 | Gen. Method 1 | 6.52, 7.78 |
| B-12 | 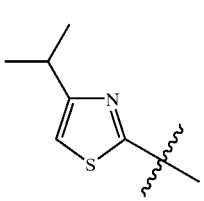 | Gen. Method 1 | 7.24, 7.64 |
| B-13 | 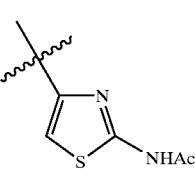 | Gen. Method 1 | 6.95, 7.60 |
| B-14 | 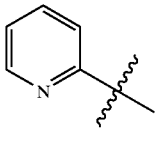 | Gen. Method 1 | 6.93, 7.41 |
| B-15 | 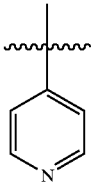 | Gen. Method 1 | 7.33, 7.60 |
| B-16 |  | Gen Method 1 | 6.96, 7.51 |

TABLE B-continued

Preparation of Enones

| Example | R$_7$ | General Method | NMR Data (δ for vinyl protons. Solvent: CDCl$_3$) or Mass Spec |
|---|---|---|---|
| B-17 | 2-CF$_3$-phenyl | Gen Method 1 | MS (APCI): 243 (M + H) |
| B-18 | 3-CF$_3$-phenyl | Gen Method 1 | MS (APCI): 243 (M + H) |
| B-19 | 4-CF$_3$-phenyl | Gen Method 1 | MS (APCI): 243 (M + H) |
| B-20 | 3-CF$_3$-5-F-phenyl | Gen Method 1 | MS (APCI): 261 (M + H) |
| B-21 | 3-CF$_3$-4-F-phenyl | Gen. Method 1 | MS (APCI): 261 (M + H) |
| B-22 | 4-CN-phenyl | Gen. Method 1 | MS (APCI): 200 (M + H) |
| B-23 | 2-CH$_3$-3-F-phenyl | Gen. Method 2 | 6.74, 7.86 |
| B-24 | 2-F-phenyl | Gen. Method 2 | 6.90, 7.73 |

TABLE B-continued

Preparation of Enones $$R_7 \diagup\!\!\!\diagdown C(O)CH(CH_3)_2$$

| Example | R₇ | General Method | NMR Data (δ for vinyl protons. Solvent: CDCl₃) or Mass Spec |
|---|---|---|---|
| B-25 | 4-fluorophenyl | Gen. Method 2 | 6.74, 7.57 |
| B-26 | 3-fluorophenyl | Gen. Method 2 | 6.80, 7.56 |
| B-27 | 3,4-difluorophenyl | Gen. Method 2 | |
| B-28 | 1H-pyrrol-3-yl | Gen. Method 1 | MS (APCI): 164 (M + H) |
| B-29 | 1H-imidazol-4-yl | Gen. Method 1 | MS (APCI): 165 (M + H) |
| B-30 | thiophen-3-yl | Gen. Method 2 | 6.59, 7.56 |
| B-31 | 1H-indol-5-yl | Gen. Method 1 | 6.82, 7.78 |
| B-32 | 2-methylthiophen-3-yl | Gen. Method 1 | 6.78, 6.99 |

TABLE B-continued

Preparation of Enones

[Structure: R7-CH=CH-C(=O)-CH(CH3)2]

| Example | R7 | General Method | NMR Data (δ for vinyl protons. Solvent: CDCl3) or Mass Spec |
|---|---|---|---|
| B-33 | 2,6-difluorophenyl | Gen. Method 2 | 7.11, 7.70 |
| B-34 | 3,5-difluorophenyl | Gen. Method 2 | 6.79, 7.49 |
| B-35 | 2,4-difluorophenyl | Gen. Method 2 | 6.84, 7.66 |
| B-36 | 3,4,5-trifluorophenyl | Gen. Method 2 | 6.73, 7.43 |

Names corresponding to the enones in Table B above are:

B-3: 4-Methyl-1-thiazol-2-yl-pent-1-en-3-one;
B-4: 4-Methyl-1-thiazol-4-yl-pent-1-en-3-one;
B-5: 4-Methyl-1-thiazol-5-yl-pent-1-en-3-one;
B-6: 4-Methyl-1-(5-methyl-thiazol-2-yl)-pent-1-en-3-one;
B-7: 4-Methyl-1-(4-methyl-thiazol-2-yl)-pent-1-en-3-one;
B-8: 4-Methyl-1-(2-methyl-thiazol-4-yl)-pent-1-en-3-one;
B-9: 4-Methyl-1-(5-methyl-thiazol-4-yl)-pent-1-en-3-one;
B-10: 1-(2-Isopropyl-thiazol-4-yl)-4-methyl-pent-1-en-3-one;
B-11: 1-(4-Isopropyl-thiazol-5-yl)-4-methyl-pent-1-en-3-one;
B-12: 1-(5-Isopropyl-thiazol-4-yl)-4-methyl-pent-1-en-3-one;
B-13: 1-(4-Isopropyl-thiazol-2-yl)-4-methyl-pent-1-en-3-one;
B-14: N-[4-(4-Methyl-3-oxo-pent-1-enyl)-thiazol-2-yl]-acetamide;
B-15: 4-Methyl-1-pyridin-2-yl-pent-1-en-3-one;
B-16: 4-Methyl-1-pyridin-4-yl-pent-1-en-3-one;
B-17: 4-Methyl-1-(2-trifluoromethyl-phenyl)-pent-1-en-3-one;
B-18: 4-Methyl-1-(3-trifluoromethyl-phenyl)-pent-1-en-3-one;
B-19: 4-Methyl-1-(4-trifluoromethyl-phenyl)-pent-1-en-3-one;
B-20: 4-Methyl-1-(3-fluoro-5-trifluoromethyl-phenyl)-pent-1-en-3-one;
B-21: 4-Methyl-1-(4-fluoro-3-trifluoromethyl-phenyl)-pent-1-en-3-one;
B-22: 4-(4-Methyl-3-oxo-pent-1-enyl)-benzonitrile;
B-23: 4-Methyl-1-(3-fluoro-2-methyl-phenyl)-pent-1-en-3-one;
B-24: 4-Methyl-1-(2-fluoro-phenyl)-pent-1-en-3-one;
B-25: 4-Methyl-1-(4-fluoro-phenyl)-pent-1-en-3-one;
B-26: 4-Methyl-1-(3-fluoro-phenyl)-pent-1-en-3-one;
B-27: 4-Methyl-1-(3,4-difluoro-phenyl)-pent-1-en-3-one;
B-28: 4-Methyl-1-(1H-pyrrol-3-yl)-pent-1-en-3-one;
B-29: 1-(1H-Imidazol-4-yl)-4-methyl-pent-1-en-3-one;
B-30: 4-Methyl-1-thiophen-3-yl-pent-1-en-3-one;
B-31: 1-(1H-Indol-5-yl)-4-methyl-pent-1-en-3-one;
B-32: 4-Methyl-1-(2-methyl-thiophen-3-yl)-pent-1-en-3-one;
B-33: 4-Methyl-1-(2,6-difluoro-phenyl)-pent-1-en-3-one;
B-34: 4-Methyl-1-(3,5-difluoro-phenyl)-pent-1-en-3-one;
B-35: 4-Methyl-1-(2,4-difluoro-phenyl)-pent-1-en-3-one; and
B-36: 4-Methyl-1-(3,4,5-trifluoro-phenyl)-pent-1-en-3-one.

Methods for the Preparation of Requisite Ketones: General Method 3. Preparation of Ketones by Hydrogenation of Enones The substituted arylpropiophenones were prepared by hydrogenation of the corresponding enones at room temperature at 50 psi in tetrahydrofuran (THF) utilizing a number of catalysts such as: 5% palladium (Pd) on barium sulfate (BaSO$_4$) or (Ph$_3$P)$_3$RhCl or 10% Pd on carbon or 5% Pd on CaCO$_3$. The catalyst was filtered off and the resulting ketone recrystallized or purified by flash chromatography.

EXAMPLE C-1

4-Methyl-1-pyridin-4-yl-pentan-3-one

The title compound was prepared according to General Method 3 using 4-methyl-1-pyridin-4-yl-pent-1-en-3-one (Example B-16; 1.81 g), (Ph$_3$P)$_3$RhCl (0.5 g), and THF (100 mL) at 50 psi. The title compound was flash chromatographed using 98:2 CH$_2$Cl$_2$:MeOH as eluent. $^1$H NMR (CDCl$_3$): δ1.15 (d, 6 H), 2.5–2.7 (m, 1 H), 2.7–2.8 (m, 2 H), 2.85–2.95 (m, 2 H), 7.1 (d, 2 H), 8.5 (d, 2 H).

EXAMPLE C-2

4-Methyl-1-(4-methyl-thiazol-5-yl)-pentan-3-one

The title compound was prepared as described in General Method 3 using 1.73 g (8.86 mmol) of 4-methyl-1-(4-methyl-thiazol-5-yl)-pent-1-en-3-one (prepared in Example B-1) and 0.4 g of 5% Pd/BaSO$_4$ in THF:MeOH (25 mL:25 mL). The crude product was chromatographed on silica gel, eluting with 2:1 hexane:EtOAc, to give the title compound. $^1$H NMR (CDCl$_3$): δ1.03 (d, 6 H), 2.35 (s, 3 H), 2.49–2.56 (m, 1 H), 2.72 (t, 2 H), 2.98 (t, 2 H), 8.49 (s, 1 H).
Synthesis of Appropriate Halogenated Heterocycles Necessary for Ketone Synthesis (General Methods 4a and 4b)

Example Starting Material—1 (SM)

(5-Bromo-thiophen-2-yl)-methanol

The title compound was prepared by reduction of 5-bromo-2-thiophenecarbaldehyde (137 mmol) with sodium borohydride (137 mmol) in MeOH (500 mL). The reaction was stirred for 2 hours at 0° C. and 2 hours at room temperature. The MeOH was evaporated, and saturated ammonium chloride was added followed by 2N HCl. The aqueous layers were extracted with EtOAc, dried (MgSO$_4$), and concentrated. Flash chromatography over silica gel using 100% CH$_2$Cl$_2$ as eluent afforded the title compound. $^1$H NMR (CDCl$_3$): δ4.74 (d, 2 H), 6.75 (m, 1 H), 6.91 (d, 1 H).

Example Starting Material—2

(4-Bromo-thiophen-2-yl)-methanol

The title compound was prepared in a similar manner to Example SM-1 by reduction of 4-bromo-2-thiophenecarboxaldehyde (122 mmol) with sodium borohydride (12 mmol) in MeOH (500 mL).
$^1$H NMR (CDCl$_3$): δ4.80 (d, 2 H), 6.93 (d, 1 H), 7.18 (d, 1 H).

Example Starting Material—3

(3-Bromo-thiophen-2-yl)-methanol

The title compound was prepared by reduction of 3-bromothiophene-2-carboxylic acid methyl ester (45 mmol) with lithium aluminum hydride (45 mmol) in THF (150 mL) at 0° C. for 1 hour and then overnight at room temperature. The reaction was worked up by addition of 1 mL of H$_2$O, 1 mL of 15% NaOH, and 3 mL of H$_2$O followed by filtration through celite. Concentration of the filtrate gave the title compound. $^1$H NMR (CDCl$_3$): δ4.80 (s, 2 H), 6.96 (d, 1 H), 7.26 (d, 1 H).

Example Starting Material—4

1-Trityl-4-iodopyrazole

The title compound was prepared by combining 4-iodopyrazole (10 g, 52 mmol), triphenylmethyl chloride (14.4 g, 51.6 mmol), triethylamine (NEt$_3$) (7.2 mL, 52 mmol), and DMF (80 mL). After stirring overnight, the mixture was poured onto ice water. The precipitated solid was collected and recrystallized to give the title compound as a solid, mp 193–194° C.
$^1$H NMR (CDCl$_3$): δ7.11 (m, 6 H), 7.32 (m, 9 H), 7.41 (s, 1 H), 7.67 (s, 1 H).

Example Starting Material—5 (SM)

(4-Bromo-thiophen-3-yl)-methanol

The title compound was prepared in a similar manner to Example SM-1 by reduction of 4-bromo-3-thiophenecarbaldehyde (*Bull. Soc. Chim. France*, 1967;11:4115) with sodium borohydride in MeOH. $^1$H NMR (CDCl$_3$): δ2.05 (s, 2 H), 7.27–7.34 (m, 2 H).

Example Starting Material—6 (SM)

(2-Bromo-thiophen-3-yl)-methanol

A solution of 10.0 g (39.0 mmol) of 2-bromo-3-bromomethyl-thiophene (*J Chem. Soc Perkin Trans. II*, 1983:813) in 130 mL of acetone was treated with a solution of 11.4 g (67.1 mmol) of AgNO$_3$ in 110 mL of H$_2$O. The mixture was stirred at room temperature for 1 hour and filtered. The solid was washed with Et$_2$O and acetone; the combined filtrate and washings were concentrated. The residue was extracted with CH$_2$Cl$_2$, and the organic layer was dried (MgSO$_4$) and concentrated. The crude product was chromatographed over silica gel, eluting with hexane:EtOAc:CH$_2$Cl$_2$ (80:5:15 to 60:30:10) to give the title compound.
$^1$H NMR (CDCl$_3$) δ1.67 (t, 1 H), 4.63 (d, 2 H), 7.03 (d, 1 H), 7.26 (d, 1 H).

Example Starting Material—7 (SM)

3-Bromo-4-ethyl-fluorobenzene

2-Bromo-4-fluoroacetophenone (10.0 g, 46.1 mmol) in THF (120 mL) was treated with BF$_3$.OEt$_2$ (22.9 g, 20.4 mL, 161 mmol) and followed by NaBH$_3$CN (7.24 g, 155 mmol) added portionwise. The resulting mixture was heated to reflux under N$_2$ overnight and then cooled to room temperature. Diethyl ether (Et$_2$O) was added; the organic layer was washed with saturated NaHCO$_3$/H$_2$O and brine, dried (MgSO$_4$), filtered, and concentrated. The resulting residue was subjected to flash silica gel chromatography, eluting with 4:1 (hexanes:EtOAc) to afford the intermediate alcohol.
$^1$H NMR (CDCl$_3$): δ1.46 (d, 3 H), 1.98 (bs, 1 H), 5.21 (q, 1 H), 7.03–7.10 (m, 1 H), 7.26 (dd, 1 H), 7.58 (dd, 1 H).

The alcohol isolated above (4.0 g, 18 mmol) was dissolved in hexanes (20 mL) and treated with trimethylsilyl chloride (11.9 g, 13.9 mL, 109 mmol), NaI (16.4 g, 109 mmol), and CH$_3$CN (5.7 mL, 109 mmol). The resulting slurry was stirred at room temperature under $N_2$ overnight. $Et_2O$ was added followed by $H_2O$. The phases were separated, and the aqueous phase was extracted again with $Et_2O$; the combined organic phases were washed with sodium bisulfite ($NaHSO_3$)/$H_2O$ and brine, dried ($MgSO_4$), filtered, and concentrated. The resulting residue was subjected to flash silica gel chromatography, eluting with hexanes to afford the title compound. $^1H$ NMR ($CDCl_3$): δ1.20 (t, 3 H), 2.72 (q, 2 H), 6.93–6.99 (m, 1 H), 7.18 (dd, 1 H), 7.27 (dd, 1 H).

Example Starting Material—8 (SM)

(2-Bromo-5-fluoro-phenyl)-methanol

2-Bromo-5-fluorobenzylbromide (2.0 g, 7.46 mmol) was dissolved in dioxane (25 mL) and $H_2O$ (25 mL), and $CaCO_3$ (3.84 g, 38.39 mmol) was added. The mixture was heated to reflux overnight. The solution was concentrated, and the residue was partitioned between $H_2O$ and $CH_2Cl_2$. The organic phase was washed with 1N HCl and brine, dried ($MgSO_4$), filtered, and concentrated to afford the title compound. $^1H$ NMR ($CDCl_3$): δ2.00 (t, 1 H), 4.72 (d, 2 H), 6.85–6.92 (m, 1 H), 7.26 (dd, 1 H), 7.48 (dd, 1 H).

The remaining halides were commercially available, as summarized in Table C below.

TABLE C

| Example | Aryl Halides Aryl |
|---|---|
| SM-9 | 3-iodo-pyridine |
| SM-10 | 3-bromo-furan |
| SM-11 | 3-bromo-thiophene |
| SM-12 | 2-bromo-thiophene |
| SM-13 | 5-bromo-pyrimidine |
| SM-14 | 2-amino-5-bromo-pyrimidine |
| SM-15 | 2-iodo-benzyl alcohol |
| SM-16 | 3-bromo-4-methyl-thiophene |
| SM-17 | 2-bromo-3-methyl-thiophene |
| SM-18 | 4-fluoro-2-iodo-toluene |
| SM-19 | 1-bromo-4-fluoro-2-methyl-benzene |

Methods for the Preparation of Requisite Ketones: General Method 4a and 4b. Preparation of Ketones via Pd-Catalyzed Coupling General Method 4a is the method described in *Tetrahedron*, 1979;35:329 and *Tetrahedron Letters*, 1991;32:2121. The appropriate aryl halide (Br or I; 1 equiv.), allylic alcohol (1–2 equiv.), tetrabutyl ammonium chloride (1 equiv.), sodium bicarbonate (2–3 equiv.), DMF (0.1–1 mL per mmol of halide), and palladium acetate (0.01–0.1 equiv.) were added to a reaction vessel. The solution was heated to 40° C. to 100° C. for 1 to 24 hours. On occasion, pyrrolidine (0.2–1 equiv.) was also added. The reaction was cooled to room temperature and partitioned between $H_2O$ and $CH_2Cl_2$. The solution was filtered through celite and the aqueous layer extracted two times with $CH_2Cl_2$. The organic extracts were washed with brine and then dried ($MgSO_4$). Purification was usually carried out by flash chromatography.

General Method 4b is the method described in *Tetrahedron*, 1979;35:329–340 with slight modifications. The appropriate aryl halide (Br or I; 1 equiv.), allylic alcohol (1–2 equiv.), sodium iodide (0.01–0.050 equiv.), sodium bicarbonate (1–3 equiv.), triphenyl phosphine (0.01–0.050 equiv.), DMF (0.1–1 mL per mmol of halide), and palladium acetate (0.01–0.1 equiv.) were added to a reaction vessel. The solution was heated to 40° C. to 100° C. for 1 to 24 hours. Pyrrolidine (0.2–1 equiv.) was also added at times. The reaction was cooled to room temperature and partitioned between $H_2O$ and $CH_2Cl_2$. The solution was filtered through celite and the aqueous layer extracted two times with $CH_2Cl_2$. The organic extracts were washed with brine and then dried ($MgSO_4$). Purification was usually carried out by flash chromatography.

EXAMPLE C-3

4-Methyl-1-pyridin-3-yl-pentan-3-one

The title compound was prepared according to General Method 4a using 3-iodo-pyridine (36.6 mmol), 4-methyl-1- penten-3-ol (54.9 mmol), tetrabutyl ammonium chloride (36.6 mmol), sodium bicarbonate (91.5 mmol), pyrrolidine (~1.5 mL), DMF (15 mL), and palladium acetate (0.51 g). The title compound was flash chromatographed eluting with EtOAc:CH$_2$Cl$_2$:hexane 50:25:25.

$^1$NMR (CDCl$_3$): δ1.15 (d, 6 H), 2.5–2.7 (m, 1 H), 2.7–2.9 (m, 2 H), 2.85–2.95 (m, 2 H), 7.2–7.3 (m, 1 H), 7.5–7.6 (m, 1 H), 8.4–8.5 (m, 2 H).

EXAMPLE C-4

1-Furan-3-yl-4-methyl-pentan-3-one

The title compound was prepared according to General Method 4a using 3-bromofuran (17 mmol), 4-methyl-1-penten-3-ol (25.5 mmol), tetrabutyl ammonium chloride (17 mmol), sodium bicarbonate (42.5 mmol), DMF (15 mL), and palladium acetate (0.9 mmol). The title compound was flash chromatographed eluting with EtOAc:hexane (5:95 to 10:90).

$^1$NMR (CDCl$_3$): δ1.05 (d, 6 H), 2.5–2.7 (m, 1 H), 2.65 (s, 4 H), 6.2 (s, 1 H), 7.25 (m, 1 H), 7.3 (m, 1 H).

EXAMPLE C-5

4-Methyl-1-thiophen-3-yl-pentan-3-one

The title compound was prepared according to General Method 4b using 3-bromothiophene (20 mmol), 4-methyl-1-penten-3-ol (30 mmol), sodium iodide (0.7 mmol), sodium bicarbonate (24 mmol), triphenylphosphine (0.6 mmol), DMF (15 mL), and palladium acetate (0.2 mmol). The title compound was flash chromatographed using EtOAc:hexane (5:95 to 10:90).

$^1$NMR (CDCl$_3$): δ1.05 (d, 6 H), 2.5–2.7 (m, 1 H), 2.7–2.8 (t, 2 H), 2.85–2.95 (t, 2 H), 6.90–9.95 (m, 2 H), 7.2–7.3 (m, 1 H).

Alternatively, the title compound could be prepared by hydrogenation (General Method 3) of the enone prepared in Example B-30.

General Method 5. Preparation of Silylated Intermediates

The appropriate alcohol (1 equiv.), and imidazole (1.2 equiv.) were added to a reaction vessel followed by CH$_2$Cl$_2$ or THF (7–10 mL per mmol of alcohol). t-Butyldimethylsilyl chloride (1.1 equiv.) was added and the reaction stirred at room temperature (3 hours to 4 days). The reaction was filtered, washed with H$_2$O and brine, dried (MgSO$_4$), and concentrated. The product was either flashed chromatographed or carried on crude.

EXAMPLE C-6

1-[5-(tert-Butyl-dimethyl-silanyloxymethyl)-thiophen-2-yl]-4-methyl-pentan-3-one The title compound was prepared according to General Method 5 using 1-(5-hydroxymethyl-thiophen-2-yl)-4-methyl-pentan-3-one (see Example C-24 below; 73.0 mmol), t-butyldimethylsilyl chloride (80.3 mmol), imidazole (80.3 mmol) and CH$_2$Cl$_2$ (300 mL). $^1$H NMR (CDCl$_3$): δ0.09 (s, 6 H), 0.92 (s, 9 H), 1.09 (d, 6 H), 2.59 (m, 1 H), 2.81 (t, 2 H), 3.06 (t, 2 H), 4.78 (s, 2 H), 6.61 (d, 1 H), 6.69 (d, 1 H).

The following ketones were prepared as indicated [either from reduction of the corresponding enones from Examples B-1 to B-36 (General Method 3) OR from the corresponding halides from Examples SM-1 to SM-19 (General Method 4a or 4b)]. In some cases, the following ketones were also prepared from silylation of an existing ketone using General Method 5:

TABLE D

Preparation of Ketones

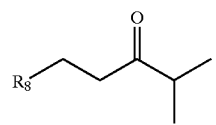

| Example | R$_8$ | General Method | Analytical Data ($^1$H NMR or MS) |
|---|---|---|---|
| C-7 | | Gen. Method 3 | (CDCl$_3$): δ 1.06 (d, 6 H), 2.56–2.63 (m, 1 H), 2.97 (t, 2 H), 3.24 (t, 2 H), 7.13 (d, 1 H), 7.60 (d, 1 H) |
| C-8 | | Gen. Method 3 | (CDCl$_3$): δ 1.04 (d, 6 H), 2.53–2.60 (m, 1 H), 2.87 (m, 2 H), 3.08 (m, 2 H), 6.96 (m, 1 H), 8.70 (m, 1 H) |
| C-9 | | Gen. Method 3 | (CDCl$_3$): δ 1.08 (d, 6 H), 2.55–2.61 (m, 1 H), 2.78 (t, 2 H), 3.15 (t, 2 H), 7.60 (s, 1 H), 8.63 (s, 1 H) |

TABLE D-continued

Preparation of Ketones

| Example | R₈ | General Method | Analytical Data (¹H NMR or MS) |
|---|---|---|---|
| C-10 | 5-methyl-thiazol-2-yl | Gen. Method 3 | (CDCl₃): δ 1.03 (d, 6 H), 2.33 (s, 3 H), 2.52–2.59 (m, 1 H), 2.88–2.92 (m, 2 H), 3.09–3.13 (m, 2 H), 7.18 (s, 1 H) |
| C-11 | 4-methyl-thiazol-2-yl | Gen. Method 3 | (CDCl₃): δ 1.05 (d, 6 H), 2.34 (s 3 H), 2.55–2.62 (m, 1 H), 2.93 (t, 2 H), 3.18 (t, 2 H), 6.65 (s, 1 H) |
| C-12 | 2-methyl-thiazol-4-yl | Gen. Method 3 | (CDCl₃): δ 1.02 (d, 6 H), 2.50–2.56 (m, 1 H), 2.62 (s, 3 H), 2.80–2.84 (m, 2 H), 2.91–2.94 (m, 2 H), 6.68 (s, 1 H) |
| C-13 | 5-methyl-thiazol-4-yl | Gen. Method 3 | (CDCl₃): δ 1.00 (d, 6 H), 2.35 (s. 3 H), 2.50–2.57 (m, 1 H), 2.86 (s, 4 H), 8.45 (s, 1 H) |
| C-14 | 2-isopropyl-thiazol-4-yl | Gen. Method 3 | (CDCl₃): δ 1.02 (d, 6 H), 1.32 (d, 6 H), 2.52–2.58 (m, 1 H), 2.83 (t, 2 H), 2.95 (t, 2 H), 3.20–3.27 (m, 1 H), 6.70 (s, 1 H) |
| C-15 | 4-isopropyl-thiazol-5-yl | Gen. Method 3 | (CDCl₃): δ 1.07 (d, 6 H), 1.26 (d, 6 H), 2.53–2.60 (m, 1 H), 2.75 (t, 2 H), 3.04 (t, 2 H), 3.07–3.14 (m, 1 H), 8.56 (s, 1 H) |
| C-16 | 5-isopropyl-thiazol-4-yl | Gen. Method 3 | (CDCl₃): δ 1.07 (d, 6 H), 1.27 (d, 6 H), 2.56–2.63 (m, 1 H), 2.89–2.97 (m, 4 H), 3.28–3.35 (m, 1 H), 8.53 (s, 1 H) |

TABLE D-continued

Preparation of Ketones $$R_8 \overset{O}{\underset{}{\diagup\hspace{-0.5em}\diagdown}} $$

| Example | R₈ | General Method | Analytical Data (¹H NMR or MS) |
|---|---|---|---|
| C-17 | 4-isopropyl-thiazol-2-yl | Gen. Method 3 | (CDCl₃): δ 1.10 (d, 6 H), 1.26 (d, 6 H), 2.60–2.65 (m, 1 H), 2.98 (t, 2 H), 2.99–3.05 (m, 1 H), 3.24 (t, 2 H), 6.68 (s, 1 H) |
| C-18 | 2-acetamido-thiazol-4-yl | Gen. Method 3 | (CDCl₃): δ 1.04 (d, 6 H), 2.20 (s, 3 H), 2.52–2.59 (m, 1 H), 2.76–2.80 (m, 2 H), 2.86–2.90 (m, 2 H), 6.51 (s, 1 H) |
| C-19 | pyridin-2-yl | Gen. Method 3 | (CDCl₃): δ 1.15 (d, 6 H), 2.5–2.7 (m, H), 2.9–3.0 (m, 2 H), 3.0–3.1 (m, 2 H), 7.05–7.15 (m, 1 H), 7.2 (d, 1 H), 7.5–7.6 (dt, 1 H), 8.5 (d, 1 H) |
| C-20 | furan-2-yl | Gen. Method 3 | (CDCl₃): δ 1.15 (d, 6 H), 2.5–2.7 (m, 1 H), 2.7–2.9 (m, 2 H), 2.85–2.95 (m, 2 H), 5.95 (m, 1 H), 6.25 (m, 1 H), 7.3 (m, 1 H) |
| C-21 | tetrahydrofuran-2-yl | Gen. Method 3 (complete reduction of C-20) | MS (APCI): 171 (M + H) |
| C-22 | thien-2-yl | Gen. Method 4b | (CDCl₃): δ 1.1 (d, 6 H), 2.5–2.7 (m, 1 H), 2.8–2.9 (t, 2 H), 3.05–3.15 (t, 2 H), 6.75–6.80 (m, 1 H), 6.85–6.95 (m, 1 H), 7.05–7.15 (m, 1 H) |
| C-23 | 5-(hydroxymethyl)thien-3-yl | Gen. Method 4b | (CDCl₃): δ 1.1 (d, 6 H), 2.5–2.7 (m, 1 H), 2.7–2.8 (m, 2 H), 2.8–2.9 (m, 2 H), 4.75 (s, 2 H), 6.85 (s, 1 H), 6.9 (s, 1 H) |
| C-24 | 5-(hydroxymethyl)thien-2-yl | Gen. Method 4b | (CDCl₃): δ 1.1 (d, 6 H), 2.5–2.7 (m, 1 H), 2.8–2.9 (t, 2 H), 3.05–3.15 (t, 2 H), 4.75 (s, 2 H), 6.65 (d, 1 H), 6.8 (d, 1 H) |
| C-25 | 2-(hydroxymethyl)thien-3-yl | Gen. Method 4b | (CDCl₃): δ 1.0 (d, 6 H), 2.4–2.5 (m, 1 H), 2.7–2.8 (m, 2 H), 2.8–2.9 (m, 2 H), 4.7 (s, 2 H), 6.75 (d, 1 H), 7.1 (d, 1 H) |

TABLE D-continued

Preparation of Ketones $$R_8\text{-CH}_2\text{CH}_2\text{-C(=O)-CH(CH}_3)_2$$

| Example | R$_8$ | General Method | Analytical Data ($^1$H NMR or MS) |
|---|---|---|---|
| C-26 | 3-(2-((tert-butyldimethylsilyloxy)methyl)thiophenyl) | Gen. Method 5 (from C-25) | (CDCl$_3$): δ 0.00 (s, 6 H), 0.82 (s, 9 H), 0.95 (d, 6 H), 2.44 (m, 1 H), 2.62 (t, 2 H), 2.72 (t, 2 H), 4.70 (s, 2 H), 6.70 (d, 1 H), 7.01 (d, 1 H) |
| C-27 | 4-(2-((tert-butyldimethylsilyloxy)methyl)thiophenyl) | Gen. Method 5 (from C-23) | (CDCl$_3$): δ 0.09 (s, 6 H), 0.85 (s. 9 H), 0.92 (d, 6 H), 2.58 (m, 1 H), 2.73 (m, 2 H), 2.82 (m, 2 H), 4.81 (s, 2 H), 6.74 (s, 1 H), 6.82 (s, 1 H) |
| C-28 | 3-fluoro-2-methylphenyl | Gen. Method 3 | (CDCl$_3$): δ 1.08 (d, 6 H), 2.21 (d, 3 H), 2.53–2.62 (m, 1 H), 2.70 (t, 2 H), 2.89 (t, 2 H), 6.84–6.92 (m, 2 H), 7.03–7.10 (m, 1 H) |
| C-29 | 2-fluorophenyl | Gen. Method 3 | |
| C-30 | 4-fluorophenyl | Gen. Method 3 | (CDCl$_3$): δ 1.05 (d, 6 H), 2.50–2.60 (m, 1 H), 2.71–2.76 (m, 2 H), 2.83–2.89 7(m, 2 H), 6.95 (m, 2 H), 7.13 (m, 2 H) |
| C-31 | 1-trityl-pyrazol-3-yl | Gen. Method 4a | $^1$HNMR (CDCl$_3$): δ 1.04 (d, 6H), 2.55 (sp, 1H), 2.64–2.74 (m, 4H), 7.11–7.17 (m, 7H), 7.26–7.35 (m, 9H), 7.48 (s, 1H) |
| C-32 | pyrrol-3-yl | Gen. Method 3 | MS (APCI): 166 (M + H) |
| C-33 | imidazol-4-yl | Gen. Method 3 | MS (APCI): 167 (M + H) |

TABLE D-continued

Preparation of Ketones

| Example | R₈ | General Method | Analytical Data (¹H NMR or MS) |
|---|---|---|---|
| C-34 | 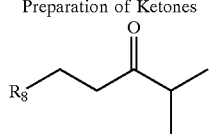 | Gen. Method 4a | MS (APCI): 179 (M + H) |
| C-35 | 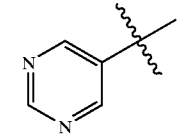 | Gen. Method 4a | MS (APCI): 194 (M + H) |
| C-36 | 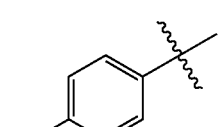 | Gen. Method 3 | MS (APCI): 200 (M − H) |
| C-37 | Ph | | Prepared as reported in Bull. Soc. Chim. Fr, 1956: 1653. |
| C-38 | 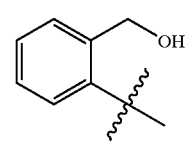 | Gen. Method 4 | MS (APCI): 206 (M) |
| C-39 | 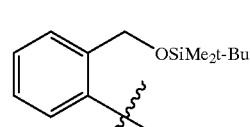 | Gen. Method 5 (from C-38) | MS (APCI): 319 (M − H) |
| C-40 | 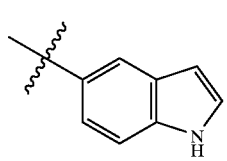 | Gen. Method 3 | ¹HNMR (CDCl₃): δ 1.09 (d, 6 H), 2.56–2.63 (m, 1 H), 2.84 (t, 2 H), 3.01 (t, 2 H), 6.49 (m, 1 H), 7.03–7.06 (m, 1 H), 7.17 (m, 1 H), 7.29–7.33 (m, 1 H), 7.46 (s, 1 H), 8.23 (s, 1H) |
| C-41 | 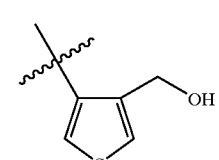 | Gen. Method 4b | (CDCl₃): δ 1.03 (d, 6 H), 2.51–2.58 (m, 1 H), 2.81–2.87 (m, 4 H), 4.60 (s, 2 H), 6.90 (d 1 H), 7.17 (d, 1 H) |
| C-42 | 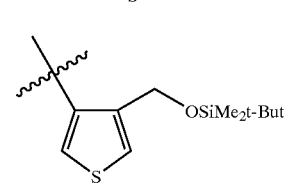 | Gen. Method 5 (from ABOVE) | (CDCl₃): δ 0.0 (s, 6 H), 0.83 (s, 9 H), 0.99 (d, 6 H), 2.50 (m, 1 H), 2.71 (m, 4 H), 4.56 (s, 2 H), 6.81 (d, 1 H), 7.06 (s, 1 H) |

TABLE D-continued

Preparation of Ketones $$R_8\text{-CH}_2\text{CH}_2\text{-C(=O)-CH(CH}_3)_2$$

| Example | R₈ | General Method | Analytical Data (¹H NMR or MS) |
|---|---|---|---|
| C-43 | 4-methyl-thiophen-3-yl | Gen. Method 4b | (CDCl₃): δ 1.09 (d, 6 H), 2.19 (s, 3 H), 2.60 (m, 1 H), 2.75–2.80 (m, 4 H), 6.85–6.90 (m, 2 H) |
| C-44 | 3-methyl-thiophen-2-yl | Gen. Method 4b | (CDCl₃): δ 1.04–1.06 (d, 6 H), 2.13 (s, 3 H), 2.51–2.58 (m, 1 H), 2.72–2.75 (t, 2 H), 2.94–2.98 (t, 2 H), 6.72–6.75 (d, 1 H), 6.97–6.98 (d, 1 H) |
| C-45 | 2-methyl-thiophen-3-yl | Gen. Method 3 | (CDCl₃): δ 1.06 (d, 6 H), 2.37 (s, 3 H), 2.52–2.59 (m, 1 H), 2.67–2.71 (t, 2 H), 2.77–2.81 (t, 2 H), 6.78–6.79 (d, 1 H), 6.98–7.00 (d, 1 H) |
| C-46 | 3-(hydroxymethyl)-thiophen-2-yl | Gen. Method 4a | (CDCl₃): δ 1.05 (d, 6 H), 2.50–2.61 (m, 1 H), 2.88 (t, 2 H), 3.12 (t, 2 H), 4.62 (d, 2 H), 6.96 (d, 1 H), 7.08 (d, 1 H) |
| C-47 | 3-(OSiMe₂t-Bu-methyl)-thiophen-2-yl | Gen. Method 5 (from C-46) | (CDCl₃): δ 0.08 (s, 6 H), 0.91 (s, 9 H), 1.08 (d, 6 H), 2.50–2.70 (m, 1 H), 2.78–2.81 (t, 2 H), 3.03–3.08 (t, 2 H), 4.63 (s, 2 H), 6.94 (d; 1 H), 7.03 (d, 1 H) |
| C-48 | 2,6-difluoro-phenyl | Gen. Method 3 | (CDCl₃): δ 1.09 (d, 6 H), 2.52–2.66 (m, 1 H), 2.71–2.76 (m, 2 H), 2.90–2.95 (m, 2 H), 6.79–6.89 (m, 2 H), 7.09–7.19 (m, 1 H) |
| C-49 | 3,5-difluoro-phenyl | Gen. Method 3 | (CDCl₃): δ 1.07 (d, 6 H), 2.50–2.64 (m, 1 H), 2.73–2.78 (m, 2 H), 2.84–2.90 (m, 2 H), 6.59–6.67 (m, 2 H), 7.69–7.72 (m, 1 H) |
| C-50 | 2,4-difluoro-phenyl | Gen. Method 3 | (CDCl₃): δ 1.06 (d, 6 H), 2.51–2.60 (m, 1 H), 2.71–2.77 (m, 2 H), 2.84–2.89 (m, 2 H), 6.72–6.81 (m, 2 H), 7.12–7.20 (m, 1 H) |

TABLE D-continued

Preparation of Ketones $$R_8 \underset{\text{structure}}{\overset{O}{\diagdown}}$$

| Example | $R_8$ | General Method | Analytical Data ($^1$H NMR or MS) |
|---|---|---|---|
| C-51 | 3,4,5-trifluorophenyl | Gen. Method 3 | (CDCl$_3$): δ 1.07 (d, 6 H), 2.49–2.61 (m, 1 H), 2.71–2.76 (m, 2 H), 2.80–2.85 (m, 2 H), 6.74–6.84 (m, 2 H) |
| C-52 | 2-methyl-5-fluorophenyl | Gen. Method 4a | |
| C-53 | 5-fluoro-2-ethylphenyl | Gen. Method 4a | (CDCl$_3$): δ 1.10 (d, 6 H), 1.19 (t, 3 H), 2.54–2.64 (m, 3 H), 2.69–2.77 (m, 2 H), 2.82–2.90 (m, 2 H), 6.80–6.87 (m, 2 H), 7.08–7.13 (m, 1 H) |
| C-54 | 4-fluoro-2-(hydroxymethyl)phenyl | Gen. Method 4a | (CDCl$_3$): δ 1.04 (d, 6 H), 2.37 (bs, 1 H), 2.50–2.66 (m, 1 H), 2.77–2.82 (m, 2 H), 2.84–2.94 (m, 2 H), 4.70 (s, 2 H), 6.88–6.91 (m, 1 H), 7.08–13 (m, 2 H) |
| C-55 | 4-fluoro-2-(t-BuMe$_2$SiOCH$_2$)phenyl | Gen. Method 5 (from C-54) | |
| C-56 | 2-methyl-4-fluorophenyl | Gen. Method 4a | |

EXAMPLE C-57

2,2,2-Trifluoro-N-[4-(4-methyl-3-oxo-pentyl)-thiazol-2-yl]-acetamide

A solution of C-18 (from Table D above; 1.21 g, 5.03 mmol) in 6N HCl (50 mL) and THF (5 mL) was refluxed for 4 hours and then cooled to room temperature. Solid NaHCO$_3$ was added portionwise with caution until pH 7.2 was achieved. The suspension was extracted with EtOAc. The combined extracts were washed with brine, dried (MgSO$_4$), and concentrated. The residue was chromatographed over silica gel, eluting with EtOAc, to give the deprotected compound. $^1$H NMR (CDCl$_3$): δ1.04 (d, 6 H), 2.52–2.59 (m, 1 H), 2.75 (m, 4 H), 6.06 (s, 1 H).

A solution of the ketone prepared above (0.75 g, 3.8 mmol) in CH$_2$Cl$_2$ (50 mL) was cooled in an ice bath, treated with NEt$_3$ (0.6 mL, 4.3 mmol) and trifluoromethyl acetic anhydride (0.6 mL, 4.3 mmol), and allowed to warm to room temperature. H$_2$O was added. The organic layer was separated, washed with brine, and dried (MgSO$_4$). Concentration gave an oil which was chromatographed over silica gel, eluting with EtOAc, to give the title compound. $^1$H NMR (CDCl$_3$): δ1.10 (d, 6 H), 2.58–2.65 (m, 1 H), 2.83–2.86 (m, 2 H), 2.91–2.95 (m, 2 H), 6.61 (s, 1 H).

Names corresponding to the ketones from Table D above are:

C-7: 4-Methyl-1-thiazol-2-yl-pentan-3-one;
C-8: 4-Methyl-1-thiazol-4-yl-pentan-3-one;
C-9: 4-Methyl-1-thiazol-5-yl-pentan-3-one;
C-10: 4-Methyl-1-(5-methyl-thiazol-2-yl)-pentan-3-one;
C-11: 4-Methyl-1-(4-methyl-thiazol-2-yl)-pentan-3-one;
C-12: 4-Methyl-1-(2-methyl-thiazol-4-yl)-pentan-3-one;
C-13: 4-Methyl-1-(5-methyl-thiazol-4-yl)-pentan-3-one;
C-14: 1-(2-Isopropyl-thiazol-4-yl)-4-methyl-pentan-3-one;
C-15: 1-(4-Isopropyl-thiazol-5-yl)-4-methyl-pentan-3-one;
C-16: 1-(5-Isopropyl-thiazol-4-yl)-4-methyl-pentan-3-one;
C-17: 1-(4-Isopropyl-thiazol-2-yl)-4-methyl-pentan-3-one;
C-18: N-[4-(4-Methyl-3-oxo-pentyl)-thiazol-2-yl]-acetamide;
C-19: 4-Methyl-1-pyridin-2-yl-pentan-3-one;
C-20: 1-Furan-2-yl-4-methyl-pentan-3-one;
C-21: 4-Methyl-1-(tetrahydro-furan-2-yl)-pentan-3-one;
C-22: 4-Methyl-1-thiophen-2-yl-pentan-3-one;
C-23: 1-(5-Hydroxymethyl-thiophen-3-yl)-4-methyl-pentan-3-one;
C-24: 1-(5-Hydroxymethyl-thiophen-2-yl)-4-methyl-pentan-3-one;
C-25: 1-(2-Hydroxymethyl-thiophen-3-yl)-4-methyl-pentan-3-one;
C-26: 1-[2-(tert-Butyl-dimethyl-silanyloxymethyl)-thiophen-3-yl]-4-methyl-pentan-3-one;
C-27: 1-[5-(tert-Butyl-dimethyl-silanyloxymethyl)-thiophen-3-yl]-4-methyl-pentan-3-one;
C-28: 1-(3-Fluoro-2-methyl-phenyl)-4-methyl-pentan-3-one;
C-29: 1-(2-Fluoro-phenyl)-4-methyl-pentan-3-one;
C-30: 1-(4-Fluoro-phenyl)-4-methyl-pentan-3-one;
C-31: 4-Methyl-1-(1-trityl-1H-pyrazol-3-yl)-pentan-3-one;
C-32: 4-Methyl-1-(1H-pyrrol-3-yl)-pentan-3-one;
C-33: 1-(1H-Imidazol-4-yl)-4-methyl-pentan-3-one;
C-34: 4-Methyl-1-(pyrimidin-5-yl)-pentan-3-one;
C-35: 1-(2-Amino-pyrimidin-5-yl)-4-methyl-pentan-3-one;
C-36: 4-(4-Methyl-3-oxo-pentyl)-benzonitrile;
C-37: 4-Methyl-1-phenyl-pentan-3-one;
C-38: 1-(2-Hydroxymethyl-phenyl)-4-methyl-pentan-3-one;
C-39: 1-[2-(tert-Butyl-dimethyl-silanyloxymethyl)-phenyl]-4-methyl-pentan-3-one.
C-40: 1-(1H-Indol-5-yl)-4-methyl-pentan-3-one;
C-41: 1-(4-Hydroxymethyl-thiophen-3-yl)-4-methyl-pentan-3-one;
C-42: 1-[4-(tert-Butyl-dimethyl-silanyloxymethyl)-thiophen-3-yl]-4-methyl-pentan-3-one;
C-43: 4-Methyl-1-(4-methyl-thiophen-3-yl)-pentan-3-one;
C-44: 4-Methyl-1-(3-methyl-thiophen-2-yl)-pentan-3-one;
C-45: 4-Methyl-1-(2-methyl-thiophen-3-yl)-pentan-3-one;
C-46: 1-(3-Hydroxymethyl-thiophen-2-yl)-4-methyl-pentan-3-one;
C-47: 1-[3-(tert-Butyl-dimethyl-silanyloxymethyl)-thiophen-2-yl]-4-methyl-pentan-3-one;
C-48: 1-(2,6-Difluoro-phenyl)-4-methyl-pentan-3-one;
C-49: 1-(3,5-Difluoro-phenyl)-4-methyl-pentan-3-one;
C-50: 1-(2,4-Difluoro-phenyl)-4-methyl-pentan-3-one;
C-51: 1-(3,4,5-Trifluoro-phenyl)-4-methyl-pentan-3-one;
C-52: 1-(5-Fluoro-2-methyl-phenyl)4-methyl-pentan-3-one;
C-53: 1-(2-Ethyl-5-fluoro-phenyl)-4-methyl-pentan-3-one;
C-54: 1-(4-Fluoro-2-hydroxymethyl-phenyl)-4-methyl-pentan-3-one;
C-55: 1-[2-(tert-Butyl-dimethyl-silanyloxymethyl)-4-fluoro-phenyl]-4-methyl-pentan-3-one; and
C-56: 1-(4-Fluoro-2-methyl-phenyl)-4-methyl-pentan-3-one.

General Method 6. Preparation of β-Ketoesters

Methyl acetoacetate was added dropwise to a slurry of hexane washed sodium hydride in anhydrous THF at 0° C. and the reaction stirred at 0° C. (15 minutes to 3 hours). N-Butyl lithium (nBuLi) was then added at 0° C. and the reaction stirred at 0° C. (15 minutes to 24 hours). A solution of the requisite ketone in THF was added, and the reaction mixture was stirred at 0° C. to room temperature for 15 minutes to 24 hours. To the reaction mixture was added acetic acid [or dilute HCl or saturated ammonium chloride $(NH_4Cl)$] with stirring, and the THF was removed on a rotoevaporator. The viscous reaction mixture was partitioned between $H_2O$ and EtOAc. After separation of the layers, the aqueous layer was again extracted with EtOAc. The combined organic extracts were dried $(MgSO_4)$ and concentrated. The aldol intermediates were either purified by flash chromatography or taken on crude.

General Method 7. Desilylation of Silyl Ether Protecting Groups

The appropriate silanyloxy compound (1 equiv.) was added to a reaction vessel followed by THF (3–5 mL per mmol of silanyloxy compound). This solution was treated with tetrabutylammonium fluoride (1.2–2.0 equiv.) and stirred at room temperature (1 hour to 1 day). The product was partitioned between EtOAc and 1N HCl. The organic layer was dried $(MgSO_4)$ and concentrated. The product was either flashed chromatographed or carried on crude.

EXAMPLE D-1

5-Hydroxy-6-methyl-5-[2-(4-methyl-thiazol-5-yl)-ethyl]-3-oxo-heptanoic acid methyl ester The title compound was prepared as described in General Method 6 from 1.00 g (8.61 mmol) of methyl acetoacetate, 0.38 g (9.50 mmol) of sodium hydride, 4.5 mL of 2.1 M nBuLi (9.45 mmol), and 1.53 g (7.75 mmol) of 4-methyl-1-(4-methyl-thiazol-5-yl)-pentan-3-one (prepared in Example C-2.) The crude compound was used without purification in the next step.

The following compounds were prepared in similar fashion from the appropriate ketone (from Examples C-1 to C-57) and were used without purification.

TABLE E

Preparation of β-Ketoesters

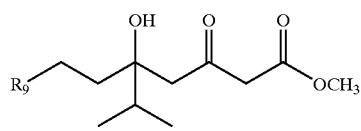

| Example | $R_9$ |
|---------|-------|
| D-2 | 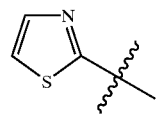 |

TABLE E-continued
Preparation of β-Ketoesters
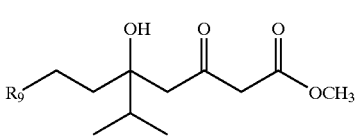
| Example | R₉ |
|---|---|
| D-3 | 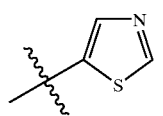 |
| D-4 | 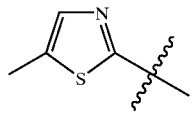 |
| D-5 | 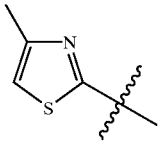 |
| D-6 | 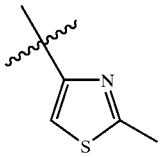 |
| D-7 | 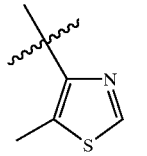 |
| D-8 | 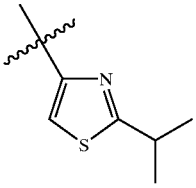 |
| D-9 | 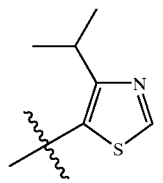 |
| D-10 | 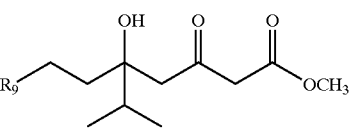 |
| D-11 | 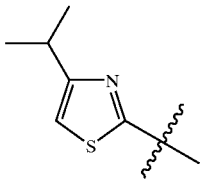 |
| D-12 | 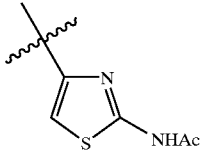 |
| D-13 | 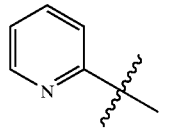 |
| D-14 | 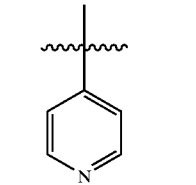 |
| D-15 | 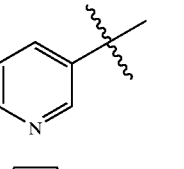 |
| D-16 | 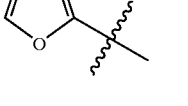 |
| D-17 | 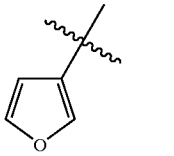 |
| D-18 | |

TABLE E-continued
Preparation of β-Ketoesters
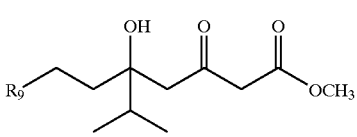
| Example | R₉ |
|---|---|
| D-19 | 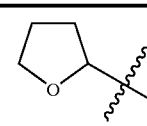 |
| D-20 | 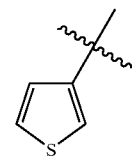 |
| D-21 | 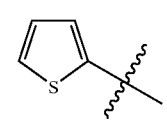 |
| D-22 | 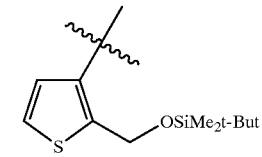 |
| D-23 | 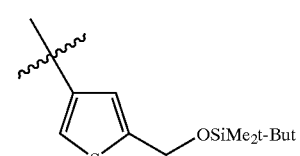 |
| D-24 | 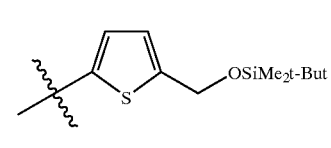 |
| D-25 | 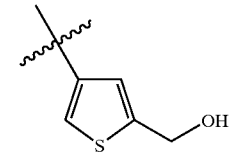 |
| D-26 | 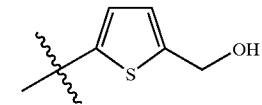 |
| D-27 | 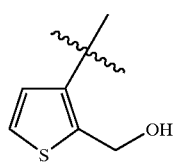 |
| D-28 | 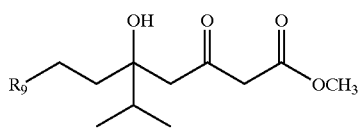 |
| D-29 | 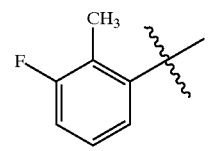 |
| D-30 | 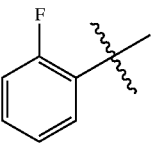 |
| D-31 | 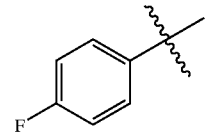 |
| D-32 | 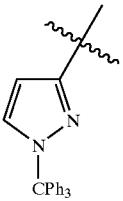 |
| D-33 |  |
| D-34 | 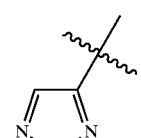 |
| D-35 | 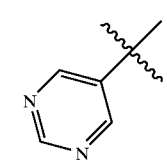 |

TABLE E-continued
Preparation of β-Ketoesters
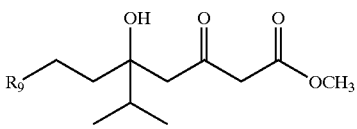
| Example | R$_9$ |
|---|---|
| D-36 | 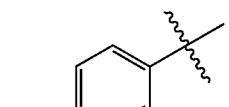 |
| D-37 | 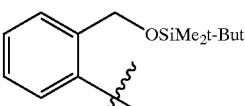 |
| D-38* | 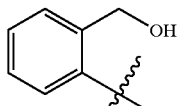 |
| D-39 | 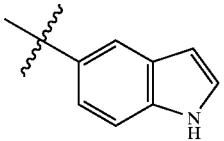 |
| D-40 | 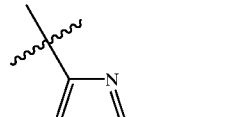 |
| D-41 | 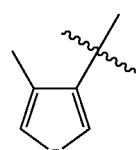 |
| D-42 | 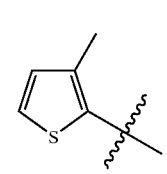 |
| D-43 | 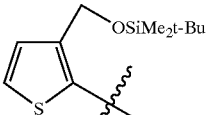 |
TABLE E-continued
Preparation of β-Ketoesters
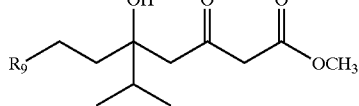
| Example | R$_9$ |
|---|---|
| D-44 | 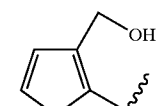 |
| D-45 | 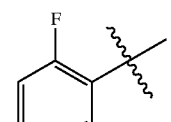 |
| D-46 | 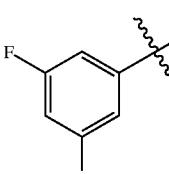 |
| D-47 | 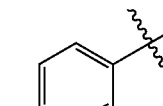 |
| D-48 | 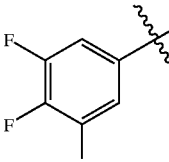 |
| D-49 | 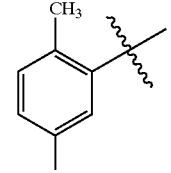 |
| D-50 | 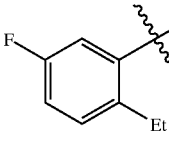 |
| D-51 | 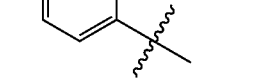 |

TABLE E-continued

Preparation of β-Ketoesters

[Structure: R₉-CH₂CH₂-C(OH)(iPr)-CH₂-C(=O)-CH₂-C(=O)-OCH₃]

| Example | R₉ |
|---|---|
| D-52** | [4-fluoro-2-(hydroxymethyl)phenyl with gem-dimethyl attachment] |

*Can be prepared from D-37 as outlined in General Method 7
**Can be prepared from D-51 as outlined in General Method 7

The compounds from Table E above are named:

D-2: 5-Hydroxy-6-methyl-3-oxo-5-(2-thiazol-2-yl-ethyl)-heptanoic acid methyl ester;
D-3: 5-Hydroxy-6-methyl-3-oxo-5-(2-thiazol-4-yl-ethyl)-heptanoic acid methyl ester;
D-4: 5-Hydroxy-6-methyl-3-oxo-5-(2-thiazol-5-yl-ethyl)-heptanoic acid methyl ester;
D-5: 5-Hydroxy-6-methyl-5-[2-(5-methyl-thiazol-2-yl)-ethyl]-3-oxo-heptanoic acid methyl ester;
D-6: 5-Hydroxy-6-methyl-5-[2-(4-methyl-thiazol-2-yl)-ethyl]-3-oxo-heptanoic acid methyl ester;
D-7: 5-Hydroxy-6-methyl-5-[2-(2-methyl-thiazol-4-yl)-ethyl]-3-oxo-heptanoic acid methyl ester;
D-8: 5-Hydroxy-6-methyl-5-[2-(5-methyl-thiazol-4-yl)-ethyl]-3-oxo-heptanoic acid methyl ester;
D-9: 5-Hydroxy-5-[2-(2-isopropyl-thiazol-4-yl)-ethyl]-6-methyl-3-oxo-heptanoic acid methyl ester;
D-10: 5-Hydroxy-5-[2-(4-isopropyl-thiazol-5-yl)-ethyl]-6-methyl-3-oxo-heptanoic acid methyl ester;
D-11: 5-Hydroxy-5-[2-(5-isopropyl-thiazol-4-yl)-ethyl]-6-methyl-3-oxo-heptanoic acid methyl ester;
D-12: 5-Hydroxy-5-[2-(4-isopropyl-thiazol-2-yl)-ethyl]-6-methyl-3-oxo-heptanoic acid methyl ester;
D-13: 5-[2-(2-Acetylamino-thiazol-4-yl)-ethyl]-5-hydroxy-6-methyl-3-oxo-heptanoic acid methyl ester;
D-14: 5-Hydroxy-6-methyl-3-oxo-5-(2-pyridin-2-yl-ethyl)-heptanoic acid methyl ester;
D-15: 5-Hydroxy-6-methyl-3-oxo-5-(2-pyridin-4-yl-ethyl)-heptanoic acid methyl ester;
D-16: 5-Hydroxy-6-methyl-3-oxo-5-(2-pyridin-3-yl-ethyl)-heptanoic acid methyl ester;
D-17: 5-(2-Furan-2-yl-ethyl)-5-hydroxy-6-methyl-3-oxo-heptanoic acid methyl ester;
D-18: 5-(2-Furan-3-yl-ethyl)-5-hydroxy-6-methyl-3-oxo-heptanoic acid methyl ester;
D-19: 5-Hydroxy-6-methyl-3-oxo-5-[2-(tetrahydro-furan-2-yl)-ethyl]-heptanoic acid methyl ester;
D-20: 5-Hydroxy-6-methyl-3-oxo-5-(2-thiophen-3-yl-ethyl)-heptanoic acid methyl ester;
D-21: 5-Hydroxy-6-methyl-3-oxo-5-(2-thiophen-2-yl-ethyl)-heptanoic acid methyl ester;
D-22: 5-{2-[2-(tert-Butyl-dimethyl-silanyloxymethyl)-thiophen-3-yl]-ethyl}-5-hydroxy-6-methyl-3-oxo-heptanoic acid methyl ester;
D-23: 5-{2-[5-(tert-Butyl-dimethyl-silanyloxymethyl)-thiophen-3-yl]-ethyl}-5-hydroxy-6-methyl-3-oxo-heptanoic acid methyl ester;
D-24: 5-{2-[5-(tert-Butyl-dimethyl-silanyloxymethyl)-thiophen-2-yl]-ethyl}-5-hydroxy-6-methyl-3-oxo-heptanoic acid methyl ester;
D-25: 5-Hydroxy-5-[2-(5-hydroxymethyl-thiophen-3-yl)-ethyl]-6-methyl-3-oxo-heptanoic acid methyl ester;
D-26: 5-Hydroxy-5-[2-(5-hydroxymethyl-thiophen-2-yl)-ethyl]-6-methyl-3-oxo-heptanoic acid methyl ester;
D-27: 5-Hydroxy-5-[2-(2-hydroxymethyl-thiophen-3-yl)-ethyl]-6-methyl-3-oxo-heptanoic acid methyl ester;
D-28: 5-[2-(3-Fluoro-2-methyl-phenyl)-ethyl]-5-hydroxy-6-methyl-3-oxo-heptanoic acid methyl ester;
D-29: 5-[2-(2-Fluoro-phenyl)-ethyl]-5-hydroxy-6-methyl-3-oxo-heptanoic acid methyl ester;
D-30: 5-[2-(4-Fluoro-phenyl)-ethyl]-5-hydroxy-6-methyl-3-oxo-heptanoic acid methyl ester;
D-31: 5-Hydroxy-6-methyl-3-oxo-5-[2-(1-trityl-1H-pyrazol-3-yl)-ethyl]-heptanoic acid methyl ester;
D-32: 5-Hydroxy-6-methyl-3-oxo-5-[2-(1H-pyrrol-3-yl)-ethyl]-heptanoic acid methyl ester;
D-33: 5-Hydroxy-5-[2-(1H-imidazol-4-yl)-ethyl]-6-methyl-3-oxo-heptanoic acid methyl ester;
D-34: 5-Hydroxy-6-methyl-3-oxo-5-(2-pyrimidin-5-yl-ethyl)-heptanoic acid methyl ester;
D-35: 5-[2-(2-Amino-pyrimidin-5-yl)-ethyl]-5-hydroxy-6-methyl-3-oxo-heptanoic acid methyl ester;
D-36: 5-[2-(4-Cyano-phenyl)-ethyl]-5-hydroxy-6-methyl-3-oxo-heptanoic acid methyl ester;
D-37: 5-{2-[2-(tert-Butyl-dimethyl-silanyloxymethyl)-phenyl]-ethyl}-5-hydroxy-6-methyl-3-oxo-heptanoic acid methyl ester;
D-38: 5-Hydroxy-5-[2-(2-hydroxymethyl-phenyl)-ethyl]-6-methyl-3-oxo-heptanoic acid methyl ester;
D-39: 5-Hydroxy-5-[2-(1H-indol-5-yl)-ethyl]-6-methyl-3-oxo-heptanoic acid methyl ester;
D-40: 5-Hydroxy-6-methyl-3-oxo-5-{2-[2-(2,2,2-trifluoro-acetylamino)-thiazol-4-yl]-ethyl}-heptanoic acid methyl ester;
D-41: 5-Hydroxy-6-methyl-5-[2-(4-methyl-thiophen-3-yl)-ethyl]-3-oxo-heptanoic acid methyl ester;
D-42: 5-Hydroxy-6-methyl-5-[2-(3-methyl-thiophen-2-yl)-ethyl]-3-oxo-heptanoic acid methyl ester;
D-43: 5-{2-[3-(tert-Butyl-dimethyl-silanyloxymethyl)-thiophen-2-yl]-ethyl)}-5-hydroxy-6-methyl-3-oxo-heptanoic acid methyl ester;
D-44: 5-Hydroxy-5-[2-(3-hydroxymethyl-thiophen-2-yl)-ethyl]-6-methyl-3-oxo-heptanoic acid methyl ester;
D-45: 5-[2-(2,6-Difluoro-phenyl)-ethyl]-5-hydroxy-6-methyl-3-oxo-heptanoic acid methyl ester;
D-46: 5-[2-(3,5-Difluoro-phenyl)-ethyl]-5-hydroxy-6-methyl-3-oxo-heptanoic acid methyl ester;
D-47: 5-[2-(2,4-Difluoro-phenyl)-ethyl]-5-hydroxy-6-methyl-3-oxo-heptanoic acid methyl ester;
D-48: 5-[2-(3,4,5-Trifluoro-phenyl)-ethyl]-5-hydroxy-6-methyl-3-oxo-heptanoic acid methyl ester;
D-49: 5-[2-(5-Fluoro-2-methyl-phenyl)-ethyl]-5-hydroxy-6-methyl-3-oxo-heptanoic acid methyl ester;
D-50: 5-[2-(2-Ethyl-5-Fluoro-phenyl)-ethyl]-5-hydroxy-6-methyl-3-oxo-heptanoic acid methyl ester;
D-51: 5-{2-[2-(tert-Butyl-dimethyl-silanyloxymethyl)-4-fluoro-phenyl]-ethyl}-5-hydroxy-6-methyl-3-oxo-heptanoic acid methyl ester; and
D-52: 5-Hydroxy-5-[2-(4-fluoro-2-hydroxymethyl-phenyl)-ethyl]-6-methyl-3-oxo-heptanoic acid methyl ester.

General Method 8. Preparation of the Intermediate 4-Hydroxy-5,6-dihydro-pyran-2-ones The aldol intermediate was dissolved in THF (1 volume) and treated with 9 to 10 volumes of NaOH (0.1N–1.0N). The reaction was stirred from 1 hour to 24 hours at room temperature. The base solution was extracted with Et$_2$O and then cooled to 0° C. The mixture was acidified to pH 4 to 5 using HCl (0.1N to 6N) or acetic acid. On occasion, the product could be isolated by filtration. Alternatively the acidified extracts were extracted with EtOAc. The organic extracts were combined, dried (MgSO$_4$) and concentrated. Purification was accomplished by trituration from Et$_2$O or flash chromatography.

EXAMPLE E-1

4-Hydroxy-6-isopropyl-6-[2-(4-methyl-thiazol-5-yl)-ethyl]-5,6-dihydro-pyran-2-one The title compound was prepared as described in General Method 8 using the crude aldol product isolated in Example D-1, 20 mL of f THF, and 200 mL of 1.0.N NaOH. The reaction mixture was stirred at room temperature for 2 hours, then poured over ice and acidified to pH 5.1. The solution was extracted with EtOAc, dried (MgSO$_4$), and concentrated. Purification by silica gel chromatography, eluting with 5:95 MeOH:CH$_2$Cl$_2$, gave the title compound.

$^1$H NMR (DMSO-d$_6$): δ0.87–0.90 (m, 6 H), 1.82–1.96 (m, 2 H), 2.07–2.18 (m, 1 H), 2.25 (s, 3 H), 2.31 (d of ABX q, 1 H), 2.60 (d of ABX q, 1 H), 2.74–2.81 (m, 2 H), 4.96 (s, 1 H), 8.78 (s, 1 H), 11.39 (s, 1 H).

The following dihydropyrones were prepared from the corresponding aldol products from Examples D-1 to D-51. The 4-hydroxy-dihydropyrones exist in different forms depending upon the solvent.

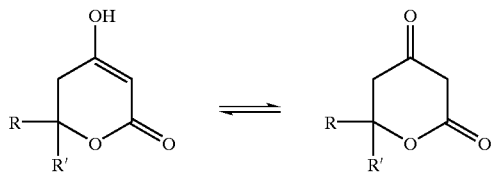

TABLE F

Preparation of Racemic 4-Hydroxy-Dihydropyrones

| Example | Aryl | R$_{10}$ | General Method | Analytical Data ($^1$H NMR or MS) |
|---|---|---|---|---|
| E-2 | 2-thiazolyl | i-Propyl | Gen. Method 8 | MS (APCI): 268 (M+H) |
| E-3 | 4-thiazolyl | i-Propyl | Gen. Method 8 | MS (APCI): 268 (M+H) |
| E-4 | 5-thiazolyl | i-Propyl | Gen. Method 8 | MS (APCI): 268 (M+H) |
| E-5 | 5-methyl-2-thiazolyl | i-Propyl | Gen. Method 8 | MS (APCI): 282 (M+H) |
| E-6 | 4-methyl-2-thiazolyl | i-Propyl | Gen. Method 8 | MS (APCI): 282 (M+H) |

TABLE F-continued

Preparation of Racemic 4-Hydroxy-Dihydropyrones

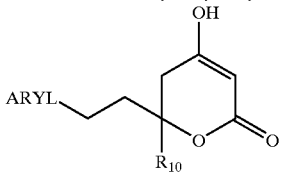

| Example | Aryl | R$_{10}$ | General Method | Analytical Data ($^1$H NMR or MS) |
|---|---|---|---|---|
| E-7 | 4-(2-methylthiazolyl) | i-Propyl | Gen. Method 8 | MS (APCI): 282 (M+H) |
| E-8 | 4-(5-methylthiazolyl) | i-Propyl | Gen. Method 8 | MS (APCI): 282 (M+H) |
| E-9 | 4-(2-isopropylthiazolyl) | i-Propyl | Gen. Method 8 | MS (APCI): 310 (M+H) |
| E-10 | 5-(4-isopropylthiazolyl) | i-Propyl | Gen. Method 8 | MS (APCI): 310 (M+H) |
| E-11 | 4-(5-isopropylthiazolyl) | i-Propyl | Gen. Method 8 | MS (APCI): 310 (M+H) |
| E-12 | 2-(4-isopropylthiazolyl) | i-Propyl | Gen. Method 8 | MS (APCI): 310 (M+H) |
| E-13 | 4-(2-acetamidothiazolyl) | i-Propyl | Gen. Method 8 | MS (APCI): 325 (M+H) |

TABLE F-continued

Preparation of Racemic 4-Hydroxy-Dihydropyrones

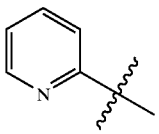

| Example | Aryl | $R_{10}$ | General Method | Analytical Data ($^1$H NMR or MS) |
|---|---|---|---|---|
| E-14 | 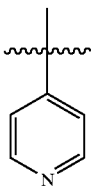 | i-Propyl | Gen. Method 8 | MS (APCI): 262 (M+H) |
| E-15 | 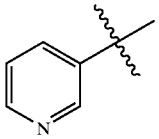 | i-Propyl | Gen. Method 8 | (CDCl$_3$): δ1.05(d, 6H), 1.7–1.9(m, 1H), 2.0–2.2(m, 2H), 2.6–2.9(ABq, 2H), 2.7–2.8(m, 2H), 3.42(s, 2H), 7.05(d, 2H), 8.5(d, 2H). |
| E-16 | 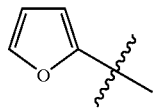 | i-Propyl | Gen. Method 8 | (CDCl$_3$): δ1.00(d, 6H), 1.7–1.9(m, 1H), 1.95–2.2(m, 2H), 2.6–2.8(ABq, 2H), 2.6–2.8(m, 2H), 3.40(s, 2H), 7.15–7.25(m, 1H), 7.4–7.5(m, 1H), 8.4–8.5(s, m, 2H). |
| E-17 | 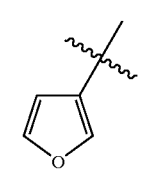 | i-Propyl | Gen. Method 8 | (CDCl$_3$): δ1.1(dd, 6H), 1.7–1.9(m, 1H), 2.0–2.2(m, 2H), 2.6–2.8(ABq, 2H), 2.7–2.9(m, 2H), 3.40(s, 2H), 6.0(m, 1H), 6.30(m, 1H), 7.3(m, 1H). |
| E-18 | 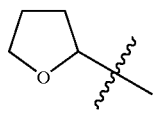 | i-Propyl | Gen. Method 8 | (CDCl$_3$): δ1.1(dd, 6H), 1.7–1.9(m, 1H), 1.95–2.2(m, 2H), 2.5–2.7(m, 2H), 2.6–2.8(ABq, 2H), 3.40(s, 2H), 6.25(s, 1H), 7.1(m, 1H), 7.18(m, 1H). |
| E-19 | 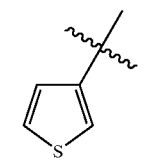 | i-Propyl | Gen. Method 8 | (CDCl$_3$): δ0.8–2.2 (m, 15H), 2.65(ABq, 2H), 3.40(ABq, 2H), 3.60–3.90(m, 3H). |
| E-20 |  | i-Propyl | Gen. Method 8 | Mp 140–142.5° C. |

TABLE F-continued

Preparation of Racemic 4-Hydroxy-Dihydropyrones

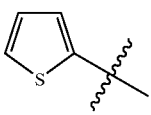

| Example | Aryl | R<sub>10</sub> | General Method | Analytical Data (¹H NMR or MS) |
|---|---|---|---|---|
| E-21 | 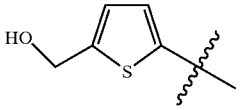 | i-Propyl | Gen. Method 8 | (CDCl$_3$): δ1.05(d, 6H), 1.8–2.0(m, 1H), 2.0–2.2(m, 2H), 2.6–2.8(ABq, 2H), 2.9–3.1(m, 2H), 3.40(s, 2H), 6.8(m, 1H), 6.9(m, 1H), 7.15(m, 1H). |
| E-22 | 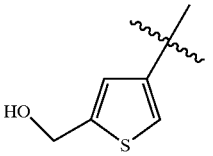 | i-Propyl | Gen. Method 7 then Gen. Method 8 | (CDCl$_3$): δ1.1(d, 6H), 1.8–2.0(m, 1H), 2.0–2.2(m, 2H), 2.6–2.8(ABq, 2H), 2.8–3.0(m, 2H), 3.40(s, 2H), 4.75(s, 2H), 6.65(d, 1H), 6.8(d, 1H). |
| E-23 | 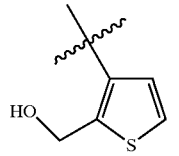 | i-Propyl | Gen. Method 7 then Gen. Method 8 | (CDCl$_3$). δ1.0(d, 6H), 1.7–1.9(m, 2H), 2.0–2.2(m, 2H), 2.6–2.8(m, Abq, 4H), 3.40(s, 2H), 4.8(d, 2H), 6.8(s, 1H), 6.9(s, 1H). |
| E-24 | 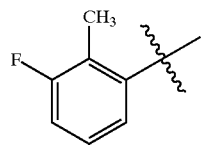 | i-Propyl | Gen. Method 7 then Gen. Method 8 | MS (APCI): 295(M–H) |
| E-25 | 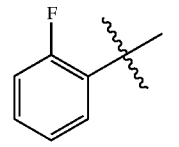 | i-Propyl | Gen. Method 8 | (DMSO-d$_6$): δ0.90 (d, 3H), 0.92(d, 3H), 1.73–1.90(m, 2H), 2.10–2.19(m, 4H), 2.28(d of ABX q, 1H), 2.58–2.65(m, 3H), 4.97(s, 1H), 6.92–6.98(m, 2H), 7.08–7.15(m, 1H), 11.39(bs, 1H). |
| E-26 |  | i-Propyl | Gen. Method 8 | (DMSO-d$_6$): δ0.89 (d, 3H), 0.91(d, 3H), 1.81–1.95(m, 2H), 2.08–2.17(m, 1H), 2.28(d of ABX q, 1H), 2.58–2.64(m, 3H), 4.96(s, 1H), 7.07–7.14(m, 2H), 7.19–7.28(m, 2H), 11.37(bs, 1H). |

TABLE F-continued

Preparation of Racemic 4-Hydroxy-Dihydropyrones

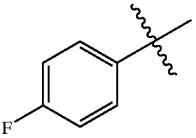

| Example | Aryl | $R_{10}$ | General Method | Analytical Data ($^1$H NMR or MS) |
|---|---|---|---|---|
| E-27 | 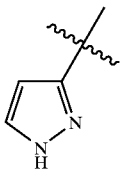 | i-Propyl | Gen. Method 8 | (DMSO-$d_6$): δ0.88 (d, 3H), 0.90(d, 3H), 1.82–1.91(m, 2H), 2.05–2.14(m, 1H), 2.32(d of ABXq, 1H), 2.54–2.62(m, 3H), 4.96(s, 1H), 7.04–7.11(m, 2H), 7.18–7.22(m, 2H), 11.35(bs, 1H). |
| E-28 | 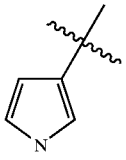 | i-Propyl | Gen. Method 8 | MS (APCI): 250(M) |
| E-29 | 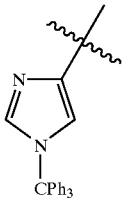 | i-Propyl | Gen. Method 8 | MS (APCI): 250(M+H) |
| E-30 | 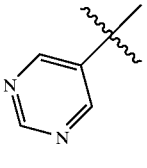 | i-Propyl | Gen. Method 8 | MS (APCI): 493(M+H) |
| E-31 | 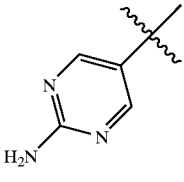 | i-Propyl | Gen. Method 8 | MS (APCI): 263(M+H) |
| E-32 | 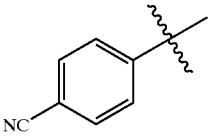 | i-Propyl | Gen. Method 8 | MS (APCI): 278(M+H) |
| E-33 |  | i-Propyl | Gen. Method 8 | MS (APCI): 286(M+H) |

TABLE F-continued

Preparation of Racemic 4-Hydroxy-Dihydropyrones

| Example | Aryl | $R_{10}$ | General Method | Analytical Data ($^1$H NMR or MS) |
|---|---|---|---|---|
| E-34 | 2-(hydroxymethyl)phenyl, α-methyl | i-Propyl | Gen. Method 8 | MS (APCI): 290(M) |
| E-35 | 4-hydroxyphenyl, α-methyl | i-Propyl | | 08/883,743 |
| E-36 | 4-hydroxyphenyl, α-methyl | Cyclopentyl | | |
| E-37 | 4-hydroxyphenyl, α-methyl | Cyclohexyl | | |
| E-38 | 4-(BOCHN)phenyl, α-methyl | i-Propyl | | |
| E-39 | 4-(BOCHN)phenyl, α-methyl | Cyclopentyl | | |
| E-40 | 4-(BOCHN)phenyl, α-methyl | Cyclohexyl | | |
| E-41 | 3-hydroxyphenyl, α-methyl | i-Propyl | | |

TABLE F-continued

Preparation of Racemic 4-Hydroxy-Dihydropyrones

| Example | Aryl | R$_{10}$ | General Method | Analytical Data ($^1$H NMR or MS) |
|---|---|---|---|---|
| E-42 | 3-OH-phenyl | Cyclopentyl | From 08/883,743 | |
| E-43 | 3-OH-phenyl | Cyclohexyl | From 08/883,743 | |
| E-44 | 3-NHBOC-phenyl | i-Propyl | From 08/883,743 | |
| E-45 | 3-NHBOC-phenyl | Cyclopentyl | From 08/883,743 | |
| E-46 | 3-NHBOC-phenyl | Cyclohexyl | From 08/883,743 | |
| E-47 | 5-indolyl | i-Propyl | Gen. Method 8 | MS (APCI): 300(M+H) |
| E-48 | 2-(NHCOCF$_3$)-thiazol-4-yl | i-Propyl | Gen. Method 8 | MS (APCI): 379(M+H) |

TABLE F-continued

Preparation of Racemic 4-Hydroxy-Dihydropyrones

| Example | Aryl | $R_{10}$ | General Method | Analytical Data ($^1$H NMR or MS) |
|---|---|---|---|---|
| E-49 | 3,4-dimethylthiophen-3-yl | i-Propyl | Gen. Method 8 | MS (APCI): 281(M+H) |
| E-50 | 3-methylthiophen-2-yl | i-Propyl | Gen. Method 8 | MS (APCI): 281(M+H) |
| E-51 | 2-(hydroxymethyl)thiophen-2-yl | i-Propyl | Gen. Method 8 | (CDCl$_3$): δ1.02–1.06 (dd, 6H), 1.80–2.00(m, 1H), 2.05–2.25(m, 2H), 2.61–2.79(ABq, 2H), 2.85–3.05(m, 2H), 3.34–3.52(AB q, 2H), 4.60(d, 2H), 6.97(d, 1H), 7.10(d, 1H). |
| E-52 | 2,6-difluorophenyl | i-Propyl | Gen. Method 8 | (CDCl$_3$)δ0.88(d, 3H), 0.91(d, 3H), 1.74–1.94(m, 2H), 2.10–2.19(m, 1H), 2.28(d of ABXq, 1 H), 2.58–2.65(m, 3 H), 4.97(s, 1H), 6.92–6.98(m, 2H), 7.08–7.15(m, 1H), 11.39(bs, 1H) |
| E-53 | 3,5-difluorophenyl | i-Propyl | Gen. Method 8 | (CDCl$_3$)δ0.88(d, 3 H), 0.91(d, 3H), 1.87–1.93(m, 2H), 2.04–2.13(m, 1H), 2.33(d of ABXq, 1 H), 2.60–2.69(m, 3 H), 4.96(s, 1H), 7.00–7.04(m, 3H), 11.35(bs, 1H) |
| E-54 | 2,4-difluorophenyl | i-Propyl | Gen. Method 8 | (DMSO)δ0.89(d, 3 H), 0.91(d, 3H), 1.77–1.94(m, 2H), 2.07–2.16(m, 1H), 2.29(d of ABXq, 1H), 2.57–2.63(m, 3H), 4.95(s, 1H), 6.95–7.01(m, 1H), 7.11–7.19(m, 1H), 7.27–7.35(m, 1H), 11.36(bs, 1H) |

TABLE F-continued

Preparation of Racemic 4-Hydroxy-Dihydropyrones

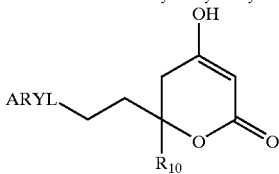

| Example | Aryl | $R_{10}$ | General Method | Analytical Data ($^1$H NMR or MS) |
|---|---|---|---|---|
| E-55 | 3,4,5-trifluorophenyl | i-Propyl | Gen. Method 8 | (CDCl$_3$)δ0.87(d, 3H), 0.89(d, 3H), 1.86–1.92(m, 2H), 2.01–2.15(m, 1H), 2.34(d of ABXq, 1H), 2.53–2.61(m, 3H), 4.94(s, 1H), 7.15–7.24(m, 2H), 11.36(bs, 1H). |
| E-56 | 2-methyl-4-fluorophenyl | i-Propyl | Gen. Method 8 | (DMSO)δ0.89(d, 3 H), 0.91(d, 3H), 1.77–1.85(m, 2H), 2.08–2.16(m+s, 4H), 2.29(d of ABXq, 1 H), 2.53–2.64(m, 3 H), 4.96(s, 1H), 6.84–6.96(m, 2H), 7.10–7.15(m, 1H), 11.36(bs, 1H) |
| E-57 | 2-ethyl-5-fluorophenyl | i-Propyl | Gen. Method 8 | (DMSO)δ0.89(d, 3 H), 0.91(d, 3H), 1.09 (t, 3H), 1.80–1.87(m, 2H), 2.08–2.17(m, 1 H), 2.28(d of ABXq, 1H), 2.47–2.51(m, partially obscured by DMSO, 2H), 2.54–2.64(m, 3H), 4.96(s, 1H), 6.88–6.95(m, 2 H), 7.15–7.18(m, 1 H), 11.38(bs, 1H). |
| E-58 | 2-(OTBDMS-methyl)-4-fluorophenyl | i-Propyl | Gen. Method 8 |  |
| E-59 | 2-(hydroxymethyl)-4-fluorophenyl | i-Propyl | Gen. Method 7 (from E-58) | (DMSO)δ0.95(d, 3 H), 0.93(d, 3H), 2.14–2.26(m, 1H), 2.35(d of ABXq, 1H), 2.53–2.62(m, partially obscured by DMSO, 2H), 2.66(d of ABXq, 1H), 4.52 (s, 2H), 5.03(s, 1H), 5.32(bs, 1H), 6.99–7.05(m, 1H), 7.15–7.22(m, 2H), 11.42 (bs, 1H) |

The compounds from Table F above are named:

E-2: 4-Hydroxy-6-isopropyl-6-(2-thiazol-2-yl-ethyl)-5,6-dihydro-pyran-2-one;

E-3: 4-Hydroxy-6-isopropyl-6-(2-thiazol-4-yl-ethyl)-5,6-dihydro-pyran-2-one;

E-4: 4-Hydroxy-6-isopropyl-6-(2-thiazol-5-yl-ethyl)-5,6-dihydro-pyran-2-one;

E-5: 4-Hydroxy-6-isopropyl-6-[2-(5-methyl-thiazol-2-yl)-ethyl]-5,6-dihydro-pyran-2-one;

E-6: 4-Hydroxy-6-isopropyl-6-[2-(4-methyl-thiazol-2-yl)-ethyl]-5,6-dihydro-pyran-2-one;

E-7: 4-Hydroxy-6-isopropyl-6-[2-(2-methyl-thiazol-4-yl)-ethyl]-5,6-dihydro-pyran-2-one;

E-8: 4-Hydroxy-6-isopropyl-6-[2-(5-methyl-thiazol-4-yl)-ethyl]-5,6-dihydro-pyran-2-one;

E-9: 4-Hydroxy-6-isopropyl-6-[2-(2-isopropyl-thiazol-4-yl)-ethyl]-5,6-dihydro-pyran-2-one;

E-10: 4-Hydroxy-6-isopropyl-6-[2-(4-isopropyl-thiazol-5-yl)-ethyl]-5,6-dihydro-pyran-2-one;

E-11: 4-Hydroxy-6-isopropyl-6-[2-(5-isopropyl-thiazol-4-yl)-ethyl]-5,6-dihydro-pyran-2-one;

E-12: 4-Hydroxy-6-isopropyl-6-[2-(4-isopropyl-thiazol-2-yl)-ethyl]-5,6-dihydro-pyran-2-one;

E-13: N-{4-[2-(4-Hydroxy-2-isopropyl-6-oxo-3,6-dihydro-2H-pyran-2-yl)-ethyl]-thiazol-2-yl}-acetamide;

E-14: 4-Hydroxy-6-isopropyl-6-(2-pyridin-2-yl-ethyl)-5,6-dihydro-pyran-2-one;

E-15: 4-Hydroxy-6-isopropyl-6-(2-pyridin-4-yl-ethyl)-5,6-dihydro-pyran-2-one;

E-16: 4-Hydroxy-6-isopropyl-6-(2-pyridin-3-yl-ethyl)-5,6-dihydro-pyran-2-one;

E-17: 6-(2-Furan-2-yl-ethyl)-4-hydroxy-6-isopropyl-5,6-dihydro-pyran-2-one;

E-18: 6-(2-Furan-3-yl-ethyl)-4-hydroxy-6-isopropyl-5,6-dihydro-pyran-2-one;

E-19: 4-Hydroxy-6-isopropyl-6-[2-(tetrahydro-furan-2-yl)-5,6-dihydro-pyran-2-one;

E-20: 4-Hydroxy-6-isopropyl-6-(2-thiophen-3-yl-ethyl)-5,6-dihydro-pyran-2-one;

E-21: 4-Hydroxy-6-isopropyl-6-(2-thiophen-2-yl-ethyl)-5,6-dihydro-pyran-2-one;

E-22: 4-Hydroxy-6-[2-(5-hydroxymethyl-thiophen-2-yl)-ethyl]-6-isopropyl-5,6-dihydro-pyran-2-one;

E-23: 4-Hydroxy-6-[2-(5-hydroxymethyl-thiophen-3-yl)-ethyl]-6-isopropyl-5,6-dihydro-pyran-2-one;

E-24: 4-Hydroxy-6-[2-(2-hydroxymethyl-thiophen-3-yl)-ethyl]-6-isopropyl-5,6-dihydro-pyran-2-one;

E-25: 6-[2-(3-Fluoro-2-methyl-phenyl)-ethyl]-4-hydroxy-6-isopropyl-5,6-dihydro-pyran-2-one;

E-26: 6-[2-(2-Fluoro-phenyl)-ethyl]-4-hydroxy-6-isopropyl-5,6-dihydro-pyran-2-one;

E-27: 6-[2-(4-Fluoro-phenyl)-ethyl]-4-hydroxy-6-isopropyl-5,6-dihydro-pyran-2-one;

E-28: 4-Hydroxy-6-isopropyl-6-[2-(1H-pyrazol-3-yl)-ethyl]-5,6-dihydro-pyran-2-one;

E-29: 4-Hydroxy-6-isopropyl-6-[2-(1H-pyrrol-3-yl)-ethyl]-5,6-dihydro-pyran-2-one;

E-30: 4-Hydroxy-6-isopropyl-6-[2-(1-trityl-1H-imidazol-4-yl)-ethyl]-5,6-dihydro-pyran-2-one;

E-31: 4-Hydroxy-6-isopropyl-6-(2-pyrimidin-5-yl-ethyl)-5,6-dihydro-pyran-2-one;

E-32: 6-[2-(2-Amino-pyrimidin-5-yl)-ethyl]-4-hydroxy-6-isopropyl-5,6-dihydro-pyran-2-one;

E-33: 4-[2-(4-Hydroxy-2-isopropyl-6-oxo-3,6-dihydro-2H-pyran-2-yl)-ethyl]-benzonitrile;

E-34: 4-Hydroxy-6-isopropyl-6-[2-(2-hydroxymethyl-phenyl)-ethyl]-5,6-dihydro-pyran-2-one;

E-47: 4-Hydroxy-6-[2-(1H-indol-5-yl)-ethyl]-6-isopropyl-5,6-dihydro-pyran-2-one;

E-48: 2,2,2-Trifluoro-N-{4-[2-(4-hydroxy-2-isopropyl-6-oxo-3,6-dihydro-2H-pyran-2-yl)-ethyl]-thiazol-2-yl}-acetamide;

E-49: 4-Hydroxy-6-isopropyl-6-[2-(4-methyl-thiophen-3-yl)-ethyl]-5,6-dihydro-pyran-2-one;

E-50: 4-Hydroxy-6-isopropyl-6-[2-(3-methyl-thiophen-2-yl)-ethyl]-5,6-dihydro-pyran-2-one;

E-51: 4-Hydroxy-6-[2-(3-hydroxymethyl-thiophen-2-yl)-ethyl]-6-isopropyl-5,6-dihydro-pyran-2-one;

E-52: 6-[2-(2,6-Difluoro-phenyl)-ethyl]-4-hydroxy-6-isopropyl-5,6-dihydro-pyran-2-one;

E-53: 6-[2-(3,5-Difluoro-phenyl)-ethyl]-4-hydroxy-6-isopropyl-5,6-dihydro-pyran-2-one;

E-54: 6-[2-(2,4-Difluoro-phenyl)-ethyl]-4-hydroxy-6-isopropyl-5,6-dihydro-pyran-2-one;

E-55: 6-[2-(3,4,5-Trifluoro-phenyl)-ethyl]-4-hydroxy-6-isopropyl-5,6-dihydro-pyran-2-one;

E-56: 6-[2-(5-Fluoro-2-methyl-phenyl)-ethyl]-4-hydroxy-6-isopropyl-5,6-dihydro-pyran-2-one;

E-57: 6-[2-(2-Ethyl-5-Fluoro-phenyl )-ethyl]-4-hydroxy-6-isopropyl-5,6-dihydro-pyran-2-one;

E-58: 6-{2-[2-(tert-Butyl-dimethyl-silanyloxymethyl)-4-fluoro-phenyl]-ethyl}-4-hydroxy-6-isopropyl-5,6-dihydro-pyran-2-one; and E-59: 6-[2-(4-Fluoro-2-hydroxymethyl-phenyl)-ethyl]-4-hydroxy-6-isopropyl-5,6-dihydro-pyran-2-one.

Alternate Synthesis of 4-Hydroxy-5,6-dihydro-pyran-2-ones via β-Hydroxyesters

General Method 9. Preparation of β-Hydroxyesters from Ketones (Table D) or Enones (Table B)

Diisopropylamine (1.25–1.4 equiv.) was cooled to −10° C. and treated with nBuLi (1.25 equiv.) over 10 to 20 minutes. The solution was stirred for 15 to 45 minutes at −10° C. and then cooled to −60° C. to −78° C. The desired acetate (1.25 equiv.) was dissolved in THF and added dropwise to the LDA solution over 30 to 90 minutes. When addition was complete, the reaction mixture was stirred at −78° C. to −40° C. for another 30 to 90 minutes. The appropriate ketone (from Examples C-1 to C-39) or enone (from Examples B-1 to B-30) was dissolved in THF and added over 15 to 30 minutes. The reaction mixture was warmed to room temperature and stirred for 3 to 18 hours. The solution was poured into 1N HCl:ice; the product was extracted into EtOAc, dried (MgSO$_4$), and concentrated. The product could be purified via chromatography or recrystallization.

EXAMPLE F-1

3-Hydroxy-4-methyl-3-(2-thiophen-3-yl-ethyl)-pentanoic acid tert-butyl ester

The title compound was prepared as described in General Method 9 using t-butyl acetate (42.6 mmol), diisopropyl amine (42.6 mmol), nBuLi (42.6 mmol), 4-methyl-1-thiophen-3-yl-pentan-3-one (Example C-5; 21.3 mmol), and THF (100 mL). The title compound was purified by flash chromatography over silica gel eluting with hexane:EtOAc 97:3. $^1$NMR (CDCl$_3$): δ0.95 (dd, 6 H), 1.47 (s, 9 H), 1.7–2.0 (m, 3 H), 2.36–2.54 (AB q, 2 H), 2.6–2.8 (m, 2 H), 6.93–6.95 (m, 2 H), 7.23–7.25 (m, 1 H).

The following hydroxyesters were prepared in similar fashion from the analogous ketones from Examples C-1 to C-57 or enones from Examples B-1 to B-36:

TABLE G
Preparation of Hydroxyesters
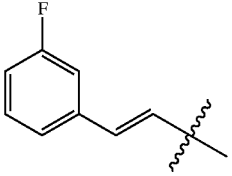
| Example | R$_{11}$ | R$_{12}$ | Analytical Data ($^1$H NMR or MS) |
|---|---|---|---|
| F-2 | 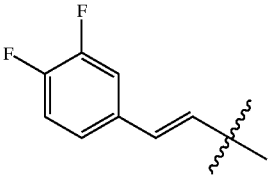 | CH$_2$Ph | (CDCl$_3$): δ 0.94 (d, 3 H), 0.96 (d, 3 H), 1.79–1.88 (m, 1 H), 2.71 (s, 2 H), 4.00 (br s, 1 H), 5.07 (d, 1H), 5.14 (d, 1 H), 6.19 (d, 1 H), 6.58 (d, 1 H), 6.90–6.70 (m, 2 H), 7.06–7.09 (m, 1 H), 7.24–7.29 (m, 5 H), 7.36–7.38 (m, 1 H). |
| F-3 | 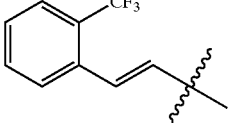 | CH$_2$Ph | |
| F-4 | 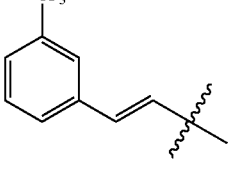 | CH$_2$Ph | MS (APCI): 393 (M + H) |
| F-5 | 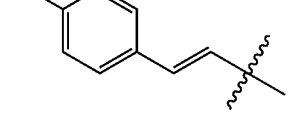 | CH$_2$Ph | MS (APCI): 393 (M + H) |
| F-6 | 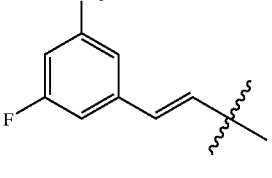 | CH$_2$Ph | MS (APCI): 393 (M + H) |
| F-7 | 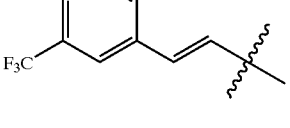 | CH$_2$Ph | MS (APCI): 411 (M + H) |
| F-8 | 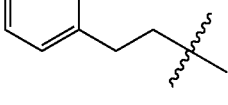 | CH$_2$Ph | MS (APCI): 411 (M + H) |
| F-9 |  | CMe$_3$ | MS (APCI): 323 (M + H) |

TABLE G-continued

Preparation of Hydroxyesters $$R_{11} \underset{OH}{\overset{}{\diagdown}} \underset{O}{\overset{}{\diagup}} OR_{12}$$

| Example | R₁₁ | R₁₂ | Analytical Data (¹H NMR or MS) |
|---|---|---|---|
| F-10 | phenethyl | CMe₃ | (CDCl₃): δ 0.95 (d, 3 H), 0.97 (d, 3 H), 1.48 (s, 9 H), 1.75–1.86 (m, 2 H), 1.88–1.96 (m, 1 H), 2.40 (d, 1 H), 2.52 (d, 1 H), 2.63–2.73 (m, 2 H), 3.92 (s, 1 H), 7.16–7.21 (m, 3 H), 7.26–7.31 (m, 2 H). |
| F-11 | styryl | CH₂Ph | MS (APCI): 326 (M + H) |
| F-12 | 4-F-styryl | CH₂Ph | (CDCl₃): δ 0.95 (d, 3 H), 0.96 (d, 3 H), 1.76–1.88 (m, 1 H), 2.71 (s, 2 H), 3.98 (bs, 1 H), 5.05 (d, 1 H), 5.13 (d, 1 H), 6.10 (d, 1 H), 6.57 (d, 1 H), 6.95–7.03 (m, 2 H), 7.23–7.31 (m, 7 H). |
| F-13 | 3-(OSiMe₂t-But-methyl)thien-4-yl-ethyl | Et | (CDCl₃): δ 0.00 (s, 9 H), 0.83 (s, 6 H), 0.99 (d, 6 H), 1.3 (t, 3 H), 1.7–2.0 (m, 3 H), 2.50 (dd, 2 H), 2.60 (t, 2 H), 3.71 (s, 1 H), 4.19 (q, 2 H), 4.66 (s, 2 H), 6.91 (d, 1 H), 7.2 (d, 1 H). |
| F-14 | 2-methylthien-3-yl-ethyl | CMe₃ | (CDCl₃): δ 0.93–0.97 (t, 6 H), 1.47 (s, 9 H), 1.6–1.80 (m, 2 H), 1.91–1.95 (m, 1 H), 2.37 (s, 3 H), 2.37–2.40 (d, 1 H), 2.48–2.51 (d, 1 H), 2.56–2.61 (m, 2 H), 3.92 (s, 1 H), 6.80 (d, 1 H), 6.99 (d, 1 H). |
| F-15 | 2-F-styryl | CH₂Ph | |
| F-16 | 3,5-di-F-styryl | CH₂Ph | (CDCl₃) δ 0.93 (d, 3 H), 0.95 (d, 3 H), 1.77–1.87 (m, 1 H), 2.70 (s, 2 H), 4.00 (s, 1 H), 5.06 (d, 1 H), 5.15 (d, 1 H), 6.18 (d, 1 H), 6.52 (d, 1 H), 6.64–6.71 (m, 1 H), 6.75–7.82 (m, 2 H), 7.24–7.28 (m, 3 H), 7.34–7.38 (m, 2 H). |

TABLE G-continued

Preparation of Hydroxyesters $$R_{11}\underset{OH}{\overset{}{\diagdown}}\underset{O}{\overset{}{\diagup}}OR_{12}$$

| Example | R₁₁ | R₁₂ | Analytical Data (¹H NMR or MS) |
|---|---|---|---|
| F-17 | [4-fluoro-2-methylphenyl-ethyl] | CMe₃ | (CDCl₃) δ 0.94 (d, 3 H), 0.96 (d, 3 H), 1.46 (s, 9 H), 1.60–1.75 (m, 2 H), 1.89–1.97 (m, 1 H), 2.30 (s, 3 H), 2.39 (d, 1 H). 2.50 (d, 1 H), 2.56–2.67 (m, 2 H), 3.97 (s, 1H), 6.77–6.86 (m, 2 H), 7.04–7.08 (m, 1 H). |

The compounds of Table G above are named:

F-2: 5-(3-Fluoro-phenyl)-3-hydroxy-3-isopropyl-pent-4-enoic acid benzyl ester;
F-3: 5-(3,4-Difluoro-phenyl)-3-hydroxy-3-isopropyl-pent-4-enoic acid benzyl ester;
F-4: 3-Hydroxy-3-isopropyl-5-(2-trifluoromethyl-phenyl)-pent-4-enoic acid benzyl ester;
F-5: 3-Hydroxy-3-isopropyl-5-(3-trifluoromethyl-phenyl)-pent-4-enoic acid benzyl ester;
F-6: 3-Hydroxy-3-isopropyl-5-(4-trifluoromethyl-phenyl)-pent-4-enoic acid benzyl ester;
F-7: 5-(3-Fluoro-5-trifluoromethyl-phenyl)-3-hydroxy-3-isopropyl-pent-4-enoic acid benzyl ester;
F-8: 5-(4-Fluoro-3-trifluoromethyl-phenyl)-3-hydroxy-3-isopropyl-pent-4-enoic acid benzyl ester;
F-9: 3-Hydroxy-3-[2-(2-hydroxymethyl-phenyl)-ethyl]-4-methyl-pentanoic acid tert-butyl ester;
F-10: 3-Hydroxy-4-methyl-3-(2-phenyl-ethyl)-pentanoic acid tert-butyl ester;
F-11: 3-Hydroxy-3-isopropyl-5-phenyl-3-pent-4-enoic acid benzyl ester;
F-12: 5-(4-Fluoro-phenyl)-3-hydroxy-3-isopropyl-pent-4-enoic acid benzyl ester;
F-13: 3-{2-[4-(tert-Butyl-dimethyl-silanyloxymethyl)-thiophen-3-yl]-ethyl}-3-hydroxy-4-methyl-pentanoic acid ethyl ester;
F-14: 3-Hydroxy-4-methyl-3-[2-(2-methyl-thiophen-3-yl)-ethyl]-pentanoic acid tert-butyl ester;
F-15: 5-(3-Fluoro-2-methyl-phenyl)-3-hydroxy-3-isopropyl-pent-4-enoic acid benzyl ester;
F-16: 5-(3,5-Difluoro-phenyl)-3-hydroxy-3-isopropyl-pent-4-enoic acid benzyl ester; and
F-17: 5-(4-Fluoro-2-methyl-phenyl)-3-hydroxy-3-isopropyl-pent-4-enoic acid tert-butyl ester.

Separation of β-Hydroxy Ester Enantiomers Via Chiral HPLC

EXAMPLE F-1 (S)

(S)-3-Hydroxy-4-methyl-3-(2-thiophen-3-yl-ethyl)-pentanoic acid tert-butyl ester The title compound was prepared by resolution on a Chiralpak AD column eluting with 1:99 isopropanol:hexane to afford both enantiomers of 3-hydroxy-4-methyl-3-(2-thiophen-3-yl-ethyl)-pentanoic acid tert-butyl ester. The S enantiomer eluted first.

¹H NMR (CDCl₃): δ0.95 (dd, 6 H), 1.47 (s, 9 H), 1.7–2.00 (m, 3 H), 2.36–2.54 (AB q, 2 H), 2.6–2.8 (m, 2 H), 6.93–6.95 (m, 2 H), 7.23–7.25 (m, 1 H).

EXAMPLE F-1 (R)

(R)-3-Hydroxy-4-methyl-3-(2-thiophen-3-yl-ethyl)-pentanoic acid tert-butyl ester The title compound was prepared as described above via resolution of Compound F-9 on a Chiralpak AD column eluting with 1:99 isopropanol:hexane to afford both enantiomers of 3-hydroxy-4-methyl-3-(2-thiophen-3-yl-ethyl)-pentanoic acid tert-butyl ester. The R enantiomer eluted second.

¹H NMR (CDCl₃): δ0.95 (dd, 6 H), 1.47 (s, 9 H), 1.7–2.00 (m, 3 H), 2.36–2.54 (AB q, 2 H), 2.6–2.8 (m, 2 H), 6.93–6.95 (m, 2 H), 7.23–7.25 (m, 1 H).

EXAMPLE F-9 (S)

(S)-3-Hydroxy-4-methyl-3-[2-(2-hydroxymethyl-phenyl)-ethyl]-pentanoic acid tert-butyl ester The title compound was prepared by resolution of Compound F-9 on a Chiralpak AD column eluting with isopropanol:hexane (1:99) to afford both enantiomers of 3-hydroxy-4-methyl-3-[2-(2-hydroxymethyl-phenyl)-ethyl]-pentanoic acid tert-butyl ester. MS (APCI): 323 (M+H).

EXAMPLE F-14 (S)

(S)-3-Hydroxy-4-methyl-3-[2-(2-methyl-thiophen-3-yl)-ethyl]-pentanoic acid tert-butyl ester The title compound was prepared by resolution on a Chiralpak AD column eluting with 0.75:0.25:99 ethanol:isopropanol:hexane to afford both enantiomers of 3-hydroxy-4-methyl-3-[2-(2-methyl-thiophen-3-yl)-ethyl]-pentanoic acid tert-butyl ester. The S enantiomer eluted first.

¹H NMR (CDCl₃): δ0.93–0.97 (t, 6 H), 1.47 (s, 9 H), 1.6–1.80 (m, 2 H), 1.91–1.95 (m, 1 H), 2.37 (s, 3 H), 2.37–2.40 (d, 1 H), 2.48–2.51 (d, 1 H), 2.56–2.61 (m, 2 H), 3.92 (s, 1 H), 6.80 (d, 1 H), 6.99 (d, 1 H).

General Method 10. Preparation of β-Hydroxyacids

The appropriate β-hydroxyester (1 equiv.) was dissolved in EtOH and treated with 1.4 to 2.0 equivalents of an alkoxide (KOH or LiOH). The mixture was stirred at room temperature or heated to reflux for 4 to 18 hours. The solution was concentrated to dryness, and the residue was partitioned between H$_2$O and Et$_2$O. The aqueous layer was separated, acidified with 1N HCl, and extracted with Et$_2$O. The solution was dried (MgSO$_4$) and concentrated.

Alternatively, the benzyl esters (compounds F-2 through F-8 and compounds F-11 and F-12) were hydrogenated as described in General Method 3 to give the corresponding acid.

EXAMPLE G-1 (S)

(S)-3-Hydroxy-4-methyl-3-(2-thiophen-3-yl-ethyl)-pentanoic acid

The title compound was prepared as described in General Method 10 using (S)-3-hydroxy-4-methyl-3-(2-thiophen-3-yl-ethyl)-pentanoic acid tert-butyl ester (Example F-1 (S); 8 mmol), LiOH (16 mmol), H$_2$O (5 mL), and MeOH (15 mL).

$^1$NMR (CDCl$_3$): δ0.98 (t, 6 H), 1.8–2.0 (m, 3 H), 2.50–2.70 (Ab q, 2 H), 2.6–2.8 (m, 2 H), 6.93–6.95 (m, 2 H), 7.23–7.25 (m, 1 H).

The following β-hydroxyacids were prepared from the corresponding esters, either by hydrolysis (General Method 10) or hydrogenolysis (as outlined in General Method 3) as noted:

TABLE H

Synthesis of β-hydroxyacids

| Example | R$_{13}$ | General Method | Chirality | Analytical Data ($^1$HNMR or MS) |
|---|---|---|---|---|
| G-1 (R) | (thiophen-3-yl-ethyl) | Gen. Method 10 | R | (CDCl$_3$): δ 0.98(t, 6H), 1.8–2.0(m, 3H), 2.50–2.70(AB q, 2H), 2.6–2.8(m, 2H), 6.93–6.95(m, 2H), 7.23–7.25(m, 1H). |
| G-1 | (thiophen-3-yl-ethyl) | Gen. Method 10 | ± | (CDCl$_3$): δ 0.92–0.95(m, 6H), 1.78–2.02(m, 3H), 2.49–2.76(m, 4H), 6.91 (m, 2H), 7.22(m, 1H). |
| G-2 | (3-fluorophenyl-ethyl) | Gen. Method 3 | ± | (CDCl$_3$) δ 0.95–1.00(m, 6H), 1.71–2.03(m, 3H), 2.49–2.56(m, 1H), 2.62–2.73(m, 3H), 3.75–3.79(m, 1H), 6.84–6.91(m, 2H), 6.96(d, 1H), 7.18–7.27(m, 1H). |
| G-3 | (3,4-difluorophenyl-ethyl) | Gen. Method 3 | ± | (CDCl$_3$): δ 0.94–0.99(m, 6H), 1.78–1.89(m, 2H), 1.92–2.01(m, 1H), 2.52(d, 1H), 2.61–2.70 (m, 3H), 3.75–3.79(m, 1H), 6.85–6.91(m, 1H), 6.94–7.09(m, 2H). |
| G-4 | (2-trifluoromethylphenyl-ethyl) | Gen. Method 3 | ± | MS (APCI): 303 (M − H) |

TABLE H-continued

Synthesis of β-hydroxyacids $$R_{13} \underset{\underset{O}{\overset{OH}{|}}}{\overset{OH}{-}} OH$$

| Example | R₁₃ | General Method | Chirality | Analytical Data (¹HNMR or MS) |
|---|---|---|---|---|
| G-5 | 3-(CF₃)-phenyl-CH₂CH₂- | Gen. Method 3 | ± | MS (APCI): 303 (M − H) |
| G-6 | 4-(CF₃)-phenyl-CH₂CH₂- | Gen. Method 3 | ± | MS (APCI): 607 (2M − H) |
| G-7 | 3-F-5-(CF₃)-phenyl-CH₂CH₂- | Gen. Method 3 | ± | MS (APCI): 321 (M − H) |
| G-8 | 4-F-3-(CF₃)-phenyl-CH₂CH₂- | Gen. Method 3 | ± | MS (APCI): 321 (M − H) |
| G-9 | 2-(HOCH₂)-phenyl-CH₂CH₂- | Gen. Method 10 | S | MS (APCI): 266 (M) Rotation: −3.8° (c = 2.0, EtOH) |
| G-10 | phenyl-CH₂CH₂- | Gen. Method 10 (using F-10) or Gen. Method 3 (using F-11) | ± | (CDCl₃): δ 0.97(d, 3H), 0.99(d, 3H), 1.80–1.93(m, 2H), 1.95–2.05(m, 1H), 2.56 (d, 1H), 2.65–2.74(m, 3H), 7.17–7.21(m, 3H), 7.26–7.32(m, 2H). |
| G-11 | 4-F-phenyl-CH₂CH₂- | Gen. Method 3 | ± | (CDCl₃): δ 0.96(d, 3H), 0.99(d, 3H), 1.76–1.89(m, 2H), 1.91–2.05(m, 1H), 2.55(d, 1H), 2.63–2.70 (m, 3H), 3.74–3.78(m, 1H), 6.93 –6.91(m, 2H), 7.11–7.16(m, 2H). |
| G-12 | 3-(OSiMe₂t-But-CH₂)-thiophen-4-yl-CH₂CH₂- | Gen. Method 10 | ± | MS (APCI): 385 (M − H) |

TABLE H-continued

Synthesis of β-hydroxyacids

| Example | R₁₃ | General Method | Chirality | Analytical Data ($^1$HNMR or MS) |
|---|---|---|---|---|
| G-13 | (2-methyl-thiophen-3-yl) | Gen. Method 10 | S | MS (APCI): 255 (M − H) |
| G-14 | (3-fluoro-2-methyl-phenyl) | Gen. Method 3 | ± | (CDCl₃) δ 0.97(d, 3H), 0.99(d, 3H), 1.66–1.86(m, 2H), 1.96–2.05(m, 1H), 2.21(d, 3H), 2.59(d, 1H), 2.65–2.73(m, 3H), 6.84–6.93(m, 2H), 7.03–6.10(m, 1H). |
| G-15 | (3,5-difluoro-phenyl) | Gen. Method 3 | ± | (CDCl₃) δ 0.96(d, 3H), 0.98(d, 3H), 1.81–1.86 (m, 2H), 1.87–2.01(m, 1H), 2.53(d, 1H), 2.64–2.78(m, 3H), 3.74–3.78(m, 1H), 6.59–6.67(m, 1H), 6.69–6.74(m, 2H). |
| G-16 | (4-fluoro-2-methyl-phenyl) | Gen. Method 10 | ± | |

The compounds of Table H above are named:

G-2: 3-[2-(3-Fluoro-phenyl)-ethyl]-3-hydroxy-4-methyl-pentanoic acid;

G-3: 3-[2-(3,4-Difluoro-phenyl)-ethyl]-3-hydroxy-4-methyl-pentanoic acid;

G-4: 3-Hydroxy-4-methyl-3-[2-(2-trifluoromethyl-phenyl)-ethyl]-pentanoic acid;

G-5: 3-Hydroxy-4-methyl-3-[2-(3-trifluoromethyl-phenyl)-ethyl]-pentanoic acid;

G-6: 3-Hydroxy-4-methyl-3-[2-(4-trifluoromethyl-phenyl)-ethyl]-pentanoic acid;

G-7: 3-[2-(3-Fluoro-5-trifluoromethyl-phenyl)-ethyl]-3-hydroxy-4-methyl-pentanoic acid;

G-8: 3-[2-(4-Fluoro-3-trifluoromethyl-phenyl)-ethyl]-3-hydroxy-4-methyl-pentanoic acid;

G-9: (S)-3-Hydroxy-3-[2-(2-hydroxymethyl-phenyl)-ethyl]-4-methyl-pentanoic acid;

G-10: 3-Hydroxy-4-methyl-3-(2-phenyl-ethyl)-pentanoic acid;

G-11: 3-[2-(4-Fluoro-phenyl)-ethyl]-3-hydroxy-4-methyl-pentanoic acid;

G-12: 3-{2-[4-(tert-Butyl-dimethyl-silanyloxy-methyl)-thiophen-3-yl]-ethyl}-3-hydroxy-4-methyl-pentanoic acid;

G-13: 3-Hydroxy-4-methyl-3-[2-(2-methyl-thiophen-3-yl)-ethyl]-pentanoic acid;

G-14: 3-[2-(3-Fluoro-2-methyl-phenyl)-ethyl]-3-hydroxy-4-methyl-pentanoic acid;

G-15: 3-[2-(3,5-Difluoro-phenyl)-ethyl]-3-hydroxy-4-methyl-pentanoic acid; and

G-16: 3-[2-(4-Fluoro-2-methyl-phenyl)-ethyl]-3-hydroxy-4-methyl-pentanoic acid.

Resolution of Racemic β-hydroxyacids Enantiomers

EXAMPLE G-2 (R)

(R)-3-[2-(3-Fluoro-phenyl)-ethyl]-3-hydroxy-4-methyl-pentanoic acid

Racemic compound G-2 (42.0 g, 165 mmol) from Table H was dissolved in 410 mL EtOAc and treated with (S)-α-methylbenzylamine (10.01 g, 82.58 mmol). The resulting slurry was placed on a steam bath and heated to reflux to dissolve the solids completely. The solution was allowed to cool to room temperature slowly overnight. The flask was then cooled to 5° C., and the solids were filtered and washed with cold EtOAc and Et₂O. The product was recrystallized from hot EtOAc (110 mL) on a steam bath, and then cooled slowly to room temperature overnight. The flask was then cooled (5° C.); the solids were filtered and washed with cold EtOAc followed by Et₂O to yield the desired compound. HPLC analysis of isolated solid (as the free acid): (AD chiralpak column, 1 mL/min., 97.5% Hexanes:2.5% IPA+ 0.1% TFA)

retention time:
19.60 min. (95.3%)
22.67 min. (4.7%)

EXAMPLE G-2 (S)

(S)-3-[2-(3-Fluoro-phenyl)-ethyl]-3-hydroxy4-methyl-pentanoic acid

A second solid was isolated from the mother liquor from Example G-2 (R) after the solution was allowed to stand for 48 hours. The mixture was cooled to 0° C. in ice bath for several hours. The solid was filtered off and washed with cold EtOAc followed by $Et_2O$. HPLC analysis of isolated solid (as the free acid): (AD chiralpak column, 1 mL/min., 97.5% Hexanes:2.5% IPA+0.1% TFA)

retention time:
18.11 min. (11.76%)
19.28 min. (88.24%).

The isolated solid was recrystallized from hot EtOAc (~100 mL) on a steam bath and cooled slowly to room temperature overnight. The mixture then was cooled in an ice bath for 2 hours. The resulting solids were filtered and washed with cold EtOAc followed by $Et_2O$ to give the desired enantiomer. The free acid was obtained by treating the salt with 1N HCl followed by extraction with EtOAc. The organic phased was washed with brine, dried ($MgSO_4$), filtered and concentrated to afford the resolved β-hydroxy acid. HPLC analysis of isolated solid (as the free acid): (AD chiralpak column, 1 mL/min., 97.5% Hexanes:2.5% IPA+0.1% TFA)

retention time:
18.20 min. (3.4%)
19.42 min. (96.6%)

EXAMPLE G-3 (R)

(R)-3-[2-(3,4-Difluoro-phenyl)-ethyl]-3-hydroxy-4-methyl-pentanoic acid

Compound G-3 (16.0 g, 58.8 mmol) from Table H was dissolved in 150 mL EtOAc and treated with (S)-α-methylbenzylamine (3.77 g, 31.14 mmol). The thick suspension that resulted was placed on a steam bath and heated to reflux. Additional EtOAc (240 mL) was added, followed by hot isopropanol (approximately 80 mL), until the solids dissolved. The solution was allowed to cool to room temperature slowly overnight. The mixture was then cooled to approximately 0° C. The resulting solids were filtered and washed with cold EtOAc followed by $Et_2O$ to yield the desired enantiomer. HPLC analysis of isolated solid (as the free acid): (AD chiralpak column, 1 mL/min., 97.5% Hexanes:2.5% IPA+0.1% TFA)

retention time:
23.80 min. (7.7%)
25.10 min. (92.3.%).

The isolated solid was dissolved in hot IPA (120 mL) and EtOAc (600 mL) on a steam bath and then cooled slowly to room temperature overnight. The flask was cooled in an ice bath for several hours and then filtered. The solids were washed with cold EtOAc followed by $Et_2O$ to yield the pure stereoisomer. The free acid was obtained by treating the salt with 1N HCl followed by extraction with EtOAc. The organic phased was washed with brine, dried ($MgSO_4$), filtered and concentrated to afford the resolved β-hydroxy acid. HPLC analysis of isolated solid (as the free acid): (AD chiralpak column, 1 mL/min., 97.5% Hexanes:2.5% IPA+0.1% TFA)

retention time: 25.90 min. (>99%).

EXAMPLE G-3 (S)

(S)-3-[2-(3,4-Difluoro-phenyl)-ethyl]-3-hydroxy-4-methyl-pentanoic acid

The mother liquor from the isolation of diastereomaric salt G-3 (R) was treated with 1N HCl and extracted with EtOAc. The organic phased was washed with brine, dried ($MgSO_4$), filtered and concentrated to liberate compound G-3. HPLC analysis indicated the isolated material was 78% (S):22% (R) based on comparison with previously isolated solid (diastereomaric salt G-3 (R)). β-Hydroxy acid G-3 (9.75 g, 35.8 mmol) was dissolved in 100 mL EtOAc and treated with (R)-α-methylbenzylamine (3.25 g, 26.86 mmol). The resulting thick suspension was placed on a steam bath and heated to reflux. Additional EtOAc (50 mL) was added, followed by hot IPA (100 mL), a little at a time until the solids dissolved. The solution was allowed to cool to room temperature overnight. The mixture was then cooled to 0° C. in an ice bath. The resulting solids were filtered and washed with cold EtOAc followed by $Et_2O$. The free acid was obtained by treating the salt with 1N HCl followed by extraction with EtOAc. The organic phased was washed with brine, dried ($MgSO_4$), filtered and concentrated to afford the resolved β-hydroxy acid. HPLC analysis of isolated material (as the free acid): (AD chiralpak column, 1 mL/min., 97.5% Hexanes:2.5% IPA+0.1% TFA)

retention time:
22.06 min. (96.9%)
24.34 min. (3.1.%).

EXAMPLE G-10 (S)

(S)-3-Hydroxy-4-methyl-3-(2-phenyl-ethyl)-pentanoic acid

Compound G-10 (15.0 g, 63.48 mmol) was dissolved in 155 mL EtOAc and treated with (S)-α-methylbenzylamine (4.23 g, 34.91 mmol). The resulting slurry was placed on a steam bath and heated to reflux at which all solids dissolved. The solution allowed to cool to room temperature slowly overnight, then cooled to -20° C. Cold EtOAc was added and the solids were filtered and washed with cold EtOAc and $Et_2O$ to yield the title compound. The free acid was obtained by treating the salt with 1N HCl followed by extraction with EtOAc. The organic phased was washed with brine, dried ($MgSO_4$), filtered and concentrated to afford the resolved β-hydroxy acid. HPLC analysis of isolated solid (as the free acid): (OD chiralpak column, 1 mL/min., 97.5% Hexanes:2.5% IPA:+0.1% Formic acid)

retention time:
20.67 min. (4.4%)
22.24 min. (95.6%).

EXAMPLE G-10 (R)

(R)-3-Hydroxy-4-methyl-3-(2-phenyl-ethyl)-pentanoic acid

The mother liquor from the isolation of diastereomeric salt G-10 (S) was treated with 1N HCl and extracted with EtOAc. The organic phase was washed with brine, dried ($MgSO_4$), filtered and concentrated to liberate the free β-hydroxy acid. HPLC analysis indicated the isolated material was 73% (R):27% (S). β-Hydroxy acid G-10 (1 equiv.)

was dissolved in 600 mL EtOAc and treated with (R)-α-methylbenzylamine (0.74 equiv.). The resulting suspension was placed on a steam bath and heated to reflux. The solution was allowed to cool to room temperature slowly and then cooled to 0° C. in an ice bath. The resulting solids were filtered off and washed with cold EtOAc followed by Et$_2$O to yield the title compound. The free acid was obtained by treating the salt with 1N HCl followed by extraction with EtOAc. The organic phased was washed with brine, dried (MgSO$_4$), filtered and concentrated to afford the resolved β-hydroxy acid. HPLC analysis of isolated solid (as the free acid): (OD chiralpak column, 1 mL/min., 97.5% Hexanes:2.5% IPA:+0.1% Formic acid)

retention time:
21.86 min. (95.6%)
23.75 min. (4.4%).

EXAMPLE G-11 (R)

(R)-3-[2-(4-Fluoro-phenyl)-ethyl]-3-hydroxy-4-methyl-pentanoic acid

Compound G-11 (37.1 g, 146 mmol) was dissolved in 375 mL EtOAc and treated with (S)-α-methylbenzylamine (4.23 g, 34.9 mmol). The resulting slurry was heated to reflux, diluted with an additional 50 to 100 mL EtOAc, and treated with hot isopropanol until the solids had completely dissolved. The solution was allowed to cool to room temperature slowly and then cooled to 0° C. in an ice bath for ~1 hour. Cold EtOAc was added; the solids were filtered off and washed with cold EtOAc and Et$_2$O to yield the title compound. HPLC analysis of isolated solid (as the free acid): (AS chiralpak column, 1 mL/min., 98% Hexanes:2% IPA:+0.1% Formic acid)

retention time:
16.81 min. (7.52%)
21.42 min. (92.48%).

The isolated solid and 450 mL EtOAc was heated to reflux and treated with hot isopropanol until the solids dissolved. The solution was allowed to cool to room temperature slowly overnight. The flask was then cooled to −10 to −15° C. and treated with cold EtOAc. The solids were filtered off and washed with cold EtOAc and Et$_2$O to yield the title compound. The free acid was obtained by treating the salt with 1N HCl followed by extraction with EtOAc. The organic phased was washed with brine, dried (MgSO$_4$), filtered and concentrated to afford the resolved β-hydroxy acid. HPLC analysis of isolated solid (as the free acid): (AS chiralpak column, 1 mL/min., 98% Hexanes:2% IPA:+0.1% Formic acid)

retention time:
16.74 min. (1.19%)
20.95 min. (98.81%).

EXAMPLE G-11 (S)

(S)-3-[2-(4-Fluoro-phenyl)-ethyl]-3-hydroxy-4-methyl-pentanoic acid

The mother liquors from the isolation of the G-11 (R) enantiomer were combined, treated with 1N HCl and extracted with EtOAc. The organic phase was washed with brine, dried (MgSO$_4$), filtered and concentrated to liberate the free β-hydroxy acid. HPLC analysis indicated the isolated material was 79% (S):21% (R). β-Hydroxy acid G-11 (22.6 g, 89.0 mmol) was dissolved in 250 mL EtOAc and treated with (R)-α-methylbenzylamine (9.17 g, 75.64 mmol). The resulting mixture was placed on a steam bath, heated to reflux, diluted with additional ~100 mL EtOAc, and treated with hot isopropanol until solids completely dissolved. The solution was allowed to cool to room temperature slowly overnight and then cooled to −10 to −15° C. Cold EtOAc was added; the solids were filtered off and washed with cold EtOAc and Et$_2$O to yield the title compound. The free acid was obtained by treating the salt with 1N HCl followed by extraction with EtOAc. The organic phased was washed with brine, dried (MgSO$_4$), filtered and concentrated to afford the resolved β-hydroxy acid. HPLC analysis of isolated solid (as the free acid): (AS chiralpak column, 1 mL/min., 98% Hexanes:2% IPA:+0.1% Formic acid)

retention time:
16.61 min. (96.17%)
20.77 min. (3.83%).

EXAMPLE G-14 (S)

(S)-3-[2-(3-Fluoro-2-methyl-phenyl)-ethyl]-3hydroxy-4-methyl-pentanoic acid

Compound G-14 (28.3 g, 105 mmol) was dissolved in 270 mL EtOAc and treated with (R)-α-methylbenzylamine (6.52 g, 53.8 mmol). No precipitate formed. After 2 hours the solvent was evaporated. To the resulting residue was added 200 mL hexanes, and the flask was refluxed on a steam bath until the solids dissolved. Et$_2$O (20 mL) was added and the solution allowed to cool to room temperature slowly overnight. The resulting solids were filtered off and washed with cold hexanes/Et$_2$O. HPLC analysis of isolated solid (as the free acid): (AS chiralpak column, 0.8 mL/min., 98% Hexanes/2% IPA/+0.1% Formic acid).

retention time:
16.38 min. (80.76%)
22.67 min. (19.24%)

The isolated solids, Et$_2$O (100 mL), and hexanes (200 mL) were heated to reflux on a steam bath. EtOAc was added until all solids dissolved (approximately 150 mL). An additional 200 mL of hexanes were added, and the mixture was brought back to reflux and then allowed to cool slowly to room temperature overnight. The flask was then cooled to approx. 5° C. for 2 hours. The resulting solids were filtered and washed with cold Et$_2$O to yield the title compound. HPLC analysis of isolated solid (as the free acid): (AS chiralpak column, 1 mL/min., 98% Hexanes/2% IPA/+0.1% Formic acid).

retention time:
12.12 min. (94.8%)
24.10 min. (5.2%)

EXAMPLE G-15 (S)

(S)-3-[2-(3,5-Difluoro-phenyl)-ethyl]-3-hydroxy-4-methyl-pentanoic acid

Compound G-15 (24.6 g, 90.5 mmol) was dissolved in 235 mL EtOAc and treated with (R)-α-methylbenzylamine (6.03 g, 49.8 mmol). The resulting slurry was placed on a steam bath and heated to reflux until all solids dissolved. The solution was allowed to cool and hexanes were added (approximately 100 mL). The solution was returned to reflux, the steam turned off, and the mixture allowed to cool to room temperature overnight. The flask was then cooled to approx. 5° C. for 1 hour. The resulting solids were filtered and washed with cold Et$_2$O. HPLC analysis of isolated solid (as the free acid): (AS chiralpak column, 1.0 mL/min., 98% Hexanes/2% IPA/+0.1% Formic acid).

retention time:
12.51 min. (92.3%)
14.83 min. (7.7%)

The solids were suspended in EtOAc (approximately 300 mL) and heated to reflux on a steam bath. When the solids did not dissolve, isopropanol (approximately 20 mL) was added gradually until the material completely dissolved. An additional 100 mL of EtOAc was added; the mixture was brought back to reflux and then allowed to cool to room temperature overnight. The flask was then cooled to approx. 5° C. for 2 hours. The resulting solids were filtered and washed with cold $Et_2O$ to yield the title compound. HPLC analysis of isolated solid (as the free acid): (AS chiralpak column, 1 mL/min., 98% Hexanes/2% IPA/+0.1% Formic acid).
retention time:
12.65 min. (98.0%)
15.10 min. (2.0%)

EXAMPLE G-16 (S)

(S)-3-[2-(4-Fluoro-2-methyl-phenyl)-ethyl]-3-hydroxy-4-methyl-pentanoic acid

Compound G-16 (enriched—62% (S)-enantiomer/38% (R) enantiomer) (11.1 g, 41.5 mmol) was dissolved in 120 mL EtOAc and treated with (S)-α-methylbenzylamine (6.52 g, 53.79 mmol). The resulting suspension was heated to reflux until all solids dissolved, at which time the solution was allowed to cool to room temperature overnight. The reaction flask was cooled to 0° C. for 1 hour. The resulting solids were filtered off and washed with cold $Et_2O$. HPLC analysis of isolated solid (as the free acid): (AS chiralpak column, 0.8 mL/min., 98% Hexanes/2% IPA/+0.1% Formic acid).
retention time:
15.86 min. (79.43%)
19.34 min. (20.57%)

The isolated solids were suspended in EtOAc (150 mL) and isopropanol (10 mL) and heated to reflux on a steam bath until all solids dissolved. The solution was allowed to cool to room temperature overnight and then cooled to 0° C. for 1 hour. The resulting solids were filtered off and washed with cold $Et_2O$ to afford the title compound. HPLC analysis of isolated solid (as the free acid): (AS chiralpak column, 0.8 mL/min., 98% Hexanes/2% IPA/+0.1% Formic acid).
retention time:
15.83 min. (92.0%)
19.34 min. (8.0%)

The isolated solids in EtOAc (130 mL) and isopropanol (6 mL) were again heated to reflux on a steam bath until the solids dissolved. The steam was shut off, and the solution was allowed to cool to room temperature overnight. The reaction flask was cooled to 0° C. for 1 hour. The resulting solids were filtered off and washed with cold $Et_2O$ to afford the title compound. HPLC analysis of isolated solid (as the free acid): (AS chiralpak column, 0.8 mL/min., 98% Hexanes/2% IPA/+0.1% Formic acid).
retention time:
15.83 min. (96.7%)
19.34 min. (3.3%)

EXAMPLE H

Bis[3-methoxy-3-oxopropanoato-(1-)-O,O'] magnesate

Monomethyl malonate (2.39 g, 20 mmol) and magnesium ethoxide (1.16 g, 10 mmol) in THF (50 mL) were stirred for 3 hours at room temperature. The solution was concentrated under vacuum to give the title compound. The product was carried on crude to the next step.

General Method 11. Preparation of Chiral (or Racemic) β-Ketoester from β-Hydroxy Acid for the Alternate Synthesis of Intermediate 4-Hydroxy-5,6-dihydro-pyran-ones A solution of the chiral β-hydroxyacid as isolated above (or the racemic entity from Table H) (1.0 equiv.), THF (30 mL), and carbonyldiimidazole (1.2–3 equiv.) was stirred for 3 to 18 hours at room temperature. Bis[3-methoxy-3-oxopropanoato (1-)-O,O'] magnesate from Example H (1 to 2 equiv.) was added, and the reaction was stirred for 6 to 72 hours at room temperature. The reaction was concentrated and the residue partitioned between EtOAc and 1N HCl. The organic layer was washed with aqueous $NaHCO_3$ and brine, dried ($MgSO_4$) and concentrated. Purification was accomplished by silica gel chromatography; alternatively, the material could be carried on crude.

EXAMPLE I-1 (S)

(S)-5-Hydroxy-6-methyl-3-oxo-5-(2-thiophen-3-yl-ethyl)-heptanoic acid ethyl ester The title compound was prepared as described in General Method 11 using (S)-3-hydroxy-4-methyl-3-(2-thiophen-3-yl-ethyl)-pentanoic acid (from Example G-1 (S); 7.81 mmol), carbonyl diimidazole (8.59 mmol), bis[3-methoxy-3-oxopropanoato(1-)-O,O']magnesate (15.62 mmol) and THF (85 mL). Purification was accomplished using silica gel chromatography, eluting with 100% $CH_2Cl_2$.

$^1$H NMR (CDCl$_3$): δ0.94 (dd, 6 H), 1.27 (t, 3 H), 1.75–190 (m, 2 H), 1.9–2.0 (m, 1 H), 2.65–2.75 (m, 3 H), 2.80 (d, 1 H), 3.48 (s, 2 H), 4.15–4.25 (m, 2 H), 6.93 (m, 2 H), 7.2–7.3 (m, 1 H).

EXAMPLE I-2 (S)

5-[2-(3-Fluoro-phenyl)-ethyl]-5-hydroxy-6-methyl-3-oxo-heptanoic acid ethyl ester, (S) enantiomer The title compound was prepared following General Method 11 from compound G-2 (S) (5.85 g, 23.00 mmol) and CDI (8.21 g, 50.61 mmol) in 100 mL of THF. After 3.5 hours stirring under $N_2$ at room temperature, bis[3-methoxy-3-oxopropanoato(1-)-O,O']magnesate (13.94 g, 48.31 mmol) was added, and the mixture was stirred at room temperature overnight. The product was purified via silica gel chromatography, eluting with 4:1 hexanes:EtOAc to afford the title compound.

$^1$H NMR (CDCl$_3$): δ0.93 (d, 3 H), 0.95 (d, 3 H), 1.27 (m, 3 H), 1.77–1.83 (m, 2 H), 1.91–2.01 (m, 1 H), 2.63–2.69 (m, 2 H), 2.71 (d, 1 H), 2.83 (d, 1 H), 3.48 (s, 2 H), 3.61 (s, 1 H), 4.19 (m, 2 H), 6.84–6.90 (m, 2 H), 6.95 (d, 1 H), 7.19–7.24 (m, 1 H).

The following β-ketoesters were prepared in similar fashion from the appropriate chiral (or racemic—Examples G-1 to G-16) β-ketoacids:

TABLE 1

Preparation of β-Ketoesters

R₁₄–CH₂CH₂–C*(OH)(iPr)–CH₂–C(O)–CH₂–C(O)–OEt

| Example | R₁₄ | Chirality | Analytical Data (¹HNMR or MS) |
|---|---|---|---|
| I-1 (R) | 3-thienyl | R | (CDCl$_3$): δ 0.94(dd, 6H), 1.27(t, 3H), 1.75–190(m, 2H), 1.9–2.0(m, 1H), 2.65–2.75(m, 3H), 2.80(d, 1H), 3.48(s, 2H), 4.15–4.25(m, 2H), 6.93(m, 2H), 7.2–7.3(m, 1H). |
| I-2(R) | 3-fluorophenyl | R | |
| I-3(R) | 3,4-difluorophenyl | R | (CDCl$_3$): δ 0.93(d, 3H), 0.95(d, 3H), 1.27(m, 3H), 1.77(m, 2H), 1.90–2.00(m, 1H), 2.62(m, 2H), 2.70(d, 1H), 2.83(d, 1H), 3.48(s, 2H), 3.61(s, 1H), 4.19(m, 2H), 6.85–6.90(m, 1H), 6.94–7.09(m, 2H). |
| I-3(S) | 3,4-difluorophenyl | S | |
| I-4 | 2-(trifluoromethyl)phenyl | ± | MS (APCI): 373 (M − H) |
| I-5 | 3-(trifluoromethyl)phenyl | ± | MS (APCI): 373 (M − H) |
| I-6 | 4-(trifluoromethyl)phenyl | ± | MS (APCI): 373 (M − H) |

TABLE 1-continued

Preparation of β-Ketoesters

R₁₄ with structure showing OH, O, O groups, isopropyl branch, and OEt ester

| Example | R₁₄ | Chirality | Analytical Data ($^1$HNMR or MS) |
|---|---|---|---|
| I-7 | 3-CF₃, 5-F phenyl | ± | MS (APCI): 391 (M − H) |
| I-8 | 4-F, 3-CF₃ phenyl | ± | MS (APCI): 391 (M − H) |
| I-9 (S) | 2-(hydroxymethyl)phenyl | S | |
| I-10 (S) | Ph | S | (CDCl₃): δ 0.93(d, 3H), 0.96(d, 3H), 1.26(t, 3H), 1.79–1.85(m, 2H), 1.93–2.02(m, 1H), 2.64–2.69(m, 2H), 2.72(d, 1H), 2.83(d, 1H), 3.48(s, 2H), 4.18(q, 2H), 7.15–7.20(m, 3H), 7.26–7.31(m, 2H). |
| I-10 (R) | Ph | R | (CDCl₃): δ 0.93(d, 3H), 0.96(d, 3H), 1.26(t, 3H), 1.79–1.85(m, 2H), 1.93–2.02(m, 1H), 2.64–2.69(m, 2H), 2.72(d, 1H), 2.83(d, 1H), 3.47(s, 2H), 4.19(q, 2H), 7.15–7.20(m, 3H), 7.25–7.31(m, 2H). |
| I-11 (R) | 4-F phenyl | R | (CDCl₃): δ 0.93(d, 3H), 0.95(d, 3H), 1.26(t, 3H), 1.75–1.81(m, 2H), 1.91–2.01(m, 1H), 2.64–2.69(m, 2H), 2.71(d, 1H), 2.83(d, 1H), 3.48(s, 2H), 4.18(q, 2H), 6.92–6.98(m, 2H), 7.10–7.15(m, 2H). |
| I-11 (S) | 4-F phenyl | S | (CDCl₃): δ 0.93(d, 3H), 0.95(d, 3H), 1.26(t, 3H), 1.75–1.81(m, 2H), 1.91–2.00(m, 1H), 2.60–2.68(m, 2H), 2.71(d, 1H), 2.83(d, 1H), 3.48(s, 2H), 4.18(q, 2H), 6.92–6.98(m, 2H), 7.10–7.15(m, 2H). |
| I-12 | 3-(OSiMe₂t-Bu-methyl)thiophen-4-yl | ± | |

TABLE 1-continued

Preparation of β-Ketoesters

| Example | R₁₄ | Chirality | Analytical Data (¹HNMR or MS) |
|---------|-----|-----------|-------------------------------|
| I-13 (S) | 2-methyl-thiophen-3-yl | S | MS (APCI): 325 (M − H) |
| I-14(S) | 3-fluoro-2-methyl-phenyl | S | (CDCl$_3$) δ 0.94(d, 3H), 0.96(d, 3H), 1.25(q, 3H), 1.69–1.76(m, 2H), 1.95–2.04(m, 1H), 2.12(d, 3H), 2.64–2.70(m, 2H), 2.72(d, 1H), 3.48(s, 2H), 3.61(s, 1H), 4.14–4.24(m, 2H), 6.82–6.92(m, 2H), 7.02–7.10(m, 1H). |
| I-15(S) | 3,5-difluoro-phenyl | S | |
| I-16(S) | 4-fluoro-2-methyl-phenyl | S | |

The compounds of Table I above are named.

I-2: (R)-5-[2-(3-Fluoro-phenyl)-ethyl]-5-hydroxy-6-methyl-3-oxo-heptanoic acid ethyl ester;

I-3: 5-[2-(3,4-Difluoro-phenyl)-ethyl]-5-hydroxy-6-methyl-3-oxo-heptanoic acid ethyl ester (R and S isomers);

I-4: 5-Hydroxy-6-methyl-3-oxo-5-[2-(2-trifluoromethyl-phenyl)-ethyl]-heptanoic acid ethyl ester;

I-5: 5-Hydroxy-6-methyl-3-oxo-5-[2-(3-trifluoromethyl-phenyl)-ethyl]-heptanoic acid ethyl ester;

I-6: 5-Hydroxy-6-methyl-3-oxo-5-[2-(4-trifluoromethyl-phenyl)-ethyl]-heptanoic acid ethyl ester;

I-7: 5-[2-(3-Fluoro-5-trifluoromethyl-phenyl)-ethyl]-5-hydroxy-6-methyl-3-oxo-heptanoic acid ethyl ester;

I-8: 5-[2-(4-Fluoro-3-trifluoromethyl-phenyl)-ethyl]-5-hydroxy-6-methyl-3-oxo-heptanoic acid ethyl ester;

I-9: (S)-5-Hydroxy-5-[2-(2-hydroxymethyl-phenyl)-ethyl]-6-methyl-3-oxo-heptanoic acid ethyl ester;

I-10: 5-Hydroxy-6-methyl-3-oxo-5-(2-phenyl-ethyl)-heptanoic acid ethyl ester (R and S isomers);

I-11: 5-[2-(4-Fluoro-phenyl)-ethyl]-5-hydroxy-6-methyl-3-oxo-heptanoic acid ethyl ester (S and R isomers);

I-12: 5-{2-[4-(tert-Butyl-dimethyl-silanyloxymethyl)-thiophen-3-yl]-ethyl}-5-hydroxy-6-methyl-3-oxo-heptanoic acid ethyl ester;

I-13: (S)-5-Hydroxy-6-methyl-5-[2-(2-methyl-thiophen-3-yl)-ethyl]-3-oxo-heptanoic acid ethyl ester;

I-14: (S)-5-[2-(3-Fluoro-2-methyl-phenyl)-ethyl]-5-hydroxy-6-methyl-3-oxo-heptanoic acid ethyl ester;

I-15: (S)-5-[2-(3,5-Difluoro-2-methyl-phenyl)-ethyl]-5-hydroxy-6-methyl-3-oxo-heptanoic acid ethyl ester; and I-16: (S)-5-[2-(4-Fluoro-2-methyl-phenyl)-ethyl]-5-hydroxy-6-methyl-3-oxo-heptanoic acid ethyl ester.

Alternate Synthesis of the Intermediate 4-Hydroxy-5,6-dihydro-pyran-2-ones (for Both Chiral and Racemic Intermediates)

EXAMPLE J-1 (S)

(S)-4-Hydroxy-6-isopropyl-6-(2-thiophen-3-yl-ethyl)-5,6-dihydro-pyran-2-one

The title compound was prepared as described in General Method 8 using (S)-hydroxy-6-methyl-3-oxo-5-(2-thiophen-3-yl-ethyl)-heptanoic acid ethyl ester (6.4 mmol), 0.1N NaOH (400 mL), and THF (40 mL). The product was triturated from Et$_2$O, mp 117–123° C.

The following chiral dihydropyrones were prepared in a similar fashion:

TABLE J
Synthesis of Chiral Dihydropyrones
| Example | R₁₅ | Chirality | Analytical Data ($^1$H NMR or MS) |
|---|---|---|---|
| J-1 (R) | 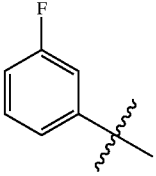 | R | mp 117–123° C. |
| J-2 (S) | 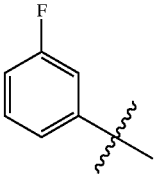 | S | (DMSO–d$_6$): δ 0.88(d, 3H), 0.90 (d, 3H), 1.89–1.93(m, 2H), 2.08–2.15(m, 1H), 2.32(d, 1H), 2.56–2.62(m, 3H), 4.96(s, 1H), 6.95–7.04(m, 3H), 7.27–7.33(m, 1H), 11.37(bs, 1H). |
| J-2 (R) | 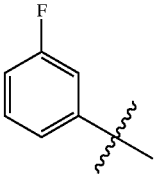 | R | (DMSO–d$_6$): δ 0.88 (d, 3H), 0.90(d, 3H), 1.88–1.93(m, 2H), 2.05–2.15(m, 1H), 2.33(d, 1H), 2.56–2.62(m, 3H), 4.96(s, 1H), 6.96–7.04(m, 3H), 7.26–7.33(m, 1H), 11.36(bs, 1H). |
| J-3 (S) | 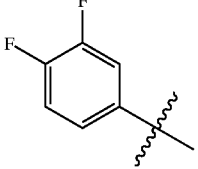 | S | (DMSO–d$_6$): δ 0.87(d, 3H), 0.90(d, 3H), 1.86–1.91(m, 2H), 2.04–2.13(m, 1H), 2.33(d, 1H), 2.55–2.61(m, 3H), 4.95(s, 1H), 6.99–7.03(m, 1H), 7.24–7.34(m, 2H). |
| J-3 (R) | 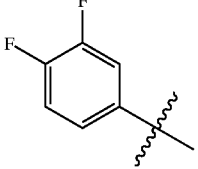 | R | (DMSO–d$_6$): δ 0.87(d, 3H), 0.90 (d, 3H), 1.86–1.91(m, 2H), 2.04–2.13(m, 1H), 2.33(d, 1H), 2.55–2.61(m, 3H), 4.95(s, 1H), 6.99–7.03(m, 1H), 7.24–7.34(m, 2H). |
| J-4 | 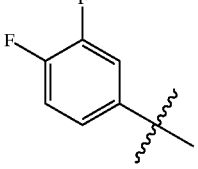 | ± | MS (APCI): 329 (M + H) |
| J-5 | 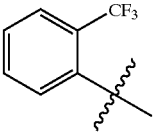 | ± | MS (APCI): 329 (M + H) |

TABLE J-continued

Synthesis of Chiral Dihydropyrones

| Example | R₁₅ | Chirality | Analytical Data (¹H NMR or MS) |
|---|---|---|---|
| J-6 | 4-(F₃C)-C₆H₄- | ± | MS (APCI): 329 (M + H) |
| J-7 | 3-CF₃-5-F-C₆H₃- | ± | MS (APCI): 347 (M + H) |
| J-8 | 4-F-3-(F₃C)-C₆H₃- | ± | MS (APCI): 347 (M + H) |
| J-9 | 2-(HOCH₂)-C₆H₄- | S | (CDCl₃): δ 1.05(d, 3H), 1.06(d, 3H), 1.8(br.s, 1H), 1.9(m, 1H), 2.03(m, 1H), 2.23(m, 1H), 2.66(d, 1H), 2.78(d, 1H), 2.81(m, 2 H), 3.4(d, 1H), 3.53(d, 1H), 4.63(d, 1H), 4.72(d, 1H), 7.24(m, 4H), |
| J-10 | 4-HO-C₆H₄- | S | FROM 08/883,743 |
| J-11 (S) | Ph | S | (DMSO-d₆): δ 0.89(d, 3H), 0.91(d, 3H), 1.81–1.98(m, 2H), 2.07–2.16(m, 1H), 2.31(d of ABX q, 1H), 2.54–2.63(m, 3H), 4.96(s, 1H), 7.13–7.18(m, 3H), 7.23–7.28(m, 2H), 11.36(bs, 1H). |
| J-11 (R) | Ph | R | (DMSO-d₆): δ 0.89(d, 3H), 0.91 (d, 3H), 1.81–1.98(m, 2H), 2.07–2.16(m, 1H), 2.31(d of ABX q, 1H), 2.55–2.63(m, 3H), 4.97(s, 1H), 7.13–7.17(m, 3H), 7.23–7.28(m, 2H), 11.35(bs, 1H). |
| J-12 (R) | 4-F-C₆H₄- | R | (DMSO-d₆) 0.87(d, 3H), 0.89(d, 3H), 1.81–1.93(m, 2H), 2.05–2.14(m, 1H), 2.31(d of ABX q, 1H), 2.54–2.62(m, 3H), 4.95(s, 1H), 7.03–7.10(m, 2H), 7.17–7.22(m, 2H). |

TABLE J-continued

Synthesis of Chiral Dihydropyrones

| Example | R$_{15}$ | Chirality | Analytical Data ($^1$H NMR or MS) |
|---|---|---|---|
| J-12 (S) | 4-fluorophenyl-CH(CH$_3$)- | S | (DMSO-d$_6$): δ 0.88(d, 3H), 0.90(d, 3H), 1.82–1.92(m, 2H), 2.05–2.14(m, 1H), 2.32(d of ABX q, 1H), 2.54–2.62(m, 3H), 4.96(s, 1H), 7.04–7.10(m, 2H), 7.17–7.22(m, 2H). |
| J-13 | 3-(hydroxymethyl)thiophen-4-yl-CH(CH$_3$)- | ± | MS (APCI): 295 (M − H) |
| J-14 (S) | 2-methylthiophen-3-yl-CH(CH$_3$)- | S | MS (APCI): 279 (M − H) |
| J-15 (S) | 3-fluoro-2-methylphenyl-CH(CH$_3$)- | S | (DMSO-d$_6$) δ 0.89(d, 3H), 0.91(d, 3H), 1.75–1.87(m, 2H), 210–2.19(m + d, 4H), 2.69 (d, 1H), 2.58–2.65(m, 3H), 4.96(s, 1H), 6.92–6.98(m, 2H), 7.08–7.15(m, 1H) |
| J-16 (S) | 3,5-difluorophenyl-CH(CH$_3$)- | S | (DMSO-d$_6$) δ 0.87(d, 3H), 0.89(d, 3H), 1.87–1.93(m, 2H), 2.04–2.13(m, 1H), 2.34(d, 1H), 2.54–2.65(m, 3H), 4.95 (s, 1H), 6.91–7.04(m, 3H). |
| J-17 (S) | 4-fluoro-2-methylphenyl-CH(CH$_3$)- | S | (DMSO-d$_6$) δ 0.89(d, 3H), 0.91(d, 3H), 1.73–1.85(m, 2H), 2.08–2.17(m, 1H), 2.20(s, 3H), 2.28(d, 1H), 2.49–2.65 (m, partially obscured by DMSO, 3H), 4.95(s, 1H), 6.86–6.98(m, 2H), 7.07–7.12 (m, 1H). |

The compounds of Table J above are named:

J-2: 6-[2-(3-Fluoro-phenyl)-ethyl]-4-hydroxy-6-isopropyl-5,6-dihydro-pyran-2-one (R and S isomers);
J-3: 6-[2-(3,4-Difluoro-phenyl)-ethyl]-4-hydroxy-6-isopropyl-5,6-dihydro-pyran-2-one (R and S isomers);
J-4: 4-Hydroxy-6-isopropyl-6-[2-(2-trifluoromethyl-phenyl)-ethyl]-5,6-dihydro-pyran-2-one;
J-5: 4-Hydroxy-6-isopropyl-6-[2-(3-trifluoromethyl-phenyl)-ethyl]-5,6-dihydro-pyran-2-one;
J-6: 4-Hydroxy-6-isopropyl-6-[2-(4-trifluoromethyl-phenyl)-ethyl]-5,6-dihydro-pyran-2-one;
J-7: 6-[2-(3-Fluoro-5-trifluoromethyl-phenyl)-ethyl]-4-hydroxy-6-isopropyl-5,6-dihydro-pyran-2-one;
J-8: 6-[2-(4-Fluoro-3-trifluoromethyl-phenyl)-ethyl]-4-hydroxy-6-isopropyl-5,6-dihydro-pyran-2-one;
J-9: (S)-4-Hydroxy-6-[2-(2-hydroxymethyl-phenyl)-ethyl]-6-isopropyl-5,6-dihydro-pyran-2-one;
J-11: 4-Hydroxy-6-isopropyl-6-(2-phenyl-ethyl)-5,6-dihydro-pyran-2-one (R and S isomers);

J-12: 6-[2-(4-Fluoro-phenyl)-ethyl]-4-hydroxy-6-isopropyl-5,6-dihydro-pyran-2-one (R and S isomers);
J-13: 4-Hydroxy-6-[2-(4-hydroxymethyl-thiophen-3-yl)-ethyl]-6-isopropyl-5,6-dihydro-pyran-2-one;
J-14: (S)-4-Hydroxy-6-isopropyl-6-[2-(2-methyl-thiophen-3-yl)-ethyl]-5,6-dihydro-pyran-2-one;
J-15: (S)-6-[2-(3-Fluoro-2-methyl-phenyl)-ethyl]-4-hydroxy-6-isopropyl-5,6-dihydro-pyran-2-one;
J-16: (S)-6-[2-(3,5-Difluoro-phenyl)-ethyl]-4-hydroxy-6-isopropyl-5,6-dihydro-pyran-2-one; and
J-17: (S)-6-[2-(4-Fluoro-2-methyl-phenyl)-ethyl]-4-hydroxy-6-isopropyl-5,6-dihydro-pyran-2-one.

Synthesis of Tosylthiolate Side Chains
General Method 12. Preparation of Nitro Intermediates The appropriate alkylbenzene (1 equiv.) was dissolved in acetic acid and acetic anhydride. To the solution was added sulfuric acid, followed by 70% nitric acid or fuming nitric acid (1 to 1.5 equiv.; ratio of concentrated sulfuric acid to nitric acid is 1:2), dropwise at 0° C. After the addition, the reaction was warmed to room temperature. The reaction mixture was kept at room temperature to 80° C. for 6 to 18 hours. The reaction mixture was poured into ice and extracted with EtOAc. The crude product was purified by either distillation or by flash silica gel chromatography.

EXAMPLE K

1-Bromo-4-tert-butyl-2-nitro-benzene

The reaction was done as described in General Method 12 using 1-bromo-4-tert-butyl-benzene (15 g), acetic acid (10 mL), nitric acid (6.5 g), and sulfuric acid (13 g), MS(APCI): 291.

General Method 13. Preparation of Benzthiazoles

To the aryl amine (1 equiv.) in MeOH or acetic acid was added sodium or potassium or ammonium thiocyanate (3–6 equiv.). The reaction was stirred at 0° C. to room temperature. This reaction mixture was cooled to 0° C. and treated dropwise with bromine (2–2.2 equiv.) or a solution of sodium bromide (2–2.2 equiv.) and bromine (2–2.2 equiv.). After the addition was complete, the reaction mixture was slowly warmed to room temperature and stirred at room temperature for 4 to 24 hours. The reaction mixture was added to sodium bicarbonate solution and extracted with EtOAc (2–4 times). The EtOAc layer was separated, washed with $H_2O$ and brine, and dried ($MgSO_4$). The organic layer was concentrated, and the residue was purified either by crystallization or by flash silica gel chromatography.

EXAMPLE L-1

5tert-Butyl-6-thiocyanato-benzothiazol-2-yl-amine

1-Bromo-4-tert-butyl-2-nitro-benzene (18 g) was reduced as described in General Method 3 using 10% palladium on charcoal (1 g) and MeOH (100 mL) in a hydrogen atmosphere (50 psi). The catalyst was filtered, and the solvents were evaporated. The residue was taken in EtOAc (100 mL) and washed with saturated sodium bicarbonate solution and $H_2O$. The solution was dried and concentrated. The residue was purified by flash chromatography to give 3-tert-butyl-phenylamine. MS (APCI): 150 (M+H).

The title compound was prepared according to General Method 13 using 3-tert-butyl-phenylamine (9.4 g, 63 mmol), sodium thiocyanate (30.7 g, 379 mmol), sodium bromide (14.3 g, 139 mmol), bromine (22.2 g, 139 mmol) and MeOH (300 mL). The crude reaction mixture was purified by flash chromatography (20% EtOAc in hexanes to 75% EtOAc in hexanes as eluents). MS (APCI): 264 (M+H).

EXAMPLE L-2

5-iso-Propyl-6-thiocyanato-benzothiazol-2-yl-amine

The title compound was prepared according to General Method 13 using 3-isopropyl-phenylamine (20.8 g, 154 mmol), sodium thiocyanate (74.8 g, 923 mmol), sodium bromide (34.8 g, 338 mmol), bromine (54.1 g, 338 mmol), and MeOH (300 mL). The crude reaction mixture was purified by flash chromatography ($CH_2Cl_2$ to 25% EtOAc in $CH_2Cl_2$ as eluents). MS (APCI): 250 (M+H).

EXAMPLE L-3, L-4, and L-5

2-Isopropyl-4-isothiocyanato-5-methyl-phenylamine, 7-Isopropyl-4-methyl-6-thiocyanato-benzothiazol-2-yl-amine, and 4-Isopropyl-7-methyl-6-thiocyanato-benzothiazol-2-yl-amine The title compounds were prepared according to General Method 13 using 2-isopropyl-5-methyl-phenylamine (contains approximately 10% of 3-isopropyl-6-methyl-phenylamine) (20.0 g, 134 mmol), sodium thiocyanate (65.3 g, 805 mmol), sodium bromide (30.4 g, 295 mmol), bromine (47.2 g, 295 mmol), and MeOH (300 mL). The crude reaction mixture was purified by flash chromatography (20% EtOAc in hexanes to 75% EtOAc in hexanes as eluents), which yielded three products:

L-3: 2-Isopropyl-4-isothiocyanato-5-methyl-phenylamine: uppermost spot on tlc: MS (APCI): 207 (M+H).
L-4: 4-Isopropyl-7-methyl-6-thiocyanato-benzothiazol-2-yl-amine: middle sport on tlc: MS (APCI): 264 (M+H), 239.
L-5: 7-Isopropyl-4-methyl-6-thiocyanato-benzothiazol-2-yl-amine: lowest spot on tlc: MS (APCI): 264 (M+H)

EXAMPLE L-6

6-tert-Butyl-4-thiocyanato-benzothiazol-2-yl-amine

The title compound was prepared according to General Method 13 using 4-tert-butyl-phenylamine (16.2 g, 109 mmol), sodium thiocyanate (53.0 g, 653 mmol), sodium bromide (24.6 g, 240 mmol), bromine (38.3 g, 240 mmol), and MeOH (300 mL). The crude product was purified by silica gel chromatography (10–50% EtOAc in hexanes as eluents). MS (APCI): 263 (M).

General Method 14. Cleavage of SCN Group

A solution of the SCN intermediate in denatured EtOH was treated with dithiothreitol (3–5 equiv.) and 0.2 M $KH_2PO_4$ (in a ratio of 4:1 EtOH:buffer). The mixture was stirred for 6 to 48 hours at 0° C. to 50° C. The solvent was evaporated, and $H_2O$ and $CHCl_3$ were added; the organic layer was washed with brine, dried ($Na_2SO_4$), filtered and concentrated. The resulting residue was flash chromatographed on silica gel.

General Method 14b. Alternate Cleavage of the SCN Group

The thiocyante (1 eq.) was dissolved in THF and treated with sodium hydrogen sulfide (3 eq.) and sodium borohydride (6 eq.). A mixture of MeOH and water (2:1) was added dropwise at 0° C., and the reaction mixture was stirred at room temperature overnight. Water and toluene were added, and the reaction was quenched with glacial acetic acid at 0° C. The organic layer was separated, washed with $H_2O$, and dried ($MgSO_4$). The organic layer was concentrated, and the crude was used without any purification.

EXAMPLE M-1

2-Amino-5-tert-butyl-benzothiazole-6-thiol

The title compound was prepared according to General Method 14 using 5-tert-butyl-6-thiocyanato-benzothiazol-2-yl-amine (Example L-1; 8 g, 30 mmol), dithiothreitol (18.7 g, 121 mmol), EtOH (200 mL), and phosphate buffer (50 mL). MS (APCI): 239 (M+H).

EXAMPLE M-2

2-Amino-5-isopropyl-benzothiazole-6-thiol and 5-Isopropyl-benzothiazole-6-thiol

The title compound was prepared according to General Method 14 using 5-isopropyl-6-thiocyanato-benzothiazol-2-yl-amine (Example L-2; 23.5 g, 94.4 mmol), dithiothreitol (58.2 g, 377 mmol), EtOH (300 mL), and phosphate buffer (150 mL). The reaction mixture was kept under reflux overnight. The reaction mixture contained a mixture of 2-amino-5-isopropyl-benzothiazole-6-thiol and 5-isopropyl-benzothiazole-6-thiol in 1:2 ratio. The crude reaction mixture was used as such without any further purification. 2-Amino-5-isopropyl-benzothiazole-6-thiol: MS (APCI): 225 (M+H); 5-Isopropyl-benzothiazole-6-thiol: MS (APCI): 210 (M+H).

EXAMPLE M-3

2-Amino-7-isopropyl-4-methyl-benzothiazole-6-thiol

The title compound was prepared according to General Method 14 using 7-isopropyl-4-methyl-6-thiocyanato-benzothiazol-2-yl-amine (Example L-5; 11.5 g, 43.7 mmol), dithiothreitol (27.0 g, 175 mmol), EtOH (200 mL), and phosphate buffer (50 mL). MS (APCI): 239 (M+H).

EXAMPLE M-4

2-Amino-6-tert-butyl-benzothiazole-4-thiol

The title compound was prepared according to General Method 14 using 6-tert-butyl-4-thiocyanato-benzothiazol-2-yl-amine (Example L-6; 2.0 g, 7.6 mmol), dithiothreitol (4.6 g, 30 mmol), phosphate buffer of pH 7 (10 mL), and EtOH (50 mL). The crude product was used further without any purification. MS (APCI): 239 (M+H).

EXAMPLE N 2-(Methyloxycarbonyl)amino-4-isopropyl-7-methyl-benzothiazole-6-thiol To 4-isopropyl-7-methyl-6-thiocyanato-benzothiazol-2-yl-amine (Example L-4; 4.0 g, 17 mmol) dissolved in $CH_2Cl_2$ (25 mL) and pyridine (5 mL), was added methyl chloroformate at 0° C. The reaction mixture was stirred at room temperature for 2 hours. $H_2O$ was added to the reaction mixture followed by EtOAc (100 mL). The organic layer was washed with 2N HCl, $H_2O$, saturated sodium bicarbonate solution and brine, and was dried ($MgSO_4$). The solvents were evaporated, and the residue was purified by flash chromatography (100% hexanes to 25% EtOAc in hexanes) to give 2-(methyloxycarbonyl)amino-4-isopropyl-7-methyl-6-thiocyanato-benzothiazole. MS (APCI): 322 (M+H).

The title compound was prepared according to General Method 14 using 2-(methyloxycarbonyl)amino-4-isopropyl-7-methyl-6-thiocyanato-benzothiazole (1.5 g, 4.7 mmol), dithiothreitol (2.9 g, 18.7 mmol), EtOH (50 mL), and phosphate buffer (15 mL). MS (APCI): 296 (M–H).

Preparation of Benzothiphenes

EXAMPLE O 3-tert-Butyl-2-mercapto-benzo[b]thiophene

A solution of 3-tert-butylbenzo[b]thiophene (2.00 g, 10.4 mmol; *J. Chem. Soc., Perkin Trans.* 1, 1972;3:414–18) in $Et_2O$ (30 mL, $N_2$ atmosphere) was treated with a 1.6 M hexane solution of nBuLi (3.75 mL, 12 mmol) and allowed to stir overnight. The mixture was then cooled to 0° C. and treated with dry precipitated sulfur (0.38 g, 12 mmol). The mixture was allowed to stir for 2 hours, then quenched with ice $H_2O$. The mixture was washed with $Et_2O$, and the aqueous layer was acidified with 1 N HCl and extracted with $Et_2O$. The organic layers were combined, dried ($MgSO_4$), and concentrated. The crude thiol was used without purification in the next step.

EXAMPLE P 2-(3,5-Dibromo-thiophen-2-yl)-propan-2-ol

A solution of 2,3,5-tribromothiophene (8.17 g, 25 mmol) in $Et_2O$ ($N_2$ atmosphere) was cooled to −78° C. and treated with a 1.6 M hexane solution of nBuLi (15.6 mL, 25 mmol). The mixture was then stirred for 10 minutes, then treated with acetone (1.84 mL, 25 mmol). The mixture was then stirred for 30 minutes and quenched with $H_2O$. The mixture was extracted with $Et_2O$; the organic layers were combined, dried ($MgSO_4$), and the solvent removed in vacuo. The residue was filtered through a plug of silica gel (gradient elution from hexanes to EtOAc) to provide the title compound.

$^1H$ NMR ($CDCl^3$): δ1.70 (s, 6 H), 2.40 (br s, 1 H), 6.89 (s, 1 H).

EXAMPLE Q (4-Bromo-5-isopropyl-thiophen-2-yl)-methanol

A solution of 2-(3,5-dibromo-thiophen-2-yl)-propan-2-ol (Example P; 7.64 g, 25 mmol) in $CH_2Cl_2$ (100 mL) was cooled to 0° C. and treated with triethylsilane (6.80 mL, 30.56 mmol) followed by triflouroacetic acid (40 mL). The mixture was stirred for 15 minutes and then concentrated in vacuo. The residue was taken up in hexanes and filtered through a plug of silica gel. The solvent was removed in vacuo, and the residue was diluted with $Et_2O$ and cooled to −78° C. ($N_2$ atmosphere). The mixture was treated with a 1.6 M hexane solution of nBuLi (15.6 mL, 25 mmol), stirred 10 minutes, and treated with a solution of 4-formylmorpholine (2.88 mL, 25 mmol) in $Et_2O$ (25 mL). The mixture was allowed to slowly come to room temperature overnight, then quenched with $H_2O$ and extracted with $Et_2O$. The organic layers were combined, dried ($MgSO_4$), and concentrated.

The residue was then taken up in MeOH (250 mL) and treated with an excess of sodium borohydride. After 30 minutes, the mixture was diluted with $Et_2O$, washed with $H_2O$, and dried ($MgSO_4$). The solvent was evaporated and the residue purified via silica gel chromatography (hexanes to 10% EtOAc:hexanes) to provide the title compound.

$^1H$ NMR ($CDCl^3$): δ1.28 (d, 6 H), 1.73 (bs, 1 H), 3.31 (sept, 1 H), 4.73 (d, 2 H). 6.82 (d, 1 H).

EXAMPLE R (4-Bromo-5-isopropyl-thiophen-2-yl-methoxy)-tert-butyl-dimethyl-silane A solution of (4-bromo-5-isopropyl-thiophen-2-yl)-methanol (Example Q; 3.4 g, 14 mmol) in $CH_2Cl_2$ (4.0 mL)

was treated with NEt₃ (2.8 mL, 20 mmol), p-dimethylaminopyridine (0.050 g), and t-butyldimethylsilylchloride (2.41 g, 16.0 mmol). The mixture was stirred for 14 hours, then diluted with Et₂O and washed with H₂O. The organic layer was dried (MgSO₄) and the solvent evaporated to provide the crude product, which was used without further purification.

$^1$H NMR (CDCl$^3$): δ0.0 (s, 6 H), 0.82 (s, 9 H), 1.17 (d, 6 H), 3.20 (sept, 1 H), 4.66 (d, 2 H), 6.60 (s, 1 H).

EXAMPLE S

5-(tert-Butyl-dimethyl-silanyloxymethyl)-2-isopropyl-3-mercapto-thiophene

A solution of (4-bromo-5-isopropyl-thiophen-2-ylmethoxy)-tert-butyl-dimethyl-silane (Example R; 4.7 g, 13.5 mmol) in Et₂O (100 mL, N₂ atmosphere) was cooled to −78° C. and treated with a 1.6 M hexane solution of nBuLi (8.42 mL, 13.5 mmol). After 10 minutes, dry triturated sulfur (0.43 g, 13.5 mmol) was added. and the mixture was allowed to warm to room temperature. After 2 hours the mixture was diluted with Et₂O and washed with 0.5 M HCl. The organic layer was dried (MgSO₄) and concentrated to give the title compound, which was used crude in the next step.

EXAMPLE T

5-tert-Butyl-4-hydroxy-2-methylbenzaldehyde

Aluminum chloride (26.6 g, 200 mmol) was added to chlorobenzene (40 mL), and the mixture was cooled to −10° C. A solution of 2-tert-butyl-5-methylphenol (16.4 g, 100 mmol) in triethyl orthoformate (32.5 g, 220 mmol) was added dropwise. When addition was complete, the reaction mixture was warmed to 0° C. to 5° C. and kept at that temperature for 6 hours. Five percent HCl (100 mL) was added, and the mixture was extracted with 1:1 EtOAC:toluene. The organic phase was extracted with 23% KOH (3×50 mL) and water (25 mL), and the water extract was combined with the KOH extracts. The pH of the combined aqueous extracts was adjusted to 4 with 37% HCl. The resulting precipitate was filtered, washed with water (3×50 mL), and dried to give the title compound. mp 171–171° C.

EXAMPLE U

Dimethylthiocarbamic acid O-(2-tert-butyl-4-formyl-5-methylphenyl)ester

Ten percent KOH (80 mL) was added to a mixture of 5-tert-butyl-4-hydroxy-2-methylbenzaldehyde (Example T 99.0 g, 515 mmol) in water (180 mL) and THF (135 mL.) The mixture was treated with a solution of N,N-dimethylthiocarbamoyl chloride (86.1 g) in THF (108 mL) over a 2-hour period with simultaneous addition of 10% KOH in order to hold the pH of the reaction mixture between 12.0 and 12.3. After approximately 70% of the dimethylthiocarbamoyl chloride-THF solution had been added, vacuum was applied to the reaction mixture to remove the THF; during this distillation, the simultaneous additions of 10% KOH and the dimethylthiocarbamoyl chloride-THF solution were continued while maintaining the pH range between 12.0 and 11.6 and the reaction temperature between 23° C. to 25° C. The distillation was continued for 10 minutes after all the dimethylthiocarbamoyl chloride solution had been added. Stirring at ambient pressure and temperature was continued for another 90 minutes, during which time the pH was stable between 11.6 and 1.75. A solution of EtOAc (150 mL) and heptane (150 mL) was added to the reaction mixture, and after stirring and settling, the layers were separated and the aqueous layer extracted with 1:1 heptane:EtOAc. The combined organic extracts were extracted with 10% KOH (2×100 mL) and water (2×90 mL) and concentrated. The residue was diluted with MeOH (120 mL). The solution was warmed to 45° C. and H₂O (20 mL) was added. The solution was cooled to room temperature. 50% NaOH (170 mg) was added, and the solution was concentrated. This residue was redissolved in MeOH (120 mL) at 50° C. and H₂O (15 mL) was added. The solution was cooled slowly to −5° C. with the addition of dimethylthiocarbamic acid O-(2-tert-butyl-4-formyl-5-methyl-phenyl) ester seed crystals to promote crystallization. The mixture was filtered and the solid washed with 4:1 MeOH:H₂O to give the title compound, mp 80–81° C.

EXAMPLE V

(5-tert-Butyl-4-mercapto-5-methyl-phenyl)methanol

Dimethylthiocarbamic acid O-(2-tert-butyl-4-formyl-5-methylphenyl) ester (Example U; 24.0 g, 85.9 mmol) was treated with tetraethylene glycol dimethyl ether (65 g), and the mixture was stirred and heated under argon to 275° C. The solution was heated at this temperature for 30 minutes. The solution was cooled. and H₂O was added. The mixture was cooled to 0° C. and filtered; the solid was washed with H₂O to give dimethyl thiocarbamic acid S-(2-tert-butyl-4-formyl-5-methyl-phenyl)ester.

The crude solid was treated with MeOH (40 mL) and THF (30 mL) followed by slow addition (20 minutes) of NaBH₄ (14.1 g of a 12 weight percent solution in 14 M NaOH), while maintaining the temperature below 8° C. The resulting solution was stirred at 20° C. to 25° C. for 90 minutes. Fifty percent NaOH (4 g) was added, and the solution was heated to reflux for 3 hours. The mixture was cooled to room temperature, treated with H₂O (110 mL) and toluene (70 mL), and acidified to pH 4 with 37% HCl. The aqueous layer was separated and extracted with toluene (2×15 mL). Concentration gave the title compound which was used without further purification in the next step.

EXAMPLE W

3-tert-Butyl-4-dimethylcarbamoylsulfanyl-benzoic acid methyl ester

A solution of 3.0 g (14.4 mmol) of 3-tert-butyl-4-hydroxy-benzoic acid methyl ester (Aust. J. Chem., 1978;31:907–916), cesium carbonate (7.04 g, 21.6 mmol), and acetonitrile (50 mL) was heated to reflux and then treated with N,N-dimethylthiocarbamoyl chloride (2.67 g, 21.6 mmol) all at once. The mixture was refluxed for 2 hours, cooled to room temperature. and quenched with 1N HCl. The solution was extracted with EtOAc; the organic layer was washed with 1N NaOH and brine, dried (MgSO₄), and concentrated. The residue was chromatographed over silica gel, eluting with 3:2 hexane:EtOAc, to give 3-tert-butyl-4-dimethylthiocarbamoyloxy-benzoic acid methyl ester.

$^1$H NMR (CDCl₃): δ1.39 (s, 9 H), 3.44 (d, 6 H), 3.90 (s, 3 H), 7.09 (d, 1 H), 7.89 (dd, 1 H), 8.12 (m, 1 H).

Neat 3-tert-butyl-4-dimethylthiocarbamoyloxy-benzoic acid methyl ester (2.71 g, 9.2 mmol) was heated to 230° C. for 2 hours and then cooled to room temperature. The material was chromatographed over silica gel, eluting with 7:3 hexane:EtOAc. to give the title compound.

$^1$H NMR (CDCl$^3$): δ1.50 (s, 9 H), 3.11 (br s. 6 H), 3.91 (s, 3 H), 7.53 (d, 1 H), 7.84 (dd, 1 H), 8.13 (d, 1 H).

EXAMPLE X (3-tert-Butyl-4-mercapto-phenyl)methanol

A solution of 2.1 g (7.1 mmol) of 3-tert-butyl-4-dimethylcarbamoylsulfanyl-benzoic acid methyl ester (Example W) in toluene (100 mL) was cooled to −78° C. and treated with 42 mL of DIBAL (1.0 M in CH$_2$Cl$_2$; 42 mmol). The reaction mixture was allowed to warm to room temperature overnight. The reaction was quenched cautiously with saturated aqueous citric acid and extracted with EtOAc (2×100 mL). The combined organic extracts were washed with brine, dried (MgSO$_4$), and concentrated. Chromatography of the residue over silica gel, eluting with 3:2 hexane:EtOAc, gave the title compound.

$^1$H NMR (CDCl$_3$): δ1.48 (s, 9 H), 1.97 (br s, 1 H), 3.61 (s, 1 H), 4.59 (s, 2 H), 7.02 (dd, 1 H), 7.20 (d, 1 H), 7.34 (d, 1 H).

EXAMPLE Y (5-tert-Butyl-4-hydroxy-2-methyl-phenyl)-acetic acid, methyl ester A solution of 8.5 g (51 mmol) of (4-hydroxy-2-methyl-phenyl)-acetic acid (*Indian J. Chem. Sect B*. 26, 1987:679–682), tert-butanol (60 g), and conc. sulfuric acid (2 mL) was stirred at 70° C. for 5 days. The solution was cooled to room temperature, poured into water, and extracted with EtOAc. The organic extract was washed with brine, dried (MgSO$_4$), and concentrated to give (5-tert-butyl-4-hydroxy-2-methyl-phenyl)-acetic acid.

$^1$H NMR (CDCl$^3$): δ1.33 (s, 9 H), 2.14 (s, 3 H), 3.54 (s, 2 H), 6.47 (s, 1 H), 7.00 (s, 1 H).

A mixture of the (5-tert-butyl-4-hydroxy-2-methyl-phenyl)-acetic acid isolated above (11.3 g, 51 mmol), MeOH (150 mL), and conc. sulfuric acid (2 mL) was refluxed overnight. The solution was cooled to room temperature and concentrated. The residue was partitioned between EtOAc and water: the organic phase was washed with brine, dried (MgSO$_4$), and concentrated. The product was chromatographed over silica gel, eluting with hexane:EtOAc, to give the title compound.

$^1$H NMR (CDCl$^3$): δ1.35 (s, 9 H), 2.16 (s, 3 H), 3.54 (s, 2 H), 3.67 (s, 3 H), 6.46 (s, 1 H), 7.01 (s, 1 H).

EXAMPLE Z (5-tert-Butyl-4-dimethylcarbamoylsulfanyl-2-methyl-phenyl)-acetic acid methyl ester A solution of 3.0 g (13 mmol) of (5-tert-butyl-4-hydroxy-2-methyl)-phenyl acetic acid, methyl ester (Example Y) in 20 mL of DMF was treated portionwise with 0.60 g (15 mmol) of NaH and stirred at room temperature for 1 hour. N,N-dimethylthiocarbamoyl chloride (2.35 g, 19 mmol) was added all at once, and the reaction mixture was stirred at 70° C. overnight. Water was added; the solution was extracted with EtOAc. The organic layer was separated, washed with brine, dried (MgSO$_4$), and concentrated. The crude material was chromatographed over silica gel, eluting with hexane:EtOAc 3:1, to give (5-tert-butyl-4-dimethylthiocarbamoyloxy-2-methyl-phenyl)-acetic acid methyl ester.

$^1$H NMR (CDCl$^3$): δ1.30 (s, 9 H), 2.22 (s, 3 H), 3.40 (d, 6 H), 3.58 (s, 2 H), 3.66 (s, 3 H), 6.80 (s, 1 H), 7.17 (s, 1 H).

The product isolated above (2.1 g, 6.5 mmol) was heated neat to 310° C. for 1 hour and then cooled to room temperature. The residue was chromatographed on silica gel, eluting with hexane:EtOAc 2:1, to give the title compound.

$^1$H NMR (CDCl$^3$): δ1.41 (s, 9 H), 2.2 (s, 3 H), 3.00–3.10 (br d, 6 H), 3.58 (s, 2 H), 3.65 (s, 3 H), 7.22–7.24 (m, 2 H).

EXAMPLE AA 2-(5-tert-Butyl-4-mercapto-2-methyl-phenyl)-ethanol

A solution of 0.68 g (2.1 mmol) of (5-tert-butyl-4-dimethylcarbamoylsulfanyl-2-methyl-phenyl)-acetic acid methyl ester (Example Z) in 20 mL of toluene was cooled to −78° C. and treated dropwise with 1.0 M DIBAL in CH$_2$Cl$_2$ (10 mL; 10 mmol). The cold bath was removed, and the mixture was stirred at room temperature for 2 hours. Saturated citric acid was added cautiously. H$_2$O and EtOAc were added, and the mixture was filtered. The filtrate was transferred to a separatory funnel where the aqueous phase was isolated and re-extracted with EtOAc. The organic extracts were combined, washed with brine, and dried (MgSO$_4$). Concentration gave an oil which was chromatographed over silica gel, eluting with 1:1 hexane:EtOAc, to give the title compound.

$^1$H NMR (CDCl$^3$): δ1.42 (s, 9 H), 2.20 (s, 3 H), 2.79 (t, 2 H), 3.49 (t, 1 H), 3.76 (t, 2 H), 7.01 (s, 1 H), 7.11 (s, 1 H).

General Method 15. Preparation of Tosyl Reagents

A solution of p-toluenesulfonyl bromide (1 equiv.), a base such as NEt$_3$ or pyridine (1–1.5 equiv.), and a solvent such as CCl$_4$ or EtOAc at 0° C. to 24° C. was treated with a solution of the appropriate thiol (1 equiv.) in CCl$_4$ or EtOAc in a dropwise fashion. Addition was complete in 0.5 to 1 hours. The reaction was allowed to warm to room temperature. H$_2$O was added; the organic layer was separated, washed with saturated aqueous NH$_4$Cl and brine, and dried (MgSO$_4$). Concentration gave a residue which could be purified either by silica gel chromatography or by trituration.

EXAMPLE BB-1

Toluene-4-thiosulfonic acid S-(2-amino-5-tert-butyl-benzothiazol-6-yl)ester

The title compound was prepared according to General Method 15 using 2-amino-5-tert-butyl-benzothiazole-6-thiol (7.0 g, 29 mmol), pyridine (2.3 g, 29 mmol), tosyl bromide (6.9 g, 29 mmol), carbon tetrachloride (100 mL), and EtOAc (100 mL). The crude reaction mixture was purified by flash chromatography (5% EtOAc in hexanes to 50% EtOAc in hexanes as eluents). MS(APCI): 393 (M+H).

EXAMPLE BB-2

Toluene-4-thiosulfonic aid S-(2-tert-butyl-4-hydroxymethyl-5-methyl-phenyl)ester A solution of (5-tert-butyl-4-mercapto-5-methyl-phenyl) methanol (from Example V), pyridine (6.12 G), and toluene (30 mL) was slowly added (over 3 hours) at 40° C. to a prestirred solution of toluenesulfonyl chloride (16.6 g) and lithium bromide (8.0 g) in THF (75 mL). The resulting mixture was stirred at 40° C. for 2 hours and then overnight at room temperature. H$_2$O (70 mL) and EtOAc (30 mL) were added. The organic layer was separated and washed with 10% HCl (2×50 mL) and H₂O(50 mL). The solution was concentrated to give a residue which was warmed to 60° C. and treated with heptane. This solution was stirred and cooled to 10° C.; the solids were filtered and washed with 1:1 toluene:heptane. Upon drying in vacuo, the title compound was obtained, mp 121–122° C.

The following tosylthiolates were prepared using the appropriate thiol and following General Method 15:

TABLE K

Thiotosylate Side Chains

| Prep. of Starting Materials | Example | Structure | $^1$H NMR or MS Data |
|---|---|---|---|
| Examples L-2 and M-2 | BB-3 | | MS (APCI): 378 |
| Examples L-2 and M-2 | BB-4 | | MS (APCI): 364 (M + H) |
| Examples L-5 and M-3 | BB-5 | | MS (APCI): 393 (M + H) |
| Examples L-4 and N | BB-6 | | MS (APCI): 451 (M + H) |
| Examples L-6 and M4 | BB-7 | | MS (APCI): 393 (M + H) |

TABLE K-continued

Thiotosylate Side Chains

| Prep. of Starting Materials | Example | Structure | ¹H NMR or MS Data |
|---|---|---|---|
| Example O | BB-8 | 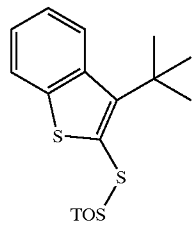 | (CDCl$_3$): δ 1.54(s, 9H), 2.43(s, 3H), 7.24(d, 2H), 7.32–7.39(m, 2H), 7.62(d, 2H,), 7.69–7.75(m, 1H), 8.17–8.21(m, 1H). |
| Examples P–S | BB-9 | 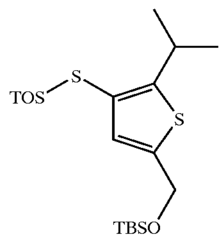 | (CDCl$_3$): δ 0.0(s, 6H), 0.82(s, 9H), 0.91(d, 6H), 2.31(s, 3H), 2.93(sept., 1H), 4.65(d, 2H), 6.60(s, 1H), 7.13(d, 2H), 7.41(d, 2H). |
| | BB-10 | | USSN 08/883,743 |
| | BB-11 | | USSN 08/883,743 |
| | BB-12 | | USSN 08/883,743 |
| Examples W and X | BB-13 | 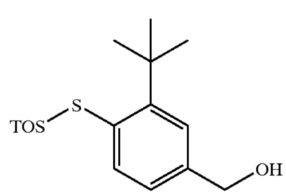 | (CDCl$_3$): δ 1.23(s, 9H), 2.40(s, 3H), 4.73(s, 2H), 7.23(m, 3H), 7.43(m, 1H), 7.46–7.50(m, 2H), 7.61(d, 1H). |

TABLE K-continued

Thiotosylate Side Chains

| Prep. of Starting Materials | Example | Structure | ¹H NMR or MS Data |
|---|---|---|---|
| Examples Y, Z, and AA | BB-14 | (structure) | (CDCl$_3$): δ 1.21(s, 9H), 2.17(s, 3H), 2.39(s, 3H), 2.85(t, 2H), 3.80(t, 2H), 7.18–7.22(m, 4H), 7.47(d, 2H). |
| Example BB-11 | BB-15 | (structure) | |
| Examples CC–FF | BB-16 | (structure) | (CDCl$_3$): δ 1.28(s, 9H), 1.69(s, 9H), 2.4(s, 3H), 6.5(d, 1H), 7.2 (d, 2H), 7.44(d, 2H), 7.61(d, 1H), 7.81(s, 1H), 8.28(br s, 1H). |
| Examples GG–LL | BB-17 | (structure) | MS (APCI): 462 (M + H) |
| Examples MM–NN | BB-18 | (structure) | (CDCl$_3$): δ 1.22(s, 9H), 2.44(s, 3H), 2.99(t, 2H), 4.03(t, 2H), 7.22(d, 2H), 7.39(d, 2H), 7.42(s, 1H), 7.66(s, 1H), 7.81(d, 2H), 7.94 (d, 2H). |

TABLE K-continued

Thiotosylate Side Chains

| Prep. of Starting Materials | Example | Structure | ¹H NMR or MS Data |
|---|---|---|---|
| Examples OO-1–VV-1 | BB-19 | 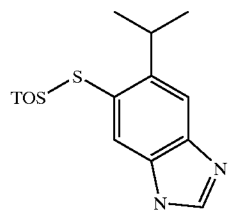 | MS (APCI): 347 (M + H). |
| Examples OO-2–VV-2 | BB-20 | | MS (APCI): 361 (M + H). |
| Examples OO-2–VV-2 | BB-21 | | MS (APCI): 375 (M − H). |
| Examples WW–AAA | BB-22 | 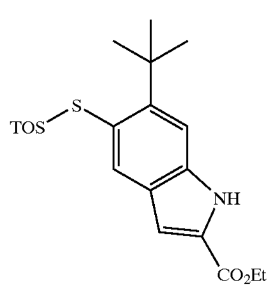 | MS (APCI): 432 (M + H) |
| Examples BBB–DDD | BB-23 | 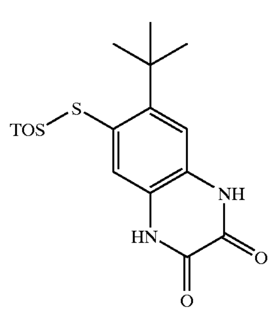 | MS (APCI): 405 (M + H) |

TABLE K-continued

Thiotosylate Side Chains

| Prep. of Starting Materials | Example | Structure | $^1$H NMR or MS Data |
|---|---|---|---|
| Example BB-1 | BB-24 | 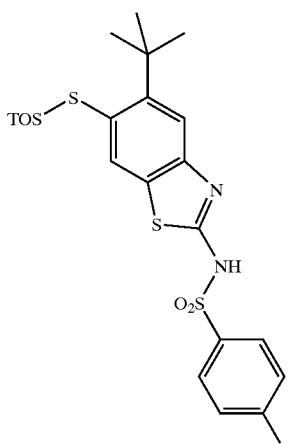 | MS (APCI): 558 (M + H) |
| Example BB-1 | BB-25 | 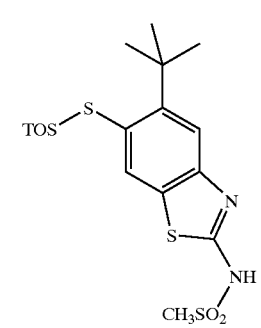 | MS (APCI): 471 (M + H) |
| Example BB-1 | BB-26 | 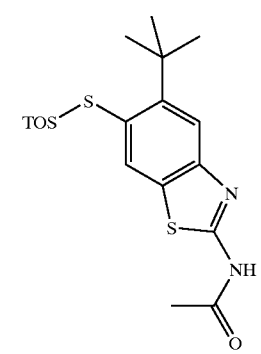 | MS (APCI): 435 (M + H) |
| Example VV-1 | BB-27 | 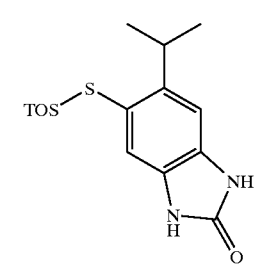 | MS (APCI): 363 (M + H) |

The compounds from Table K above are named:

BB-3: Toluene-4-thiosulfonic acid S-(2-amino-5-isopropyl-benzothiazol-6-yl)ester;

BB-4: Toluene-4-thiosulfonic acid S-(5-isopropyl-benzothiazol-6-yl)ester;,

BB-5: Toluene-4-thiosulfonic acid S-(2-amino-7-isopropyl-4-methyl-benzothiazol-6-yl)ester;

BB-6: Toluene-4-thiosulfonic acid S-(4-isopropyl-2-methoxycarbonylamino-7-methyl-benzothiazol-6-yl) ester;
BB-7: Toluene-4-thiosulfonic acid S-(2-amino-6-tert-butyl-benzothiazol-4-yl)ester;
BB-8: Toluene-4-thiosulfonic acid S-(3-tert-butyl-benzo[b]thiophen-2-yl)ester;
BB-9: Toluene-4-thiosulfonic acid S-[5-(tert-butyl-silanyloxymethyl)-2-isopropyl-thiophen-3-yl]ester;
BB-13: Toluene-4-thiosulfonic acid S-(2-tert-butyl-4-hydroxymethyl-phenyl)ester;
BB-14: Toluene-4-thiosulfonic acid S-[2-tert-butyl-4-(2-hydroxy-ethyl)-5-methyl-phenyl]ester; and
BB-15: Benzenesulfonothioic acid, 4-methyl-, S-[2-(1,1-dimethylethyl]-5-methyl-4-[[[[(5-trifluoromethyl)-2-pyridinyl]sulfonyl]amino]phenyl]ester;
BB-16: 6-tert-Butyl-5-(toluene-4-sulfonylsulfanyl)-indole-1-carboxylic acid tert-butyl ester;
BB-17: 6-tert-Butyl-5-(toluene-4-sulfonylsulfanyl)-2,3-dihydro-indole-1-carboxylic acid tert-butyl ester;
BB-18: Toluene-4-thiosulfonic acid S-[6-tert-butyl-1-(4-cyanobenzenesulfonyl)-2,3-dihydro-1H-indol-5-yl]ester;
BB-19: Toluene-4-thiosulfonic acid S-(6-isopropyl-3H-benzoimidazol-5-yl)ester;
BB-20: Toluene-4-thiosulfonic acid S-(6-tert-butyl-3H-benzoimidzol-5-yl) ester;
BB-21: Toluene-4-thiosulfonic acid S-(6-tert-butyl-2-oxo-2.3-dihydro-1H-benz-oimidzol-5-yl)ester;
BB-22: 6-tert-Butyl-5-(toluene-4-sulfonylsulfanyl)-1H-indole-2-carboxylic acid ethyl ester;
BB-23: Toluene-4-thiosulfonic acid S-(7-tert-butyl-2,3-dioxo-1,2,3,4-tetrahydro-quinoxalin-6-yl)ester;
BB-24: Toluene-4-thiosulfonic acid S-[5-tert-butyl-2-(4-cyanobenzenesulfonyl-amino)-benzothiazol-6-yl)]ester;
BB-25: Toluene-4-thiosulfonic acid S-(6-tert-butyl-2-methanesulfonylamino-benzothiazol-6-yl)ester;
BB-26: Toluene-4-thiosulfonic acid S-(2-acetylamino-5-tert-butyl-benzothiazol-6-yl)ester; and
BB-27: Toluene-4-thiosulfonic acid S-(6-isopropyl-2-oxo-2,3-dihydro-1H-benzimidazol-5-yl)ester.

EXAMPLE BB-15

Benzenesulfonothioic acid, 4-methyl-, S-[2-(1,1-dimethylethyl)-5-methyl-4-[[[[(5-trifluoromethyl)-2-pyridinyl]sulfonyl]amino]phenyl]ester Compound BB-11 (0.5 g, 1.43 mmol) was dissolved in pyridine (5 mL) and CH$_2$Cl$_2$ (2 mL). To this solution was added 0.53 g (2.16 mmol) of 5-(trifluoromethyl)pyridine-2-sulfonyl chloride (*J. Amer. Chem. Soc.*, 1997;119(15):3627–3628), and the reaction mixture was stirred under N$_2$ at room temperature overnight. 1N HCl was then added; the mixture was extracted with EtOAc, washed with 1 N HCl and brine, dried (MgSO$_4$), filtered, and concentrated. The resulting residue was chromatographed over silica gel, eluting with 9:1 CH$_2$Cl$_2$:EtOAc to afford the desired product.

$^1$H NMR (CDCl$_3$): δ1.13 (s, 9 H), 2.19 (s, 3 H), 2.42 (s, 3 H), 6.83 (s, 1 H), 7.22 (d, 2 H), 7.40 (s, 1 H) 7.45 (d, 2 H), 8.08 (d, 1 H), 8.15 (m, 1 H), 8.99 (s, 1 H).

EXAMPLE BB-24

Toluene-4-thiosulfonic acid S-[5-tert-butyl-2-(4-cyanobenzenesulfonyl-amino)-benzothiazol-6-yl)] ester The title compound was prepared as described in Example BB-15 using toluene-4-thiosulfonic acid S-(2-amino-5-tert-butyl-benzothiazol-6-yl)ester (prepared in Example BB-1; 1.0 g, 3.37 mmol), 4-cyanobenzenesulfonyl chloride (0.68 g, 3.37 mmol), pyridine (10 mL) and CH$_2$Cl$_2$ (3 mL). The crude product was purified by flash silica gel chromatography (20%–70% EtOAc in hexanes as eluents). MS(APCI): 558 (M+H).

EXAMPLE BB-25

Toluene-4-thiosulfonic acid S-(6-tert-butyl-2-methanesulnoylamino-benzothiazol-6yl) ester The title compound was prepared as described in Example BB-15 using toluene-4-thiosulfonic acid S-(2-amino-5-tert-butyl-benzothiazol-6-yl)ester (prepared in Example BB-1; 1.75 g, 4.47 mmol), methanesulfonyl chloride (1.02 g, 8.94 mmol), pyridine (3 mL), DMAP (0.3 g) and CH$_2$Cl$_2$ (20 mL). The crude product was purified by flash silica gel chromatography (20%–70% EtOAc in hexanes as eluents). MS(APCI): 471 (M+H).

EXAMPLE BB-26

Toluene-4-thiosulfonic acid S-(2-acetylamino-5-tert-butyl-benzothiazol-6-yl)ester The title compound was prepared as described in Example BB-15 using toluene-4-thiosulfonic acid S-(2-amino-5-tert-butyl-benzothiazol-6-yl)ester (prepared in Example BB-1; 1.75 g, 4.47 mmol), acetyl chloride (4 mL), pyridine (5 mL), DMAP (0.3 g) and CH$_2$Cl$_2$ (20 mL). The crude product was purified by flash silica gel chromatography (20%–70% EtOAc in hexanes as eluents). MS(APCI): 435 (M+H).

EXAMPLE BB-27

Toluene-4-thiosulfonic acid S-(6-isopropyl-2-oxo-2,3-dihydro-1H-benzimidazol-5-yl) ester Toluene-4-thiosulfonic acid S-(1,2-diamino-5-isopropyl-phenyl)ester (prepared in Example VV-1 below; 0.5 g, 1.5 mmol) and triphosgene (0.15 g, 0.5 mmol) were dissolved in THF (30 mL). NEt$_3$ (1 mL) was added, and the reaction mixture was stirred at 90° C. for 1.5 hours. The crude reaction mixture was subjected to flash silica gel chromatography (EtOAc to 2%–10% MeOH in CH$_2$Cl$_2$ as eluents). MS(APCI): 363 (M+H).

EXAMPLE CC (5-tert-Butyl-2-methyl-phenyl)-carbamic acid tert-butyl ester 5-tert-Butyl-2-methyl-phenylamine (50 g, 307 mmol) in 500 mL of hexanes was treated with di-t-butyl dicarbonate (80.3 g, 368 mmol.). The reaction mixture was kept under reflux overnight. After cooling to room temperature, the reaction mixture was diluted with EtOAc, washed with saturated NaHCO$_3$ solution and brine, and dried (MgSO$_4$). After evaporation of the solvents, the crude reaction mixture was purified by flash silica gel chromatography to give the title compound. MS(APCI): 262 (M–H).

EXAMPLE DD (5-tert-Butyl-2-methyl-4-thiocyanto-phenyl)-carbamic acid tert-butyl ester Thiocyanation was performed as described in the General Method 13 using (5-tert-butyl-2-methyl-phenyl)-carbamic acid tert-butyl ester (prepared in Example CC; 4.32 g, 15.82 mmol), sodium thiocyanate (7.7 g, 94.95 mmol), sodium bromide (1.95 g, 18.98 mmol), bromine (3.03 g, 18.98 mmol), and methanol (50 mL). MS(APCI): (M+H).

EXAMPLE EE (5-tert-Butyl-4-mercapto-2-methyl-phenyl)-carbamic acid tert-butyl ester The title compound was prepared according to General Method 14 using (5-tert-butyl-2-methyl-4-thiocyantophenyl)-carbamic acid tert-butyl ester (prepared in Example DD; 30 g, 93.75 mmol), dithiothreitol (29 g, 187.5 mmol) and phosphate buffer (50 mL). MS(APCI): 294 (M−H).

EXAMPLE FF 6-tert-Butyl-5-mercapto-indole-1-carboxylic acid tert-butyl ester (5-tert-Butyl-4-mercapto-2-methyl-phenyl)-carbamic acid tert-butyl ester (prepared in Example EE; 20 g, 68 mmol) was dissolved in 100 mL of THF, cooled to −40° C., and treated dropwise with sec-butyllithium (1.3 M, 156 mL, 203 mmol). After the addition was complete, the reaction mixture was stirred at −30° C. to −45° C. for 30 minutes. To the mixture was added DMF (14.8 g, 203.39 mmol), and the solution was stirred at −35° C. for 30 minutes. The reaction mixture was slowly warmed to room temperature and was quenched with saturated $NH_4Cl$ solution. EtOAc (200 mL) was added; the organic layer was washed with brine, dried ($MgSO_4$) and concentrated. The residue was dissolved in 100 mL of THF and 2 mL of concentrated HCl and stirred at room temperature for 1 hour. The solution was diluted with EtOAc, washed with $NaHCO_3$ solution and brine, and dried ($MgSO_4$). The crude product was purified by flash silica gel chromatography to give the title compound. MS(APCI): 304 (M−H).

EXAMPLE BB-16

6-tert-Butyl-5-(toluene-4-sulfonylsulfanyl)-indole-1-carboxylic acid tert-butyl ester The title compound was prepared according to General Method 15 using 6-tert-butyl-5-mercapto-indole-1-carboxylic acid tert-butyl ester (prepared in Example FF), pyridine, tosyl bromide, carbon tetrachloride, and EtOAc.

EXAMPLE GG 6-tert-Butyl-indole-1-carboxylic acid tert-butyl ester (5-tert-Butyl-2-methyl-phenyl)-carbamic acid tert-butyl ester (prepared in Example CC; 19.7 g, 75 mmol) in 100 mL of THF was cooled to −40° C. To it was added tert-butyllithium (1.5 M, 100 mL, 150 mmol), dropwise with stirring, at −45° C. to −35° C. After the addition was complete, the reaction was stirred at −35° C. for another 15 minutes. DMF (10.97 g, 150 mmol) was added dropwise, and the reaction mixture was stirred at −35° C. for 30 minutes, followed by slow warming to room temperature. The reaction was quenched with saturated $NH_4Cl$ solution and diluted with EtOAc. The organic layer was washed with brine, dried ($MgSO_4$), and concentrated. The residue was dissolved in 100 mL of THF and 2 mL of concentrated HCl and stirred at room temperature for 1 hour. EtOAc was added, and the solution was washed with saturated $NaHCO_3$ solution and brine and dried ($MgSO_4$). Concentration gave a residue that was purified by flash silica gel chromatography (5%–50% EtOAc in hexanes). MS(APCI): 274 (M+H).

EXAMPLE HH 6-tert-Butyl-2,3-dihydro-indole-1-carboxylic acid tert-butyl ester 6-tert-Butyl indole-1-carboxylic acid tert-butyl ester (prepared in Example GG; 13.0 g, 48 mmol) was taken up in 500 mL of AcOH. 20% Pd/C (2 g) was added, and the mixture was shaken under a hydrogen atmosphere of 50 psi. The catalyst was filtered, and the filtrate was concentrated. The residue was dissolved in EtOAc, washed with saturated $NaHCO_3$ solution and brine, and dried ($MgSO_4$). Concentration gave the title compound which was used without purification in the next step.

EXAMPLE II 6-tert-Butyl-2,3-dihydro-1H-indole 6-tert-Butyl-2,3-dihydro-indole-1-carboxylic acid tert-butyl ester (Prepared in Example HH; 12.0 g) in $CH_2Cl_2$ (100 mL) was cooled to 0° C. and treated with HCl gas for 10 minutes. The reaction mixture was warmed to room temperature and stirred for 1 hour. The solvents were evaporated; the residue was dissolved in EtOAc, washed with saturated $NaHCO_3$ solution and brine, and dried ($MgSO_4$) Concentration gave the title compound which was used without any further purification. MS(APCI): 176 (M+H).

EXAMPLE JJ 6-tert-Butyl-5-thiocyanato-2,3-dihydro-1H-indole

The title compound was prepared according to General Method 13 using 6-tert-butyl-2,3-dihydro-1H-indole (prepared in Example 11: 8.3 g, 47 mmol), MeOH (100 mL), sodium thiocyante (23.1 g, 284.57 mmol), NaBr (5.86 g, 56.92 mmol) and bromine (9.1 g, 56.92 mmol). The crude reaction mixture was purified by flash silica gel chromatography (5%–75% EtOAc in hexanes). MS(APCI): 233 (M+H).

EXAMPLE KK 6-tert-Butyl-5-thiocyanato-2,3-dihydro-indole-1-carboxylic acid tert-butyl ester The title compound was prepared in the manner described in Example CC using 6-tert-butyl-5-thiocyanato-2,3-dihydro-1H-indole (prepared in Example JJ; 2.0 g, 8.6 mmol), di-t-butyl dicarbonate (2.35 g, 10.8 mmol) and hexanes (150 mL). The crude product was purified by flash silica gel chromatography.

EXAMPLE LL 6-tert-Butyl-5-mercapto-2,3-dihydro-indole-1-carboxylic acid tert-butyl ester The title compound was prepared according to General Method 14 using 6-tert-butyl-5-thiocyanato-2,3-dihydroindole-1-carboxylic acid tert-butyl ester (prepared in Example KK; 2.0 g, 6.6 mmol), dithiothreitol (1.21 g, 7.9 mmol), EtOH (100 mL), and phosphate buffer (pH: 7.5. 10 mL). The crude product was used without any purification.

EXAMPLE BB-17

6-tert-Butyl-5-(toluene-4-sulfonylsulfanyl)-2,3-dihydro-indole-1-carboxylic acid tert-butyl ester The title compound was prepared according to General Method 15 using 6-tert-Butyl-5-mercapto-2,3-dihydroindole-1-carboxylic acid tert-butyl ester (prepared in Example FF), pyridine, tosyl bromide, carbon tetrachloride, and EtOAc.

EXAMPLE MM 4-(6-tert-Butyl-5-thiocyanato-2,3-dihydro-indole-1-sulfonyl)-benzonitrile 6-tert-Butyl-5-thiocyanato-2,3-dihydro-1H-indole (prepared in Example JJ; 4.5 g, 19 mmol) was taken in $CH_2Cl_2$ (50 mL) and treated with 4-cyanophenylsulfonyl chloride (3.91 g, 19.4 mmol) and pyridine (5 mL). The reaction mixture was stirred overnight, quenched with saturated $NaHCO_3$ solution, and diluted with EtOAc. The organic layer was separated, dried ($MgSO_4$), and concentrated. The crude product was purified by flash chromatography (20%–75% EtOAc in hexanes as eluents). MS(APCI): 397 ($M^+$).

EXAMPLE NN 4-(6-tert-Butyl-5-mercapto-2,3-dihydro-indole-1-sulfonyl)-benzonitrile The title compound was prepared according to the General Method 14b using 4-(6-tert-butyl-5-thiocyanato-2,3-dihydro-indole-1-sulfonyl)-benzonitrile (prepared in Example MM; 6.0 g, 15 mmol), sodium hydrogen sulfide (2.53 g, 45.3 mmol), sodium borohydride (3.43 g, 90.7 mmol), MeOH (10 mL), water (5 mL), and AcOH (5 mL). The crude product was used further without any purification.

EXAMPLE OO-1

2,2,2-Trifluoro-N-(5-isopropyl-2-nitro-phenyl)-acetamide

Trifluoroacetic anhydride (50 mL) was cooled to 0° C. and treated dropwise with 3-isopropyl-phenylamine (5 g, 37.03 mmol). To the resulting solution was added potassium nitrate (4.12 g, 101.11 mmol). After 1 hour, the reaction mixture was warmed to room temperature and stirred overnight. The reaction mixture was diluted carefully with ice water and extracted with EtOAc (4×100 mL). The organic layer was washed with saturated $NaHCO_3$ solution and brine, dried ($MgSO_4$), and concentrated. The crude product was used further without any purification. MS(APCI): 275 (M–H).

EXAMPLE OO-2

N-(5-tert-Butyl-2-nitro-phenyl)-2,2,2-trifluoro-acetamide

The title compound was prepared following the procedure used in Example OO-1 using trifluoroacetic anhydride (300 mL), 3-tert-butyl-phenylamine (144 g, 951 mmol), and potassium nitrate (106 g, 1047 mmol). The crude product was used further without any purification. MS(APCI): 289 (M–H).

EXAMPLE PP-1

5-Isopropyl-2-nitro-phenylamine 2,2,2-Trifluoro-N-(5-isopropyl-2-nitro-phenyl)-acetamide (prepared in Example OO-1; 9.4 g, 34 mmol) was dissolved in MeOH (30 mL) and treated with 7% aqueous potassium carbonate solution. The reaction mixture was stirred overnight at room temperature. The reaction was diluted with water (30 mL) and extracted with EtOAc (3×50 mL). The organic layer was washed with saturated $NaHCO_3$ solution and brine, dried ($MgSO_4$), and concentrated. The crude product was used further without any purification. MS(APCI): 181 (M+H).

EXAMPLE PP-2

5-tert-Butyl-2-nitro-phenylamine

The title compound was prepared as outlined in Example PP-1 from N-(5-tert-butyl-2-nitro-phenyl)-2,2,2-trifluoro-acetamide (prepared in Example OO-2; 248 g, 855 mmol), MeOH (500 mL), and 7% aqueous potassium carbonate solution. The crude product was used without any purification. MS(APCI): 195 (M+H).

EXAMPLE QQ-1

5-Isopropyl-2-nitro-4-thiocyanato-phenylamine

The title compound was prepared according to General Method 13 using 5-isopropyl-2-nitro-phenylamine (prepared in Example PP-1; 5.4 g, 30 mmol), sodium thiocyanate (14.6 g, 180 mmol), sodium bromide (3.7 g, 35.99 mmol), bromine (5.75 g, 36.0 mmol), and MeOH (100 mL). The crude reaction mixture was purified by flash silica gel chromatography (5%–50% EtOAc in hexanes as eluents). MS(APCI): 238 (M+H).

EXAMPLE QQ-2

5-tert-Butyl-2-nitro-4-thiocyanato-phenylamine

The title compound was prepared according to the General Method 13 using 5-tert-butyl-2-nitro-phenylamine (prepared in Example PP-2; 170 g, 876 mmol), ammonium thiocyanate (400 g, 5260 mmol), bromine (140 g, 876 mmol), and MeOH (500 mL). The crude reaction mixture was purified by flash silica gel chromatography (5%–50% EtOAc in hexanes as eluents). MS(APCI): 252 (M+H).

EXAMPLE RR-1

4-Isopropyl-5-thiocyanato-benzene-1,2-diamine

5-Isopropyl-2-nitro-4-thiocyanato-phenylamine (prepared in Example QQ-1; 7.83 g, 33 mmol) was hydrogenated using Raney nickel (2 g) and THF (100 mL) in the presence of hydrogen (50 psi) as described in General Method 3. MS(APCI): 208(M+H).

EXAMPLE RR-2

4-tert-Butyl-5-thiocyanato-benzene-1,2-diamine 5-tert-Butyl-2-nitro-4-thiocyanato-phenylamine (prepared in Example QQ-2; 3 g, 12 mmol) was hydrogenated using Raney nickel (0.75 g) in the presence of hydrogen as described in General Method 3. MS(APCI): 222(M+H).

EXAMPLE SS-1

(2-tert-Butyoxycarbonylamino-4-isopropyl-5-thiocyanato-phenyl)-carbamic acid tert-butyl ester Boc protection was performed as described in Example CC using 4-isopropyl-5-thiocyanato-benzene-1,2-diamine (prepared in Example RR-1; 4.49 g, 21.7 mmol), di-t-butyl dicarbonate (11.3 g, 52.0 mmol), hexanes (150 mL), and EtOAc (50 mL). The crude product was purified by flash silica gel chromatography. MS(APCI): 406 (M–H).

EXAMPLE SS-2

(2-tert-Butoxycarbonylamino-4-tert-Butyl-5-thiocyanato-phenyl)-carbamic acid tert-butyl ester Boc protection was performed as described in Example CC using 4-tert-butyl-5-thiocyanato-benzene-1,2-diamine (prepared in Example RR-2; 9.78 g, 44.2 mmol), di-t-butyl dicarbonate (23.2 g, 106 mmol), hexanes (150 mL), and EtOAc (50 mL). The crude product was purified by flash silica gel chromatography. MS(APCI): 422 (M+H).

EXAMPLE TT-1

(2-tert-Butyoxycarbonylamino-4-isopropyl-5-mercapto-phenyl)-carbamic acid tert-butyl ester The title compound was prepared according to General Method 14b using (2-tert-butyoxycarbonylamino-4-isopropyl-5-thiocyanato-phenyl)-carbamic acid tert-butyl ester (prepared in Example SS-1; 9 g, 22 mmol), sodium hydrogen sulfide (3.7 g, 66 mmol), sodium borohydride (5.02 g, 132 mmol), MeOH (20 mL), $H_2O$ (5 mL), and AcOH (2 mL). The crude product was used without any purification. MS(APCI): 381 (M–H).

EXAMPLE TT-2

(2-tert-Butoxycarbonylamino-4-tert-Butyl-5-mercapto-phenyl)-carbamic acid tert-butyl ester The title compound was prepared according to General Method 14b using (2-tert-butoxycarbonylamino-4-tert-butyl-5-thiocyanato-phenyl)-carbamic acid tert-butyl ester (prepared in Example SS-2; 18 g, 43 mmol), sodium hydrogen sulfide (7.2 g, 128 mmol), sodium borohydride (9.7 g, 256 mmol), MeOH (150 mL), $H_2O$ (50 mL), and AcOH (10 mL). The crude product was used without purification.

EXAMPLE UU-1

Toluene-4-thiosulfonic acid S-(4,5-bis-tert-butoxycarbonylamino-2-isopropyl-phenyl) ester The title compound was prepared according to the General Method 15 using (2-tert-butyoxycarbonylamino-4-isopropyl-5-mercapto-phenyl)-carbamic acid tert-butyl ester (prepared in Example TT-1; 22.1 mmol), tosyl bromide (5.2 g, 22 mmol), pyridine (5 mL), and EtOAc (50 mL). The crude product was purified by flash chromatography (5%–60% EtOAc in hexanes as eluents). $^1$H-NMR (CDCl$^3$): δ0.97 (s, 6 H), 1.53 (s, 18 H), 2.4 (s, 3 H), 3.2 (m, 1 H), 7.11 (br s, 1 H), 7.22 (d, 2 H), 7.28 (s, 1 H), 7.36 (s, 1 H), 7.5 (d, 2 H), 7.75 (br s, 1 H).

EXAMPLE UU-2

Toluene-4-thiosulfonic acid S-(4,5-bis-tert-butoxycarbonylamino-2-tert-butyl-phenyl) ester The title compound was prepared according to the General Method 15 using (2-tert-butoxycarbonylamino-4-tert-butyl-5-mercapto-phenyl)-carbamic acid tert-butyl ester (prepared in Example TT-2; 16.9 g, 42.8 mmol), tosyl bromide (10.04 g, 42.76 mmol), pyridine (10 mL), and EtOAc (150 mL). The crude product was purified by flash chromatography (5%–60% EtOAc in hexanes as eluents). $^1$H-NMR (CDCl$^3$): δ1.19 (s, 9 H), 1.53 (s, 18 H), 2.42 (s, 3 H), 6.42 (br s, 1 H), 7.22 (d, 2 H), 7.28 (s, 1 H), 7.5 (m, 3 H), 7.87 (br s, 1 H).

EXAMPLE VV-1

Toluene-4-thiosulfonic acid S-(4,5-diamino-2-isopropyl-phenyl)ester

Toluene-4-thiosulfonic acid S-(4,5-bis-tert-butoxycarbonylamino-2-isopropyl-phenyl)ester (prepared in Example UU-1; 8.88 g, 16.6 mmol) was dissolved in $CH_2Cl_2$ (25 mL), and HCl gas was bubbled through the solution for 15 minutes. The reaction mixture was stirred at room temperature for 90 minutes. The solvents were evaporated, and the residue was dissolved in MeOH (10 mL) and treated with pH 7.5 buffer. The precipitate that formed was filtered and dried. MS(APCI): 337 (M+H).

EXAMPLE VV-2

Toluene-4-thiosulfonic acid S-(4,5-diamino-2-tert-butyl-phenyl) ester

The title compound was prepared as described in Example VV-1 from toluene-4-thiosulfonic acid S-(4,5-bis-tert-butoxycarbonylamino-2-tert-butyl-phenyl) ester (prepared in Example UU-2; 15 g, 28 mmol), $CH_2Cl_2$ (100 mL), and HCl gas. MS(APCI): 351 (M+H).

EXAMPLE BB-19

Toluene-4-thiosulfonic acid S-(6-isopropyl-3H-benzoimidazol-5-yl)

Toluene-4-thiosulfonic acid S-(1,2-diamino-5-isopropyl-phenyl)ester (prepared in Example VV-1; 0.5 g) was dissolved in 96% formic acid (0.5 mL) and refluxed for 3 hours. After cooling, toluene (10 mL) and water (5 mL) were added. The organic layer was concentrated. the residue was taken in EtOAc (20 mL), washed with $H_2O$, and dried (MgSO$_4$). Concentration gave the crude title compound which was purified by flash chromatography (20%–100% EtOAc in hexanes to 2%–8% MeOH in $CH_2Cl_2$ as eluents). MS(APCI): 347 (M+H).

EXAMPLE BB-20

Toluene-4-thiosulfonic acid S-(6-tert-butyl-3H-benzoimidzol-5-yl) ester

The title compound was prepared using the procedure outlined in Example BB-19 from toluene-4-thiosulfonic acid S-(1,2-diamino-5-tert-butyl-phenyl)ester (prepared in Example VV-2; 0.5 g), and 96% formic acid (0.5 mL) The crude product was purified by flash chromatography (20%–100% EtOAc in hexanes to 2%–8% MeOH in $CH_2Cl_2$ as eluents). MS(APCI): 361 (M+H).

EXAMPLE BB-21

Toluene-4-thiosulfonic acid S-(6-tert-butyl-2-oxo-2, 3-dihydro-1H-benz-oimidzol-5-yl)ester Toluene-4-thiosulfonic acid S-(4,5-diamino-2-tert-butyl-phenyl)ester (prepared in Example VV-2; 0.4 g, 1.2 mmol) and triphosgene (0.12 g, 0.41 mmol) were taken in THF (30 mL). To it triethylamine (1 mL) was added. The reaction mixture was kept at 90° C. for 1.5 hours. The crude reaction mixture was subjected to flash silica gel chromatography (EtOAc to 2%–1 0% MeOH in $CH_2Cl_2$ as eluents). MS(APCI): 375 (M–H).

Preparation of 2-substitued-Indoles for the Synthesis of BB-22

EXAMPLE WW 4-tert-Butyl-1-methyl-2-nitrobenzene

Nitration was performed as described in General Method 12 using tert-butyl-4-methylbenzene (25 g), concentrated $H_2SO_4$ (92 g), 70% $HNO_3$ (82 g), and $H_2O$ (25 g). The crude product was purified via distillation under vacuum.

EXAMPLE XX 3-(4-tert-Butyl-2-nitro-phenyl)-2-oxo-propionic acid ethyl ester

The title compound was prepared by adapting the procedure described by Gagliardi S., el al., in *J. Med. Chem.*, 1998;41:1568 using potassium (1.66 g, 42.4 mmol), $Et_2O$ (200 mL), EtOH (10 mL), diethyl oxalate (7.56 g, 51.8 mmol), and 4-tert-butyl-1-methyl-2-nitrobenzene (prepared in ExampleWW; 10.0 g, 51.8 mmol). MS(APCI): 294 (M+H).

EXAMPLE YY 6-tert-Butyl-1H-indole-2-carboxylic acid ethyl ester

A mixture of 3-(4-tert-butyl-2-nitro-phenyl)-2-oxo-propionic acid ethyl ester (prepared in Example XX; 9.1 g, 31 mmol), iron powder (15.3 g, 274 mmol), EtOH (70 mL), and glacial AcOH (70 mL) was refluxed for 2 hours. After cooling, the resulting mixture was evaporated. THF (100 mL) was added to the residue, and the suspension was filtered on florisil, eluting with a large amount of THF. The solvents were evaporated, and the residue was purified by flash silica gel chromatography (5%–30% EtOAc in hexanes as eluents). MS(APCI): 246 (M+H).

EXAMPLE ZZ 6-tert-Butyl-5-thiocyanato-1H-indole-2-carboxylate ethyl ester

The title compound was prepared according to General Method 13 using 6-tert-butyl-1H-indole-2-carboxylic acid ethyl ester (prepared in Example YY; 3.5 g, 14 mmol), ammonium thiocyanate (1.63 g, 21.4 mmol), bromine (3.42 g, 21.4 mmol), and MeOH (50 mL). The crude product was purified by flash silica gel chromatography (5%–50% EtOAc in hexanes as eluents). MS(APCI): 301 (M–H).

EXAMPLE AAA (6-tert-Butyl-5-mercapto-1H-indole-2-carboxylic acid ethyl ester The title compound was prepared according to the general Method 14b using (6-tert-butyl-5-thiocyanato-1H-indole-2-carboxylic acid ethyl ester (prepared in Example ZZ; 0.25 g, 0.83 mmol), sodium hydrogen sulfide (0.13 g, 2.48 mmol), sodium borohydride (0.188 g, 4.98 mmol), MeOH (5 mL), and AcOH (1 mL). MS(APCI): 278 (M+H).

EXAMPLE BB-22

6-tert-Butyl-5-(toluene-4-sulfonylsulfanyl)-1H-indole-2-carboxylic acid ethyl ester The title compound was prepared according to General Method 15 using (6-tert-Butyl-5-mercapto-1H-indole-2-carboxylic acid ethyl ester (prepared in Example AAA), pyridine, tosyl bromide, carbon tetrachloride, and EtOAc.

Preparation of Quinoxalones for the Synthesis of BB-23

Example BBB (5-tert-Butyl-2-nitro-4-thiocyanatophenyl)-oxalmic acid methyl ester 5-tert-Butyl-2-nitro-4-thiocyanato-phenylamine (prepared in Example QQ-2; 2.5 g, 10.0 mmol) and methyl chloroxoacetate (5 mL) were dissolved in $CH_2Cl_2$ (50 mL) and treated with pyridine (5 mL.) The reaction mixture was stirred at room temperature overnight, quenched with saturated $NaHCO_3$ solution, and diluted with EtOAc (100 mL). The organic layer was washed with dil HCl and brine, dried ($MgSO_4$), and concentrated. The crude product was used without purification. MS(APCI): 336 (M–H).

EXAMPLE CCC 6-tert-Butyl-7-thiocyanato-1,4-dihydro-quinoline-2,3-dione (5-tert-Butyl-2-nitro-4-thiocyanatophenyl)-oxalmic acid methyl ester (prepared in Example BBB; 3.91 g, 1 1.6 mmol) was taken up in THF (100 mL) and treated with Raney nickel (1 g). The reaction mixture was shaken in a hydrogen atmosphere (50 psi). The catalyst was filtered; the filtrate was concentrated, and the residue was triturated with EtOAc/hexanes to obtain the title compound. MS(APCI): 274 (M–H).

EXAMPLE DDD 6-tert-Butyl-7-mercapto-1,4-dihydro-quinoxaline-2,3-dione

The title compound was prepared according to General Method 14b using 6-tert-butyl-7-thiocyanato-1,4-dihydro-quinoxaline-2,3-dione (prepared in Example CCC; 1.5 g, 9.1 mmol), sodium hydrogen sulfide (0.51 g, 27 mmol), sodium borohydride (2.1 g, 55 mmol), MeOH (30 mL), H20 (3 mL), and glacial AcOH (5 mL). The crude product was used without purification. MS(APCI): 251 (M+H).

EXAMPLE BB-23

Toluene-4-thiosulfonic acid S-(7-tert-butyl-2,3-dioxo-1,2,3,4-tetrahydro-quinoxalin-6-yl) ester The title compound was prepared according to the General Method 15 using 6-tert-butyl-7-mercapto-1,4-dihydro-quinoxaline-2,3-dione (prepared in Example DDD, 9.1 mmol), tosyl bromide (2.1 g, 9.1 mmol), pyridine (2 mL), EtOAc (50 mL). The crude product was purified by flash silica gel chromatography (5%–10% MeOH in $CH_2Cl_2$) as eluents. MS(APCI): 405 (M+H).

General Method 16a. Coupling of the Dihydropyrone and the Thiotosylate

The appropriate dihydropyrone intermediate (1 equiv.) from Table F or Table J was added to a reaction flask followed by DMF (1–12 mL per mmol of dihydropyrone). Potassium carbonate ($K_2CO_3$) (4–8 equiv.) was added followed by the appropriate thiotosylate reagent (1.1–1.5 eq.) from Table K. The reaction was stirred at room temperature (2.5 hours to overnight). The reaction was worked up by pouring into a mixture of EtOAc and either 1N HCl or saturated aqueous $NH_4Cl$. The layers were separated and the aqueous layer extracted again with EtOAc. The combined organic extracts were washed with brine, dried (MgSO$_4$), and concentrated. The final compounds were purified via recrystallization, trituration, or silica gel gel chromatography.

General Method 16b. Coupling of the Dihydropyrone and the Thiotosylate

The appropriate dihydropyrone intermediate (1 equiv.) from Examples E-1 to E-46 or Examples J-1 to J-12 and the appropriate thiotosylate reagent (1.0–1.5 equiv.) from Examples BB-1 to BB-14 were added to a reaction flask, followed by acetonitrile (1–12 mL per mmol of dihydropyrone) and triethylamine (NEt$_3$; 2–4 equiv.) The reaction was stirred at room temperature (2.5 hours to overnight.) The NEt$_3$ and solvent were evaporated, and the reaction was poured into a mixture of EtOAc and either saturated aqueous NH$_4$Cl or water. The aqueous layer was extracted with EtOAc; the combined organic extracts were dried (MgSO$_4$), and concentrated. The final compounds were purified via recrystallization, trituration, or silica gel gel chromatography.

EXAMPLE 1

3-(2-tert-Butyl-4-hydroxymethyl-5-methyl-phenylsulfanyl)-4-hydroxy-6-isopropyl-6-(2-pyridin-4-yl-ethyl)-5,6-dihydro-pyran-2-one The title compound was prepared as described in General Method 16a using 4-hydroxy-6-isopropyl-6-(2-pyridin-4-yl-ethyl)-5,6-dihydro-pyran-2-one (Example E-15; 0.8 mmol), toluene-4-thiosulfonic acid S-(2-tert-butyl-4-hydroxymethyl-5-methyl-phenyl)ester (Example BB-2; 0.9 mmol), potassium carbonate (3.1 mmol) in DMF (5 mL). The product was triturated from Et$_2$O, mp 140–155° C. MS (APCI): 470 (M+H).

EXAMPLE 2

3-(2-tert-Butyl-4-hydroxymethyl-5-methyl-phenylsulfanyl)4-hydroxy-6-isopropyl-6-(2-pyridin-3-yl-ethyl)-5,6-dihydro-pyran-2-one The title compound was prepared as described in General Method 16a using 4-hydroxy-6-isopropyl-6-(2-pyridin-3-yl-ethyl)-5,6-dihydro-pyran-2-one (Example E-16; 0.92 mmol), toluene-4-thiosulfonic acid S-(2-tert-butyl-4-hydroxymethyl-5-methyl-phenyl)ester (Example BB-2; 1.01 mmol), potassium carbonate (3.67 mmol) in DMF (5 mL). The product was triturated from Et$_2$O, mp 122–125° C. MS (APCI): 470 (M+H).

EXAMPLE 3

3-(2-tert-Butyl-4-hydroxymethyl-5-methyl-phenylsulfanyl)-4-hydroxy-6-isopropyl-6-(2-pyridin-2-yl-ethyl)-5,6-dihydro-pyran-2-one The title compound was prepared as described in General Method 16a using 4-hydroxy-6-isopropyl-6-(2-pyridin-2-yl-ethyl)-5,6-dihydro-pyran-2-one (Example E-14; 0.8 mmol), toluene-4-thiosulfonic acid S-(2-tert-butyl-4-hydroxymethyl-5-methyl-phenyl)ester (Example BB-2; 0.9 mmol), potassium carbonate (3.1 mmol) in DMF (5 mL). The product was triturated from Et$_2$O. mp 100–110° C. MS (APCI): 470 (M+H).

EXAMPLE 4

3-(2-tert-Butyl-4-hydroxymethyl-5-methyl-phenylsulfanyl)-6-(2-furan-3-yl-ethyl)-4-hydroxy-6-isopropyl-5,6-dihydro-pyran-2-one The title compound was prepared as described in General Method 16a using 6-(2-furan-3-yl-ethyl)-4-hydroxy-6-isopropyl-5,6-dihydro-pyran-2-one (Example E-18; 1 mmol), toluene-4-thiosulfonic acid S-(2-tert-butyl-4-hydroxymethyl-5-methyl-phenyl)ester (Example BB-2; 1.1 mmol), potassium carbonate (4 mmol) in DMF (4 mL). The product was flash chromatographed over silica gel using 70:20:10 hexane:EtOAc:CH$_2$Cl$_2$, mp 62–70° C. MS (APCI): 457 (M–H)

EXAMPLE 5

3-(2-tert-Butyl-4-hydroxymethyl-5-methyl-phenylsulfanyl)-6-(2-furan-2-yl-ethyl)-4-hydroxy-6-isopropyl-5,6-dihydro-pyran-2-one The title compound was prepared as described in General Method 16a using 6-(2-furan-2-yl-ethyl)-4-hydroxy-6-isopropyl-5,6-dihydro-pyran-2-one (Example E-17; 1 mmol), toluene-4-thiosulfonic acid S-(2-tert-butyl-4-hydroxymethyl-5-methyl-phenyl)ester (Example BB-2; 1.1 mmol), potassium carbonate (4 mmol) in DMF (5 mL), mp 64–110° C. MS (APCI): 457 (M–H).

EXAMPLE 6

3-(2-tert-Butyl-4-hydroxymethyl-5-methyl-phenylsulfanyl)-4-hydroxy-6-isopropyl-6-[2-(tetrahydro-furan-2-yl)-ethyl]-5,6-dihydro-pyran-2-one The title compound was prepared as described in General Method 16a using 4-hydroxy-6-isopropyl-6-[2-(tetrahydro-furan-2-yl)-ethyl]-5,6-dihydro-pyran-2-one (Example E-19; 0.98 mmol), toluene-4-thiosulfonic acid S-(2-tert-butyl-4-hydroxymethyl-5-methyl-phenyl)ester (Example BB-; 1.18 mmol), potassium carbonate (3.93 mmol) in DMF (5 mL). Flash chromatographed over silica gel using 10:90 EtOAc:CH$_2$Cl$_2$, mp 57–59° C. MS (APCI): 461 (M–H).

EXAMPLE 7

3-(2-tert-Butyl-4-hydroxymethyl-5-methyl-phenylsulfanyl)-4-hydroxy-6-isopropyl-6-(2-thiophen-3-yl-ethyl)-5,6-dihydro-pyran-2-one The title compound was prepared as described in General Method 16a using 4-hydroxy-6-isopropyl-6-(2-thiophen-3-yl-ethyl)-5,6-dihydro-pyran-2-one (Example E-20; 0.84 mmol), toluene-4-thiosulfonic acid S-(2-tert-butyl-4-hydroxymethyl-5-methyl-phenyl)ester (Example BB-2; 0.92 mmol), potassium carbonate (3.35 mmol) in DMF (4 mL). The product was purified via flash chromatography over silica gel eluting with 10:90 EtOAc:CH$_2$Cl$_2$, mp 63–70° C. MS (APCI): 475 (M+H).

EXAMPLE 8

3-(2-tert-Butyl-4-hydroxymethyl-5-methyl-phenylsulfanyl)-4-hydroxy-6-isopropyl-6-(2-thiophen-2-yl-ethyl)-5,6-dihydro-pyran-2-one The title compound was prepared as described in General Method 16a using 4-hydroxy-6-isopropyl-6-(2-thiophen-2-yl-ethyl)-5,6-dihydro-pyran-2-one (Example E-21; 1 mmol), toluene-4-thiosulfonic acid S-(2-tert-butyl-4-hydroxymethyl-5-methyl-phenyl)ester (Example BB-2; 1.2 mmol), potassium carbonate (4 mmol) in DMF (3 mL). The product was isolated via flash chromatography over silica gel using 10:90 EtOAc:CH$_2$Cl$_2$, mp 73–77° C. MS (APCI): 475 (M+H).

EXAMPLE 9

3-(2-tert-Butyl)-4-hydroxymethyl-5-methyl-phenylsulfanyl)-4-hydroxy-6-[2-(5-hydroxymethyl-thiophen-3-yl)-ethyl]-6-isopropyl-5,6-dihydro-pyran-2-one The title compound was prepared as described in General Method 16a using 4-hydroxy-6-f2-(5-hydroxymethylthiophen-3-yl)-ethyl-6-isopropyl-5,6-dihydro-pyran-2-one (Example E-23; 0.67 mmol), toluene-4-thiosulfonic acid S-(2-tert-butyl-4-hydroxymethyl-5-methyl-phenyl)ester (Example BB-2; 0.74 mmol), potassium carbonate (2.7 mmol) in DMF (5 mL), mp 76–80° C. MS (APCI): 503 (M–H).

EXAMPLE 10

3-(2-tert-Butyl-4-hydroxymethyl-5-methyl-phenylsulfanyl)-4-hydroxy-6-[2-(2-hydroxymethyl-thiophen-3-yl)-ethyl]-6-isopropyl-5,6-dihydro-pyran-2-one The title compound was prepared as described in General Method 16b using 4-hydroxy-6-[2-(2-hydroxymethyl-thiophen-3-yl)-ethyl]-6-isopropyl-5,6-dihydro-pyran-2-one (Example E-24; 1 mmol), toluene-4-thiosulfonic acid S-(2-tert-butyl-4-hydroxymethyl-5-methyl-phenyl)ester (Example BB-2; 1.05 mmol), NEt$_3$ (2.2 mmol) in acetonitrile (5 mL). The product was chromatographed over silica gel using 97.5:2.5 CH$_2$Cl$_2$:MeOH, mp 87–90° C. MS (APCI): 503 (M–H).

EXAMPLE 11

3-(4-Amino-2-tert-butyl-5-methyl-phenylsulfanyl)-4-hydroxy-6-[2-(2-hydroxymethyl-thiophen-3-yl)-ethyl]-6-isopropyl-5,6-dihydro-pyran-2-one The title compound was prepared as described in General Method 16b using 4-hydroxy-6-[2-(2-hydroxymethyl-thiophen-3-yl)-ethyl]-6-isopropyl-5,6-dihydro-pyran-2-one (Example E-24; 1 mmol), toluene-4-thiosulfonic acid S-(4-amino-2-tert-butyl-5-methyl-phenyl)ester (Example BB-11; 1.05 mmol), NEt$_3$ (2.2 mmol) in acetonitrile (5 mL). The product was triturated from Et$_2$O, mp 107–115° C. MS (APCI): 488 (M–H).

EXAMPLE 12 (S)

(S)-3-(2-tert-Butyl-4-hydroxymethyl-5-methyl-phenylsulfanyl)-4-hydroxy-6-isopropyl-6-(2-thiophen-3-yl-ethyl)-5,6-dihydro-pyran-2-one The title compound was prepared as described in General Method 16a using (S)-4-hydroxy-6-isopropyl-6-(2-thiophen-3-yl-ethyl)-5,6-dihydro-pyran-2-one (Example J-1 (S); 2.68 mmol), toluene-4-thiosulfonic acid S-(2-tert-butyl-4-hydroxymethyl-5-methyl-phenyl)ester (Example BB-2; 3.22 mmol), potassium carbonate (10.74 mmol) in DMF (5 mL), mp 64–70° C. MS (APCI): 475 (M+H).

EXAMPLE 13

(S)-3-(2-Amino-5-tert-butyl-benzothiazol-6-ylsulfanyl)-4-hydroxy-6-isopropyl-6-phenethyl-5,6-dihydro-pyran-2-one The title compound was prepared according to the General Method 16a using tolune-4-thiosulfonic acid S-(2-amino-5-tert-butyl-benzothiazol-6-yl)ester (Example BB-1; 0.6 g, 1.53 mmol), (S)-4-hydroxy-6-isopropyl-6-phenylethyl-5,6-dihydro-pyran-2-one (Example J-11 (S); 0.4 g, 1.53 mmol), potassium carbonate (0.8 g), and DMF (DMF; 5 mL). The crude reaction mixture was purified by flash chromatography (25% EtOAc in hexanes to 50% EtOAc in hexanes to 10% MeOH in EtOAc as eluents), mp 186–188° C. MS (APCI): 497 (M+H).

EXAMPLE 14

(S)-3-(2-Amino-5-isopropyl-benzothiazol-6-ylsulfanyl)-4-hydroxy-6-isopropyl-6-phenethyl-5,6-dihydro-pyran-2-one The title compound was prepared according to the General Method 16b using (S)-4-hydroxy-6-isopropyl-6-phenethyl-5,6-dihydro-pyran-2-one (Example J-11 (S); 0.5 g, 1.92 mmol), toluene-4-thiosulfonic acid S-(2-amino-5-isopropyl-benzothiazol-6-yl)ester (Example BB-3; 0.73 g, 1.92 mmol), NEt$_3$ (0.39 g, 3.84 mmol), and acetonitrile (10 mL). The crude compound was purified by flash silica gel chromatography (25% EtOAc in hexanes to 100% EtOAc to 5% MeOH in EtOAc as eluents), mp 197–199° C. MS (APCI): 483 (M+H).

EXAMPLE 15

6-1-2-(4-Fluoro-phenyl)-ethyl]-4-hydroxy-6-isopropyl-3-(5-isopropyl-benzothiazol-6-ylsulfanyl)-5,6-dihydro-pyran-2-one The title compound was prepared according to General Method 16b using 6-[(4-fluoro-phenyl)-ethyl]-4-hydroxy-6-isopropyl-5,6-dihydropyran-2-one (Example E-27; 0.5 g, 1.8 mmol), toluene-4-thiosulfonic acid S-(5-isopropyl-benzothiazol-6-yl)ester (Example BB-4; 0.65 g, 1.8 mmol), NEt$_3$ (0.22 g, 2.16 mmol), and acetonitrile (10 mL). The crude compound was purified by flash silica gel chromatography (25% EtOAc in hexanes to 100% EtOAc to 5% MeOH in EtOAc as eluents), mp 104–105° C. MS (APCI ): 486.

EXAMPLE 16

3-(2-Amino-5-isopropyl-benzothiazol-6-yl-sulfanyl)-6-[2-(4-fluoro-phenyl)-ethyl]-phenethyl-4-hydroxy-6-isopropyl-5,6-dihydro-pyran-2-one The title compound was prepared according to General Method 16b using 6-[(4-fluoro-phenyl)-ethyl]-4-hydroxy-6-isopropyl-, 5,6-dihydro-pyran-2-one (Example E-27; 0.5 g, 1.8 mmol), toluene-4-thiosulfonic acid S-(2-amino-5-isopropyl-benzothiazol-6-yl)ester (Example BB-3; 0.68 g, 1.8 mmol), NEt$_3$ (0.36 g, 3.6 mmol), and acetonitrile (20 mL). The crude compound was purified by flash silica gel chromatography (25% EtOAc in hexanes to 100% EtOAc to 5% MeOH in EtOAc as eluents), mp 204–206° C. MS (APCI): 501 (M+H).

EXAMPLE 17

(S)-3-(2-Amino-7-isopropyl-4-methyl-benzothiazol-6-yl-sulfanyl)-4-hydroxy-6-isopropyl-6-phenethyl-5,6-dihydro-pyran-2-one The title compound was prepared according to General Method 16a using toluene-4-thiosulfonic acid S-(2-amino-7-isopropyl-4-methyl-benzothiazol-6-yl)ester (Example BB-5; 0.75 g, 1.92 mmol), (S)-4-hydroxy-6-isopropyl-6-phenylethyl-5,6-dihydro-pyran-2-one (Example J-11 (S); 0.5 g, 1.92 mmol), potassium carbonate (1.0 g), and DMF (5 mL). The crude reaction mixture was purified by flash chromatography (25% EtOAc in hexanes to 50% EtOAc in hexanes to 5% MeOH in EtOAc as eluents), mp 160–162° C. MS (APCI): 497 (M+H).

EXAMPLE 18

(S)-3-(2-Amino-7-isopropyl-4-methyl-benzothiazol-6-ylsulfanyl)-4-hydroxy-6-[2-(4-hydroxyl-phenyl)-ethyl]-6-isopropyl-5,6-dihydro-pyran-2-one The title compound was prepared according to General Method 16a using toluene-4-thiosulfonic acid S-(2-amino-7-isopropyl-4-methyl-benzothiazol-6-yl)ester (Example BB-5; 0.35 g, 1.27 mmol), (S)4-hydroxy-6-[2-(4-hydroxy-phenyl)-ethyl]-6-isopropyl-5,6-dihydro-pyran-2-one (Example J-10; 0.35 g, 1.27 mmol), potassium carbonate (0.7 g), and DMF (5 mL). The crude reaction mixture was purified by flash chromatography (20% EtOAc in hexanes to 50% EtOAc in hexanes to 5% MeOH in EtOAc as eluents), mp 232–234° C. MS (APCI): 513 (M+H).

EXAMPLE 19

(S)-(6-{4-Hydroxy-6-[2-(4-hydroxy-phenyl)-ethyl]-6-isopropyl-2-oxo-5,6-dihydro-2H-pyran-3-ylsulfanyl}-4-isopropyl-7-methyl-benzothiazol-2-yl)-carbamic acid methyl ester The title compound was prepared according to General Method 16a using toluene-4-thiosulfonic acid S-[2-(methyloxycarbonyl)amino]-4-isopropyl-7-methyl-benzothiazol-6-yl)ester (Example BB-6; 0.65 g, 1.5 mmol), (S)-4-hydroxy-6-[2-(4-hydroxy-phenyl)-ethyl]-6-isopropyl-5,6-dihydro-pyran-2-one (Example J-10 (S); 0.4 g, 1.5 mmol), potassium carbonate (0.7 g), and DMF (5 mL). The crude reaction mixture was purified by flash chromatography (30% EtOAc in hexanes to 100% EtOAc as eluents), mp 150–151° C. MS (APCI): 571 (M+H).

EXAMPLE 20

(S)-3-(2-Amino-6-tert-butyl-benzothiazol-4-ylsulfanyl)-4-hydroxy-6-[2-(4-hydroxy-phenyl)-ethyl]-6-isopropyl-5,6-dihydro-pyran-2-one The title compound was prepared according to General Method 16a using toluene-4-thiosulfonic acid S-(2-amino-6-tert-butyl-benzothiazol-4-yl)ester (Example BB-7; 0.28 g, 0.73 mmol), (S)-4-hydroxy-6-[2-(4-hydroxy-phenyl)-ethyl]-6-isopropyl-5,6-dihydro-pyran-2-one (Example J-10 (S); 0.2 g, 0.73 mmol), potassium carbonate (0.7 g), and DMF (5 mL). The crude reaction mixture was purified by flash chromatography (30% EtOAc in hexanes to 100% EtOAc to 10% MeOH in $CH_2Cl_2$ in as eluents), mp 168–179° C. MS (APCI): 513 (M+H).

EXAMPLE 21

(S)-3-(3-tert-Butyl-benzo[b]thiophen-2-ylsulfanyl)-4-hydroxy-6-[2-(4-hydroxy-phenyl)-ethyl]-6-isopropyl-5,6-dihydro-pyran-2-one The title compound was prepared according to General Method 16a using (S)-4-hydroxy-6-[2-(4-hydroxy-phenyl)-ethyl]-6-isopropyl-5,6-dihydro-pyran-2-one (Example J-10 (S); 0.052 g, 0.19 mmol), toluene-4-thiosulfonic acid S-(3-tert-butyl-benzo[b]thiophen-2-yl)ester (Example BB-8; 0.080 g, 0.21 mmol), potassium carbonate (0.029 g, 0.21 mmol), and DMF (1.0 mL). The product was purified via column chromatography (eluting with 1:1 hexanes:EtOAc) to provide a solid. mp 207° C.

$^1$H NMR (DMSO-$d_6$): δ0.86–0.92 (m, 6 H), 1.56 (s, 9 H), 1.85–1.95 (m, 2 H), 2.09–2.21 (m, 3 H), 2.52 (d, 1 H), 2.92 (d, 1 H), 6.62 (d, 2 H), 6.93 (d, 2 H), 7.12 (t, 1 H), 7.21 (t, 1 H), 7.40 (d, 1 H), 7.89 (d, 1 H), 9.14 (s, 1 H).

EXAMPLE 22

3-(3-tert-Butyl-benzo[b]thiophen-2-yl-sulfanyl)-4-hydroxy-6-[2-(2-hydroxymethyl-phenyl)-ethyl]-6-isopropyl-5,6-dihydro-pyran-2-one The title compound was prepared according to General Method 16a using 4-hydroxy-6-[2-(2-hydroxymethyl-phenyl)-ethyl]-6-isopropyl-5,6-dihydro-pyran-2-one (Example E-34; 0.20 g, 0.73 mmol), toluene-4-thiosulfonic acid S-(3-tert-butyl-benzo[b]thiophen-2-yl)ester (Example BB-8; 0.302 g, 0.803 mmol), potassium carbonate (0.11 g, 0.80 mmol), and DMF (2.0 mL). The product was purified via column chromatography (eluting with EtOAc) to the title compound, mp 92–94° C.

$^1$H NMR (DMSO-$d_6$): δ0.93–0.99 (m, 6 H), 1.61 (s, 9 H), 2.13–2.28 (m, 3 H), 2.47–2.71 (m, 3 H), 2.99 (d, 1 H), 4.50 (dd, 2 H), 7.09–7.28 (m, 5 H), 7.35 (d, 1 H), 7.42 (d, 1 H), 7.93 (d, 1 H).

EXAMPLE 23

4-Hydroxy-3-(5-hydroxymethyl-2-isopropyl-thiophen-3-ylsulfanyl)-6-isopropyl-6-(2-thiophen-3-yl-ethyl)-5,6-dihydro-pyran-2-one The title compound was prepared according to General Method 16b using 4-hydroxy-6-isopropyl-6-(2-thiophen-3-yl-ethyl)-5,6-dihydro-pyran-2-one (Example E-20; 0.200 g, 0.75 mmol), toluene-4-thiosulfonic acid S-[5-(tert-butyl-dimethyl-silanyloxymethyl)-2-isopropyl-thiophen-3-yl] ester (Example BB-9; 0.377 g, 0.83 mmol), NEt$_3$ (0.209 mL, 1.50 mmol), and acetonitrile (1.5 mL). As part of the purification, the silylether was cleaved by dissolving the crude coupled product in THF (50 mL) and then treated with a 1.0 M THF solution of tetrabutylammoniumflouride (1.5 mL, 1.5 mmol). After 30 minutes, the mixture was diluted with $H_2O$ and extracted with EtOAc. The organic layers were then combined, dried (MgSO$_4$), and concentrated. The resulting residue was then submitted to column chromatography (eluting with 3% MeOH in $CH_2Cl_2$) to provide the title compound, mp 52–54° C.

$^1$H NMR (CDCl$_3$): δ0.96–1.03 (m, 6 H), 1.32 (t, 6 H), 1.92–2.09 (m, 2 H), 2.17–2.26 (m, 1 H), 2.49 (d, 1 H), 2.66 (t, 2 H), 2.93 (d, 1 H), 3.71 (sept., 1 H), 4.57 (s, 2 H), 6.71 (s, 1 H), 6.79 (d, 1 H), 6.84 (bs, 1 H), 7.23–7.24 (m, 1 H), 7.83 (s, 1 H).

EXAMPLE 24

3-(2-tert-Butyl-4-hydroxymethyl-5-methyl-phenylsulfanyl)-4-hydroxy-6-isopropyl-6-[2-(4-methyl-thiazol-5-yl)-ethyl]-5,6-dihydro-pyran-2-one The title compound was prepared according to General Method 16a using 4-hydroxy-6-isopropyl-6-[2-(4-methyl-thiazol-5-yl)-ethyl]-5,6-dihydro-pyran-2-one (Example E-1; 0.22 g, 0.78 mmol), toluene-4-thiosulfonic acid S-(2-tert-butyl-4-hydroxymethyl-5-methyl-phenyl)ester (Example BB-2, 0.33 g, 0.90 mmol), potassium carbonate (1.0 g, 7.2 mmol), and DMF (4 mL). The product was chromatographed on silica gel, eluting with 10% MeOH in $CH_2Cl_2$, to give the title compound, mp 138–141° C.

$^1$H NMR (DMSO-$d_6$): δ0.90–0.96 (m, 6 H), 1.46 (s, 9 H), 1.85 (s, 3 H), 1.95–2.00 (m, 2 H), 2.15–2.23 (m, 4 H), 2.70–2.82 (m, 3 H), 2.93 (d of ABX q, 1 H), 4.34 (s, 2 H), 4.92 (br s, 1 H), 6.66 (s, 1 H), 7.24 (s, 1 H), 8.79 (s, 1 H).

EXAMPLE 25

3-(2-tert-Butyl-4-hydroxymethyl-5-methyl-phenylsulfanyl)-4-hydroxy-6-isopropyl-6-(2-thiazol-2-yl-ethyl)-5,6-dihydro-pyran-2-one The title compound was prepared according to General Method 16a using 4-hydroxy-6-isopropyl-6-(2-thiazol-2-yl-ethyl)-5,6-dihydro-pyran-2-one (Example E-2; 0.25 g, 0.95 mmol), toluene-4-thiosulfonic acid S-(2-tert-butyl-4- hydroxymethyl-5-methyl-phenyl)ester (Example BB-2; 0.42 g, 1.15 mmol), potassium carbonate (0.52 g, 3.76 mmol), and DMF (5 mL). The product was chromatographed on silica gel, eluting with 5% MeOH in $CH_2Cl_2$, to give the title compound, mp 108–110° C.

$^1$H NMR (DMSO-$d_6$): δ0.91–0.95 (m, 6 H), 1.46 (s, 9 H), 1.92 (s, 3 H), 2.18–2.24 (m, 3 H), 2.77 (d of ABX q, 1 H), 2.96 (d of ABX q, 1 H), 3.06 (br t, 2 H), 4.34 (s, 2 H), 4.90 (br s, 1 H), 6.68 (s, 1 H), 7.24 (s, 1 H), 7.57 (d, 1 H), 7.67 (d, 1 H).

EXAMPLE 26

3-(2-tert-Butyl-4-hydroxymethyl-5-methyl-phenylsulfanyl)-4-hydroxy-6-isopropyl-6-[2-(4-methyl-thiazol-2-yl)-ethyl]-5,6-dihydro-pyran-2-one The title compound was prepared according to General Method 16a using 4-hydroxy-6-isopropyl-6-[2-(4-methyl-thiazol-2-yl)-ethyl]-5,6-dihydro-pyran-2-one (Example E-6; 0.33 g, 1.2 mmol), toluene-4-thiosulfonic acid S-(2-tert-butyl-4-hydroxymethyl-5-methyl-phenyl)ester (Example BB-2, 0.51 g, 1.4 mmol), potassium carbonate (0.48 g, 3.5 mmol), and DMF (5 mL). The product was chromatographed on silica gel, eluting with 5% MeOH in $CH_2Cl_2$, to give the title compound, mp 98–100° C.

$^1$H NMR (DMSO-$d_6$): δ0.86–0.92 (m, 6 H), 1.42 (s, 9 H), 1.87 (s, 3 H), 2.15–2.20 (m, 3 H), 2.25 (s, 3 H), 2.71 (d of ABX q, 1 H), 2.83–2.95 (m, 3 H), 4.30 (s, 2 H), 4.89 (br s, 1 H), 6.64 (s, 1 H), 7.04 (s, 1 H), 7.20 (d, 1 H).

EXAMPLE 27

N-(4-{2-[5-(2-tert-Butyl-4-hydroxymethyl-5-methyl-phenylsulfanyl)-4-hydroxy-2-isopropyl-6-oxo-3,6-dihydro-2H-pyran-2-yl]-ethyl}-thiazol-2-yl)-acetamide The title compound was prepared according to General Method 16a using N-{4-[2-(4-hydroxy-2-isopropyl-6-oxo-3,6-dihydro-2H-pyran-2-yl)-ethyl]-thiazol-2-yl}-acetamide (Example E-13: 0.49 g, 1.5 mmol), toluene-4-thiosulfonic acid S-(2-tert-butyl-4-hydroxymethyl-5-methyl-phenyl) ester (Example BB-2; 0.66 g, 1.8 mmol), potassium carbonate (0.83 g, 6.0 mmol), and DMF (5 mL). The product was chromatographed on silica gel, eluting with 5% MeOH in $CH_2Cl_2$, to give the title compound, mp 128–130° C.

$^1$H NMR (DMSO-$d_6$): δ0.86–0.92 (m, 6 H), 1.42 (s, 9 H), 1.85 (s, 3 H), 2.05 (m, 5 H), 2.17 (m, 1 H), 2.59–2.67 (m, 3 H), 2.92 (d of ABX q, 1 H), 4.30 (s, 2 H), 4.89 (br s, 1 H), 6.25 (s, 1 H), 6.75 (s, 1 H), 7.20 (d, 1 H), 11.92 (br s, 1 H), 12.00 (s, 1 H).

TABLE L

Final Dihydropyrones

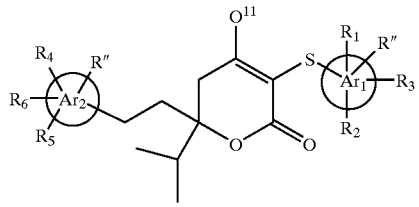

| Example | $Ar_2$ | Chirality at C-6 | $Ar_1$ | General Method | Melting Point (° C.) | Mass Spe (APCI) |
|---|---|---|---|---|---|---|
| 28 | 5-methyl-thiazol-2-yl | ± | 2-tert-butyl-4-hydroxymethyl-5-methyl-phenyl | 16a | 103–105 | 490 (M + H) |
| 29 | thiazol-5-yl | ± | 2-tert-butyl-4-hydroxymethyl-5-methyl-phenyl | 16a | 120–124 | 476 (M + H) |

TABLE L-continued
Final Dihydropyrones
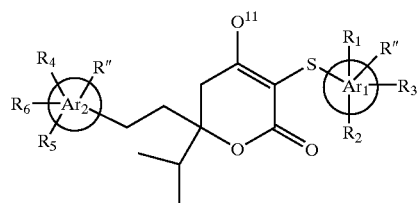
| Example | Ar₂ | Chirality at C-6 | Ar₁ | General Method | Melting Point (° C.) | Mass Spe (APCI) |
|---|---|---|---|---|---|---|
| 30 | | ± | | 16a | 118–121 | 490 (M + H) |
| 31 | | ± | | 16a | 105–108 | 490 (M + H) |
| 32 | | ± | | 16b | 97–100 | 518 (M + H) |
| 33 | | ± | | 16b | 109–112 | 518 (M + H) |
| 34 | | ± | | 16b | 108–112 | 518 (M + H) |

TABLE L-continued
Final Dihydropyrones
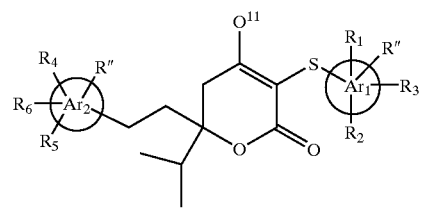
| Example | Ar₂ | Chirality at C-6 | Ar₁ | General Method | Melting Point (° C.) | Mass Spe (APCI) |
|---|---|---|---|---|---|---|
| 35 | 3-thienyl | ± | 4-tBu-2-Me-5-NH₂-phenyl | 16a | 93–98 | 460 (M + H) |
| 36 | 3-furyl | ± | 4-tBu-2-Me-5-NH₂-phenyl | 16a | 96–101 | 453 (M + H) |
| 37 | 5-(hydroxymethyl)-2-thienyl | ± | 4-tBu-2-Me-5-OH-phenyl | 16a | 90–96 | |
| 38 | 5-(hydroxymethyl)-2-thienyl | ± | 4-tBu-2-Me-5-NH₂-phenyl | 16a | 104–106 | 490 (M + H) |
| 39 | 5-(hydroxymethyl)-2-thienyl | ± | 4-tBu-2-Me-5-CH₂OH-phenyl | 16a | 110–117 | |

TABLE L-continued

Final Dihydropyrones

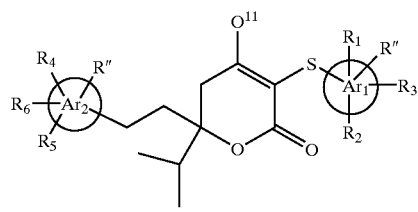

| Example | Ar$_2$ | Chirality at C-6 | Ar$_1$ | General Method | Melting Point (° C.) | Mass Spe (APCI) |
|---|---|---|---|---|---|---|
| 40 | 3-pyrazolyl (NH) | ± | 4-tBu-2-methyl-5-(hydroxymethyl)phenyl | 16a | 136–138 | 459 (M + H) |
| 41 | 3-pyrazolyl (NH) | ± | 4-tBu-2-methyl-5-amino-phenyl | 16a | 134–135 | 444 (M + H) |
| 42 | 5-pyrimidinyl | ± | 4-tBu-2-methyl-5-(hydroxymethyl)phenyl | 16a | 221–223 | 471 (M + H) |
| 43 | 5-pyrimidinyl | ± | 4-tBu-2-methyl-5-amino-phenyl | 16a | 120–122 | 456 (M + H) |
| 44 | 2-amino-5-pyrimidinyl | ± | 4-tBu-2-methyl-5-(hydroxymethyl)phenyl | 16a | 145–148 | 486 (M + H) |

TABLE L-continued

Final Dihydropyrones

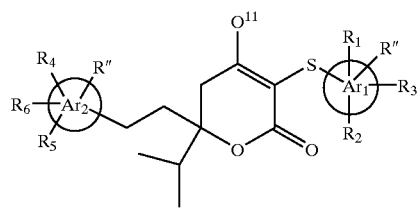

| Example | Ar₂ | Chirality at C-6 | Ar₁ | General Method | Melting Point (° C.) | Mass Spe (APCI) |
|---|---|---|---|---|---|---|
| 45 | 2-amino-pyrimidin-5-yl | ± | 4-tert-butyl-2-methyl-5-amino-phenyl | 16a | 137–140 | 471 (M + H) |
| 46 | thiazol-4-yl | ± | 4-tert-butyl-2-methyl-5-(hydroxymethyl)-phenyl | 16a | 115–118 | 476 (M + H) |
| 47 | Ph | S | 6-isopropyl-benzothiazol-5-yl | 16b | 197–199 | 468 (M + H) |
| 48 | 4-hydroxyphenyl | S | 6-isopropyl-benzothiazol-5-yl | 16b | 142 | 483 (M) |
| 49 | 4-fluorophenyl | ± | 2-amino-4-methyl-7-isopropyl-benzothiazol-6-yl | 16a | 158–160 | |

TABLE L-continued
Final Dihydropyrones
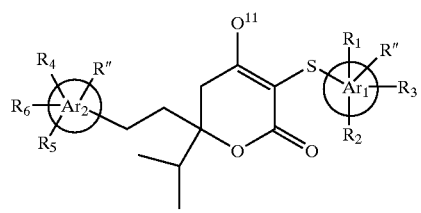
| Example | Ar$_2$ | Chirality at C-6 | Ar$_1$ | General Method | Melting Point (° C.) | Mass Spe (APCI) |
|---|---|---|---|---|---|---|
| 50 | HO-⌬- | S | tBu-⌬(tBu)-benzothiazol-2-amine | 16a | 232–234 | 513 (M + H) |
| 51 | HO-⌬- | S | iPr-⌬-benzothiazol-2-amine | 16b | 204–206 | |
| 52 | thiophen-3-yl | R | tBu-⌬(Me)-CH$_2$OH phenyl | 16a | 73–85 | 475 (M + H) |
| 53 | 2-CF$_3$-phenyl | ± | iPr-⌬-benzothiazol-2-amine | 16b | 107–109 | 551 (M + H) |
| 54 | pyridin-3-yl | ± | tBu-⌬(Me)-NH$_2$ phenyl | 16a | 118–123 | |

TABLE L-continued
Final Dihydropyrones
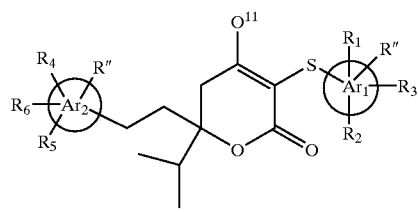
| Example | Ar$_2$ | Chirality at C-6 | Ar$_1$ | General Method | Melting Point (° C.) | Mass Spe (APCI) |
|---|---|---|---|---|---|---|
| 55 | | ± | | 16a | 80–87 | |
| 56 | | ± | | 16a | 70–73 | |
| 57 | | ± | | 16a | | 461 (M + H) |
| 58 | | ± | | 16a | 89–91 | 489 (M + H) |
| 59 | | ± | | 16a | | 669 |

TABLE L-continued

Final Dihydropyrones

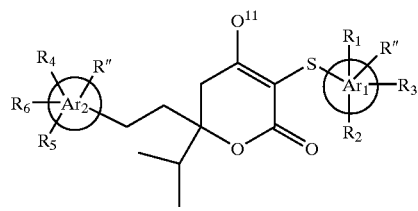

| Example | Ar₂ | Chirality at C-6 | Ar₁ | General Method | Melting Point (° C.) | Mass Spe (APCI) |
|---|---|---|---|---|---|---|
| 60 | 3-pyridyl | I | 4-tert-butyl-2-methyl-5-(5-trifluoromethylpyridin-2-ylsulfonamido)phenyl | 16a | | 663 |
| 61 | indol-5-yl | ± | 4-tert-butyl-2-methyl-5-hydroxymethylphenyl | 16a | 95–96 | 508 (M + H) |
| 62 | 3-hydroxymethylthiophen-2-yl | ± | 4-tert-butyl-5-amino-2-methylphenyl | 16b | 107–113 | 488 (M − H) |
| 63 | 2-methylthiophen-3-yl | S | 4-tert-butyl-2-methyl-5-hydroxymethylphenyl | 16a | 115 | 487 (M − H) |
| 64 | 3-methylthiophen-2-yl | ± | 4-tert-butyl-2-methyl-5-hydroxymethylphenyl | 16a | 86–90 | 487 (M − H) |

TABLE L-continued
Final Dihydropyrones
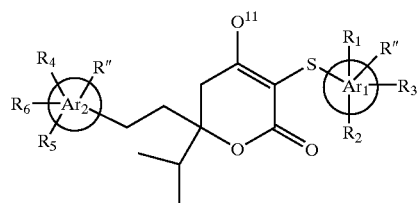
| Example | Ar$_2$ | Chirality at C-6 | Ar$_1$ | General Method | Melting Point (° C.) | Mass Spe (APCI) |
|---|---|---|---|---|---|---|
| 65 | | ± | | 16a | 98–101 | 472 (M − H) |
| 66 | | ± | | 16a | | 489 (M + H) |
| 67 | | ± | | 16a | 104–106 | 488 (M − H) |
| 68 | | ± | | 16a | 104–105 | 498 (M + H) |
| 69 | | ± | | 16a followed by NaOH deprotection | 125–126 | 494 (M + H) |

TABLE L-continued
Final Dihydropyrones
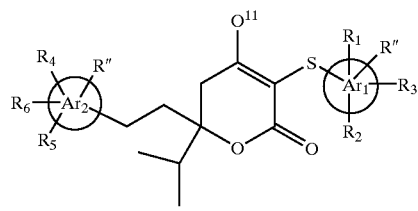
| Example | Ar₂ | Chirality at C-6 | Ar₁ | General Method | Melting Point (° C.) | Mass Spe (APCI) |
|---|---|---|---|---|---|---|
| 70 | HO-C₆H₄- | S | 5-tBu-6-indoline-N-SO₂-C₆H₄-CN | 16a | 138–140 | 647 (M + H) |
| 71 | HO-C₆H₄- | S | 5-tBu-6-indole-NBOC | 16a | 171–173 | 580 (M + H) |
| 72 | HO-C₆H₄- | S | 5-tBu-6-indole-NH | 16a followed by NaOH deprotection | 103–105 | 480 (M + H) |
| 73 | C₆H₅- | S | 5-tBu-6-indole-NH | 16a followed by NaOH deprotection | 123–125 | 464 (M + H) |

TABLE L-continued
Final Dihydropyrones
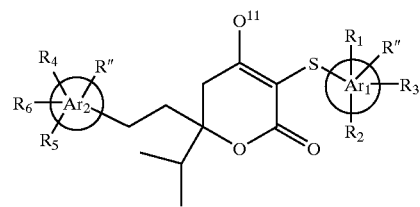
| Example | Ar$_2$ | Chirality at C-6 | Ar$_1$ | General Method | Melting Point (° C.) | Mass Spe (APCI) |
|---|---|---|---|---|---|---|
| 74 | 4-F-phenyl | S | 5-tert-butyl-2-amino-benzothiazol-6-yl | 16a | 122–124 | 515 (M + H) |
| 75 | phenyl | S | 5-isopropyl-1H-benzimidazol-6-yl | 16a | 222–224 | 451 (M + H) |
| 76 | phenyl | S | 5-isopropyl-2-oxo-2,3-dihydro-1H-benzimidazol-6-yl | 16a | 158–160 | 467 (M + H) |
| 77 | phenyl | S | 5-tert-butyl-1H-benzimidazol-6-yl | 16a | 203–205 | 465 (M + H) |

TABLE L-continued
Final Dihydropyrones
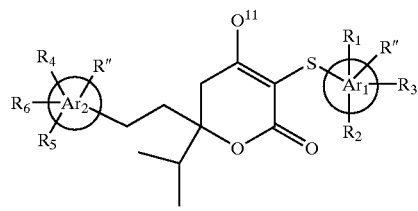
| Example | Ar$_2$ | Chirality at C-6 | Ar$_1$ | General Method | Melting Point (° C.) | Mass Spe (APCI) |
|---|---|---|---|---|---|---|
| 78 | phenyl | S | 5-tert-butyl-benzimidazol-2(3H)-one-6-yl | 16a | 232–234 | 481 (M + H) |
| 79 | phenyl | S | 5-tert-butyl-2-(methanesulfonamido)benzothiazol-6-yl | 16a | 152–153 | 573 (M − H) |
| 80 | phenyl | S | 5-tert-butyl-2-(ethoxycarbonyl)indol-6-yl | 16a | 192–194 | 536 (M + H) |
| 81 | phenyl | S | 5-tert-butyl-2-carboxyindol-6-yl | Saponification of Example 80 with LiOH | 123–125 | 506 (M − H) |

TABLE L-continued
Final Dihydropyrones
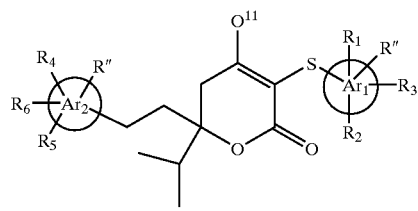
| Example | Ar₂ | Chirality at C-6 | Ar₁ | General Method | Melting Point (° C.) | Mass Spe (APCI) |
|---|---|---|---|---|---|---|
| 82 | 3-thienyl | ± | 5-tert-butyl-2-aminobenzothiazol-6-yl | 16a | 190–192 | 503 (M + H) |
| 83 | 3-fluorophenyl | ± | 5-tert-butyl-2-aminobenzothiazol-6-yl | 16a | 193–195 | 515 (M + H) |
| 84 | 3-fluoro-2-methylphenyl | ± | 5-tert-butyl-2-aminobenzothiazol-6-yl | 16a | 180–182 | 529 (M + H) |
| 85 | 3,5-difluorophenyl | S | 5-tert-butyl-2-aminobenzothiazol-6-yl | 16a | 173–175 | 533 (M + H) |

TABLE L-continued

Final Dihydropyrones

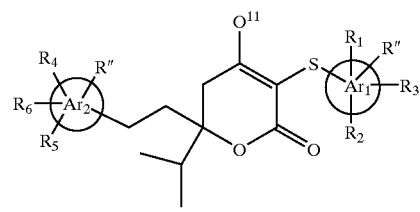

| Example | Ar$_2$ | Chirality at C-6 | Ar$_1$ | General Method | Melting Point (° C.) | Mass Spe (APCI) |
|---|---|---|---|---|---|---|
| 86 | phenyl (gem-dimethyl) | S | 6-tert-butyl-2-(NHCOMe)-benzothiazole | 16a | 175–177 | 539 (M + H) |
| 87 | thiophen-3-yl (gem-dimethyl) | S | 6-tert-butyl-2-[NHSO$_2$(4-CN-C$_6$H$_4$)]-benzothiazole | 16a | 221–222 | 668 (M + H) |
| 88 | 4-fluoro-2-methylphenyl (gem-dimethyl) | S | 6-tert-butyl-2-amino-benzothiazole | 16a | >173 | 529 (M + H) |
| 89 | 2-amino-thiazol-4-yl (gem-dimethyl) | ± | 4-tert-butyl-2-methyl-5-(hydroxymethyl)phenyl | 16a followed by NH$_3$/MeOH deprotection | 208–210 | 491 (M + 1) |

TABLE L-continued

Final Dihydropyrones

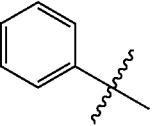

| Example | Ar$_2$ | Chirality at C-6 | Ar$_1$ | General Method | Melting Point (° C.) | Mass Spe (APCI) |
|---|---|---|---|---|---|---|
| 90 | 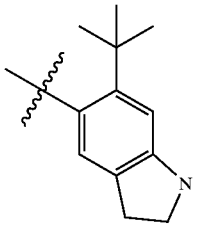 | + | 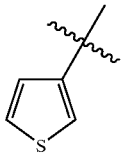 | 16a followed by HCl (g) deprotection | | 482 (M + 1) |
| 91 | 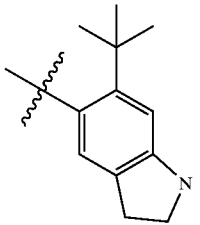 | + | 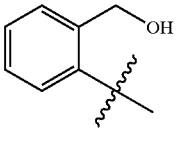 | 16a followed by HCl (g) deprotection | | 472 (M + 1) |
| 92 | 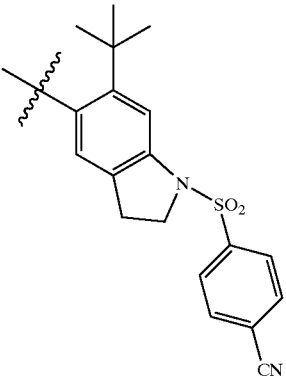 | ± | | 16a | 155–157 | 659 (M − 1) |

The Table L above shows the compounds of the invention as racemic; however, the R and S forms are within the scope of the invention. The S form is the preferred.

The compound names corresponding to Examples 28–60 in Table L above are:

Example 28: 3-(2-tert-Butyl-4-hydroxymethyl-5-methyl-phenylsulfanyl)-4-hydroxy-6-isopropyl-6-[2-(5-methyl-thiazol-2-yl)-ethyl]-5,6-dihydro-pyran-2-one;

Example 29: 3-(2-tert-Butyl-4-hydroxymethyl-5-methyl-phenylsulfanyl)-4-hydroxy-6-isopropyl-6-(2-thiazol-5-yl-ethyl)-5,6-dihydro-pyran-2-one Example 30: 3-(2-tert-Butyl-4-hydroxymethyl-5-methyl-phenylsulfanyl)-4-hydroxy-6-isopropyl-6-[2-(2-methyl-thiazol-4-yl)-ethyl]-5,6-dihydro-pyran-2-one;

Example 31: 3-(2-tert-Butyl-4-hydroxymethyl-5-methyl-phenylsulfanyl)-4-hydroxy-6-isopropyl-6-[2-(5-methyl-thiazol-4-yl)-ethyl]-5,6-dihydro-pyran-2-one;

Example 32: 3-(2-tert-Butyl-4-hydroxymethyl-5-methyl-phenylsulfanyl)-4-hydroxy-6-isopropyl-6-[2-(2-isopropyl-thiazol-4-yl)-ethyl]-5,6-dihydro-pyran-2-one;

Example 33: 3-(2-tert-Butyl-4-hydroxymethyl-5-methyl-phenylsulfanyl)-4-hydroxy-6-isopropyl-6-[2-(4-isopropyl-thiazol-5-yl)-ethyl]-5,6-dihydro-pyran-2-one;

Example 34: 3-(2-tert-Butyl-4-hydroxymethyl-5-methyl-phenylsulfanyl)-4-hydroxy-6-isopropyl-6-[2-(5-isopropy)-thiazol-4-yl)-ethyl]-5,6-dihydro-pyran-2-one;

Example 35: 3-(4-Amino-2-tert-butyl-5-methyl-phenylsulfanyl)-4-hydroxy-6-isopropyl-6-(2-thiophen-3-yl-ethyl)-5,6-dihydro-pyran-2-one;

Example 36: 3-(4-Amino-2-tert-butyl-5-methyl-phenylsulfanyl)-6-(2-furan-3-yl-ethyl)-4-hydroxy-6-isopropyl-5,6-dihydro-pyran-2-one;

Example 37: 3-(2-tert-Butyl-4-hydroxy-5-methyl-phenylsulfanyl)-4-hydroxy-6-[2-(5-hydroxymethyl-thiophen-2-yl)-ethyl]-6-isopropyl-5,6-dihydro-pyran-2-one;

Example 38: 3-(4-Amino-2-tert-butyl-5-methyl-phenylsulfanyl)-4-hydroxy-6-[2-(5-hydroxymethyl-thiophen-2-yl)-ethyl]-6-isopropyl-5,6-dihydro-pyran-2-one;

Example 39: 3-(2-tert-Butyl-4-hydroxymethyl-5-methyl-phenylsulfanyl)-4-hydroxy-6-[2-(5-hydroxymethyl-thiophen-2-yl)-ethyl]-6-isopropyl-5,6-dihydro-pyran-2-one;

Example 40: 3-(2-tert-Butyl-4-hydroxymethyl-5-methyl-phenylsulfanyl)-4-hydroxy-6-isopropyl-6-[2-(1H-pyrazol-3-yl)-ethyl]-5,6-dihydro-pyran-2-one;

Example 41: 3-(4-Amino-2-tert-butyl-5-methyl-phenylsulfanyl)-4-hydroxy-6-isopropyl-[2-(1H-pyrazol-3-yl)-ethyl]-5,6-dihydro-pyran-2-one;

Example 42: 3-(2-tert-Butyl-4-hydroxymethyl-5-methyl-phenylsulfanyl)-4-hydroxy-6-isopropyl-6-(2-pyrimidin-5-yl-ethyl)-5,6-dihydro-pyran-2-one;

Example 43: 3-(4-Amino-2-tert-butyl-5-methyl-phenylsulfanyl)-4-hydroxy-6-isopropyl-6-(2-pyrimidin-5-yl-ethyl)-5,6-dihydro-pyran-2-one;

Example 44: 6-[2-(2-Amino-pyrimidin-5-yl)-ethyl]-3-(2-tert-butyl-4-hydroxymethyl-5-methyl-phenylsulfanyl)-4-hydroxy-6-isopropyl-5,6-dihydro-pyran-2-one;

Example 45: 3-(4-Amino-2-tert-butyl-5-methyl-phenylsulfanyl)-6-[2-(2-amino-pyrimidin-5-yl)-ethyl]-4-hydroxy-6-isopropyl-5,6-dihydro-pyran-2-one;

Example 46: 3-(2-tert-Butyl-4-hydroxymethyl-5-methyl-phenylsulfanyl)-4-hydroxy-6-isopropyl-6-(2-thiazol-4-yl-ethyl)-5,6-dihydro-pyran-2-one;

Example 47: (S)-4-Hydroxy-6-isopropyl-3-(5-isopropyl-benzothiazol-6-ylsulfanyl)-6-phenethyl-5,6-dihydro-pyran-2-one;

Example 48: (S)-4-Hydroxy-6-[2-(4-hydroxy-phenyl)-ethyl]-6-isopropyl-3-(5-isopropyl-benzothiazol-6-ylsulfanyl)-5,6-dihydro-pyran-2-one;

Example 49: 3-(2-Amino-7-isopropyl-4-methyl-benzothiazol-6-ylsulfanyl)-6-[2-(4-fluoro-phenyl)-ethyl]-4-hydroxy-6-isopropyl-5,6-dihydro-pyran-2-one;

Example 50: (S)-3-(2-Amino-5-tert-butyl-benzothiazol-6-ylsulfanyl)-4-hydroxy-6-[2-(4-hydroxy-phenyl)-ethyl]-6-isopropyl-5,6-dihydro-pyran-2-one;

Example 51: (S)-3-(2-Amino-5-isopropyl-benzothiazol-6-ylsulfanyl)-4-hydroxy-6-[2-(4-hydroxy-phenyl)-ethyl]-6-isopropyl-5,6-dihydro-pyran-2-one;

Example 52: (R)-3-(2-tert-Butyl-4-hydroxymethyl-5-methyl-phenylsulfanyl)-4-hydroxy-6-isopropyl-6-(2-thiophen-3-yl-ethyl)-5,6-dihydro-pyran-2-one;

Example 53: 3-(2-Amino-5-isopropyl-benzothiazol-6-ylsulfanyl)-4-hydroxy-6-isopropyl-6-[2-(2-trifluoromethyl-phenyl)-ethyl]-5,6-dihydro-pyran-2-one;

Example 54: 3-(4-Amino-2-tert-butyl-5-methyl-phenylsulfanyl)-4-hydroxy-6-isopropyl-6-(2-pyridin-3-yl-ethyl)-5,6-dihydro-pyran-2-one;

Example 55: 3-(2-tert-Butyl-5-methyl-phenylsulfanyl)-4-hydroxy-6-[2-(5-hydroxymethyl-thiophen-2-yl)-ethyl]-6-isopropyl-5,6-dihydro-pyran-2-one;

Example 56: 3-(4-Amino-2-tert-butyl-5-methyl-phenylsulfanyl)-4-hydroxy-6-isopropyl-6-[2-(tetrahydro-furan-2-yl)-ethyl]-5,6-dihydro-pyran-2-one;

Example 57: 3-(2-tert-Butyl-4-hydroxymethyl-phenylsulfanyl)-4-hydroxy-6-isopropyl-6-(2-thiophen-3-yl-ethyl)-5,6-dihydro-pyran-2-one;

Example 58: 3-[2-tert-Butyl-4-(2-hydroxy-ethyl)-5-methyl-phenylsulfanyl]-4-hydroxy-6-isopropyl-6-(2-thiophen-3-yl-ethyl)-5,6-dihydro-pyran-2-one;

Example 59: 5-Trifluoromethyl-pyridine-2-sulfonic acid {5-tert-butyl-4-[4-hydroxy-6-isopropyl-2-oxo-6-(2-thiophen-3-yl-ethyl)-5,6-dihydro-2H-pyran-3-ylsulfanyl]-2-methyl-phenyl}-amide; and Example 60: 5-Trifluoromethyl-pyridine-2-sulfonic acid {5-tert-butyl-4-[4-hydroxy-6-isopropyl-2-oxo-6-(2-pyridin-3-yl-ethyl)-5,6-dihydro-2H-pyran-3-ylsulfanyl]-2-methyl-phenyl}-amide:

Example 61: 3-(2-tert-Butyl-4-hydroxymethyl-5-methyl-phenylsulfanyl)-4-hydroxy-6-[2-(1H-indol-5-yl)-ethyl]-6-isopropyl-5,6-dihydro-pyran-2-one;

Example 62: 3-(2-tert-Butyl-4-hydroxymethyl-5-methyl-phenylsulfanyl)-4-hydroxy-6-isopropyl-6-[2-(2-methyl-thiophen-3-yl)-ethyl]-5,6-dihydro-pyran-2-one;

Example 63: (S)-3-(2-tert-Butyl-4-hydroxymethyl-5-methyl-phenylsulfanyl)-4-hydroxy-6-isopropyl-6-[2-(2-methyl-thiophen-3-yl)-ethyl]-5,6-dihydro-pyran-2-one;

Example 64: 3-(2-tert-Butyl-4-hydroxymethyl-5-methyl-phenylsulfanyl)-4-hydroxy-6-isopropyl-6-[2-(3-methyl-thiophen-2-yl)-ethyl]-5,6-dihydro-pyran-2-one;

Example 65: 3-(4-Amino-2-tert-butyl-5-methyl-phenylsulfanyl)-4-hydroxy-6-isopropyl-6-[2-(3-methyl-thiophen-2-yl)-ethyl]-5,6-dihydro-pyran-2-one;

Example 66: 3-(2-tert-Butyl-4-hydroxymethyl-5-methyl-phenylsulfanyl)-4-hydroxy-6-isopropyl-6-[2-(4-methyl-thiophen-3-yl)-ethyl]-5,6-dihydro-pyran-2-one;

Example 67: 3-(4-Amino-2-tert-butyl-5-methyl-phenylsulfanyl)-4-hydroxy-6-[2-(4-hydroxymethyl-thiophen-3-yl)-ethyl]-6-isopropyl-5,6-dihydro-pyran-2-one;

Example 68: 4-Hydroxy-6-[2-(2-hydroxymethyl-phenyl)-ethyl]-6-isopropyl-3-(5-isopropyl-benzothiazol-6-ylsulfanyl)-5,6-dihydro-pyran-2-one;

Example 69: 4-Hydroxy-3-(6-tert-butyl-indol-5-ylsulfanyl)-6-[2-(2-hydroxymethyl-phenyl)-ethyl]6-isopropyl-5,6-dihydropyran-2-one;

Example 70: (S)-N-[6-tert-Butyl-5-(4-hydroxy-6-isopropyl-2-oxo-6-[2-(4-hydroxy-phenyl)ethyl]-5,6-dihydro-2H-pyran-3-ylsulfanyl)-indolin-1yl]-(4-cyanophenyl) sulfonamide;

Example 71: (S)-6-tert-Butyl-5-{4-hydroxy-6-[2-(4-hydroxy-phenyl)-ethyl]-6-isopropyl-2-oxo-5,6-dihydro-2H-pyran-3-ylsulfanyl}-indole-1-carboxylic acid tert-butyl ester;

Example 72: (S)-3-(6-tert-Butyl-indol-5-yl-sulfanyl)-4-hydroxy 6-[2-(4-hydroxy-phenyl)-ethyl]6-isopropyl-5,6-dihydro-pyran-2-one;

Example 73: (S)-3-(6-tert-Butyl-1H-indol-5-yl-sulfanyl)-4-hydroxy-6-isopropyl-6-(2-phenethyl)-5,6-dihydro-pyran-2-one;

Example 74: (S)-3-(2-Amino-5-tert-butyl-benzothiazol-6-ylsulfanyl)-6-[2-(4-fluoro-phenyl)-ethyl]-4-hydroxy-6-isopropyl-5,6-dihydro-pyran-2-one;

Example 75: (S)-4-Hydroxy-6-isopropyl-3-(6-isopropyl-3H-benzoimidazol-5-ylsulfanyl)-6-(2-phenethyl)-5,6-dihydro-pyran-2-one;

Example 76: (S)-5-(4-Hydroxy-6-isopropyl-2-oxo-6-phenethyl-5,6-dihydro-2H-pyran-3-ylsulfanyl)-6-isopropyl-1,3-dihydro-benzoimidazol-2-one;

Example 77: (S)-3-(6-tert-Butyl-3H-benzoimidazol-5-ylsulfanyl)-4-hydroxy-6-isopropyl-6-(2-phenethyl)-5,6-dihydro-pyran-2-one;

Example 78: (S)-5-tert-Butyl-6-(4-hydroxy-6-isopropyl-2-oxo-6-(2-phenethyl)-5,6-dihydro-2H-pyran-3-ylsulfanyl)-1,3-dihydro-benzoimidazol-2-one;

Example 79: (S)-N-[5-tert-Butyl-6-(4-hydroxy-6-isopropyl-2-oxo-6-phenethyl-5,6-dihydro-2H-pyran-3-ylsulfanyl)-benzothiazol-2-yl]-methanesulfonamide;

Example 80: 6-tert-Butyl-5-(4-hydroxy-6-isopropyl-2-oxo-6-phenethyl-5,6-dihydro-2H-pyran-3-ylsulfanyl)-1H-indole-2-carboxylic acid ethyl ester;

Example 81: 6-tert-Butyl-5-(4-hydroxy-6-isopropyl-2-oxo-6-phenethyl-5,6-dihydro-2H-pyran-3-ylsulfanyl)-1H-indole-2-carboxylic acid;

Example 82: 3-(2-Amino-5-tert-butyl-benzothiazol-6-ylsulfanyl)-4-hydroxy-6-isopropyl-6-[(2-(3-thiophenyl)-ethyl)-5,6-dihydro-pyran-2-one;

Example 83: (S)-3-(2-Amino-5-tert-butyl-benzothiazol-6-ylsulfanyl)-6-[2-(3-fluoro-phenyl)-ethyl]-4-hydroxy-6-isopropyl-5,6-dihydro-pyran-2-one;

Example 84: 3-(2-Amino-5-tert-butyl-benzothiazol-6-ylsulfanyl)-6-[2-(3-fluoro-2-methyl-phenyl)-ethyl]-4-hydroxy-6-isopropyl-5,6-dihydro-pyran-2-one;

Example 85: (S)-3-(2-Amino-5-tert-butyl-benzothiazol-6-ylsulfanyl)-6-[2-(3,5-difluoro-phenyl)-ethyl]-4-hydroxy-6-isopropyl-5,6-dihydro-pyran-2-one;

Example 86: (S)-N-[5-tert-Butyl-6-(4-hydroxy-6-isopropyl-2-oxo-6-(2-phenethyl)-5,6-dihydro-2H-pyran-3-ylsulfanyl)-benzothiazol-2-yl]-acetamide;

Example 87: (S)-N-{5-tert-Butyl-6-(4-hydroxy-6-isopropyl-2-oxo-6-(2-thiophen-3-yl-ethyl-5,6-dihydro-2H-pyran-3-ylsulfanyl)-benzothiazol-2-yl}-4-cyanobenzenesulfonamide;

Example 88: (S)-3-(2-Amino-5-tert-butyl-benzothiazol-6-ylsulfanyl)-6-[2-(4-fluoro-2-methyl-phenyl)-ethyl]-4-hydroxy-6-isopropyl-5,6-dihydro-pyran-2-one;

Example 89: 6-[2-(2-Amino-thiazol-4-yl)-ethyl]-3-(2-tert-butyl-4-hydroxymethyl-5-methyl-phenylsulfanyl)-4-hydroxy-6-isopropyl-5,6-dihydro-pyran-2-one;

Example 90: (S)-3-(6-tert-Butyl-2,3-dihydro-1H-indol-5-ylsulfanyl)-4-hydroxy-6-[2-(4-hydroxy-phenyl)-ethyl]-6-isopropyl-5,6-dihydro-pyran-2-one;

Example 91: (S)-3-(6-tert-Butyl-2,3-dihydro-1H-indol-5-ylsulfanyl)-4-hydroxy-6-isopropyl-6-[(2-(3-thiophenyl)-ethyl)-5,6-dihydro-pyran-2-one; and Example 92: 4-(6-tert-Butyl-5-{4-hydroxy-6-[2-(2-hydroxymethyl-phenyl)-ethyl]-6-isopropyl-2-oxo-5,6-dihydro-2H-pyran-3-ylsulfanyl}-2,3-dihydro-indole-1-sulfonyl)-benzonitrile.

Other compounds which can be prepared by the above methods include:

3-(4-Amino-2-tert-butyl-5-methyl-phenylsulfanyl)-4-hydroxy-6-[2-(3-hydroxymethyl-thiophen-2-yl)-ethyl]-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(3-methyl-thiophen-2-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(2-methyl-thiophen-3-yl)-ethyl]-5,6-dihydro-pyran-2-one;

3-(4-Amino-2-tert-butyl-5-methyl-phenylsulfanyl)-4-hydroxy-6-[2-(4-hydroxymethyl-thiophen-3-yl)-ethyl]-6-isopropyl-5,6-dihydro-pyran-2-one 3-(2-tert-Butyl-4-hydroxymethyl-5-methyl-phenylsulfanyl)-4-hydroxy-6-isopropyl-6-[2-(4-methyl-thiophen-3-yl)-ethyl]-5,6-dihydro-pyran-2-one;

3-(2-Cyclopentyl-4-hydroxymethyl-5-methyl-phenylsulfanyl)-4-hydroxy-6-isopropyl-6-(2-thiophen-3-yl-ethyl)-5,6-dihydro-pyran-2-one;

3-(4-Amino-2-cyclopentyl-5-methyl-phenylsulfanyl)-4-hydroxy-6-[2-(2-hydroxymethyl-thiophen-3-yl)-ethyl]-6-isopropyl-5,6-dihydro-pyran-2-one;

3-(4-Amino-2-cyclopentyl-5-methyl-phenylsulfanyl)-4-hydroxy-6-[2-(4-hydroxymethyl-thiophen-3-yl)-ethyl]-6-isopropyl-5,6-dihydro-pyran-2-one;

3-(6-tert-Butyl-1-hydroxy-indan-5-ylsulfanyl)-4-hydroxy-6-isopropyl-6-(2-thiophen-3-yl-ethyl)-5,6-dihydro-pyran-2-one;

3-(6-tert-Butyl-1-hydroxy-indan-5-ylsulfanyl)-4-hydroxy-6-[2-(2-hydroxymethyl-thiophen-3-yl)-ethyl]-6-isopropyl-5,6-dihydro-pyran-2-one;

3-(6-tert-Butyl-1-hydroxy-indan-5-ylsulfanyl)-4-hydroxy-6-[2-(4-hydroxymethyl-thiophen-3-yl)-ethyl]-6-isopropyl-5,6-dihydro-pyran-2-one;

3-(4-Amino-2-tert-butyl-5-methyl-phenylsulfanyl)-4-hydroxy-6-[2-(2-hydroxymethyl-furan-3-yl)-ethyl]-6-isopropyl-5,6-dihydro-pyran-2-one;

3-(4-Amino-2-tert-butyl-5-methyl-phenylsulfanyl)-4-hydroxy-6-[2-(3-hydroxymethyl-furan-2-yl)-ethyl]-6-isopropyl-5,6-dihydro-pyran-2-one;

3-(4-Amino-2-tert-butyl-5-methyl-phenylsulfanyl)-4-hydroxy-6-[2-(4-hydroxymethyl-furan-3-yl)-ethyl]-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(2-methyl-furan-3-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(3-methyl-furan-2-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(4-methyl-furan-3-yl)-ethyl]-5,6-dihydro-pyran-2-one;

3-(2-Cyclopentyl-4-hydroxymethyl-5-methyl-phenylsulfanyl)-6-(2-furan-3-yl-ethyl)-4-hydroxy-6-isopropyl-5,6-dihydro-pyran-2-one;

3-(6-tert-Butyl-1-hydroxy-indan-5-ylsulfanyl)-6-(2-furan-3-yl-ethyl)-4-hydroxy-6-isopropyl-5,6-dihydro-pyran-2-one;

3-(4-Amino-2-tert-butyl-5-methyl-phenylsulfanyl)-4-hydroxy-6-[2-(4-hydroxymethyl-thiazol-5-yl)-ethyl]-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(4-methyl-thiazol-5-yl)-ethyl]-5,6-dihydro-pyran-2-one;

3-(4-Amino-2-tert-butyl-5-methyl-phenylsulfanyl)-4-hydroxy-6-[2-(5-hydroxymethyl-thiazol-4-yl)-ethyl]-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(5-methyl-thiazol-4-yl)-ethyl]-5,6-dihydro-pyran-2-one;

6-[2-(2-Amino-thiazol-4-yl)-ethyl]-3-(2-tert-butyl-4-hydroxymethyl-5=methyl-phenylsulfanyl)-4-hydroxy-6-isopropyl-5,6-dihydro-pyran-2-one;

6-[2-(2-Amino-thiazol-5-yl)-ethyl]-3-(2-tert-butyl-4-hydroxymethyl-5-methyl-phenylsulfanyl)-4-hydroxy-6-isopropyl-5,6-dihydro-pyran-2-one;

3-(2-tert-Butyl-4-hydroxymethyl-5-methyl-phenylsulfanyl)-4-hydroxy-6-isopropyl-6-(2-isothiazol-4-yl-ethyl)-5,6-dihydro-pyran-2-one;

3-(2-tert-Butyl-4-hydroxymethyl-5-methyl-phenylsulfanyl)-4-hydroxy-6-isopropyl-6-(2-isothiazol-5-yl-ethyl)-5,6-dihydro-pyran-2-one;

3-(2-tert-Butyl-4-hydroxymethyl-5-methyl-phenylsulfanyl)-4-hydroxy-6-isopropyl-6-(2-isothiazol-3-yl-ethyl)-5,6-dihydro-pyran-2-one;

3-(2-tert-Butyl-4-hydroxymethyl-5-methyl-phenylsulfanyl)-4-hydroxy-6-isopropyl-6-[2-(4-methyl-oxazol-5-yl)-ethyl]-5,6-dihydro-pyran-2-one;

3-(4-Amino-2-tert-butyl-5-methyl-phenylsulfanyl)-4-hydroxy-6-[2-(1H-indol-5-yl)-ethyl]-6-isopropyl-5,6-dihydro-pyran-2-one;

3-(2-tert-Butyl-4-hydroxymethyl-5-methyl-phenylsulfanyl)-4-hydroxy-6-[2-(1H-indol-5-yl)-ethyl]-6-isopropyl-5,6-dihydro-pyran-2-one;

3-(4-Amino-2-tert-butyl-5-methyl-phenylsulfanyl)-4-hydroxy-6-[2-(1H-indazol-5-yl)-ethyl]-6-isopropyl-5,6-dihydro-pyran-2-one;

3-(2-tert-Butyl-4-hydroxymethyl-5-methyl-phenylsulfanyl)-4-hydroxy-6-[2-(1H-indazol-5-yl)-ethyl]-6-isopropyl-5,6-dihydro-pyran-2-one;

3-(4-Amino-2-tert-butyl-5-methyl-phenylsulfanyl)-6-[2-(1H-benzoimidazol-5-yl)-ethyl]-4-hydroxy-6-isopropyl-5,6-dihydro-pyran-2-one;

6-[2-(1H-Benzoimidazol-5-yl)-ethyl]-3-(2-tert-butyl-4-hydroxymethyl-5-methyl-phenylsulfanyl)-4-hydroxy-6-isopropyl-5,6-dihydro-pyran-2-one;

3-(4-Amino-2-tert-butyl-5-methyl-phenylsulfanyl)-6-[2-(3-amino-1H-indazol-5-yl)-ethyl]-4-hydroxy-6-isopropyl-5,6-dihydro-pyran-2-one;

6-[2-(3-Amino-1H-indazol-5-yl)-ethyl]-3-(2-tert-butyl-4-hydroxymethyl-5-methyl-phenylsulfanyl)-4-hydroxy-6-isopropyl-5,6-dihydro-pyran-2-one;

3-(4-Amino-2-tert-butyl-5-methyl-phenylsulfanyl)-4-hydroxy-6-[2-(1H-indol-4-yl)-ethyl]-6-isopropyl-5,6-dihydro-pyran-2-one;

3-(2-tert-Butyl-4-hydroxymethyl-5-methyl-phenylsulfanyl)-4-hydroxy-6-[2-(1H-indol-4-yl)-ethyl]-6-isopropyl-5,6-dihydro-pyran-2-one;

3-(4-Amino-2-tert-butyl-5-methyl-phenylsulfanyl)-4-hydroxy-6-[2-(1H-indazol-4-yl)-ethyl]-6-isopropyl-5,6-dihydro-pyran-2-one;

3-(2-tert-Butyl-4-hydroxymethyl-5-methyl-phenylsulfanyl)-4-hydroxy-6-[2-(1H-indazol-4-yl)-ethyl]-6-isopropyl-5,6-dihydro-pyran-2-one;

3-(4-Amino-2-tert-butyl-5-methyl-phenylsulfanyl)-6-[2-(3-amino-1H-indazol-4-yl)-ethyl]-4-hydroxy-6-isopropyl-5,6-dihydro-pyran-2-one;

6-[2-(3-Amino-1H-indazol-4-yl)-ethyl]-3-(2-tert-butyl-4-hydroxymethyl-5-methyl-phenylsulfanyl)-4-hydroxy-6-isopropyl-5,6-dihydro-pyran-2-one;

3-(2-tert-Butyl-6-hydroxymethyl-5-methyl-pyridin-3-ylsulfanyl)-6-[2-(4-fluoro-phenyl)-ethyl]-4-hydroxy-6-isopropyl-5,6-dihydro-pyran-2-one;

3-(2-tert-Butyl-5-methyl-pyridin-3-ylsulfanyl)-4-hydroxy-6-[2-(2-hydroxymethyl-phenyl)-ethyl]-6-isopropyl-5,6-dihydro-pyran-2-one;

3-(3-tert-Butyl-2-hydroxymethyl-6-methyl-pyridin-4-ylsulfanyl)-6-[2-(4-fluoro-phenyl)-ethyl]-4-hydroxy-6-isopropyl-5,6-dihydro-pyran-2-one;

3-(5-tert-Butyl-2-methyl-pyridin-4-ylsulfanyl)-4-hydroxy-6-[2-(2-hydroxymethyl-phenyl)-ethyl]-6-isopropyl-5,6-dihydro-pyran-2-one;

3-(4-tert-Butyl-5-hydroxymethyl-thiophen-3-ylsulfanyl)-6-[2-(4-fluoro-phenyl)-ethyl]-4-hydroxy-6-isopropyl-5,6-dihydro-pyran-2-one;

3-(4-tert-Butyl-thiophen-3-ylsulfanyl)-4-hydroxy-6-[2-(2-hydroxymethyl-phenyl)-ethyl]-6-isopropyl-5,6-dihydro-pyran-2-one;

6-[2-(4-Amino-phenyl)-ethyl]-3-(2-tert-butyl-5-methyl-thiophen-3-ylsulfanyl)-4-hydroxy-6-isopropyl-5,6-dihydro-pyran-2-one;

3-(2-tert-Butyl-5-methyl-thiophen-3-ylsulfanyl)-4-hydroxy-6-[2-(2-hydroxymethyl-phenyl)-ethyl]-6-isopropyl-5,6-dihydro-pyran-2-one;

6-[2-(4-Amino-phenyl)-ethyl]-3-(4-tert-butyl-5-hydroxymethyl-thiophen-3-ylsulfanyl)-4-hydroxy-6-isopropyl-5,6-dihydro-pyran-2-one;

6-[2-(4-Amino-phenyl)-ethyl]-3-(3-tert-butyl-4-hydroxymethyl-5-methyl-thiophen-2-ylsulfanyl)-4-hydroxy-6-isopropyl-5,6-dihydro-pyran-2-one;

3-(3-tert-Butyl-5-methyl-thiophen-2-ylsulfanyl)-4-hydroxy-6-[2-(2-hydroxymethyl-phenyl)-ethyl]-6-isopropyl-5,6-dihydro-pyran-2-one;

3-(3-tert-Butyl-4-hydroxymethyl-5-methyl-thiophen-2-ylsulfanyl)-6-[2-(4-fluoro-phenyl)-ethyl]-4-hydroxy-6-isopropyl-5,6-dihydro-pyran-2-one;

3-(3-tert-Butyl-4-hydroxymethyl-5-methyl-thiophen-2-ylsulfanyl)-4-hydroxy-6-isopropyl-6-(2-thiophen-3-yl-ethyl)-5,6-dihydro-pyran-2-one;

3-(6-tert-Butyl-2,3-dihydro-1H-indol-5-ylsulfanyl)-6-[2-(4-fluoro-phenyl)-ethyl]-4-hydroxy-6-isopropyl-5,6-dihydro-pyran-2-one;

3-(6-tert-Butyl-2,3-dihydro-1H-indol-5-ylsulfanyl)-4-hydroxy-6-[2-(2-hydroxymethyl-phenyl)-ethyl]-6-isopropyl-5,6-dihydro-pyran-2-one;

3-(6-tert-Butyl-1H-indol-5-ylsulfanyl)-6-[2-(4-fluoro-phenyl)-ethyl]-4-hydroxy-6-isopropyl-5,6-dihydro-pyran-2-one;

3-(6-tert-Butyl-1H-indol-5-ylsulfanyl)-4-hydroxy-6-[2-(2-hydroxymethyl-phenyl)-ethyl]-6-isopropyl-6-dihydro-pyran-2-one;

3-(7-tert-Butyl-1,2,3,4-tetrahydro-quinolin-6-ylsulfanyl)-6-[2-(4-fluoro-phenyl)-ethyl]-4-hydroxy-6-isopropyl-5,6-dihydro-pyran-2-one;

3-(7-tert-Butyl-1,2,3,4-tetrahydro-quinolin-6-ylsulfanyl)-4-hydroxy-6-[2-(2-hydroxymethyl-phenyl)-ethyl]-6-isopropyl-5,6-dihydro-pyran-2-one;

N-(7-tert-Butyl-6-{6-[2-(4-fluoro-phenyl)-ethyl]-4-hydroxy-6-isopropyl-2-oxo-5,6-dihydro-2H-pyran-3-ylsulfanyl}-4-methyl-benzothiazol-2-yl)-acetamide;

N-(7-tert-Butyl-6-{4-hydroxy-6-[2-(2-hydroxymethyl-phenyl)-ethyl]-6-isopropyl-2-oxo-5,6-dihydro-2H-pyran-3-ylsulfanyl}-4-methyl-benzothiazol-2-yl)-acetamide;

N-(7-tert-Butyl-6-{6-[2-(4-fluoro-phenyl)-ethyl]-4-hydroxy-6-isopropyl-2-oxo-5,6-dihydro-2H-pyran-3-ylsulfanyl}-4-methyl-benzothiazol-2-yl)-methanesulfonamide.

N-(7-tert-Butyl-6-{4-hydroxy-6-[2-(2-hydroxymethyl-phenyl)-ethyl]-6-isopropyl-2-oxo-5,6-dihydro-2H-pyran-3-ylsulfanyl}-4-methyl-benzothiazol-2-yl)-methanesulfonamide;

3-(7-tert-Butyl-2-dimethylamino-4-methyl-benzothiazol-6-ylsulfanyl)-6-[2-(4-fluoro-phenyl)-ethyl]-4-hydroxy-6-isopropyl-5,6-dihydro-pyran-2-one;

3-(7-tert-Butyl-2-dimethylamino-4-methyl-benzothiazol-6-ylsulfanyl)-4-hydroxy-6-[2-(2-hydroxymethyl-phenyl)-ethyl]-6-isopropyl-5,6-dihydro-pyran-2-one;

3-(7-tert-Butyl-2-hydroxy-4-methyl-benzothiazol-6-ylsulfanyl)-6-[2-(4-fluoro-phenyl)-ethyl]-4-hydroxy-6-isopropyl-5,6-dihydro-pyran-2-one;

3-(7-tert-Butyl-2-hydroxy-4-methyl-benzothiazol-6-ylsulfanyl)-4-hydroxy-6-[2-(2-hydroxymethyl-phenyl)-ethyl]-6-isopropyl-5,6-dihydro-pyran-2-one;

3-(2-tert-Butyl-6-hydroxymethyl-5-methyl-pyridin-3-ylsulfanyl)-4-hydroxy-6-isopropyl-6-(2-thiophen-3-yl-ethyl)-5,6-dihydro-pyran-2-one;

3-(3-tert-Butyl-2-hydroxymethyl-6-methyl-pyridin-4-ylsulfanyl)-4-hydroxy-6-isopropyl-6-(2-thiophen-3-yl-ethyl)-5,6-dihydro-pyran-2-one;

3-(6-tert-Butyl-2,3-dihydro-1H-indol-5-ylsulfanyl)-4-hydroxy-6-[2-(2-hydroxymethyl-thiophen-3-yl)-ethyl]-6-isopropyl-5,6-dihydro-pyran-2-one;

3-(6-tert-Butyl-1H-indol-5-ylsulfanyl)-4-hydroxy-6-[2-(2-hydroxymethyl-thiophen-3-yl)-ethyl]-6-isopropyl-5,6-dihydro-pyran-2-one;

3-(7-tert-Butyl-1,2,3,4-tetrahydro-quinolin-6-ylsulfanyl)-4-hydroxy-6-[2-(2-hydroxymethyl-thiophen-3-yl)-ethyl]-6-isopropyl-5,6-dihydro-pyran-2-one;

N-{7-tert-Butyl-6-[4-hydroxy-6-isopropyl-2-oxo-6-(2-thiophen-3-yl-ethyl)-5,6-dihydro-2H-pyran-3-ylsulfanyl]-4-methyl-benzothiazol-2-yl}-acetamide;

N-{7-tert-Butyl-6-[4-hydroxy-6-isopropyl-2-oxo-6-(2-thiophen-3-yl-ethyl)-5,6-dihydro-2H-pyran-3-ylsulfanyl]-4-methyl-benzothiazol-2-yl}-methanesulfonamide;

3-(7-tert-Butyl-2-dimethylamino-4-methyl-benzothiazol-6-ylsulfanyl)-4-hydroxy-6-isopropyl-6-(2-thiophen-3-yl-ethyl)-5,6-dihydro-pyran-2-one;

3-(7-tert-Butyl-2-hydroxy-4-methyl-benzothiazol-6-ylsulfanyl)-4-hydroxy-6-isopropyl-6-(2-thiophen-3-yl-ethyl)-5,6-dihydro-pyran-2-one;

(S)-3-(2-tert-Butyl-4-hydroxymethyl-5-methyl-phenylsulfanyl)-6-cyclohexyl-4-hydroxy-6-(2-thiophen-3-yl-ethyl)-5,6-dihydro-pyran-2-one;

(S)-3-(2-tert-Butyl-4-hydroxymethyl-5-methyl-phenylsulfanyl)-6-cyclopentyl-4-hydroxy-6-(2-thiophen-3-yl-ethyl)-5,6-dihydro-pyran-2-one;

(S)-3-(2-tert-Butyl-4-hydroxymethyl-5-methyl-phenylsulfanyl)-4-hydroxy-6-n-pentyl-6-(2-thiophen-3-yl-ethyl)-5,6-dihydro-pyran-2-one;

3-(2-tert-Butyl-4-hydroxymethyl-5-methyl-phenylsulfanyl)-6-cyclohexyl-4-hydroxy-6-(2-thiophen-2-yl-ethyl)-5,6-dihydro-pyran-2-one;

3-(2-tert-Butyl-4-hydroxymethyl-5-methyl-phenylsulfanyl)-6-cyclopentyl-4-hydroxy-6-(2-thiophen-2-yl-ethyl)-5,6-dihydro-pyran-2-one;

3-(2-tert-Butyl-4-hydroxymethyl-5-methyl-phenylsulfanyl)-4-hydroxy-6-n-pentyl-6-(2-thiophen-2-yl-ethyl)-5,6-dihydro-pyran-2-one;

3-(4-Amino-2-tert-butyl-5-methyl-phenylsulfanyl)-6-cyclohexyl-4-hydroxy-6-[2-(2-hydroxymethyl-thiophen-3-yl)-ethyl]-5,6-dihydro-pyran-2-one;

3-(4-Amino-2-tert-butyl-5-methyl-phenylsulfanyl)-6-cyclopentyl-4-hydroxy-6-[2-(2-hydroxymethyl-thiophen-3-yl)-ethyl]-5,6-dihydro-pyran-2-one;

3-(4-Amino-2-tert-butyl-5-methyl-phenylsulfanyl)-4-hydroxy-6-[2-(2-hydroxymethyl-thiophen-3-yl)-ethyl]-6-n-pentyl-5,6-dihydro-pyran-2-one;

(S)-3-(2-Amino-5-tert-butyl-benzothiazol-6-ylsulfanyl)-4-hydroxy-6-n-pentyl-6-phenethyl-5,6-dihydro-pyran-2-one;

(S)-3-(2-Amino-5-tert-butyl-benzothiazol-6-ylsulfanyl)-6-cyclohexyl-4-hydroxy-6-phenethyl-5,6dihydro-pyran-2-one;

(S)-3-(2-Amino-5-tert-butyl-benzothiazol-6-ylsulfanyl)-6-cyclopentyl-4-hydroxy-6-phenethyl-5,6-dihydro-pyran-2-one;

(S)-4-Hydroxy-6-[2-(4-hydroxy-phenyl)-ethyl]-6-propyl-3-(5-isopropyl-benzothiazol-6-ylsulfanyl)-5,6-dihydro-pyran-2-one;

(S)-6-Cyclohexyl-4-hydroxy-6-[2-(4-hydroxy-phenyl)-ethyl]-3-(5-isopropyl-benzothiazol-6-ylsulfanyl)-5,6-dihydro-pyran-2-one;

(S)-6-Cyclopentyl-4-hydroxy-6-[2-(4-hydroxy-phenyl)-ethyl]-3-(5-isopropyl-benzothiazol-6-ylsulfanyl)-5,6-dihydro-pyran-2-one;

(S)-3-(6-tert-Butyl-1H-indol-5-yl-sulfanyl)-4-hydroxy-6-propyl-6-(2-phenethyl)-5,6-dihydro-pyran-2-one;

(S)-3-(6-tert-Butyl-1H-indol-5-yl-sulfanyl)-6-cyclohexyl-4-hydroxy-6-(2-phenethyl)-5,6-dihydro-pyran-2-one;

(S)-3-(6-tert-Butyl-1H-indol-5-yl-sulfanyl)-6-cyclopentyl-4-hydroxy-6-(2-phenethyl)-5,6-dihydro-pyran-2-one;

(S)-3-(6-tert-Butyl-1H-indol-5-yl-sulfanyl)-4-hydroxy-6-pentyl-6-(2-phenethyl)-5,6-dihydro-pyran-2-one;

(S)-3-(2-Amino-5-tert-butyl-benzothiazol-6-ylsulfanyl)-6-[2-(3-fluoro-phenyl)-ethyl]-4-hydroxy-6-propyl-5,6-dihydro-pyran-2-one;

(S)-3-(2-Amino-5-tert-butyl-benzothiazol-6-ylsulfanyl)-6-[2-(3-fluoro-phenyl)-ethyl]-4-hydroxy-6-pentyl-5,6-dihydro-pyran-2-one;

(S)-3-(2-Amino-5-tert-butyl-benzothiazol-6-ylsulfanyl)-6-cyclohexyl-6-[2-(3-fluoro-phenyl)-ethyl]-4-hydroxy-5,6-dihydro-pyran-2-one; and (S)-3-(2-Amino-5-tert-butyl-benzothiazol-6-ylsulfanyl)-6-cyclopentyl-6-[2-(3-fluoro-phenyl)-ethyl]-4-hydroxy-5,6-dihydro-pyran-2-one.

The compounds of the present invention were evaluated for their in vitro inhibition of HIV protease and for their antiviral efficacy in HIV infected lymphocytes and the results shown in Table 1. Two reference agents are included and are shown below.

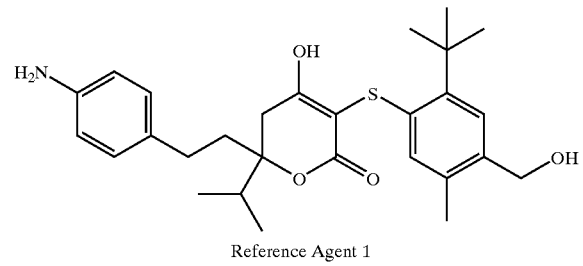

Reference Agent 1

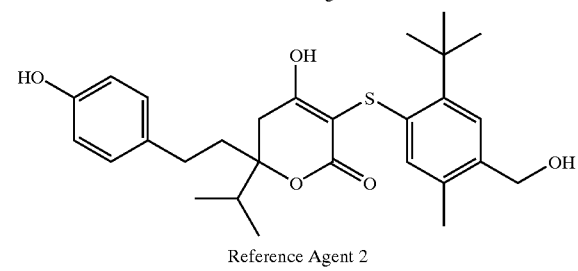

Reference Agent 2

The two Reference Agents 1 and 2 are the two best compounds as disclosed by Hagen, et al., *J. Med. Chem.*, 1997;40:3707–3711). These reference compounds were recognized to have particularly good antiviral activity due in part to the polar substituents placed on the phenyl and phenethylmoieties. In a subsequent disclosure by S. Vander Roest, et al., 37th Interscience Conference on Antimicrobial Agents and Chemotherapy, Sep. 28–Oct. 1, 1997, Toronto, Canada Abstract I-84), it was revealed that Reference Agents 1 and 2 had comparatively good pharmacokinetics in mice relative to a large series of related polar substituted phenyl and phenethyl derivatives. Thus, Reference Agents 1 and 2, represent excellent comparative agents for the compounds of the current invention both in vitro and in vivo.

The following sections provide the experimental methodology for the in vitro and in vivo assays employed to demonstrate the efficacy and advantages of the compounds of the current invention.

HIV Protease Assay

Materials

Recombinant HIV-1 protease (>96% purity) and HIV protease substrate III (the undecapeptide H-His-Lys-Ala-Arg-Val-Leu-Nph-Glu-Ala-Nle-Ser-NH$_2$, 97% purity) were purchased from Bachem Bioscience, Inc. (King of Prussia, Pa.).

Method

The methods employed follow the procedures of Tummino, et al., *Archives of Biochemistry and Biophysics*, 1995;316:523). For determination of Ki values, HIV-1 protease, 6.0 nM final concentration, was added to a solution containing inhibitor, 40 μM substrate III and 1.0% Me$_2$SO in assay buffer: 80 mM MES, 160 mM NaCl, 1.0 mM EDTA 0.1% polyethylene glycol (Mr 8000) pH 6.2 at 37° C. (total volume, 100 & 1). Polyethylene glycol was used in the assay in place of glycerol since the former was reported to be a more effective stabilizing agent in the protease (Jordan, et al., *J. Biol. Chem.*, 1992;267:20028). The final inhibitor concentrations used were 0 (0.1, 0.2, in some experiments), 0.5, 1, 2, 5, 10, 20, 50, and 100 μM. The solution was mixed, incubated for 5 minutes and the reaction quenched by addition of trifluoracetic acid, 2% final. The (leu-p-nitrophe) bond of the substrate is cleaved by the enzyme and substrate arid products separated by reverse-phase HPLC. Absorbance was measured at 220 nm, peak areas determined, and percentage conversion to product used to calculate percentage control (=[% conversion (+inhibitor)/% conversion (−inhibitor)]×100).

Cellular Infection Assay

Compounds were tested in lymphocyte derived CEM cells using the XTT cytopathic procedures and were performed at Southern Research Institute (Buckheit, et al., *Antiviral Res.*, 1993;21:247; see also Weislow, et al., *J. Nat. Cancer Inst.*, 1989;81:577). Compound concentrations were 0.32, 1, 3.2, 10, 32, and 100 uM. The $EC_{50}$ represents the concentration of agent which reduces HIV cytopathic effects 50% relative to untreated control. Cellular toxicity of the agents are estimated from the $TC_{50}$ which represents the concentration of the agent which inhibits 50% of the viability of uninfected cells.

Table 1 contains the results of the HIV protease assay Ki and the antiviral efficacy ($EC_{50}$, $TC_{50}$, TI) screening, where TI is the therapeutic index ($TC_{50}/EC_{50}$)

Mouse Blood Levels

Charles River CD-1 mice were dosed with a 25 mg/kg drug solution orally by gavage. For oral dosing the compounds were dissolved in 0.1N NaOH (20% final volume) and then 0.5% methylcellulose (80% final volume) was added. Blood was drawn and pooled from 5 mice at each time point via heart puncture and was placed in a 15 mL centrifuge tube containing heparin. The plasma stored in 200 μL aliquots at −80° C. until assayed.

Plasma was thawed at room temperature and then 400 μL of acetonitrile was added to each vial and vortexed. Following centrifugation the supernatant was removed and evaporated in a nitrogen evaporator at 48° C. Residue was then resolublized in 200 μL of a 75% water/25% $CH_3CN$ solution for HPLC analysis. HPLC analysis used a Zorbax RX-C8 column (4.6×150 mm) with a 25 mM potassium phosphate buffer with 0.1% TFA, pH 3.0. Mobile phases consisted of varying percentages of two buffer mixtures: Buffer A—90% buffer, 10% $CH_3CN$, and Buffer B—30% buffer, 70% $CH_3CN$. Absorbance was determined at a wavelength of 260 nM.

A standard curve ranging from 0.5 to 50 μg/mL was used for each drug tested. Ten times final concentration solutions of drug in water were prepared from stock solutions of 1 mg/mL drug in DMSO. The final 1:10 dilution was then done in mouse plasma obtained from mice described above.

The results from testing the reference agents and the compounds of this invention are shown in Table 2.

Rat and Dog Blood Levels

The procedure for pharmacokinetics analysis in dogs and rats was similar. For dog studies, two dogs received a single oral 10 mg/kg dose of the HIV protease inhibitor as a solution. The protease inhibitor was dissolve in 0.1N NaOH followed by buffering or diluting with isotonic phosphate buffer or water depending on solubility. For rat studies, two male rats received a single oral 10 mg/kg gavage dose of the HIV protease inhibitor suspended in 0.5% methylcellulose. For the IV administration, the compounds were dissolved in 0.1N sodium hydroxide at a concentration of 10 mg/ml. The IV dose was given bolus. Blood samples were collected prior to dosing and at 0.25, 0.5, 1, 1.5, 2, 3, 4, 8, 12, and 24 hours postdose. Plasma samples were analyzed for the HIV protease inhibitor using a HPLC procedure. The method involved plasma protein precipitation with acetonitrile, reverse-phase chromatographic separation of the HIV protease inhibitor and internal standard, and quantitation by UV detection. Some plasma samples were concentrated by evaporation prior to injection. Pharmacokinetic parameters were determined by noncompartmental analysis of individual rat-plasma concentration-time curves using WinNonlin. Maximum concentration (Cmax) and time for these to occur (tmax) were recorded as observed. Area under concentration-time curve (AUC) values were obtained using the linear trapezoidal rule. The results of the pharmacokinetic studies in dogs and rats are shown in Table 3.

Table 1 indicates that the compounds of the present invention have good to excellent activity toward inhibiting the HIV protease enzyme (Ki's) as well as activity in HIV infected cells, protecting the cells from HIV pathogenicity at μM and sub-μM concentrations. The two reference agents in Table 1, which represent the best of the hydroxylated and aminated compounds from the art, are wholly comparable to the compounds of the current invention at the antiviral level. Yet the current invention relies not only on the antiviral activity but on the unexpected finding that certain heterocycles could sufficiently mimic the polar groups of the reference agents while effecting significant gains in pharmacokinetic parameters due in part to reduced metabolism of the amines and phenols of the reference agents.

In Table 2, the results from mouse pharmacokinetic studies are shown for the reference agents and certain of the compounds of the present invention. In Table 3, the oral pharmacokinetics of certain compounds and the reference agents in rats and dogs are shown. Table 4 shows the pharmacokinetics in rats compared to the reference agents.

The results in Table 2 show a clear improvement in Cmax and T1/2 of the compounds of the invention relative to the Reference Agents. The results from Table 3 show that the pharmacokinetic advantages of the compounds of the current invention are not limited to mice but are manifest in rats and dogs. Such data all support the unexpected observation that select heterocycles mimic the polar hydroxylated and aminated phenyl groups, yet posses unexpectedly good pharmacokinetics relative to the best Reference Agents.

TABLE 1

Inhibition of HIV-Protease and Antiviral Efficacy in a CEM Cell Infection Assay

| | Inhib of HIV | Antiviral Efficacy | | |
|---|---|---|---|---|
| Example | Protease KI (nM) | $EC_{50}$ (μM) | $TC_{50}$ (μM) | TI |
| 1 | 1.5 | 1.5 | 296 | 197 |
| 2 | 0.9 | 0.9 | 216 | 240 |
| 4 | 0.35 | 1.0 | 199 | 199 |
| 5 | 0.78 | 0.75 | 190 | 253 |
| 7 | 0.17 | 0.3 | 110 | 366 |
| 8 | 0.35 | 0.5 | 80.5 | 161 |
| 9 | 0.19 | 1.8 | 210 | 117 |
| 11 | 0.23 | 0.29 | 133 | 458 |
| 12 | 0.07 | 0.14 | 91 | 650 |
| 13 | | 0.28 | 42 | 152 |
| 14 | 0.67 | 2.5 | 75 | 30 |
| 16 | | 11 | 114 | 10.4 |
| 17 | | 2.7 | 42 | 16 |
| 18 | | 1.1 | 117 | 105 |
| 22 | 0.85 | 1.5 | 66 | 43 |

TABLE 1-continued

Inhibition of HIV-Protease and Antiviral Efficacy in a CEM Cell Infection Assay

| Example | Inhib of HIV Protease KI (nM) | Antiviral Efficacy EC$_{50}$ ($\mu$M) | TC$_{50}$ ($\mu$M) | TI |
|---|---|---|---|---|
| 24 |  | 0.37 | 164 | 443 |
| 25 | 0.57 | 0.7 | 216 | 308 |
| 26 | 0.45 | 0.8 | 171 | 213 |
| 28 | 0.24 | 1.9 | 229 | 120 |
| 32 | 1.6 | 23 | 91 | 4 |
| 33 |  | 1.4 | 101 | 72 |
| 35 | 0.88 | 1.5 | 72 | 48 |
| 36 | 1.7 | 2.2 | 170 | 77 |
| 37 | 0.37 | 4.2 | 100 | 24 |
| 38 | 0.33 | 1.1 | 124 | 113 |
| 40 | 0.28 | 5.6 | >320 | >57 |
| 41 | 6.5 | 20 | 195 | 10 |
| 42 |  | 1.3 | >200 | >159 |
| 48 | 0.4 | 0.37 | 29 | 78 |
| 55 | 1.7 | 8.3 | 66 | 8 |
| 56 | 11 | 10 | 210 | 21 |
| 59 | 0.08 | 0.6 | 66 | 110 |
| 61 | 0.98 | 0.68 | 46 | 68 |
| 65 | 1.2 | 1.1 | 60 | 54 |
| 69 | 0.67 | 0.18 | 55 | 306 |
| 70 | 0.82 | 1.3 | 8 | 6 |
| 73 | 0.54 | 0.61 | 42 | 69 |
| 79 | 2.1 | 2.2 | 125 | 56 |
| 82 | 1.1 | 0.7 | 76 | 109 |
| 83 | 0.44 | 0.26 | 61 | 235 |
| 84 | 0.8 | 0.47 | 93 | 198 |
| 89 | 0.95 | 3.5 | >200 | >57 |
| Ref1 | 0.43 | 0.5 | >100 | >200 |
| Ref2 | 0.22 | 0.6 | >100 | >166 |

TABLE 2

Pharmacokinetic Evaluation of HIV Protease Inhibitors in Mice Following an Orar Dose of 25 mg/kg

| Example | Cmax[a] ($\mu$M) | T 1/2[b] (hr) |
|---|---|---|
| Ref 1 | 23 | 2.2 |
| Ref 2 | 17 | 2.0 |
| 2 | 46 | 7.3 |
| 4 | 54 | 5.6 |
| 7 | 40 | 3.5 |
| 12 | 95 | 9.5 |
| 25 | 33 | 3.3 |

[a]The maximum concentration reached within the plasma.
[b]The half life of the agents.

TABLE 3

Pharmacokinetic Evaluation of HIV Protease Inhibitors in Rats and Dogs Following an Oral Dose of 10 mg/kg

| | Rats | | Dogs | |
|---|---|---|---|---|
| Example | Cmax[a] ($\mu$M) | T 1/2[b] (hr) | Cmax ($\mu$M) | T 1/2[b] (hr) |
| Ref 1 | 16 | 3.4 | 140 | 1.25 |
| Ref 2 | 3.4 | 0.55 | 40 | 0.52 |
| 12 | 30 | 11.5 | 149 | 1.75 |
| 13 | 5.1 | 8.6 | — | — |
| 25 | 6.0 | 12.0 | — | — |

[a]The maximum concentration reached within the plasma.
[b]The half life of the agents.

TABLE 4

Pharmacokinetic Evaluation of HIV Protease Inhibitors in Rats Following an IV Dose of 10 mg/kg

| Example | C(0) ($\mu$M) | T 1/2[a] (hr) |
|---|---|---|
| Ref 1 | 86 | 3.7 |
| Ref 2 | 100 | 3.9 |
| 12 | 160 | 12.0 |
| 25 | 120 | 8.0 |
| 69 | 335 | 4.5 |
| 83 | 199 | 4.0 |

[a]The half life of the agents.

What is claimed is:
1. A compound of Formula I

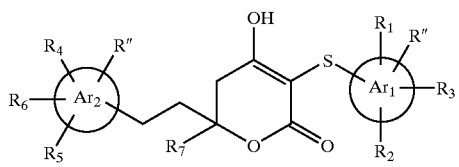

or a pharmaceutically acceptable salt thereof wherein
$R_1$ is H, a straight or branched alkyl of 1–6 carbons or a carbocycle of 3–6 carbons;
$R_2$ is H, a straight or branched alkyl of 1–5 carbons;
$R_3$ is H, $(CR'_2)_nOR$, $(CR'_2)_nN(R)_2$, $(CR'_2)_nNR'COR$, $(CR'_2)_nCO_2R$, $(CR'_2)_nOCOR$, $(CR'_2)_nCON(R)_2$, $(CR'_2)_n$ $OCON(R)_2$, $(CR'_2)_nR$, $(CR'_2)_nNR'CON(R)_2$, $(CR'_2)_n$ $NR'CO_2R$, $(CR'_2)_nOSO_2N(R)_2$, $(CR'_2)_n$ $NR'SO_2OR$, $(CR'_2)_nNR'SO_2N(R)_2$, $(CR'_2)_nOSO_2R$, $(CR'_2)_n$ $NR'SO_2R$, $(CR'_2)_nSO_2R$, $(CR'_2)_nNR'CSN(R)_2$, $(CR'_2)_n$ $NR'C(NR')N(R)_2$, $(CR'_2)_nSO_2N(R)_2$, $(CR'_2)_nC$ $(NR')N(R)_2$, $(CR'_2)_nCOR$, $O(CR'_2)_mOR$, $NR(CR'_2)_m$ $OR$, F, Cl, Br, $CF_3$, CN, or =O;
$R_4$, $R_5$, and $R_6$ are independently H, a straight or branched alkyl of 1–6 carbons, a cycloalkyl of 3–6 carbons, $(CR'_2)_nOR$, $(CR'_2)_nN(R)_2$, F, Cl, Br, CN, $CF_3$, =O, $(CR'_2)_pNR'COR$, $(CR'_2)_pSO_pR$, $(CR'_2)_pR$, $(CR'_2)_p$ $OCOR$, $O(CR'_2)_mOR$, $NR(CR'_2)_mOR$, $(CR'_2)_p$ $NR'CON(R)_2$, $(CR'_2)_pOCON(R)_2$, $(CR'_2)_pNR'CO_2R$, $(CR'_2)_pCOR$, $(CR'_2)_pCO_2R$, $(CR'_2)_pCON(R)_2$, $(CR'_2)_p$ $NR'SO_2R$, $(CR'_2)_pSO_2N(R)_2$, $(CR'_2)_pNR'SO_2OR$, $(CR'_2)_pOSO_2N(R)_2$, $(CR'_2)_pNR'SO_2N(R)_2$, $(CR'_2)_pC$ $(NR')N(R)_2$, $(CR'_2)_pNR'C(NR')N(R)_2$, $(CR'_2)_pHet$;
any two of $R_1$–$R_3$ or $R_4$–$R_6$ may together form a ring of 5–6 total atoms which may contain 0–3 heteroatoms;
n is an integer of from 0 to 3;
m is an integer of from 2 to 4;
p is an integer from 0 to 2;
$R_7$ is a straight or branched alkyl of 1–6 carbons or a carbocycle of 3–6 carbons;
R is independently H, a straight or branched alkyl of 1–4 carbons, $(CH_2)_nPh$, or a $(CH_2)_n$heterocycle of 5–6 atoms containing 1–2 heteroatoms and wherein the $(R)_2$ in $N(R)_2$ may form a heterocycle containing the nitrogen, all optionally substituted by F, Cl, Br, OR', CN, $CO_2R'$, $N(R')_2$, $NR'COR'$, $CF_3$, or =O;
R' is independently H, a straight or branched alkyl of 1–4 carbons, or phenyl;
R" is independently H, a straight or branched alkyl of 1–4 carbons, F, Cl, Br, OR', or $N(R')_2$;

Ar$_1$ is phenyl and Ar$_2$ is Het;
wherein Het is a heterocycle of from 5–6 atoms having from 1–4 heteroatoms or a fused heterocycle of from 9–10 atoms having 1–3 heteroatoms Ar$_2$ is Het wherein Het is a heterocycle of from 5–6 atoms having 1–4 heteroatoms selected from furan, pyrrole, thiophene, oxazole, isoxazole, thiazole, pyrazole, 1,2,3-triazole, 1,2,4-triazole, tetrazole, pyridine, pyridazine, pyrimidine, or pyrazine, or a fused heterocycle of from 9–10 atoms having from 1–3 heteroatoms selected from: benzofuran, indole, indoline, benzothiophene, benzimidazole, benzthiazole, benzoxazole, quinoline, isoquinoline, cinnoline, quinazoline and quinoxaline.

2. A compound according to claim 1 wherein:
R$_1$ is a straight or branched alkyl of from 1 to 4 carbons or a carbocycle of from 3 to 5 carbons and
R$_2$ is H or a straight or branched alkyl of from 1 to 3 carbons.

3. A compound according to claim 1 wherein:
R$_1$ is isopropyl or t-butyl;
R$_2$ is H, methyl, or ethyl;
R$_3$ is H, (CR'$_2$)$_n$OR, (CR'$_2$)$_n$N(R)$_2$, (CR'$_2$)$_n$NR'COR, (CR'$_2$)$_n$CO$_2$R, (CR'$_2$)$_n$OCOR, (CR'$_2$)$_n$CON(R)$_2$, (CR'$_2$)$_n$ OCON(R)$_2$, (CR'$_2$)$_n$NR'CON(R)$_2$, (CR'$_2$)$_n$NR'CO$_2$R, (CR'$_2$)$_n$OSO$_2$N(R)$_2$, (CR'$_2$)$_n$NR'SO$_2$OR, (CR'$_2$)$_n$ NR'SO$_2$N(R)$_2$, (CR'$_2$)$_n$OSO$_2$R, (CR'$_2$)$_n$NR'SO$_2$R, (CR'$_2$)$_n$SO$_p$R, (CR'$_2$)$_n$NR'CSN(R)$_2$, (CR'$_2$)$_n$COR, O(CR'$_2$)$_m$OR, NR(CR'$_2$)$_m$OR, F, Cl, Br, CF$_3$, CN, or =O;
R$_4$, R$_5$, and R$_6$ are independently H, a straight or branched alkyl of 1–6 carbons, a cycloalkyl of 3–6 carbons, (CH$_2$)$_n$OR, (CH$_2$)$_n$N(R)$_2$, F, Cl, Br, CN, CF$_3$, =O, (CR'$_2$)$_p$NR'COR, (CR'$_2$)$_p$SO$_p$R, (CR'$_2$)$_p$NR'CON(R)$_2$, (CR'$_2$)$_p$OCON(R)$_2$, (CR'$_2$)$_p$NR'CO$_2$R, (CR'$_2$)$_p$COR, (CR'$_2$)$_p$CO$_2$R, (CR'$_2$)$_p$CON(R)$_2$, (CR'$_2$)$_p$NR'SO$_2$R, (CR'$_2$)$_p$SO$_2$N(R)$_2$, (CR'$_2$)$_p$NR'SO$_2$OR, (CR'$_2$)$_p$OSO$_2$N(R)$_2$, (CR'$_2$)$_p$Het and any two of R$_1$–R$_3$ or R$_4$–R$_6$ may together form a ring of 5–6 total atoms which may contain 0–2 heteroatoms;
n is an integer of 0 to 3;
m is an integer of 2 to 4;
p is 0 to 2;
R$_7$ is a straight or branched alkyl of 1–6 carbons or a carbocycle of 3–6 carbons;
R is H, a straight or branched alkyl of 1–4 carbons, (CH$_2$)$_n$Ph, or a (CH$_2$)$_n$heterocycle of 5–6 atoms containing 1–2 heteroatoms and wherein the (R)$_2$ in N(R)$_2$ may form a heterocycle containing the nitrogen, all optionally substituted by F, Cl, Br, OR', N(R')$_2$, NR'COR', CF$_3$, or =O;
R' is H, a straight or branched alkyl of 1–4 carbons, or phenyl;
R" is H, a straight or branched alkyl of 1–4 carbons, F, Cl, Br, OR', or N(R')$_2$;
Ar$_1$ is phenyl; and
Ar$_2$ is Het wherein Het is a heterocycle of from 5–6 atoms having 1–4 heteroatoms selected from: furan, pyrrole, thiophene, oxazole, isoxazole, thiazole, pyrazole, 1,2,3-triazole, 1,2,4-triazole, tetrazole, pyridine, pyridazine, pyrimidine, or pyrazine or a fused heterocycle of from 9–10 atoms having from 1–3 heteroatoms selected from: benzofuran, indole, indoline, benzothiophene, benzimidazole, benzthiazole, benzoxazole, quinoline, isoquinoline, cinnoline, quinazoline and quinoxaline.

4. A compound according to claim 1 wherein:
R$_1$ is isopropyl or t-butyl;
R$_2$ is H, methyl or ethyl;
R$_3$ is H, (CH$_2$)$_n$OR, (CH$_2$)$_n$N(R)$_2$, (CH$_2$)$_n$NR'COR, (CH$_2$)$_n$CON(R)$_2$, (CH$_2$)$_n$OCON(R)$_2$, (CH$_2$)$_n$NR'CON(R)$_2$, (CH$_2$)$_n$NR'CO$_2$R, (CH$_2$)$_n$OSO$_2$N(R)$_2$, (CH$_2$)$_n$NR'SO$_2$OR, (CH$_2$)$_n$NR'SO$_2$N(R)$_2$, (CH$_2$)$_n$OSO$_2$R, (CH$_2$)$_n$NR'SO$_2$R, (CH$_2$)$_n$SO$_2$R, (CH$_2$)$_n$NR'CSN(R)$_2$, (CH$_2$)$_n$COR, O(CH$_2$)$_m$OR', NR(CH$_2$)$_m$OR', or C(CH$_3$)$_2$OR';
R$_4$, R$_5$, and R$_6$ are independently H, a straight or branched alkyl of 1–6 carbons, a cycloalkyl of 3–6 carbons, (CH$_2$)$_n$OR, (CH$_2$)$_n$N(R)$_2$, F, Cl, Br, CN, CF$_3$, =O, (CH$_2$)$_p$NR'COR, (CH$_2$)$_p$NR'CON(R)$_2$, (CH$_2$)$_p$OCON(R)$_2$, (CH$_2$)$_p$NR'CO$_2$R, (CH$_2$)$_p$COR, (CH$_2$)$_p$CON(R)$_2$, (CH$_2$)$_p$NR'SO$_2$R, (CH$_2$)$_p$NR'SO$_2$OR, (CH$_2$)$_p$OSO$_2$N(R)$_2$, wherein p is 0 to 2, or R$_4$ and R$_5$ may together form a ring of 5–6 total atoms which may contain 0–2 heteroatoms;
n is an integer of 0 to 3;
m is an integer of 2 to 4;
R$_7$ is a straight or branched alkyl of 1–6 carbons or a carbocycle of 3–6 carbons;
R is H, a straight or branched alkyl of 1–4 carbons, (CH$_2$)$_n$Ph, or a (CH$_2$)$_n$heterocycle of 5–6 atoms containing 1–2 heteroatoms and wherein the (R)$_2$ in N(R)$_2$ may be a heterocycle containing the nitrogen, all optionally substituted by F, Cl, Br, OR', N(R')$_2$, NR'COR', or =O;
R' is H, a straight or branched alkyl of 1–4 carbons, or phenyl;
R" is H, a straight or branched alkyl of 1–4 carbons, F, Cl, Br, OR', or N(R')$_2$;
Ar$_1$ is phenyl; and
Ar$_2$ is a heterocycle of 5–6 atoms having from 1–4 heteroatoms selected from: furan, pyrrole, thiophene, oxazole, isoxazole, thiazole, pyrazole, 1,2,3-triazole, 1,2,4-triazole, tetrazole, pyridine, pyridazine, pyrimidine, pyrazine, tetrahydrofuran, tetrahydrothiophene, pyrrolidine, piperazine, piperidine, morpholine. thiomorpholine. oxolane, dioxane, sulfolane; or a fused heterocycle of 9–10 atoms having from 1–3 heteroatoms selected from: benzofuran, indole, indoline, benzothiophene, benzimidazole, benzthiazole, benzoxazole, quinoline, isoquinoline, cinnoline, quinazoline and quinoxaline.

5. A compound according to claim 1 wherein:
R$_1$ is H, a straight or branched alkyl of 1–6 carbons or a carbocycle of 3–6 carbons;
R$_2$ is H, a straight or branched alkyl of 1–5 carbons;
R$_3$ is H, (CH$_2$)$_n$OR, (CH$_2$)$_n$N(R)$_2$, (CH$_2$)$_n$NR'COR, (CH$_2$)$_n$CON(R)$_2$, (CH$_2$)$_n$OCON(R)$_2$, (CH$_2$)$_n$NR'CON(R)$_2$(CH$_2$)$_n$NR'CO$_2$R, (CH$_2$)$_n$OSO$_2$N(R)$_2$, (CH$_2$)$_n$NR'SO$_2$OR, (CH$_2$)$_n$NR'SO$_2$N(R)$_2$, (CH$_2$)$_n$OSO$_2$R, (CH$_2$)$_n$NR'SO$_2$R, (CH$_2$)$_n$SO$_2$R, (CH$_2$)$_n$COR, O(CH$_2$)$_m$OR, NR(CH$_2$)$_m$OR, C(CH$_3$)$_2$OR', F, Cl, Br, CF$_3$, or =O;
R$_4$, R$_5$, and R$_6$ are independently H, a straight or branched alkyl of 1–6 carbons, a cycloalkyl of 3–6 carbons, (CH$_2$)$_n$OR, (CH$_2$)$_n$N(R)$_2$, F, Cl, Br, =O, (CH$_2$)$_p$NR'COR, (CH$_2$)$_p$NR'CON(R)$_2$, (CH$_2$)$_p$OCON(R)$_2$, (CH$_2$)$_p$NR'CO$_2$R, (CH$_2$)$_p$COR, (CH$_2$)$_p$CON(R)$_2$, (CH$_2$)$_p$NR'SO$_2$R, (CH$_2$)$_p$NR'SO$_2$OR, (CH$_2$)$_p$OSO$_2$N(R)$_2$, wherein p is 0 to 2;

$R_4$ and $R_5$ may together form a ring of 5–6 total atoms which may contain 0–2 heteroatoms;

n is an integer of 0 to 3;

m is an integer of 2 to 4;

$R_7$ is methyl, ethyl, isopropyl, cyclopropyl, cyclobutyl, cyclopentyl or cyclohexyl;

R is H, a straight or branched alkyl of 1–4 carbons, $(CH_2)_nPh$, or a $(CH_2)_n$heterocycle of 5–6 atoms containing 1–2 heteroatoms and wherein the $(R)_2$ in $N(R)_2$ may be a heterocycle containing the nitrogen, all optionally substituted by F, Cl, Br, OR', $N(R')_2$, NR'COR', or =O;

R' is H, a straight or branched alkyl of 1–4 carbons, or phenyl;

R" is H, a straight or branched alkyl of 1–4 carbons, F, Cl, Br, OR', or $N(R')_2$;

$Ar_1$ is phenyl; and $Ar_2$ is Het wherein Het is a heterocycle of 5–6 atoms having from 1–4 heteroatoms selected from: furan, pyrrole, thiophene, oxazole, isoxazole, thiazole, pyrazole, 1,2,3-triazole, 1,2,4-triazole, tetrazole, pyridine, pyridazine, pyrimidine, pyrazine, tetrahydrofuran, tetrahydrothiophene, pyrrolidine, piperazine, piperidine, morpholine, thiomorpholine, oxolane, dioxane, sulfolane; or a fused heterocycle of from 9–10 atoms having 1–3 heteroatoms selected from: benzofuran, indole, indoline, benzothiophene, benzimidazole, benzthiazole, benzoxazole, quinoline, isoquinoline, cinnoline, quinazoline and quinoxaline.

6. A compound according to claim 1 wherein:

$R_1$ is isopropyl or t-butyl;

$R_2$ is H or methyl;

$R_3$ is H, $(CH_2)_nOR$, $(CH_2)_nN(R)_2$, $(CH_2)_nOCON(R)_2$, $(CH_2)_nNR'CON(R)_2$, $(CH_2)_nNR'CO_2R$, $(CH_2)_nOSO_2N(R)_2$, $(CH_2)_nNR'SO_2OR$, $(CH_2)_nNR'SO_2N(R)_2$, $(CH_2)_nNR'SO_2R$, $(CH_2)_nSO_2R$, $O(CH_2)_mOR'$, $NR(CH_2)_mOR'$, or $C(CH_3)_2OR'$;

$R_4$, $R_5$, and $R_6$ are independently H, a straight or branched alkyl of 1–6 carbons, a cycloalkyl of 3–6 carbons, $(CH_2)_nOR$, $(CH_2)_nN(R)_2$, F, Cl, Br, =O, $(CH_2)_pNR'COR$, $(CH_2)_pNR'CON(R)_2$, $(CH_2)_pOCON(R)_2$, $(CH_2)_pNR'CO_2R$, $(CH_2)_pCOR$, $(CH_2)_pCON(R)_2$, $(CH_2)_pNR'SO_2R$, $(CH_2)_pNR'SO_2OR$, $(CH_2)_pOSO_2N(R)_2$, wherein p is 0 to 2;

$R_4$ and $R_5$ may together form a ring of 5–6 total atoms which may contain 0–2 heteroatoms;

n is an integer of 0 to 3;

m is an integer of 2 to 4;

$R_7$ is a straight or branched alkyl of 1–6 carbons or a carbocycle of 3–6 carbons;

R is H, a straight or branched alkyl of 1–4 carbons, $(CH_2)_nPh$, or a $(CH_2)_n$heterocycle of 5–6 atoms having from 1–2 heteroatoms and wherein the $(R)_2$ in $N(R)_2$ may be a heterocycle containing the nitrogen, all optionally substituted by F, Cl, Br, OR', $N(R')_2$, NR'COR', or =O;

R' is H, a straight or branched alkyl of 1–4 carbons, or phenyl;

R" is H, a straight or branched alkyl of 1–4 carbons, F, Cl, Br, OR', or $N(R')_2$;

$Ar_1$ is phenyl; and $Ar_2$ is furan, pyrrole, thiophene, oxazole, isoxazole, thiazole, pyrazole, tetrazole, or pyridine.

7. A compound according to claim 1 wherein:

$R_1$ is H, a straight or branched alkyl of 1–6 carbons or a carbocycle of 3–6 carbons;

$R_2$ is H, methyl or ethyl or isopropyl;

$R_3$ is H, $(CH_2)_nOR$, $(CH_2)_nN(R)_2$, $(CH_2)_nNRCOR$, $(CH_2)_nCON(R)_2$, $(CH_2)_nOCON(R)_2$, $(CH_2)_nNR'CON(R)_2$, $(CH_2)_nNR'CO_2R$, $(CH_2)_nOSO_2N(R)_2$, $(CH_2)_nNR'SO_2OR$, $(CH_2)_nNR'SO_2N(R)_2$, $(CH_2)_nOSO_2R$, $(CH_2)_nNR'SO_2R$, $(CH_2)_nSO_2R$, $O(CH_2)_mOR$, $NR(CH_2)_mOR'$, $C(CH_3)_2OR'$, or =O;

$R_4$, $R_5$, and $R_6$ are independently H, a straight or branched alkyl of 1–6 carbons, a cycloalkyl of 1–6 carbons, $(CH_2)_nOR$, $(CH_2)_nN(R)_2$, F, Cl, Br; =O, $(CH_2)_pNR'COR$, $(CH_2)_pNR'CON(R)_2$, $(CH_2)_pOCON(R)_2$, $(CH_2)_pNR'CO_2R$, $(CH_2)_pCOR$, $(CH_2)_pCON(R)_2$, $(CH_2)_pNR'SO_2R$, $(CH_2)_pNR'SO_2R$, $(CH_2)_pOSO_2N(R)_2$, wherein p is 0 to 2;

$R_4$ and $R_5$ may together form a ring of 5–6 total atoms which may contain 0–2 heteroatoms;

n is an integer of 0 to 3;

m is an integer of 2 to 4;

$R_7$ is a straight or branched alkyl of 1–6 carbons or a carbocycle of 3–6 carbons;

R is H, a straight or branched alkyl of 1–4 carbons, $(CH_2)_nPh$, or a $(CH_2)_n$heterocycle of 5–6 atoms containing 1–2 heteroatoms and wherein the $(R)_2$ in $N(R)_2$ may be a heterocycle having nitrogen, all optionally substituted by F, Cl, Br, OR', $N(R')_2$, NR'COR', or =O;

R' is H, a straight or branched alkyl of 1–4 carbons, or phenyl;

R" is H, a straight or branched alkyl of 1–4 carbons, F, Cl, Br, OR', or $N(R')_2$;

$Ar_1$ is phenyl; and $Ar_2$ is Het wherein Het is a heterocycle of 5–6 atoms having from 1–4 heteroatoms selected from: furan, pyrrole, thiophene, oxazole, isoxazole, thiazole, pyrazole, 1,2,3-triazole, 1,2,4-triazole, tetrazole, pyridine, pyridazine, pyrimidine, or pyrazine; or a fused heterocycle of 9–10 atoms having 1–3 heteroatoms selected from: benzofuran, indole, indoline, benzothiophene, benzimidazole, benzthiazole, benzoxazole, quinoline, isoquinoline, cinnoline, quinazoline and quinoxaline.

8. A compound according to claim 1 wherein:

$R_1$ is isopropyl or t-butyl;

$R_2$ is H, methyl, or ethyl;

$R_3$ is $CH_2OH$, $NH_2$, $OCH_2CH_2OH$, NHCOR, $OSO_2N(R)_2$, $NR'SO_2OR$, $NR'SO_2R$, or $OSO_2R$;

$R_4$, $R_5$ and $R_6$ are independently H, a straight or branched alkyl of 1–6 carbons, a cycloalkyl of 1–6 carbons, $(CH_2)_nOR$, $(CH_2)_nN(R)_2$, F, Cl, Br, =O, $(CH_2)_pNR'COR$, $(CH_2)_pNR'CON(R)_2$, $(CH_2)_pOCON(R)_2$, $(CH_2)_pNR'CO_2R$, $(CH_2)_pCOR$, $(CH_2)_pCON(R)_2$, $(CH_2)_pNR'SO_2R$, $(CH_2)_pNR'SO_2OR$, $(CH_2)_pOSO_2N(R)_2$, wherein p is 0 to 2;

$R_4$ and $R_5$ may together form a ring of 5–6 total atoms which may contain 0–2 heteroatoms;

$R_7$ is a straight or branched alkyl of 1–6 carbons or a carbocycle of 3–6 carbons, R is H, a straight or branched alkyl of 1–4 carbons, $(CH_2)_nPh$, or a $(CH_2)_n$heterocycle of 5–6 atoms having from 1–2 heteroatoms and wherein the $(R)_2$ in $N(R)_2$ may be a heterocycle having nitrogen, all optionally substituted by F, Cl, Br, OR', $N(R')_2$, NR'COR', or =O;

R' is H, a straight or branched alkyl of 1–4 carbons, or phenyl;

R" is H, a straight or branched alkyl of from 1–4 carbons, F, Cl, Br, OR', or N(R')$_2$;

Ar$_1$ is phenyl; and

Ar$_2$ is a heterocycle of 5–6 atoms having from 1–4 heteroatoms selected from: furan, pyrrole, thiophene, oxazole, isoxazole, thiazole, pyrazole, 1,2,3-triazole, 1,2,4-triazole, tetrazole, pyridine, pyridazine, pyrimidine, pyrazine, tetrahydrofuran, tetrahydrothiophene, pyrrolidine, piperazine, piperidine, morpholine, thiomorpholine, oxolane, dioxane, sulfolane; or a fused heterocycle of 9–10 atoms having from 1–3 heteroatoms selected from: benzofuran, indole, indoline, benzothiophene, benzimidazole, benzthiazole, benzoxazole, quinoline, isoquinoline, cinnoline, quinazoline and quinoxaline.

9. A compound according to claim 1 wherein:

R$_1$ is H, methyl, ethyl, isopropyl, or t-butyl;

R$_2$ is H, methyl, ethyl, or isopropyl;

R$_3$ is H, NH$_2$, OH, CH$_2$OR, CH$_2$N(R)$_2$, CH$_2$CON(R)$_2$, CH$_2$OSO$_2$N(R)$_2$, CH$_2$NHSO$_2$OR, CH$_2$NHSO$_2$R, CH$_2$OSO$_2$R, Cl, Br, or OCH$_2$CH$_2$OH;

R$_4$, R$_5$, and R$_6$ are independently H, methyl, ethyl, isopropyl, OH, NH$_2$, CH$_2$OR, CH$_2$N(R)$_2$, =O, F, Cl, Br, or CH$_2$NRCOR;

R$_7$ is methyl, ethyl, isopropyl, cyclopropyl, cyclobutyl, or cyclopentyl;

R is H, methyl, ethyl, Ph, CH$_2$Ph, and wherein the (R)$_2$ in N(R)$_2$ may be a heterocycle having a nitrogen;

R" is H, F, or CH$_3$;

Ar$_1$ is phenyl; and

Ar$_2$ is furan, thiophene, oxazole, isoxazole, imidazale, thiazole, pyrazole, pyridine, benzofuran, benzothiophene, benzimidazole, benzthiazole, quinoline, or isoquinoline.

10. A compound according to claim 1 wherein:

R$_1$ is isopropyl or t-butyl;

R$_2$ is H, methyl, or ethyl;

R$_3$ is H, NH$_2$, OH, CH$_2$OR, CH$_2$N(R)$_2$, CH$_2$CON(R)$_2$, OSO$_2$N(R)$_2$, NHSO$_2$OR, NHSO$_2$R, OSO$_2$R, or OCH$_2$CH$_2$OH;

R$_4$, R$_5$, and R$_6$ are independently H, methyl, ethyl, isopropyl, OH, NH$_2$, CH$_2$OR, CH$_2$N(R)$_2$, =O, F, Cl, Br, or CH$_2$NRCOR;

R$_7$ is methyl, ethyl, isopropyl, cyclopropyl, cyclobutyl, or cyclopentyl;

R is H, methyl, ethyl, Ph, CH$_2$Ph, and wherein the (R)$_2$ in N(R)$_2$ may be a heterocycle containing the nitrogen:

R" is H, F, or CH$_3$;

Ar$_1$ is phenyl; and

Ar$_2$ is furan, thiophene, oxazole, isoxazole, imidazale, thiazole, pyrazole, pyridine, benzofuran, benzothiophene, benzimidazole, benzthiazole, quinoline, or isoquinoline.

11. A compound according to claim 1 wherein:

R$_1$ is isopropyl or t-butyl;

R$_2$ is H, methyl, or ethyl;

R$_3$ is NH$_2$, CH$_2$OH, OCH$_2$CH$_2$OH, or CH$_2$CH$_2$OH;

R$_4$, R$_5$, and R$_6$ are independently H, NH$_2$, CH$_2$OH, =O, methyl, ethyl, or isopropyl;

R$_7$ is isopropyl;

R" is H, F, or CH$_3$;

Ar$_1$ is phenyl; and

Ar$_2$ is furan, thiophene, imidazole, thiazole, pyrazole, or pyridine.

12. A compound according to claim 1 and selected from:

3-(2-tert-Butyl-4-hydroxymethyl-5-methyl-phenylsulfanyl)-4-hydroxy-6-isopropyl-6-(2-pyridin-4-yl-ethyl)-5,6-dihydro-pyran-2-one;

3-(2-tert-Butyl-4-hydroxymethyl-5-methyl-phenylsulfanyl)-4-hydroxy-6-isopropyl-6-(2-pyridin-3-yl-ethyl)-5,6-dihydro-pyran-2-one;

3-(2-tert-Butyl-4-hydroxymethyl-5-methyl-phenylsulfanyl)-4-hydroxy-6-isopropyl-6-(2-pyridin-2-yl-ethyl)-5,6-dihydro-pyran-2-one 3-(2-tert-Butyl-4-hydroxymethyl-5-methyl-phenylsulfanyl)-6-(2-furan-3-yl-ethyl)-4-hydroxy-6-isopropyl-5,6-dihydro-pyran-2-one;

3-(2-tert-Butyl-4-hydroxymethyl-5-methyl-phenylsulfanyl)-6-(2-furan-2-yl-ethyl)-4-hydroxy-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(tetrahydro-furan-2-yl)-ethyl]-5,6-dihydro-pyran-2-one;

3-(2-tert-Butyl-4-hydroxymethyl-5-methyl-phenylsulfanyl)-4-hydroxy-6-isopropyl-6-(2-thiophen-3-yl -ethyl)-5,6-dihydro-pyran-2-one;

3-(2-tert-Butyl-4-hydroxymethyl-5-methyl-phenylsulfanyl)-4-hydroxy-6-isopropyl-6-(2-thiophen-2-yl-ethyl)-5,6-dihydro-pyran-2-one;

3-(2-tert-Butyl-4-hydroxymethyl-5-methyl-phenylsulfanyl)-4-hydroxy-6-[2-(5-hydroxymethyl-thiophen-3-yl)-ethyl]-6-isopropyl-5,6-dihydro-pyran-2-one;

3-(2-tert-Butyl-4-hydroxymethyl-5-methyl-phenylsulfanyl)-4-hydroxy-6-[2-(2-hydroxymethyl-thiophen-3-yl)-ethyl]-6-isopropyl-5,6-dihydro-pyran-2-one;

3-(4-Amino-2-tert-butyl-5-methyl-phenylsulfanyl)-4-hydroxy-6-[2-(2-hydroxymethyl-thiophen-3-yl)-ethyl]-6-isopropyl-5,6-dihydro-pyran-2-one;

(S)-3-(2-Amino-5-tert-butyl-benzothiazol-6-ylsulfanyl)-4-hydroxy-6-isopropyl-6-phenethyl-5,6-dihydro-pyran-2-one;

(S)-3-(2-Amino-5-isopropyl-benzothiazol-6-ylsulfanyl)-4-hydroxy-6-isopropyl-6-phenethyl-5,6-dihydro-pyran-2-one;

6-[-2-(4-Fluoro-phenyl)-ethyl]-4-hydroxy-6-isopropyl-3-(5-isopropyl-benzothiazol-6-ylsulfanyl)-5,6-dihydro-pyran-2-one;

3-(2-Amino-5-isopropyl-benzothiazol-6-yl-sulfanyl)-6-[2-(4-fluoro-phenyl)-ethyl]-phenethyl-4-hydroxy-6-isopropyl-5,6-dihydro-pyran-2-one;

(S)-3-(2-Amino-7-isopropyl-4-methyl-benzothiazol-6-yl-sulfanyl)-4-hydroxy-6-isopropyl-6-phenethyl-5,6-dihydro-pyran-2-one;

(S)-3-(2-Amino-7-isopropyl-4-methyl-benzothiazol-6-ylsulfanyl)-4-hydroxy-6-[2-(4-hydroxyl-phenyl)-ethyl]-6-isopropyl-5 6-dihydro-pyran-2-one;

(S)-(6-{4-Hydroxy-6-[2-(4-hydroxy-phenyl)-ethyl]-6-isopropyl-2-oxo-5,6-dihydro-2H-pyran-3-ylsulfanyl}-4-isopropyl-7-methyl-benzothiazol-2-yl)-carbamic acid methyl ester;

(S)-3-(2-Amino-6-tert-butyl-benzothiazol-4-ylsulfanyl)-4-hydroxy-6-[2-(4-hydroxy-phenyl)-ethyl]-6-isopropyl-5,6-dihydro-pyran-2-one;

(S)-3-(3-tert-Butyl-benzo[b]thiophen-2-ylsulfanyl)-4-hydroxy-6-[2-(4-hydroxy-phenyl)-ethyl]-6-isopropyl-5,6-dihydro-pyran-2-one;

3-(3-tert-Butyl-benzo[b]thiophen-2-yl-sulfanyl)-4-hydroxy-6-[2-(2-hydroxymethyl-phenyl)-ethyl]-6-isopropyl-5,6-dihydro-pyran-2-one;

4-Hydroxy-3-(5-hydroxymethyl-2-isopropyl-thiophen-3-ylsulfanyl)-6-isopropyl-6-(2-thiophen-3-yl-ethyl)-5,6-dihydro-pyran-2-one:

3-(2-tert-Butyl-4-hydroxymethyl-5-methyl-phenylsulfanyl)-4-hydroxy-6-isopropyl-6-[2-(4-methyl-thiazol-5-yl)-ethyl]-5,6-dihydro-pyran-2-one;

3-(2-tert-Butyl-4-hydroxymethyl-5-methyl-phenylsulfanyl)-4-hydroxy-6-isopropyl-6-(2-thiazol-2-yl-ethyl)-5,6-dihydro-pyran-2-one;

3-(2-tert-Butyl-4-hydroxymethyl-5-methyl-phenylsulfanyl)4-hydroxy-6-isopropyl-6-[2-(4-methyl-thiazol-2-yl)-ethyl]-5,6-dihydro-pyran-2-one;

N-(4-{2-[5-(2-tert-Butyl-4-hydroxymethyl-5-methyl-phenylsulfanyl)-4-hydroxy-2-isopropyl-6-oxo-3,6-dihydro-2H-pyran-2-yl]-ethyl}-thiazol-2-yl)-acetamide;

3-(2-tert-Butyl-4-hydroxymethyl-5-methyl-phenylsulfanyl)-4-hydroxy-6-isopropyl-6-[2-(5-methyl-thiazol-2-yl)-ethyl]-5,6-dihydro-pyran-2-one;

3-(2-tert-Butyl-4-hydroxymethyl-5-methyl-phenylsulfanyl)-4-hydroxy-6-isopropyl-6-(2-thiazol-5-yl-ethyl)-5,6-dihydro-pyran-2-one;

3-(2-tert-Butyl-4-hydroxymethyl-5-methyl-phenylsulfanyl)-4-hydroxy-6-isopropyl-6-[2-(2-methyl-thiazol-4-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(5-methyl-thiazol-4-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(2-isopropyl-thiazol-4-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(4-isopropyl-thiazol-5-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(5-isopropyl-thiazol-4-yl)-ethyl]-5,6-dihydro-pyran-2-one;

3-(4-Amino-2-tert-butyl-5-methyl-phenylsulfanyl)-4-hydroxy-6-isopropyl-6-(2-thiophen-3-yl-ethyl)-5,6-dihydro-pyran-2-one;

3-(4-Amino-2-tert-butyl-5-methyl-phenylsulfanyl)-6-(2-furan-3-yl-ethyl)-4-hydroxy-6-isopropyl-5,6-dihydro-pyran-2-one;

3-(2-tert-Butyl-4-hydroxy-5-methyl-phenylsulfanyl)-4-hydroxy-6-[2-(5-hydroxymethyl-thiophen-2-yl)-ethyl]-6-isopropyl-5,6-dihydro-pyran-2-one;

3-(4-Amino-2-tert-butyl-5-methyl-phenylsulfanyl)-4-hydroxy-6-[2-(5-hydroxymethyl-thiophen-2-yl)-ethyl]-6-isopropyl-5,6-dihydro-pyran-2-one, 3-(2-tert-Butyl-4-hydroxymethyl-5-methyl-phenylsulfanyl)-4-hydroxy-6-[2-(5-hydroxymethyl-thiophen-2-yl)-ethyl]-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(1H-pyrazol-3-yl)-ethyl]-5,6-dihydro-pyran-2-one;

3-(4-Amino-2-tert-butyl-5-methyl-phenylsulfanyl)-4-hydroxy-6-isopropyl-[2-(1H-pyrazol-3-yl)-ethyl]-5 6-dihydro-pyran-2-one;

3-(2-tert-Butyl-4-hydroxymethyl-5-methyl-phenylsulfanyl)-4-hydroxy-6-isopropyl-6-(2-pyrimidin-5-yl-ethyl)-5 46-dihydro-pyran-2-one;

3-(4-Amino-2-tert-butyl-5-methyl-phenylsulfanyl)-4-hydroxy-6-isopropyl-6-(2-pyrimidin-5-yl-ethyl)-5,6-dihydro-pyran-2-one;

6-[2-(2-Amino-pyrimidin-5-yl)-ethyl]-3-(2-tert-butyl-4-hydroxymethyl-5-methyl-phenylsulfanyl)-4-hydroxy-6-isopropyl-5,6-dihydro-pyran-2-one;

3-(4-Amino-2-tert-butyl-5-methyl-phenylsulfanyl)-6-[2-(2-amino-pyrimidin-5-yl)-ethyl]-4-hydroxy-6-isopropyl-5,6-dihydro-pyran-2-one;

3-(2-tert-Butyl-4-hydroxymethyl-5-methyl-phenylsulfanyl)-4-hydroxy-6-isopropyl-6-(2-thiazol-4-yl-ethyl)-5,6-dihydro-pyran-2-one;

(S)-4-Hydroxy-6-isopropyl-3-(5-isopropyl-benzothiazol-6-ylsulfanyl)-6-phenethyl-5,6-dihydro-pyran-2-one;

(S)-4-Hydroxy-6-[2-(4-hydroxy-phenyl)-ethyl]-6-isopropyl-3-(5-isopropyl-benzothiazol-6-ylsulfanyl)-5,6-dihydro-pyran-2-one;

3-(2-Amino-7-isopropyl-4-methyl-benzothiazol-6-ylsulfanyl)-6-[2-(4-fluoro-phenyl)-ethyl]-4-hydroxy-6-isopropyl-5,6-dihydro-pyran-2-one;

(S)-3-(2-Amino-5-tert-butyl-benzothiazol-6-ylsulfanyl)-4-hydroxy-6-[2-(4-hydroxy-phenyl)-ethyl]-6-isopropyl-5,6-dihydro-pyran-2-one;

(S)-3-(2-Amino-5-isopropyl-benzothiazol-6-ylsulfanyl)-4-hydroxy-6-[2-(4-hydroxy-phenyl)-ethyl]-6-isopropyl-5,6-dihydro-pyran-2-one;

(R)-3-(2-tert-Butyl-4-hydroxymethyl-5-methyl-phenylsulfanyl)-4-hydroxy-6-isopropyl-6-(2-thiophen-3-yl-ethyl)-5,6-dihydro-pyran-2-one;

3-(2-Amino-5-isopropyl-benzothiazol-6-ylsulfanyl)-4-hydroxy-6-isopropyl-6-[2-(2-trifluoromethyl-phenyl)-ethyl]-5,6-dihydro-pyran-2-one;

3-(4-Amino-2-tert-butyl-5-methyl-phenylsulfanyl)-4-hydroxy-6-isopropyl-6-(2-pyridin-3-yl-ethyl)-5,6-dihydro-pyran-2-one;

3-(2-tert-Butyl-5-methyl-phenylsulfanyl)-4-hydroxy-6-[2-(5-hydroxymethyl-thiophen-2-yl)-ethyl]-6-isopropyl-5,6-dihydro-pyran-2-one;

3-(4-Amino-2-tert-butyl-5-methyl-phenylsulfanyl)-4-hydroxy-6-isopropyl-6-[2-(tetrahydro-furan-2-yl)-ethyl]-5,6-dihydro-pyran-2-one;

3-(2-tert-Butyl-4-hydroxymethyl-phenylsulfanyl)-4-hydroxy-6-isopropyl-6-(2-thiophen-3-yl-ethyl)-5,6-dihydro-pyran-2-one;

3-[2-tert-Butyl-4-(2-hydroxy-ethyl)-5-methyl-phenylsulfanyl]4-hydroxy-6-isopropyl-6-(2-thiophen-3-yl-ethyl)-5,6-dihydro-pyran-2-one;

5-Trifluoromethyl-pyridine-2-sulfonic acid {5-tert-butyl-4-[4-hydroxy-6-isopropyl-2-oxo-6-(2-thiophen-3-yl-ethyl)-5,6-dihydro-2H-pyran-3-ylsulfanyl]-2-methyl-phenyl}-amide;

5-Trifluoromethyl-pyridine-2-sulfonic acid {5-tert-butyl-4-[4-hydroxy-6-isopropyl-2-oxo-6-(2-pyridin-3-yl-ethyl)-5,6-dihydro-2H-pyran-3-ylsulfanyl]-2-methyl-phenyl}-amide;

3-(2-tert-Butyl-4-hydroxymethyl-5-methyl-phenylsulfanyl)-4-hydroxy-6-[2-(1H-indol-5-yl)-ethyl]-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(2-methyl-thiophen-3-yl)-ethyl]-5,6-dihydro-pyran-2-one;

(S)-3-(2-tert-Butyl-4-hydroxymethyl-5-methyl-phenylsulfanyl)-4-hydroxy-6-isopropyl-6-[2-(2-methyl-thiophen-3-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(3-methyl-thiophen-2-yl)-ethyl]-5,6-dihydro-pyran-2-one;

3-(4-Amino-2-tert-butyl-5-methyl-phenylsulfanyl)-4-hydroxy-6-isopropyl-6-[2-(3-methyl-thiophen-2-yl)-ethyl]-5,6-dihydro-pyran-2-one:

3-(2-tert-Butyl-4-hydroxymethyl-5-methyl-phenylsulfanyl)-4-hydroxy-6-isopropyl-6-[2-(4-methyl-thiophen-3-yl)-ethyl]-5,6-dihydro-pyran-2-one;

3-(4-Amino-2-tert-butyl-5-methyl-phenylsulfanyl)-4-hydroxy-6-[2-(4-hydroxymethyl-thiophen-3-yl)-ethyl]-6-isopropyl-5,6-dihydro-pyran-2-one;

4-Hydroxy-6-[2-(2-hydroxymethyl-phenyl)-ethyl]-6-isopropyl-3-(5-isopropyl-benzothiazol-6-ylsulfanyl)-5,6-dihydro-pyran-2-one;

4-Hydroxy-3-(6-tert-butyl-indol-5-ylsulfanyl)-6-[2-(2-hydroxymethyl-phenyl)-ethyl]6-isopropyl-5,6dihydropyran-2-one;

(S)-N-[6-tert-Butyl-5-(4-hydroxy-6-isopropyl-2-oxo-6-[2-(4-hydroxy-phenyl)ethyl]-5,6-dihydro-2H-pyran-3-ylsulfanyl)-indolin-1-yl]-(4-cyanophenyl)sulfonamide;

(S)-6-tert-Butyl-5-{4-hydroxy-6-[2-(4-hydroxy-phenyl)-ethyl]-6-isopropyl-2-oxo-5,6-dihydro-2H-pyran-3-ylsulfanyl}-indole-1-carboxylic acid tert-butyl ester;

(S)-3-(6-tert-Butyl-indol-5-yl-sulfanyl)-4-hydroxy6-[2-(4-hydroxy-phenyl)-ethyl]-6-isopropyl-5,6-dihydro-pyran-2-one;

(S)-3-(6-tert-Butyl-1H-indol-5-yl-sulfanyl)-4-hydroxy-6-isopropyl-6-(2-phenethyl)-5,6-dihydro-pyran-2-one;

(S)-3-(2-Amino-5-tert-butyl-benzothiazol-6-ylsulfanyl)-6-[2-(4-fluoro-phenyl)-ethyl]-4-hydroxy-6-isopropyl-5,6-dihydro-pyran-2-one;

(S)-4-Hydroxy-6-isopropyl-3-(6-isopropyl-3H-benzoimidazol-5-ylsulfanyl)-6-(2-phenethyl)-5,6-dihydro-pyran-2-one;

(S)-5-(4-Hydroxy-6-isopropyl-2-oxo-6-phenethyl-5,6-dihydro-2H-pyran-3-ylsulfanyl)-6-isopropyl-1,3-dihydro-benzoimidazol-2-one;

(S)-3-(6-tert-Butyl-3H-benzoimidazol-5-yl-sulfanyl)-4-hydroxy-6-isopropyl-6-(2-phenethyl)-5,6-dihydro-pyran-2-one;

(S)-5-tert-Butyl-6-(4-hydroxy-6-isopropyl-2-oxo-6-(2-phenethyl)-5,6-dihydro-2H-pyran-3-ylsulfanyl)-1,3-dihydro-benzoimidazol-2-one;

(S)-N-[5-tert- Butyl-6-(4-hydroxy-6-isopropyl-2-oxo-6-phenethyl-5,6-dihydro-2H-pyran-3-ylsulfanyl)-benzothiazol-2-yl]-methanesulfonamide, 6-tert-Butyl-5-(4-hydroxy-6-isopropyl-2-oxo-6-phenethyl-5,6-dihydro-2H-pyran-3-ylsulfanyl)-1H-indole-2-carboxylic acid ethyl ester;

6-tert-Butyl-5-(4-hydroxy-6-isopropyl-2-oxo-6-phenethyl-5,6-dihydro-2H-pyran-3-ylsulfanyl)-1H-indole-2-carboxylic acid;

3-(2-Amino-5-tert-butyl-benzothiazol-6-ylsulfanyl)-4-hydroxy-6-isopropyl-6-[(2-(3-thiophenyl)-ethyl)-5,6-dihydro-pyran-2-one;

(S)-3-(2-Amino-5-tert-butyl-benzothiazol-6-ylsulfanyl)-6-[2-(3-fluoro-phenyl)-ethyl]-4-hydroxy-6-isopropyl-5,6-dihydro-pyran-2-one;

3-(2-Amino-5-tert-butyl-benzothiazol-6-ylsulfanyl)-6-[2-(3-fluoro-2-methyl-phenyl)-ethyl]-4-hydroxy-6-isopropyl-5,6-dihydro-pyran-2-one;

(S)-3-(2-Amino-5-tert-butyl-benzothiazol-6-ylsulfanyl)-6-[2-(3,5-difluoro-phenyl)-ethyl]-4-hydroxy-6-isopropyl-5,6-dihydro-pyran-2-one;

(S)-N-[5-tert-Butyl-6-(4-hydroxy-6-isopropyl-2-oxo-6-(2-phenethyl)-5,6-dihydro-2H-pyran-3-ylsulfanyl)-benzothiazol-2-yl]-acetamide;

(S)-N-{5-tert-Butyl-6-(4-hydroxy-6-isopropyl-2-oxo-6-(2-thiophen-3-yl-ethyl-5,6-dihydro-2H-pyran-3-ylsulfanyl)-benzothiazol-2-yl}-4-cyanobenzenesulfonamide;

(S)-3-(2-Amino-5-tert-butyl-benzothiazol-6-ylsulfanyl)-6-[2-(4-fluoro-2-methyl-phenyl)-ethyl]-4-hydroxy-6-isopropyl-5,6-dihydro-pyran-2-one;

6-[2-(2-Amino-thiazol4-yl)-ethyl]-3-(2-tert-butyl-4-hydroxymethyl-5-methyl-phenylsulfanyl)-4-hydroxy-6-isopropyl-5,6-dihydro-pyran-2-one;

(S)-3-(6-tert-Butyl-2,3-dihydro-1H-indol-5-ylsulfanyl)-4-hydroxy-6-[2-(4-hydroxy-phenyl)-ethyl]-6-isopropyl-5,6-dihydro-pyran-2-one;

(S)-3-(6-tert-Butyl-2,3-dihydro-1H-indol-5-ylsulfanyl)-4-hydroxy-6-isopropyl-6-[(2-(3-thiophenyl)-ethyl)-5,6-dihydro-pyran-2-one; and 4-(6-tert-Butyl-5-{4-hydroxy-6-[2-(2-hydroxymethyl-phenyl)-ethyl]-6-isopropyl-2-oxo-5,6-dihydro-2H-pyran-3-ylsulfanyl}-2,3-dihydro-indole-1-sulfonyl)-benzonitrile.

13. A compound according to claim 1 and selected from:

3-(4-Amino-2-tert-butyl-5-methyl-phenylsulfanyl)-4-hydroxy-6-[2-(3-hydroxymethyl-thiophen-2-yl)-ethyl]-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(3-methyl-thiophen-2-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(2-methyl-thiophen-3-yl)-ethyl]-5,6-dihydro-pyran-2-one;

3-(4-Amino-2-tert-butyl-5-methyl-phenylsulfanyl)-4-hydroxy-6-[2-(4-hydroxymethyl-thiophen-3-yl)-ethyl]-6-isopropyl-5,6-dihydro-pyran-2-one 3-(2-tert-Butyl-4-hydroxymethyl-5-methyl-phenylsulfanyl)-4-hydroxy-6-isopropyl-6-[2-(4-methyl-thiophen-3-yl)-ethyl]-5,6-dihydro-pyran-2-one;

3-(2-Cyclopentyl-4-hydroxymethyl-5-methyl-phenylsulfanyl)-4-hydroxy-6-isopropyl-6-(2-thiophen-3-yl-ethyl)-5,6-dihydro-pyran-2-one;

3-(4-Amino-2-cyclopentyl-5-methyl-phenylsulfanyl)-4-hydroxy-6-[2-(2-hydroxymethyl-thiophen-3-yl)-ethyl]-6-isopropyl-5,6-dihydro-pyran-2-one;

3-(4-Amino-2-cyclopentyl-5-methyl-phenylsulfanyl)-4-hydroxy-6-[2-(4-hydroxymethyl-thiophen-3-yl)-ethyl]-6-isopropyl-5,6-dihydro-pyran-2-one;

3-(6-tert-Butyl-1-hydroxy-indan-5-ylsulfanyl)-4-hydroxy-6-isopropyl-6-(2-thiophen-3-yl-ethyl)-5,6-dihydro-pyran-2-one; and 3-(6-tert-Butyl-1-hydroxy-indan-5-ylsulfanyl)-4-hydroxy-6-[2-(2-hydroxymethyl-thiophen-3-yl)-ethyl]-6-isopropyl-5,6-dihydro-pyran-2-one.

14. A compound according to claim 1 and selected from:

3-(6-tert-Butyl-1-hydroxy-indan-5-ylsulfanyl)-4-hydroxy-6-[2-(4-hydroxymethyl-thiophen-3-yl)-ethyl]-6-isopropyl-5,6-dihydro-pyran-2-one;

3-(4-Amino-2-tert-butyl-5-methyl-phenylsulfanyl)-4-hydroxy-6-[2-(2-hydroxymethyl-furan-3-yl)-ethyl]-6-isopropyl-5,6-dihydro-pyran-2-one;

3-(4-Amino-2-tert-butyl-5-methyl-phenylsulfanyl)-4-hydroxy-6-[2-(3-hydroxymethyl-furan-2-yl)-ethyl]-6-isopropyl-5,6-dihydro-pyran-2-one;

3-(4-Amino-2-tert-butyl-5-methyl-phenylsulfanyl)-4-hydroxy-6-[2-(4-hydroxymethyl-furan-3-yl)-ethyl]-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(2-methyl-furan-3-yl)-ethyl]-5,6-dihydro-pyran-2-one;

3-(2-tert-Butyl-4-hydroxymethyl-5-methyl-phenylsulfanyl)-4-hydroxy-6-isopropyl-6-[2-(3-methyl-furan-2-yl)-ethyl]-5,6-dihydro-pyran-2-one; and 3-(2-tert-Butyl-4-hydroxymethyl-5-methyl-phenylsulfanyl)-4-hydroxy-6-isopropyl-6-[2-(4-methyl-furan-3-yl)-ethyl]-5,6-dihydro-pyran-2-one.

15. A compound according to claim 1 and selected from:

3-(2-Cyclopentyl-4-hydroxymethyl-5-methyl-phenylsulfanyl)-6-(2-furan-3-yl-ethyl)-4-hydroxy-6-isopropyl-5,6-dihydro-pyran-2-one and 3-(6-tert-Butyl-1-hydroxy-indan-5-ylsulfanyl)-6-(2-furan-3-yl-ethyl)-4-hydroxy-6-isopropyl-5,6-dihydro-pyran-2-one.

16. A compound according to claim 1 and selected from:

3-(4-Amino-2-tert-butyl-5-methyl-phenylsulfanyl)-4-hydroxy-6-[2-(4-hydroxymethyl-thiazol-5-yl)-ethyl]-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(4-methyl-thiazol-5-yl)-ethyl]-5,6-dihydro-pyran-2-one;

3-(4-Amino-2-tert-butyl-5-methyl-phenylsulfanyl)-4-hydroxy-6-[2-(5-hydroxymethyl-thiazol-4-yl)-ethyl]-6-isopropyl-5,6-dihydro-pyran-2-one;

3-(2-tert-Butyl-4-hydroxymethyl-5-methyl-phenylsulfanyl)-4-hydroxy-6-isopropyl-6-[2-(5-methyl-thiazol-4-yl)-ethyl]-5,6-dihydro-pyran-2-one;

6-[2-(2-Amino-thiazol-4-yl)-ethyl]-3-(2-tert-butyl-4-hydroxymethyl-5-methyl-phenylsulfanyl)-4-hydroxy-6-isopropyl-5,6-dihydro-pyran-2-one;

6-[2-(2-Amino-thiazol-5-yl)-ethyl]-3-(2-tert-butyl-4-hydroxymethyl-5-methyl-phenylsulfanyl)-4-hydroxy-6-isopropyl-5,6-dihydro-pyran-2-one;

3-(2-tert-Butyl-4-hydroxymethyl-5-methyl-phenylsulfanyl)-4-hydroxy-6-isopropyl-6-(2-isothiazol-4-yl-ethyl)-5,6-dihydro-pyran-2-one;

3-(2-tert-Butyl-4-hydroxymethyl-5-methyl-phenylsulfanyl)-4-hydroxy-6-isopropyl-6-(2-isothiazol-5-yl-ethyl)-5,6-dihydro-pyran-2-one;

3-(2-tert-Butyl-4-hydroxymethyl-5-methyl-phenylsulfanyl)-4-hydroxy-6-isopropyl-6-(2-isothiazol-3-yl-ethyl)-5,6-dihydro-pyran-2-one; and 3-(2-tert-Butyl-4-hydroxymethyl-5-methyl-phenylsulfanyl)-4-hydroxy-6-isopropyl-6-[2-(4-methyl-oxazol-5-yl)-ethyl]-5,6-dihydro-pyran-2-one.

17. A compound according to claim 1 and selected from:

3-(4-Amino-2-tert-butyl-5-methyl-phenylsulfanyl)-4-hydroxy-6-[2-(1H-indol-5-yl)-ethyl]-6-isopropyl-5,6-dihydro-pyran-2-one;

3-(2-tert-Butyl-4-hydroxymethyl-5-methyl-phenylsulfanyl)-4-hydroxy-6-[2-(1H-indazol-5-yl)-ethyl]-6-isopropyl-5,6-dihydro-pyran-2-one;

3-(4-Amino-2-tert-butyl-5-methyl-phenylsulfanyl)-4-hydroxy-6-[2-(1H-indazol-5-yl)-ethyl]-6-isopropyl-5,6-dihydro-pyran-2-one;

3-(2-tert-Butyl-4-hydroxymethyl-5-methyl-phenylsulfanyl)-4-hydroxy-6-[2-(1H-indazol-5-yl)-ethyl]-6-isopropyl-5,6-dihydro-pyran-2-one;

3-(4-Amino-2-tert-butyl-5-methyl-phenylsulfanyl)-6-[2-(1H-benzoimidazol-5-yl)-ethyl]-4-hydroxy-6-isopropyl-5,6-dihydro-pyran-2-one;

6-[2-(1H-Benzoimidazol-5-yl)-ethyl]-3-(2-tert-butyl-4-hydroxymethyl-5-methyl-phenylsulfanyl)-4-hydroxy-6-isopropyl)-5,6-dihydro-pyran-2-one;

3-(4-Amino-2-tert-butyl-5-methyl-phenylsulfanyl)-6-[2-(3-amino-1H-indazol-5-yl)-ethyl]-4-hydroxy-6-isopropyl-5,6-dihydro-pyran-2-one; and 6-[2-(3-Amino-1H-indazol-5-yl)-ethyl]-3-(2-tert-butyl-4-hydroxymethyl-5-methyl-phenylsulfanyl)-4-hydroxy-6-isopropyl-5,6-dihydro-pyran-2-one.

18. A compound according to claim 1 and selected from:

3-(4-Amino-2-tert-butyl-5-methyl-phenylsulfanyl)-4-hydroxy-6-[2-(1H-indol-4-yl)-ethyl]-6-isopropyl-5,6-dihydro-pyran-2-one;

3-(2-tert-Butyl-4-hydroxymethyl-5-methyl-phenylsulfanyl)-4-hydroxy-6-[2-(1H-indol-4-yl)-ethyl]-6-isopropyl-5,6-dihydro-pyran-2-one;

3-(4-Amino-2-tert-butyl-5-methyl-phenylsulfanyl)-4-hydroxy-6-[2-(1H-indazol-4-yl)-ethyl]-6-isopropyl-5,6-dihydro-pyran-2-one;

3-(2-tert-Butyl-4-hydroxymethyl-5-methyl-phenylsulfanyl)-4-hydroxy-6-[2-(1H-indazol-4-yl)-ethyl]-6-isopropyl-5,6-dihydro-pyran-2-one;

3-(4-Amino-2-tert-butyl-5-methyl-phenylsulfanyl)-6-[2-(3-amino-1H-indazol-4-yl)-ethyl]-4-hydroxy-6-isopropyl-5,6-dihydro-pyran-2-one; and 6-[2-(3-Amino-1H-indazol-4-yl)-ethyl]-3-(2-tert-butyl-4-hydroxymethyl-5-methyl-phenylsulfanyl)-4-hydroxy-6-isopropyl-5,6-dihydro-pyran-2-one.

19. A compound according to claim 1 and selected from:

3-(4-tert-Butyl-5-hydroxymethyl-thiophen-3-ylsulfanyl)-6-[2-(4-fluoro-phenyl)-ethyl]-4-hydroxy-6-isopropyl-5,6-dihydro-pyran-2-one;

3-(4-tert-Butyl-thiophen-3-ylsulfanyl)-4-hydroxy-6-[2-(2-hydroxymethyl-phenyl)-ethyl]-6-isopropyl-5,6-dihydro-pyran-2-one;

6-[2-(4-Amino-phenyl)-ethyl]-3-(2-tert-butyl-5-methyl-thiophen-3-ylsulfanyl)-4-hydroxy-6-isopropyl-5,6-dihydro-pyran-2-one;

3-(2-tert-Butyl-5-methyl-thiophen-3-ylsulfanyl)-4-hydroxy-6-[2-(2-hydroxymethyl-phenyl)-ethyl]-6-isopropyl-5,6-dihydro-pyran-2-one;

6-[2-(4-Amino-phenyl)-ethyl]-3-(4-tert-butyl-5-hydroxymethyl-thiophen-3-ylsulfanyl)-4-hydroxy-6-isopropyl-5,6-dihydro-pyran-2-one;

6-[2-(4-Amino-phenyl)-ethyl]-3-(3-tert-butyl-4-hydroxymethyl-5-methyl-thiophen-2-ylsulfanyl)-4-hydroxy-6-isopropyl-5,6-dihydro-pyran-2-one;

3-(3-tert-Butyl-5-methyl-thiophen-2-ylsulfanyl)-4-hydroxy-6-[2-(2-hydroxymethyl-phenyl)-ethyl]-6-isopropyl-5,6-dihydro-pyran-2-one;

3-(3-tert-Butyl-4-hydroxymethyl-5-methyl-thiophen-2-ylsulfanyl)-6-[2-(4-fluoro-phenyl)-ethyl]-4-hydroxy-6-isopropyl-5,6-dihydro-pyran-2-one; and 3-(3-tert-Butyl-4-hydroxymethyl-5-methyl-thiophen-2-ylsulfanyl)-4-hydroxy-6-isopropyl-6-(2-thiophen-3-yl-ethyl)-5,6-dihydro-pyran-2-one.

20. A compound according to claim 1 and selected from:

3-(2-tert-Butyl-6-hydroxymethyl-5-methyl-pyridin-3-ylsulfanyl)-4-hydroxy-6-isopropyl-6-(2-thiophen-3-yl-ethyl)-5,6-dihydro-pyran-2-one;

3-(3-tert-Butyl-2-hydroxymethyl-6-methyl-pyridin-4-ylsulfanyl)-4-hydroxy-6-isopropyl-6-(2-thiophen-3-yl-ethyl)-5,6-dihydro-pyran-2-one;

3-(6-tert-Butyl-2,3-dihydro-1H-indol-5-ylsulfanyl)-4-hydroxy-6-[2-(2-hydroxymethyl-thiophen-3-yl)-ethyl]-6-isopropyl-5,6-dihydro-pyran-2-one;

3-(6-tert-Butyl-1H-indol-5-ylsulfanyl)-4-hydroxy-6-[2-(2-hydroxymethyl-thiophen-3-yl)-ethyl]-6-isopropyl-5,6-dihydro-pyran-2-one;

3-(7-tert-Butyl-1,2,3,4-tetrahydro-quinolin-6-ylsulfanyl)-4-hydroxy-6-[2-(2-hydroxymethyl-thiophen-3-yl)-ethyl]-6-isopropyl-5,6-dihydro-pyran-2-one;

N-{7-tert-Butyl-6-[4-hydroxy-6-isopropyl-2-oxo-6-(2-thiophen-3-yl-ethyl)-5,6-dihydro-2H-pyran-3-ylsulfanyl]-4-methyl-benzothiazol-2-yl}-acetamide;

N-{7-tert-Butyl-6-[4-hydroxy-6-isopropyl-2-oxo-6-(2-thiophen-3-yl-ethyl)-5,6-dihydro-2H-pyran-3-ylsulfanyl]-4-methyl-benzothiazol-2-yl}-methanesulfonamide;

3-(7-tert-Butyl-2-dimethylamino-4-methyl-benzothiazol-6-ylsulfanyl)-4-hydroxy-6-isopropyl-6-(2-thiophen-3-yl-ethyl)-5,6-dihydro-pyran-2-one;

3-(7-tert-Butyl-2-hydroxy-4-methyl-benzothiazol-6-ylsulfanyl)-4-hydroxy-6-isopropyl-6-(2-thiophen-3-yl-ethyl)-5,6-dihydro-pyran-2-one;

(S)-3-(2-tert-Butyl-4-hydroxymethyl-5-methyl-phenylsulfanyl)-6-cyclohexyl-4-hydroxy-6-(2-thiophen-3-yl-ethyl)-5,6-dihydro-pyran-2-one;

(S)-3-(2-tert-Butyl-4-hydroxymethyl-5-methyl-phenylsulfanyl)-6-cyclopentyl-4-hydroxy-6-(2-thiophen-3-yl-ethyl)-5,6-dihydro-pyran-2-one;

(S)-3-(2-tert-Butyl-4-hydroxymethyl-5-methyl-phenylsulfanyl)-4-hydroxy-6-n-pentyl-6-(2-thiophen-3-yl-ethyl)-5,6-dihydro-pyran-2-one;

3-(2-tert-Butyl-4-hydroxymethyl-5-methyl-phenylsulfanyl)-6-cyclohexyl-4-hydroxy-6-(2-thiophen-2-yl-ethyl)-5,6-dihydro-pyran-2-one;

3-(2-tert-Butyl-4-hydroxymethyl-5-methyl-phenylsulfanyl)-6-cyclopentyl-4-hydroxy-6-(2-thiophen-2-yl-ethyl)-5,6-dihydro-pyran-2-one;

3-(2-tert-Butyl-4-hydroxymethyl-5-methyl-phenylsulfanyl)-4-hydroxy-6-n-pentyl-6-(2-thiophen-2-yl-ethyl)-5,6-dihydro-pyran-2-one;

3-(4-Amino-2-tert-butyl-5-methyl-phenylsulfanyl)-6-cyclohexyl-4-hydroxy-6-[2-(2-hydroxymethyl-thiophen-3-yl)-ethyl]-5,6-dihydro-pyran-2-one;

3-(4-Amino-2-tert-butyl-5-methyl-phenylsulfanyl)-6-cyclopentyl-4-hydroxy-6-[2-(2-hydroxymethyl-thiophen-3-yl)-ethyl]-5,6-dihydro-pyran-2-one;

3-(4-Amino-2-tert-butyl-5-methyl-phenylsulfanyl)-4-hydroxy-6-[2-(2-hydroxymethyl-thiophen-3-yl)-ethyl]-6-n-pentyl-5,6-dihydro-pyran-2-one;

(S)-3-(2-Amino-5-tert-butyl-benzothiazol-6-ylsulfanyl)-4-hydroxy-6-n-pentyl)-6-phenethyl-5,6-dihydro-pyran-2-one;

(S)-3-(2-Amino-5-tert-butyl-benzothiazol-6-ylsulfanyl)-6-cyclohexyl-4-hydroxy-6-phenethyl-5,6-dihydro-pyran-2-one;

(S)-3-(2-Amino-5-tert-butyl-benzothiazol-6-ylsulfanyl)-6-cyclopentyl-4-hydroxy-6-phenethyl-5,6-dihydro-pyran-2-one;

(S)-4-Hydroxy-6-[2-(4-hydroxy-phenyl)-ethyl]-6-propyl-3-(5-isopropyl-benzothiazol-6-ylsulfanyl)-5,6-dihydro-pyran-2-one;

(S)-6-Cyclohexyl-4-hydroxy-6-[2-(4-hydroxy-phenyl)-ethyl]-3-(5-isopropyl-benzothiazol-6-ylsulfanyl)-5,6-dihydro-pyran-2-one;

(S)-6-Cyclopentyl-4-hydroxy-6-[2-(4-hydroxy-phenyl)-ethyl]-3-(5-isopropyl-benzothiazol-6-ylsulfanyl)-5,6-dihydro-pyran-2-one;

(S)-3-(6-tert-Butyl-1H-indol-5-yl-sulfanyl)-4-hydroxy-6-propyl-6-(2-phenethyl)-5,6-dihydro-pyran-2-one;

(S)-3-(6-tert-Butyl-1H-indol-5-yl-sulfanyl)-6-cyclohexyl-4-hydroxy-6-(2-phenethyl)-5,6-dihydro-pyran-2-one;

(S)-3-(6-tert-Butyl-1H-indol-5-yl-sulfanyl)-6-cyclopentyl-4-hydroxy-6-(2-phenethyl)-5,6-dihydro-pyran-2-one;

(S)-3-(6-tert-Butyl-1H-indol-5-yl-sulfanyl)-4-hydroxy-6-pentyl-6-(2-phenethyl)-5,6-dihydro-pyran-2-one;

(S)-3-(2-Amino-5-tert-butyl-benzothiazol-6-ylsulfanyl)-6-[2-(3-fluoro-phenyl)-ethyl]-4-hydroxy-6-propyl-5,6-dihydro-pyran-2-one;

(S)-3-(2-Amino-5-tert-butyl-benzothiazol-6-ylsulfanyl)-6-[2-(3-fluoro-phenyl)-ethyl]-4-hydroxy-6-pentyl-5,6-dihydro-pyran-2-one;

(S)-3-(2-Amino-5-tert-butyl-benzothiazol-6-ylsulfanyl)-6-cyclohexyl-6-[2-(3-fluoro-phenyl)-ethyl]-4-hydroxy-5,6-dihydro-pyran-2-one; and (S)-3-(2-Amino-5-tert-butyl-benzothiazol-6-ylsulfanyl)-6-cyclopentyl-6-[2-(3-fluoro-phenyl)-ethyl]-4-hydroxy-5,6-dihydro-pyran-2-one.

21. A compound according to claim 1 named (S)-3-(2-tert-Butyl-4-hydroxymethyl-5-methyl-phenylsulfanyl)-4-hydroxy-6-isopropyl-6-(2-thiophen-3-yl-ethyl)-5,6-dihydro-pyran-2-one.

22. A compound selected from:

5-Hydroxy-6-methyl-5-[2-(4-methyl-thiazol-5-yl)-ethyl]-3-oxo-heptanoic acid methyl ester;

5-Hydroxy-6-methyl-3-oxo-5-(2-thiazol-2-yl-ethyl)-heptanoic acid methyl ester;

5-Hydroxy-6-methyl-3-oxo-5-(2-thiazol-4-yl-ethyl)-heptanoic acid methyl ester;

5-Hydroxy-6-methyl-3-oxo-5-(2-thiazol-5-yl-ethyl)-heptanoic acid methyl ester;

5-Hydroxy-6-methyl-5-[2-(5-methyl-thiazol-2-yl)-ethyl]-3-oxo-heptanoic acid methyl ester;

5-Hydroxy-6-methyl-5-[2-(4-methyl-thiazol-2-yl)-ethyl]-3-oxo-heptanoic acid methyl ester;

5-Hydroxy-6-methyl-5-[2-(2-methyl-thiazol-4-yl)-ethyl]-3-oxo-heptanoic acid methyl ester;

5-Hydroxy-6-methyl-5-[2-(5-methyl-thiazol-4-yl)-ethyl]-3-oxo-heptanoic acid methyl ester;

5-Hydroxy-5-[2-(2-isopropyl-thiazol-4-yl)-ethyl]-6-methyl-3-oxo-heptanoic acid methyl ester;

5-Hydroxy-5-[2-(4-isopropyl-thiazol-5-yl)-ethyl]-6-methyl-3-oxo-heptanoic acid methyl ester;

5-Hydroxy-5-[2-(5-isopropyl-thiazol-4-yl)-ethyl]-6-methyl-3-oxo-heptanoic acid methyl ester;

5-Hydroxy-5-[2-(4-isopropyl-thiazol-2-yl)-ethyl]-6-methyl-3-oxo-heptanoic acid methyl ester;

5-[2-(2-Acetylamino-thiazol-4-yl)-ethyl]-5-hydroxy-6-methyl-3-oxo-heptanoic acid methyl ester;

5-Hydroxy-6-methyl-3-oxo-5-(2-pyridin-2-yl-ethyl)-heptanoic acid methyl ester;

5-Hydroxy-6-methyl-3-oxo-5-(2-pyridin-4-yl-ethyl)-heptanoic acid methyl ester;

5-Hydroxy-6-methyl-3-oxo-5-(2-pyridin-3-yl-ethyl)-heptanoic acid methyl ester;

5-(2-Furan-2-yl-ethyl)-5-hydroxy-6-methyl-3-oxo-heptanoic acid methyl ester;

5-(2-Furan-3-yl-ethyl)-5-hydroxy-6-methyl-3-oxo-heptanoic acid methyl ester;

5-Hydroxy-6-methyl-3-oxo-5-[2-(tetrahydro-furan-2-yl)-ethyl]-heptanoic acid methyl ester;

5-Hydroxy-6-methyl-3-oxo-5-(2-thiophen-3-yl-ethyl)-heptanoic acid methyl ester;

5-Hydroxy-6-methyl-3-oxo-5-(2-thiophen-2-yl-ethyl)-heptanoic acid methyl ester;

5-{2-[2-(tert-Butyl-dimethyl-silanyloxymethyl)-thiophen-3-yl]-ethyl}-5-hydroxy-6-methyl-3-oxo-heptanoic acid methyl ester;

5-{2-[5-(tert-Butyl-dimethyl-silanyloxymethyl)-thiophen-3-yl]-ethyl}-5-hydroxy-6-methyl-3-oxo-heptanoic acid methyl ester;

5-{2-[5-(tert-Butyl-dimethyl-silanyloxymethyl)-thiophen-2-yl]-ethyl}-5-hydroxy-6-methyl-3-oxo-heptanoic acid methyl ester;

5-Hydroxy-5-[2-(5-hydroxymethyl-thiophen-3-yl)-ethyl]-6-methyl-3-oxo-heptanoic acid methyl ester;

5-Hydroxy-5-[2-(5-hydroxymethyl-thiophen-2-yl)-ethyl]-6-methyl-3-oxo-heptanoic acid methyl ester;

5-Hydroxy-5-[2-(2-hydroxymethyl-thiophen-3-yl)-ethyl]-6-methyl-3-oxo-heptanoic acid methyl ester;
5-[2-(3-Fluoro-2-methyl-phenyl)-ethyl]-5-hydroxy-6-methyl-3-oxo-heptanoic acid methyl ester;
5-[2-(2-Fluoro-phenyl)-ethyl]-5-hydroxy-6-methyl-3-oxo-heptanoic acid methyl ester;
5-[2-(4-Fluoro-phenyl)-ethyl]-5-hydroxy-6-methyl-3-oxo-heptanoic acid methyl ester;
5-Hydroxy-6-methyl-3-oxo-5-[2-(1-trityl-1H-pyrazol-3-yl)-ethyl]-heptanoic acid methyl ester;
5-Hydroxy-6-methyl-3-oxo-5-[2-(1H-pyrrol-3-yl)-ethyl]-heptanoic acid methyl ester;
5-Hydroxy-5-[2-(1H-imidazol-4-yl)-ethyl]-6-methyl-3-oxo-heptanoic acid methyl ester;
5-Hydroxy-6-methyl-3-oxo-5-(2-pyrimidin-5-yl-ethyl)-heptanoic acid methyl ester;
5-[2-(2-Amino-pyrimidin-5-yl)-ethyl]-5-hydroxy-6-methyl-3-oxo-heptanoic acid methyl ester;
5-[2-(4-Cyano-phenyl)-ethyl]-5-hydroxy-6-methyl-3-oxo-heptanoic acid methyl ester;
5-Hydroxy-5-[2-(2-hydroxymethyl-phenyl)-ethyl]-6-methyl-3-oxo-heptanoic acid methyl ester;
5-{2-[2-(tert-Butyl-dimethyl-silanyloxymethyl)-phenyl]-ethyl}-5-hydroxy-6-methyl-3-oxo-heptanoic acid methyl ester;
5-Hydroxy-5-[2-(1H-indol-5-yl)-ethyl]-6-methyl-3-oxo-heptanoic acid methyl ester;
5-Hydroxy-6-methyl-3-oxo-{5-2-[2-(2,2,2-trifluoro-acetylamino)-thiazol-4-yl]-ethyl}-heptanoic acid methyl ester;
5-Hydroxy-6-methyl-5-[2-(4-methyl-thiophen-3-yl)-ethyl]-3-oxo-heptanoic acid methyl ester;
5-Hydroxy-6-methyl-5-[2-(3-methyl-thiophen-2-yl)-ethyl]-3-oxo-heptanoic acid methyl ester;
5-{2-[3-(tert-Butyl-dimethyl-silanyloxymethyl)-thiophen-2-yl]-ethyl}-5-hydroxy-6-methyl-3-oxo-heptanoic acid methyl ester;
5-Hydroxy-5-[2-(3-hydroxymethyl-thiophen-2-yl)-ethyl]-6-methyl-3-oxo-heptanoic acid methyl ester;
5-[2-(2,6-Difluoro-phenyl)-ethyl]-5-hydroxy-6-methyl-3-oxo-heptanoic acid methyl ester;
5-[2-(3,5-Difluoro-phenyl)-ethyl]-5-hydroxy-6-methyl-3-oxo-heptanoic acid methyl ester;
5-[2-(2,4-Difluoro-phenyl)-ethyl]-5-hydroxy-6-methyl-3-oxo-heptanoic acid methyl ester;
5-[2-(3,4,5-Trifluoro-phenyl)-ethyl]-5-hydroxy-6-methyl-3-oxo-heptanoic acid methyl ester;
5-[2-(5-Fluoro-2-methyl-phenyl)-ethyl]-5-hydroxy-6-methyl-3-oxo-heptanoic acid methyl ester;
5-[2-(2-Ethyl-5-Fluoro-phenyl)-ethyl]-5-hydroxy-6-methyl-3-oxo-heptanoic acid methyl ester;
5-{2-[2-(tert-Butyl-dimethyl-silanyloxymethyl)-4-fluoro-phenyl]-ethyl}-5-hydroxy-6-methyl-3-oxo-heptanoic acid methyl ester; and
5-Hydroxy-5-[2-(4-fluoro-2-hydroxymethyl-phenyl)-ethyl]-6-methyl-3-oxo-heptanoic acid methyl ester.

23. A compound selected from:
4-Hydroxy-6-isopropyl-6-[2-(4-methyl-thiazol-5-yl)-ethyl]-5,6-dihydro-pyran-2-one;
4-Hydroxy-6-isopropyl-6-(2-thiazol-2-yl-ethyl)-5,6-dihydro-pyran-2-one;
4-Hydroxy-6-isopropyl-6-(2-thiazol-4-yl-ethyl)-5,6-dihydro-pyran-2-one;
4-Hydroxy-6-isopropyl-6-(2-thiazol-5-yl-ethyl)-5,6-dihydro-pyran-2-one;
4-Hydroxy-6-isopropyl-6-[2-(5-methyl-thiazol-2-yl)-ethyl]-5,6-dihydro-pyran-2-one;
4-Hydroxy-6-isopropyl-6-[2-(4-methyl-thiazol-2-yl)-ethyl]-5,6-dihydro-pyran-2-one;
4-Hydroxy-6-isopropyl-6-[2-(2-methyl-thiazol-4-yl)-ethyl]-5,6-dihydro-pyran-2-one;
4-Hydroxy-6-isopropyl-6-[2-(5-methyl-thiazol4-yl)-ethyl]-5,6-dihydro-pyran-2-one;
4-Hydroxy-6-isopropyl-6-[2-(2-isopropyl-thiazol-4-yl)-ethyl]-5,6-dihydro-pyran-2-one;
4-Hydroxy-6-isopropyl-6-[2-(4-isopropyl-thiazol-5-yl)-ethyl]-5,6-dihydro-pyran-2-one;
4-Hydroxy-6-isopropyl-6-[2-(5-isopropyl -thiazol-4-yl)-ethyl]-5,6-dihydro-pyran-2-one;
4-Hydroxy-6-isopropyl-6-[2-(4-isopropyl-thiazol-2-yl)-ethyl]-5,6-dihydro-pyran-2-one;
N-{4-[2-(4-Hydroxy-2-isopropyl-6-oxo-3,6-dihydro-2H-pyran-2-yl)-ethyl]-thiazol-2-yl}-acetamide;
4-Hydroxy-6-isopropyl-6-(2-pyridin-2-yl-ethyl)-5,6-dihydro-pyran-2-one;
4-Hydroxy-6-isopropyl-6-(2-pyridin-4-yl-ethyl)-5,6-dihydro-pyran-2-one;
4-Hydroxy-6-isopropyl-6-(2-pyridin-3-yl-ethyl)-5,6-dihydro-pyran-2-one;
6-(2-Furan-2-yl-ethyl)-4-hydroxy-6-isopropyl-5,6-dihydro-pyran-2-one;
6-(2-Furan-3-yl-ethyl)-4-hydroxy-6-isopropyl-5,6-dihydro-pyran-2-one;
4-Hydroxy-6-isopropyl-6-[2-(tetrahydro-furan-2-yl)-5,6-dihydro-pyran-2-one;
4-Hydroxy-6-isopropyl-6-(2-thiophen-3-yl-ethyl)-5,6-dihydro-pyran-2-one;
4-Hydroxy-6-isopropyl-6-(2-thiophen-2-yl-ethyl)-5,6-dihydro-pyran-2-one;
4-Hydroxy-6-[2-(5-hydroxymethyl-thiophen-2-yl)-ethyl]-6-isopropyl-5,6-dihydro-pyran-2-one;
4-Hydroxy-6-[2-(5-hydroxymethyl-thiophen-3-yl)-ethyl]-6-isopropyl-5,6-dihydro-pyran-2-one;
4-Hydroxy-6-[2-(2-hydroxymethyl-thiophen-3-yl)-ethyl]-6-isopropyl-5,6-dihydro-pyran-2-one;
6-[2-(3-Fluoro-2-methyl-phenyl)-ethyl]-4-hydroxy-6-isopropyl-5,6-dihydro-pyran-2-one;
6-[2-(2-Fluoro-phenyl)-ethyl]-4-hydroxy-6-isopropyl-5,6-dihydro-pyran-2-one;
6-[2-(4-Fluoro-phenyl)-ethyl]-4-hydroxy-6-isopropyl-5,6-dihydro-pyran-2-one;
4-Hydroxy-6-isopropyl-6-[2-(1H-pyrazol-3-yl)-ethyl]-5,6-dihydro-pyran-2-one;
4-Hydroxy-6-isopropyl-6-[2-(1H-pyrrol-3-yl)-ethyl]-5,6-dihydro-pyran-2-one;
4-Hydroxy-6-isopropyl-6-[2-( 1-trityl-1H-imidazol-4-yl)-ethyl]-5,6-dihydro-pyran-2-one;
4-Hydroxy-6-isopropyl-6-(2-pyrimidin-5-yl)-ethyl)-5,6-dihydro-pyran-2-one;
6-[2-(2-Amino-pyrimidin-5-yl)-ethyl]-4-hydroxy-6-isopropyl-5,6-dihydro-pyran-2-one;
4-[2-(4-Hydroxy-2-isopropyl-6-oxo-3,6-dihydro-2H-pyran-2-yl)-ethyl]-benzonitrile
4-Hydroxy-6-isopropyl-6-[2-(2-hydroxymethyl-phenyl)-ethyl]-5,6-dihydro-pyran-2-one;
4-Hydroxy-6-[2-(1H-indol-5-yl)-ethyl]-6-isopropyl-5,6-dihydro-pyran-2-one;
2,2,2-Trifluoro-N-{4-[2-(4-hydroxy-2-isopropyl-6-oxo-3,6-dihydro-2H-pyran-2-yl)-ethyl]-thiazol-2-yl}-acetamide;
4-Hydroxy-6-isopropyl-6-[2-(4-methyl-thiophen-3-yl)-ethyl]-5,6-dihydro-pyran-2-one;
4-Hydroxy-6-isopropyl-6-[2-(3-methyl-thiophen-2-yl)-ethyl]-5,6-dihydro-pyran-2-one;
4-Hydroxy-6-[2-(3-hydroxymethyl-thiophen-2-yl)-ethyl]-6-isopropyl-5,6-dihydro-pyran-2-one 6-[2-(2,6-Difluoro-phenyl)-ethyl]-4-hydroxy-6-isopropyl-5,6-dihydro-pyran-2-one;

6-[2-(3,5-Difluoro-phenyl)-ethyl]-4-hydroxy-6-isopropyl-5,6-dihydro-pyran-2-one;

6-[2-(2,4-Difluoro-phenyl)-ethyl]-4-hydroxy-6-isopropyl-5,6-dihydro-pyran-2-one;

6-[2-(3,4,5-Trifluoro-phenyl)-ethyl]-4-hydroxy-6-isopropyl-5,6-dihydro-pyran-2-one;

6-[2-(5-Fluoro-2-methyl-phenyl)-ethyl]-4-hydroxy-6-isopropyl-5,6-dihydro-pyran-2-one;

6-[2-(2-Ethyl-5-Fluoro-phenyl)-ethyl]-4-hydroxy-6-isopropyl-5,6-dihydro-pyran-2-one;

6-{2-[2-(tert-Butyl-dimethyl-silanyloxymethyl)-4-fluoro-phenyl]-ethyl}-4-hydroxy-6-isopropyl-5,6-dihydro-pyran-2-one; and 6-[2-(4-Fluoro-2-hydroxymethyl-phenyl)-ethyl]-4-hydroxy-6-isopropyl-5,6-dihydro-pyran-2-one.

24. A compound selected from:

(S)-5-Hydroxy-6-methyl-3-oxo-5-(2-thiophen-3-yl-ethyl)-heptanoic acid ethyl ester;

(R)-5-Hydroxy-6-methyl-3-oxo-5-(2-thiophen-3-yl-ethyl)-heptanoic acid ethyl ester;

5-[2-(3-Fluoro-phenyl)-ethyl]-5-hydroxy-6-methyl-3-oxo-heptanoic acid ethyl ester, (S) enantiomer;

(R)-5-[2-(3-Fluoro-phenyl)-ethyl]-5-hydroxy-6-methyl-3-oxo-heptanoic acid ethyl ester;

5-[2-(3,4-Difluoro-phenyl)-ethyl]-5-hydroxy-6-methyl-3-oxo-heptanoic acid ethyl ester (R and S isomers);

5-Hydroxy-6-methyl-3-oxo-5-[2-(2-trifluoromethyl-phenyl)-ethyl]-heptanoic acid ethyl ester;

5-Hydroxy-6-methyl-3-oxo-5-[2-(3-trifluoromethyl-phenyl)-ethyl]-heptanoic acid ethyl ester;

5-Hydroxy-6-methyl-3-oxo-5-[2-(4-trifluoromethyl-phenyl)-ethyl]-heptanoic acid ethyl ester;

5-[2-(3-Fluoro-5-trifluoromethyl-phenyl)-ethyl]-5-hydroxy-6-methyl-3-oxo-heptanoic acid ethyl ester;

5-[2-(4-Fluoro-3-trifluoromethyl-phenyl)-ethyl]-5-hydroxy-6-methyl-3-oxo-heptanoic acid ethyl ester;

(S)-5-Hydroxy-5-[2-(2-hydroxymethyl-phenyl)-ethyl]-6-methyl-3-oxo-heptanoic acid ethyl ester;

(R)-5-Hydroxy-5-[2-(2-hydroxymethyl-phenyl)-ethyl]-6-methyl-3-oxo-heptanoic acid ethyl ester;

5-Hydroxy-6-methyl-3-oxo-5-(2-phenyl-ethyl)-heptanoic acid ethyl ester (R and S isomers);

5-[2-(4-Fluoro-phenyl)-ethyl]-5-hydroxy-6-methyl-3-oxo-heptanoic acid ethyl ester (S and R isomers);

5-{2-[4-(tert-Butyl-dimethyl-silanyloxymethyl)-thiophen-3-yl]-ethyl}-5-hydroxy-6-methyl-3-oxo-heptanoic acid ethyl ester;

(S)-5-Hydroxy-6-methyl-5-[2-(2-methyl-thiophen-3-yl)-ethyl]-3-oxo-heptanoic acid ethyl ester;

(S)-5-[2-(3-Fluoro-2-methyl-phenyl)-ethyl]-5-hydroxy-6-methyl-3-oxo-heptanoic acid ethyl ester;

(S)-5-[2-(3,5-Difluoro-2-methyl-phenyl)-ethyl]-5-hydroxy-6-methyl-3-oxo-heptanoic acid ethyl ester; and (S)-5-[2-(4-Fluoro-2-methyl-phenyl)-ethyl]-5-hydroxy-6-methyl-3-oxo-heptanoic acid ethyl ester.

25. A compound of Formula 1A

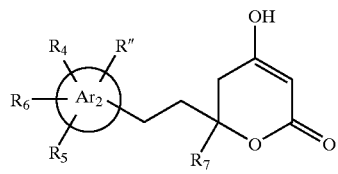

wherein $R_4$, $R_5$, and $R_6$ are independently H, a straight or branched alkyl of 1–6 carbons, a cycloalkyl of 3–6 carbons, $(CR'_2)_nOR$, $(CR'_2)_nN(R)_2$, F, Cl, Br, CN, $CF_3$, $=O$, $(CR'_2)_pNR'COR$, $(CR'_2)_pSO_pR$, $(CR'_2)_pR$, $(CR'_2)_p$ $OCOR$, $O(CR'_2)_mOR$, $NR(CR'_2)_mOR$, $(CR'_2)_pNR'CON(R)_2$, $(CR'_2)_pOCON(R)_2$, $(CR'_2)_pNR'CO_2R$, $(CR'_2)_p$ $COR$, $(CR'_2)_pCO_2R$, $(CR'_2)_pCON(R)_2$, $(CR'_2)_p$ $NR'SO_2R$, $(CR'_2)_pSO_2N(R)_2$, $(CR'_2)_pNR'SO_2OR$, $(CR'_2)_pOSO_2N(R)_2$, $(CR'_2)_pNR'SO_2N(R)_2$, $(CR'_2)_pC$ $(NR')N(R)_2$, $(CR'_2)_pNR'C(NR')N(R)_2$, $(CR'_2)_pHet$;

any two of $R_4$–$R_6$ may together form a ring of 5–6 total atoms which may contain 0–3 heteroatoms;

n is an integer of from 0 to 3;

p is an integer from 0 to 2;

$R_7$ is a straight or branched alkyl of 1–6 carbons or a carbocycle of 3–6 carbons;

R is independently H, a straight or branched alkyl of 1–4 carbons, $(CH_2)_nPh$, or a $(CH)_n$heterocycle of 5–6 atoms containing 1–2 heteroatoms and wherein the $(R)_2$ in $N(R)_2$ may form a heterocycle containing the nitrogen, all optionally substituted by F, Cl, Br, OR', CN, $CO_2R'$, $N(R')_2$, NR'COR', $CF_3$, or $=O$;

R' is independently H, a straight or branched alkyl of 1–4 carbons, or phenyl;

R" is independently H, a straight or branched alkyl of 1–4 carbons, F, Cl, Br, OR', or $N(R')_2$;

$Ar_2$ is phenyl or Het wherein Het is a heterocycle of from 5–6 atoms having from 1–4 heteroatoms.

26. A compound selected from:

3-Hydroxy-4-methyl-3-(2-thiophen-3-yl-ethyl)-pentanoic acid tert-butyl ester;

5-(3-Fluoro-phenyl)-3-hydroxy-3-isopropyl-pent-4-enoic acid benzyl ester;

5-(3,4-Difluoro-phenyl)-3-hydroxy-3-isopropyl-pent-4-enoic acid benzyl ester;

3-Hydroxy-3-isopropyl-5-(2-trifluoromethyl-phenyl)-pent-4-enoic acid benzyl ester;

3-Hydroxy-3-isopropyl-5-(3-trifluoromethyl-phenyl)-pent-4-enoic acid benzyl ester;

3-Hydroxy-3-isopropyl-5-(4-trifluoromethyl-phenyl)-pent-4-enoic acid benzyl ester;

5-(3-Fluoro-5-trifluoromethyl-phenyl)-3-hydroxy-3-isopropyl-pent-4-enoic acid benzyl ester;

5-(4-Fluoro-3-trifluoromethyl-phenyl)-3-hydroxy-3-isopropyl-pent-4-enoic acid benzyl ester;

3-Hydroxy-3-[2-(2-hydroxymethyl-phenyl)-ethyl]-4-methyl-pentanoic acid tert-butyl ester;

3-Hydroxy-4-methyl-3-(2-phenyl-ethyl)-pentanoic acid tert-butyl ester;

3-Hydroxy-3-isopropyl-5-phenyl-3-pent-4-enoic acid benzyl ester;

5-(4-Fluoro-phenyl)-3-hydroxy-3-isopropyl-pent-4-enoic acid benzyl ester;

3-{2-[4-(tert-Butyl-dimethyl-silanyloxymethyl)-thiophen-3-yl]-ethyl}-3-hydroxy-4-methyl-pentanoic acid ethyl ester;

3-Hydroxy-4-methyl-3-[2-(2-methyl-thiophen-3-yl)-ethyl]-pentanoic acid tert-butyl ester;

5-(3-Fluoro-2-methyl-phenyl)-3-hydroxy-3-isopropyl-pent-4-enoic acid benzyl ester;

5-(3,5-Difluoro-phenyl)-3-hydroxy-3-isopropyl-pent-4-enoic acid benzyl ester; and 5-(4-Fluoro-2-methyl-phenyl)-3-hydroxy-3-isopropyl-pent-4-enoic acid tert-butyl ester.

27. A compound selected from:

(S)-3-Hydroxy-4-methyl-3-(2-thiophen-3-yl-ethyl)-pentanoic acid;

(R)-3-Hydroxy-4-methyl-3-(2-thiophen-3-yl-ethyl)-pentanoic acid;

(+/−)-3-Hydroxy-4-methyl-3-(2-thiophen-3-yl-ethyl)-pentanoic acid;

3-[2-(3-Fluoro-phenyl)-ethyl]-3-hydroxy4-methyl-pentanoic acid;

3-[2-(3,4-Difluoro-phenyl)-ethyl]-3-hydroxy-4-methyl-pentanoic acid;

3-Hydroxy-4-methyl-3-[2-(2-trifluoromethyl-phenyl)-ethyl]-pentanoic acid;

3-Hydroxy-4-methyl-3-[2-(3-trifluoromethyl-phenyl)-ethyl]-pentanoic acid;

3-Hydroxy-4-methyl-3-[2-(4-trifluoromethyl-phenyl)-ethyl]-pentanoic acid;

3-[2-(3-Fluoro-5-trifluoromethyl-phenyl)-ethyl]-3-hydroxy-4-methyl-pentanoic acid;

3-[2-(4-Fluoro-3-trifluoromethyl-phenyl)-ethyl]-3-hydroxy-4-methyl-pentanoic acid;

(S)-3-Hydroxy-3-[2-(2-hydroxymethyl-phenyl)-ethyl]-4-methyl-pentanoic acid;

(R)-3-Hydroxy-3-[2-(2-hydroxymethyl-phenyl)-ethyl]-4-methyl-pentanoic acid;

3-Hydroxy-4-methyl-3-(2-phenyl-ethyl)-pentanoic acid;

3-[2-(4-Fluoro-phenyl)-ethyl]-3-hydroxy-4-methyl-pentanoic acid;

3-{2-[4-(tert-Butyl-dimethyl-silanyloxy-methyl)-thiophen-3-yl]-ethyl}-3-hydroxy-4-methyl-pentanoic acid;

3-Hydroxy-4-methyl-3-[2-(2-methyl-thiophen-3-yl)-ethyl]-pentanoic acid;

3-[2-(3-Fluoro-2-methyl-phenyl)-ethyl]-3-hydroxy-4-methyl-pentanoic acid;

3-[2-(3,5-Difluoro-phenyl)-ethyl]-3-hydroxy-4-methyl-pentanoic acid; and

3-[2-(4-Fluoro-2-methyl-phenyl)-ethyl]-3-hydroxy-4-methyl-pentanoic acid.

28. A compound selected from:

(S)-4-Hydroxy-6-isopropyl-6-(2-thiophen-3-yl-ethyl)-5,6-dihydro-pyran-2-one;

(R)-4-Hydroxy-6-isopropyl-6-(2-thiophen-3-yl-ethyl)-5,6-dihydro-pyran-2-one;

6-[2-(3-Fluoro-phenyl)-ethyl]-4-hydroxy-6-isopropyl-5,6-dihydro-pyran-2-one (R and S isomers);

6-[2-(3,4-Difluoro-phenyl)-ethyl]-4-hydroxy-6-isopropyl-5,6-dihydro-pyran-2-one (R and S isomers);

4-Hydroxy-6-isopropyl-6-[2-(2-trifluoromethyl-phenyl)-ethyl]-5,6-dihydro-pyran-2-one;

4-Hydroxy-6-isopropyl-6-[2-(3-trifluoromethyl-phenyl)-ethyl]-5,6-dihydro-pyran-2-one;

4-Hydroxy-6-isopropyl-6-[2-(4-trifluoromethyl-phenyl)-ethyl]-5,6-dihydro-pyran-2-one;

6-[2-(3-Fluoro-5-trifluoromethyl-phenyl)-ethyl]-4-hydroxy-6-isopropyl-5,6-dihydro-pyran-2-one;

6-[2-(4-Fluoro-3-trifluoromethyl-phenyl)-ethyl]-4-hydroxy-6-isopropyl-5,6-dihydro-pyran-2-one;

(S)-4-Hydroxy-6-[2-(2-hydroxymethyl-phenyl)-ethyl]-6-isopropyl-5,6-dihydro-pyran-2-one;

(R)-4-Hydroxy-6-[2-(2-hydroxymethyl-phenyl)-ethyl]-6-isopropyl-5,6-dihydro-pyran-2-one;

4-Hydroxy-6-isopropyl-6-(2-phenyl-ethyl)-5,6-dihydro-pyran-2-one (R and S isomers);

6-[2-(4-Fluoro-phenyl)-ethyl]-4-hydroxy-6-isopropyl-5,6-dihydro-pyran-2-one (R and S isomers);

4-Hydroxy-6-[2-(4-hydroxymethyl-thiophen-3-yl)-ethyl]-6-isopropyl-5,6-dihydro-pyran-2-one;

(S)-4-Hydroxy-6-isopropyl-6-[2-(2-methyl-thiophen-3-yl)-ethyl]-5,6-dihydro-pyran-2-one;

(S)-6-[2-(3-Fluoro-2-methyl-phenyl)-ethyl]4-hydroxy-6-isopropyl-5,6-dihydro-pyran-2-one;

(S)-6-[2-(3,5-Difluoro-phenyl)-ethyl]-4-hydroxy-6-isopropyl-5,6-dihydro-pyran-2-one; and (S)-6-[2-(4-Fluoro-2-methyl-phenyl)-ethyl]-4-hydroxy-6-isopropyl-5,6-dihydro-pyran-2-one.

29. A compound and the R and S isomer thereof selected from:

3-[2-(3-Fluoro-phenyl)-ethyl]-3-hydroxy-1-imidazol-1-yl-4-methyl-pentan-1-one;

3-Hydroxy-1-imidazol-1-yl-4-methyl-3-phenethyl-pentan-1-one;

3-[2-(3,4-Difluoro-phenyl)-ethyl]-3-hydroxy-1-imidazol-1-yl-4-methyl-pentan-1-one;

3-Hydroxy-1-imidazol-1-yl-4-methyl-3-[2-(2-trifluoromethyl-phenyl)-ethyl]-pentan-1-one;

3-[2-(4-Fluoro-3-trifluoromethyl-phenyl)-ethyl]-3-hydroxy-1-imidazol-1-yl-4-methyl-pentan-1-one;

3-Hydroxy-1-imidazol-1-yl-4-methyl-3-[2-(3-trifluoromethyl-phenyl)-ethyl]-pentan-1-one;

3-[2-(4-Fluoro-2-trifluoromethyl-phenyl)-ethyl]-3-hydroxy-1-imidazol-1-yl-4-methyl-pentan-1-one;

3-Hydroxy-1-imidazol-1-yl-4-methyl-3-[2-(4-trifluoromethyl-phenyl)-ethyl]-pentan-1-one;

3-[2-(4-Fluoro-phenyl)-ethyl]-3-hydroxy-1-imidazol-1-yl-4-methyl-pentan-1-one;

3-Hydroxy-1-imidazol-1-yl-4-methyl-3-[2-thiophen-3-yl-ethyl)-pentan-1-one; and

3-Hydroxy-3-[2-(2-hydroxymethyl-phenyl)-ethyl]-1-imidazol-1-yl-4-methyl-pentan-1-one.

30. A pharmaceutical composition for the treatment of infection or disease caused by a retrovirus, which comprises an amount of the compound of claim 1 sufficient to provide an antivirally effective dosage of the compound in the range of about 0.01 to about 100 mg/kg-day and a pharmaceutically effective carrier.

31. A method of treatment of infection or disease caused by a retrovirus, which comprises administering to a subject in need of such treatment a compound of claim 1.

32. A method of treatment of infection or disease caused by a retrovirus, which comprises administering to a subject in need of such treatment a compound of claim 1 in combination with an HIV reverse transcriptase inhibitor.

33. A method of treatment of infection or disease caused by a retrovirus, which comprises administering to a subject in need of such treatment a compound according to claim 1 and another antiretroviral agent.

* * * * *